(12) United States Patent
Brown

(10) Patent No.: US 12,109,110 B2
(45) Date of Patent: *Oct. 8, 2024

(54) PERCUTANEOUS TRICUSPID VALVE REPAIR DEVICES AND METHODS

(71) Applicant: Tangent Cardiovascular, Inc., Forestville, CA (US)

(72) Inventor: Nathan Daniel Brown, Forestville, CA (US)

(73) Assignee: Tangent Cardiovascular, Inc., Forestville, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/358,760

(22) Filed: Jul. 25, 2023

(65) Prior Publication Data

US 2023/0372088 A1 Nov. 23, 2023

Related U.S. Application Data

(63) Continuation of application No. 18/308,589, filed on Apr. 27, 2023.

(Continued)

(51) Int. Cl.
*A61F 2/24* (2006.01)
*A61F 2/848* (2013.01)

(52) U.S. Cl.
CPC .......... *A61F 2/2415* (2013.01); *A61F 2/2445* (2013.01); *A61F 2/2487* (2013.01); *A61F 2002/8483* (2013.01)

(58) Field of Classification Search
CPC .... A61F 2/2457; A61F 2/2418; A61F 2/2454; A61F 2/246; A61F 2/2409; A61F 2/2442;

(Continued)

(56) References Cited

U.S. PATENT DOCUMENTS 7,189,199 B2   3/2007  McCarthy et al.
7,431,692 B2 * 10/2008 Zollinger .............. A61F 2/2487
                                                    600/37

(Continued)

FOREIGN PATENT DOCUMENTS

EP    3270794    1/2018
EP    3930628    1/2022

(Continued)

OTHER PUBLICATIONS

International Seach Report and Written Opinion for International Application No. PCT/US2023/020277, Notification mailed Sep. 19, 2023.

(Continued)

*Primary Examiner* — Seema Mathew
(74) *Attorney, Agent, or Firm* — Knobbe, Martens, Olson & Bear, LLP

(57) ABSTRACT

A first ventricular surface anchor can be placed against a first right ventricular surface, wherein the first ventricular surface anchor is connected to a first tension member. A first tension anchor against a tension anchor surface of a heart, wherein the first tension anchor is connected to a second tension member. The first tension member connected to the first ventricular surface anchor can extend towards the second tension member connected to the first tension anchor; and the first tension member and the second tension member, can be draw the first right ventricular surface toward the first tension anchor. The surface anchor can include a nitinol frame forming an outer perimeter and a hole. The nitinol frame can have an austenite state in a deployed configuration when a temperature of the nitinol frame is body temperature. The surface anchor can also include a grommet comprising a distal tubular portion connected to a proximal finger portion.

19 Claims, 92 Drawing Sheets

Related U.S. Application Data

(60) Provisional application No. 63/379,404, filed on Oct. 13, 2022, provisional application No. 63/336,850, filed on Apr. 29, 2022.

(58) Field of Classification Search
CPC .... A61F 2/2487; A61F 2/2451; A61F 2/2445; A61F 2/2415; A61F 2/24; A61B 17/0469; A61F 17/0485; A61B 2017/00243; A61B 2017/00783; A61B 2017/0464; A61B 2017/0496
See application file for complete search history.

(56) References Cited

U.S. PATENT DOCUMENTS

| | | | |
|---|---|---|---|
| 7,695,425 | B2 | 4/2010 | Schweich et al. |
| 8,979,750 | B2 | 3/2015 | Van Bladel et al. |
| 9,801,720 | B2 | 10/2017 | Gilmore et al. |
| 9,999,507 | B2 | 6/2018 | Sutherland et al. |
| 10,010,315 | B2 | 7/2018 | Cahalane et al. |
| 10,039,643 | B2 * | 8/2018 | Gilmore ............ A61B 17/0401 |
| 10,052,095 | B2 | 8/2018 | Gilmore et al. |
| 10,058,323 | B2 | 8/2018 | Maisano |
| 10,076,414 | B2 | 9/2018 | Rourke et al. |
| 10,405,978 | B2 | 9/2019 | Maisano et al. |
| 10,463,492 | B2 | 11/2019 | Tylis et al. |
| 10,543,090 | B2 * | 1/2020 | Griswold ........... A61B 17/0469 |
| 10,575,953 | B2 | 3/2020 | Van Bladel et al. |
| 10,617,525 | B2 | 4/2020 | Annest et al. |
| 10,660,755 | B2 | 5/2020 | Gilmore et al. |
| 10,682,229 | B2 * | 6/2020 | Guidotti ............ A61B 17/0401 |
| 10,828,160 | B2 | 11/2020 | Sutherland et al. |
| 10,918,374 | B2 | 2/2021 | Groothuis et al. |
| 10,925,731 | B2 * | 2/2021 | Bishop ................. A61F 2/2457 |
| 11,051,942 | B2 | 7/2021 | Van Bladel et al. |
| 11,071,628 | B2 * | 7/2021 | Gross ................... A61F 2/2451 |
| 11,097,090 | B2 | 8/2021 | Vasilyev et al. |
| 11,147,673 | B2 * | 10/2021 | McAfee ............... A61F 2/2457 |
| 11,344,310 | B2 * | 5/2022 | Herman ............. A61B 17/0401 |
| 11,357,629 | B1 | 6/2022 | Gross ................... A61F 2/2466 |
| 11,684,475 | B2 * | 6/2023 | Bishop ................. A61F 2/2457 623/2.11 |
| 2005/0251159 | A1 * | 11/2005 | Ewers ..................... A61B 17/10 606/153 |
| 2006/0030886 | A1 * | 2/2006 | Clark ................. A61B 17/0057 606/232 |
| 2007/0213582 | A1 * | 9/2007 | Zollinger ........... A61B 17/0401 600/37 |
| 2010/0023118 | A1 * | 1/2010 | Medlock ........... A61B 17/0487 606/228 |
| 2011/0288635 | A1 * | 11/2011 | Miller .................. A61F 2/2457 606/228 |
| 2011/0301698 | A1 * | 12/2011 | Miller .................. A61F 2/2442 623/2.1 |
| 2015/0250590 | A1 * | 9/2015 | Gries ................ A61B 17/0401 623/2.11 |
| 2016/0051252 | A1 * | 2/2016 | Smith ................ A61B 17/0466 606/232 |
| 2016/0135953 | A1 * | 5/2016 | Alon ..................... A61F 2/2466 623/2.11 |
| 2016/0367367 | A1 * | 12/2016 | Maisano .............. A61B 17/068 |
| 2017/0189187 | A1 * | 7/2017 | Ruiz .................. A61B 17/0487 |
| 2017/0216031 | A1 * | 8/2017 | Machold .......... A61B 17/00234 |
| 2017/0340443 | A1 * | 11/2017 | Stearns ................. A61F 2/2466 |
| 2018/0289474 | A1 * | 10/2018 | Rajagopal ............ A61F 2/2418 |
| 2018/0318083 | A1 * | 11/2018 | Bolling .............. A61B 17/0401 |
| 2018/0360439 | A1 * | 12/2018 | Niland ............... A61B 17/0483 |
| 2019/0015205 | A1 * | 1/2019 | Rajagopal .......... A61B 17/0401 |
| 2019/0117400 | A1 * | 4/2019 | Medema ............... A61F 2/2457 |
| 2019/0117401 | A1 * | 4/2019 | Cortez, Jr. ......... A61B 17/0469 |
| 2019/0151093 | A1 * | 5/2019 | Keidar .................. A61F 2/2487 |
| 2019/0167428 | A1 * | 6/2019 | Tobis ................... A61B 17/068 |
| 2019/0183648 | A1 * | 6/2019 | Trapp .................... A61F 2/2463 |
| 2019/0240014 | A1 * | 8/2019 | Tegels .................. A61F 2/2418 |
| 2019/0343633 | A1 * | 11/2019 | Garvin ................. A61F 2/2457 |
| 2020/0069426 | A1 | 3/2020 | Conklin et al. |
| 2021/0030537 | A1 * | 2/2021 | Tegels .................. A61F 2/2409 |
| 2021/0038378 | A1 | 2/2021 | Sutherland et al. |
| 2021/0298728 | A1 | 9/2021 | Lashinski et al. |
| 2021/0338429 | A1 * | 11/2021 | Cortez, Jr. ......... A61B 17/0469 |
| 2021/0378824 | A1 * | 12/2021 | Popp .................... A61F 2/2466 |
| 2022/0031457 | A1 * | 2/2022 | McAfee ............... A61F 2/2487 |
| 2022/0039957 | A1 * | 2/2022 | Machold ............ A61B 17/0401 |
| 2022/0047389 | A1 * | 2/2022 | Tobis ................... A61F 2/2487 |
| 2022/0054270 | A1 * | 2/2022 | Manash ................ A61F 2/2457 |
| 2022/0079627 | A1 * | 3/2022 | Awtrey ................ A61B 17/842 |
| 2022/0192654 | A1 * | 6/2022 | Young .............. A61B 17/06166 |
| 2022/0249232 | A1 * | 8/2022 | Cournane ............. A61F 2/2463 |
| 2022/0287843 | A1 * | 9/2022 | Trapp .................... A61F 2/2463 |
| 2022/0362022 | A1 * | 11/2022 | Dorff .................... A61F 2/2445 |
| 2022/0401087 | A1 * | 12/2022 | Zarbatany .......... A61B 17/0057 |
| 2023/0048179 | A1 * | 2/2023 | Zarbatany ............. A61F 2/2466 |
| 2023/0059371 | A1 * | 2/2023 | Hariton ............ A61M 25/0102 |
| 2023/0218291 | A1 * | 7/2023 | Zarbatany .......... A61B 17/0401 606/144 |
| 2023/0320856 | A1 * | 10/2023 | Zarbatany .......... A61B 17/0487 623/2.11 |
| 2023/0346545 | A1 * | 11/2023 | Brown ................. A61F 2/2415 |
| 2023/0404756 | A1 * | 12/2023 | Pham ................. A61B 17/0401 |
| 2024/0148506 | A1 * | 5/2024 | Han ..................... A61L 27/3625 |
| 2024/0148507 | A1 * | 5/2024 | Scheinblum .......... A61F 2/2457 |

FOREIGN PATENT DOCUMENTS

| | | |
|---|---|---|
| WO | WO 2020/096862 | 5/2020 |
| WO | WO 2020/197854 | 10/2020 |
| WO | WO 2020/236417 | 11/2020 |
| WO | WO 2021/034538 | 2/2021 |
| WO | WO 2021/240289 | 12/2021 |

OTHER PUBLICATIONS

ISA PCT/US2023/020277, dated Jun. 27, 2023; 3 pages.
Khan et al. "Transcatheter Pledget-Assisted Suture Tricuspid Annuloplasty (PASTA) to create double-orifice valve" Catheterization and Cardiovascular Interventions., (dated Sep. 1, 2018) vol. 92, No. 3, pp. 1-17.

* cited by examiner

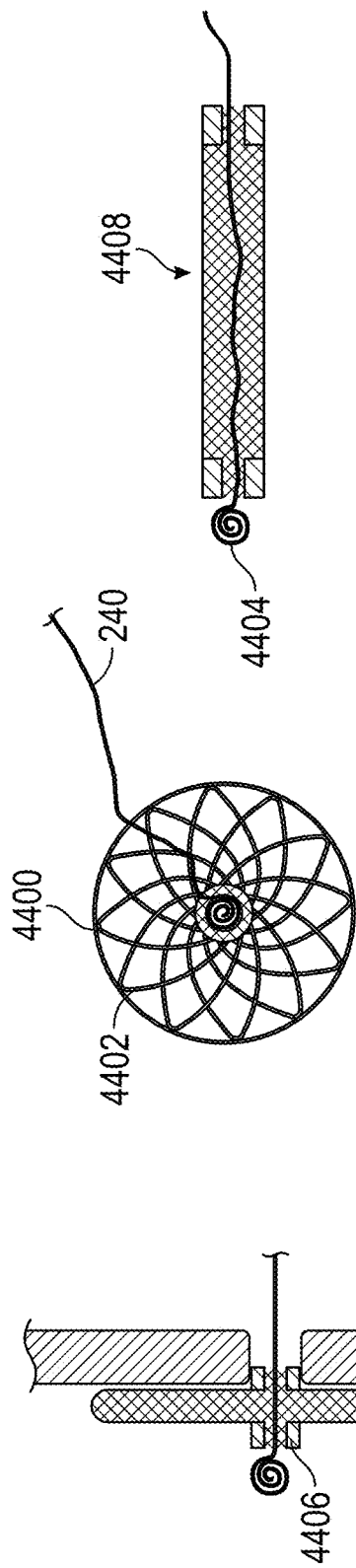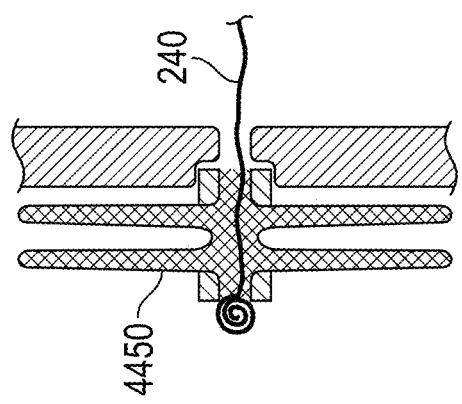
FIG. 44A
FIG. 44B

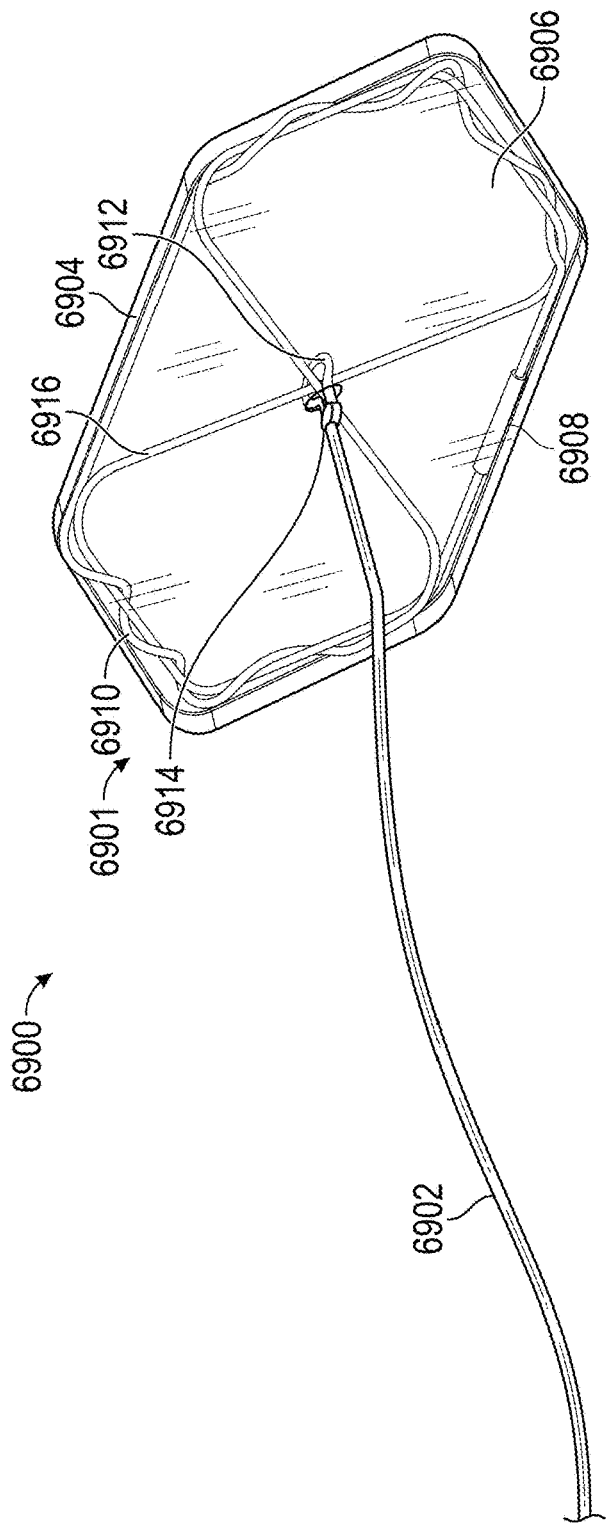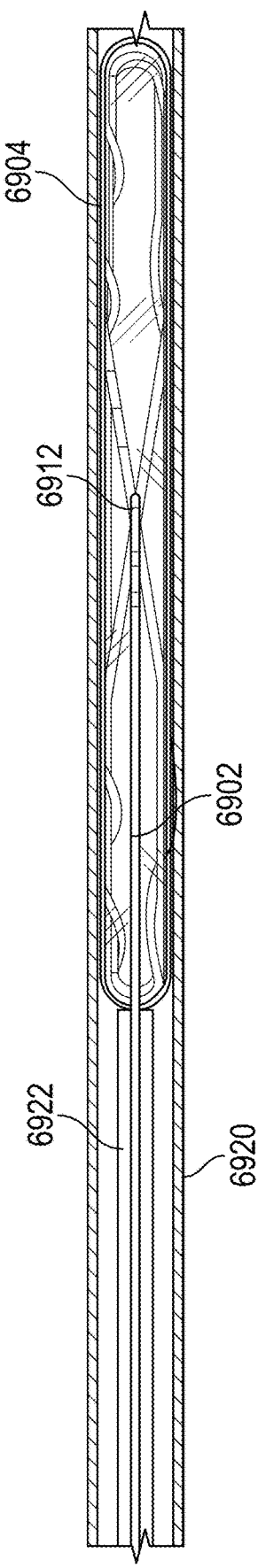
FIG. 69A
FIG. 69B

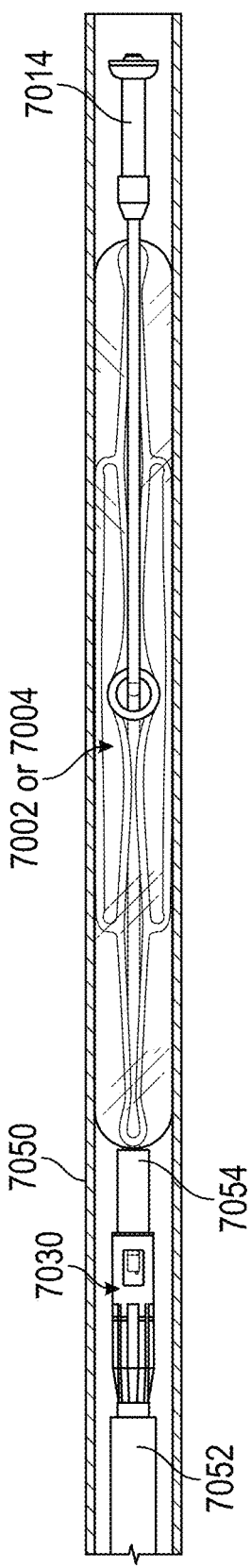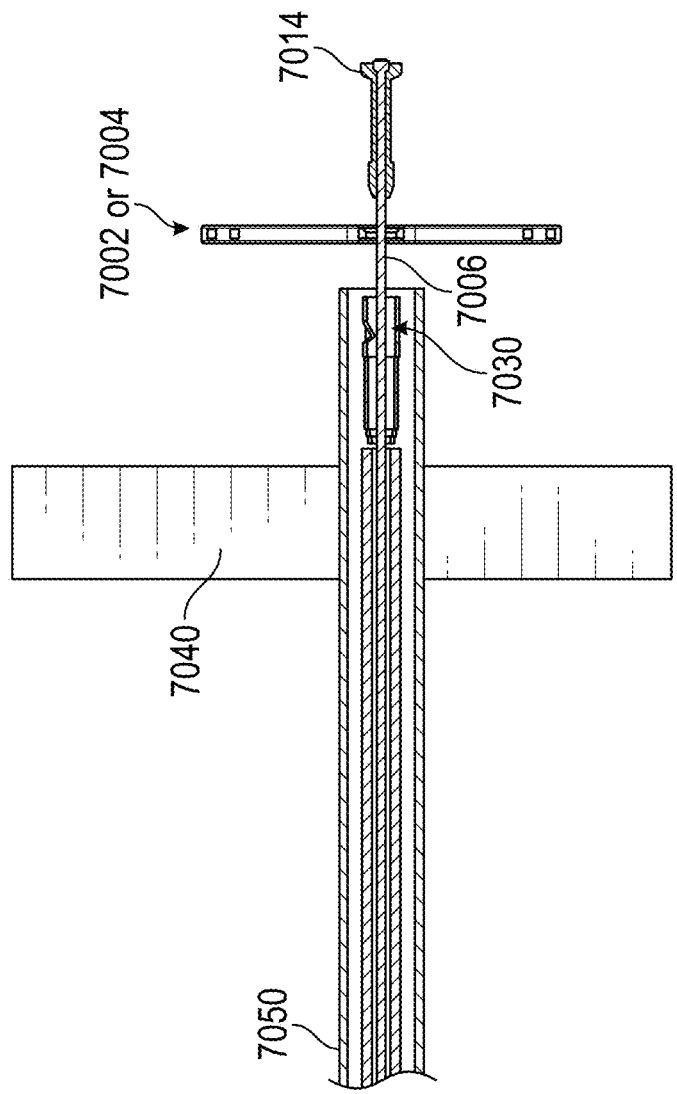

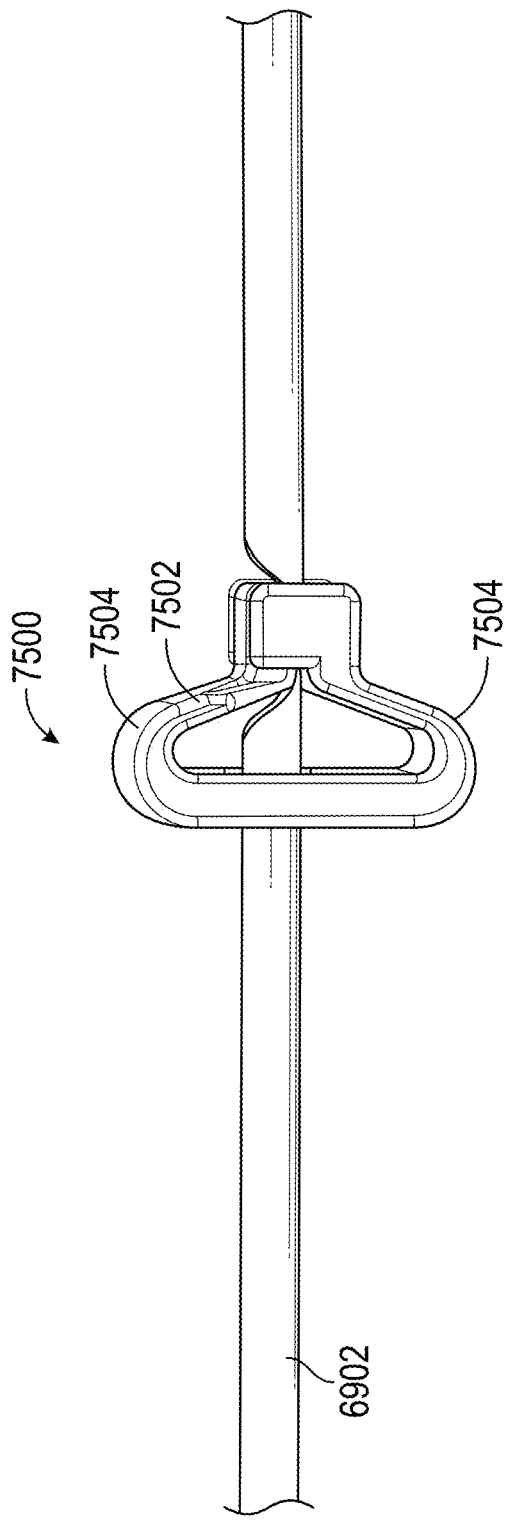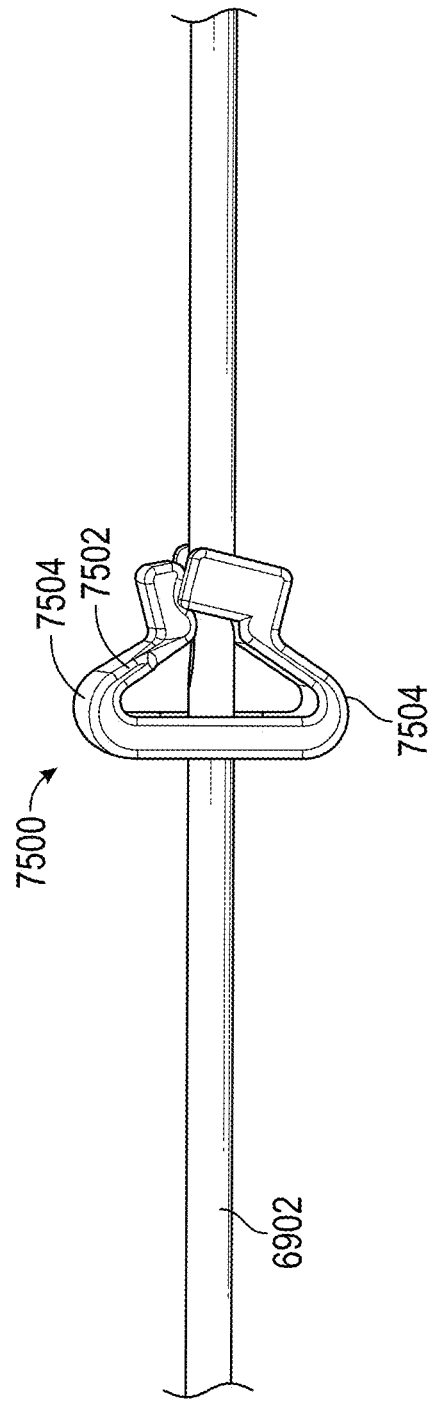
FIG. 75A
FIG. 75B

PERCUTANEOUS TRICUSPID VALVE REPAIR DEVICES AND METHODS

INCORPORATION BY REFERENCE TO ANY PRIORITY APPLICATIONS

This application is a continuation of U.S. patent application Ser. No. 18/308,589, filed Apr. 27, 2023, which claims priority to U.S. Provisional Application No. 63/379,404, filed on Oct. 13, 2022 and U.S. Provisional Application No. 63/336,850, filed on Apr. 29, 2022, the entirety of each of these priority applications are hereby incorporated by reference herein for all purposes.

BACKGROUND

Field

The present disclosure generally relates to percutaneous repair of a heart valve and in certain embodiments percutaneous repair of a tricuspid valve.

Description of the Related Art

Functional tricuspid regurgitation (FTR) is a result of one or several pathophysiological abnormalities of the heart which may include tricuspid valve annular dilatation, annular shape, right or left ventricular disfunction, right or left ventricular shape, right or left sided heart failure, pulmonary hypertension (primary or secondary to mitral valve regurgitation), and valve leaflet tethering. It is currently estimated that 1.6 million people in the United States suffer from moderate to severe tricuspid regurgitation and only 8,000 of these people undergo tricuspid valve surgery annually. Historical treatment options for patients suffering from tricuspid regurgitation have been medical management and tricuspid valve surgery. Most tricuspid valve surgeries are in conjunction with left heart valve surgery, for instance, mitral valve surgery. Few isolated tricuspid valve surgeries are performed and those that are performed are associated with high operative mortality (8-10%). FTR, particularly moderate to severe FTR, has been shown to be a strong independent determinant of mortality and is associated with more heart failure signs and symptoms, reduced cardiac output and impaired renal function. Thus, there is a distinct need for less invasive approaches to treating functional tricuspid regurgitation.

SUMMARY

Certain embodiments of the disclosure comprise drawing the anterior portion of the tricuspid annulus toward the posterior septal portion of the tricuspid annulus, near the coronary sinus ostium, thereby reducing the annular dimension in the region of the valve where tricuspid regurgitation is most prevalent. The vector of force transmission in certain embodiments can be substantially across the orifice of the valve and very close to the annular plane which makes force transmission very efficient and effective for optimal reduction of the tricuspid valve diameter. The utilization of the space created by the right ventricular outflow tract (RVOT), with the anchors abutted against the right ventricular surface of the anterior tricuspid annulus, can provide a large and robust area for safely placing tissue anchors, herein also referred to as surface anchors, and distributing force over a large surface area, minimizing stresses in the tissue. Utilizing multiple tissue anchors which each can be attached to a tensioning element and spanning 1-3, or more, centimeters of the tricuspid annulus, or a single tissue anchor spanning such distance with 2 or more individually attached tension members, can further reduce tissue stresses by distributing the force application over a larger surface area and dividing the required tensioning force over multiple tensioning elements. The ability to control the tension on each tensioning element individually allows the implanting user to tailor the reduction in tricuspid annular diameter to achieve optimal leaflet coaptation and minimize any distortion of the right coronary artery (RCA). Placing one or more anchoring elements across the inferior interatrial septum, with the anchoring element abutted against the left atrial wall above the mitral valve, provides a very secure location for anchor fixation and force transmittal that has not been previously utilized in tricuspid valve repair. The muscle tissue in this region of the interatrial septum is thick and closely adhered to the left ventricular myocardium providing a relatively immobile location by which force can be transmitted. This location is also near the tricuspid annular plane and substantially across from the anterior annulus (such that a line drawn between the anterior annulus and the septal anchor location passes through or near or close to the center of the tricuspid valve orifice) which results in an optimal force vector for reducing the tricuspid valve annular dimension.

Other embodiments disclosed within include implanting the septal anchoring element(s) substantially within or abutted against the left ventricular myocardial tissue inferior to the coronary sinus and/or it's ostia or across the left ventricular myocardium from the coronary sinus to the left ventricular chamber with the anchoring element abutted against the left ventricular wall. These areas have also not been previously utilized and share the same advantages of optimal force vectoring, robust and stable tissue, relatively immobile tissue, and large surface area for anchor apposition as does the location on the left atrial wall with the tensioning member passing through the inferior interatrial septum. Furthermore, embodiments disclosed herein describe methods and designs for implantation of large surface area tissue anchors. These anchoring elements are unique in that they can be compressed or folded into a small lumen for catheter deliver but expand into a much larger surface area element upon exiting the catheter. Some of the anchoring elements disclosed herein abut against the surfaces of cardiac tissues, with a tensioning element passing through the cardiac tissues to another chamber of the heart. The result is an anchoring element that distributes force over a large surface area to minimize tissue stresses and which exerts such force substantially over the outer surface of the heart chamber wall, including against the endocardial surface, which is tougher than the myocardial tissue layers, which minimizes the risk of tearing the tissue or dehiscence of the tissue anchor.

In certain embodiments, facilitation of less invasive approaches for treating FTR could require the need to cross through the tissue of the heart, from one chamber to another chamber, while the heart is beating, for the purpose of passing implantation instruments or implants from one chamber to an adjacent chamber. In certain embodiments, the first step in passing a device across the tissue may include passing a guidewire across the tissue which can then be used as a rail for passing catheters, instruments, or implants. This can prove to be challenging as the tissues of the heart are in constant motion and the guidewire and tissue can easily deflect relative to each other when attempting to push the guidewire through the tissue, even when the guidewire is energized with radio frequency current. Traditional guiding catheters with a free distal end may not provide enough stabilization to prevent deflection of the guidewire or tissue and facilitate passage of the guidewire. Thus, there is a need for a catheter and method that can better stabilize the guidewire when crossing tissues in the heart.

Certain embodiments of the disclosure comprise first attaching a stabilizing catheter to the myocardium of a heart valve annulus, or the tissue near (within 15 millimeters) the annulus, and second passing a guidewire through the internal diameter of the stabilizing catheter such that the distal end of the guidewire is extended out of the distal end of the stabilizing catheter and through the myocardial tissue of the heart valve annulus into a chamber of the heart adjacent to the chamber by which the stabilizing catheter is present. The stabilizing catheter can be firmly adhered or attached to the tissue of the heart such that it guides the precise location where the guidewire will first contact and penetrate the tissue, such that the stabilizing catheter prevents buckling, bowing or bending of the guidewire under the compressive forces imparted on the guidewire when being pushed through the tissue and such that the stabilizing catheter counteracts the force exerted on the tissue by the guidewire while the guidewire is pushed through the tissue. These benefits prevent the guidewire from skiving against the tissue, deflecting relative to the tissue or pushing the tissue away from the guidewire.

In some embodiments disclosed within the distal end of the stabilizing catheter forms a helical coil with a sharpened distal tip. When the tip of the stabilizing catheter is pressed into contact with the tissue and the stabilizing catheter is subsequently rotated the force imparted at the tip of the stabilizing catheter coil can puncture the tissue. Continuing to rotate the stabilizing catheter causes the coil to screw into and imbed in the tissue. Once screwed into the tissue, the distal coil can resist or impart force in any direction from or against the tissue. The distal coil can be removed from the tissue by rotating the stabilizing catheter in the direction opposite of the direction used to penetrate the tissue.

In some embodiments disclosed within the stabilizing catheter is screwed into the right atrial side of the anterior tricuspid valve annulus. The stabilizing catheter could be screwed into the annulus partially, such that the tip of the stabilizing catheter does not exit the annular tissue into the right ventricular space, or it could be screwed completely through the annulus such the tip of the stabilizing catheter does exit into the right ventricle.

Other embodiments disclosed within include winding the distal end of a guidewire into a helical coil, with a sharpened tip, such that the guidewire can be screwed into and through tissues of the heart by applying a torque to the wire, with minimal compressive force. Yet another embodiment disclosed within includes constructing a helical threat in the distal tapered section of a dilator such that rotating the dilator while in contact with tissues of the heart causes the dilator to advance through the tissue of the heart with minimal compressive force.

In some aspects, the techniques described herein relate to a method of tricuspid valve repair including: anchoring a first ventricular surface anchor against a first right ventricular surface, wherein the first ventricular surface anchor is connected to a first tension member; anchoring a first tension anchor against a tension anchor surface of a heart, wherein the first tension anchor is connected to a second tension member; extending the first tension member connected to the first ventricular surface anchor towards the second tension member connected to the first tension anchor; and with the first tension member and the second tension member, drawing the first right ventricular surface toward the first tension anchor.

In some aspects, the techniques described herein relate to a method, further including: anchoring a second tension anchor to another tension anchor surface of the heart, wherein the second tension anchor is connected to a third tension member; wherein the third tension member is connected to the first tension member and the second tension member via a tension member lock.

In some aspects, the techniques described herein relate to a method, wherein the tension anchor surface is against a left atrial surface of an interatrial septum inferior to a Fossa Ovalis.

In some aspects, the techniques described herein relate to a method, wherein the tension anchor surface is against a left atrial surface of an interatrial septum inferior and posterior to a Fossa Ovalis.

In some aspects, the techniques described herein relate to a method, wherein the tension anchor surface is at a right ventricular surface of an interventricular septum.

In some aspects, the techniques described herein relate to a method, wherein the tension anchor surface is at a left ventricular surface of an interventricular septum.

In some aspects, the techniques described herein relate to a method, wherein the tension anchor surface is at a coronary sinus close to a right atrium.

In some aspects, the techniques described herein relate to a method, further including anchoring a second ventricular surface anchor against a right ventricular surface near an anterior portion of a tricuspid annulus; wherein the second ventricular surface anchor is connected to a third tension member; wherein a center of the first ventricular surface anchor is spaced between 0.5 and 4 centimeters from a center of the second ventricular surface anchor; and extending the first tension member connected to the first ventricular surface anchor and the second tension member connected to the second ventricular surface anchor towards the first tension anchor; and with the first tension member, the second tension member, and the third tension member, drawing the first right ventricular surface and the right ventricular surface near the anterior portion of the tricuspid annulus toward the first tension anchor.

In some aspects, the techniques described herein relate to a method, further including anchoring a third ventricular surface anchor against a right ventricular surface near a posterior portion of a tricuspid annulus; wherein the third ventricular surface anchor is connected to a fourth tension member; wherein a center of the third ventricular surface anchor is spaced between 0.5 and 4 centimeters from a center of the second ventricular surface anchor and a center of the third ventricular surface anchor is spaced between 0.5 and 4 centimeters from a center of the first ventricular surface anchor; and extending the first tension member connected to the first ventricular surface anchor, the second tension member connected to the second ventricular surface anchor, and the third tension member connected to the third ventricular surface anchor towards the first tension anchor; and with the first tension member, the second tension member, the third tension member, and the fourth tension member, drawing the first right ventricular surface, the right ventricular surface near the anterior portion of the tricuspid annulus, and the right ventricular surface near the posterior portion of the tricuspid annulus toward the first tension anchor.

In some aspects, the techniques described herein relate to a method, wherein the first right ventricular surface is near an anterior portion of a tricuspid annulus.

In some aspects, the techniques described herein relate to a method, wherein the first right ventricular surface is within a right ventricular outflow tract.

In some aspects, the techniques described herein relate to a method, wherein the first right ventricular surface is within a pulmonary artery proximal to a pulmonary valve.

In some aspects, the techniques described herein relate to a method, further including anchoring a second tension anchor against a second tension anchor surface of a heart with a third tension member; wherein the third tension member connects the second tension anchor to the first tension anchor.

In some aspects, the techniques described herein relate to a method, further including anchoring a third tension anchor against a third tension anchor surface of a heart with a fourth tension member; wherein the fourth tension member connects the third tension anchor to the first tension anchor.

In some aspects, the techniques described herein relate to a method, further including anchoring a fourth tension anchor against a fourth tension anchor surface of a heart with a fifth tension member; wherein the fifth tension member connects the fourth tension anchor to the first tension anchor.

In some aspects, the techniques described herein relate to a method, wherein drawing the first right ventricular surface toward the first tension anchor further includes: advancing a tensioning lock over the first tension member and the second tension member to a location proximal the first tension anchor to draw the first right ventricular surface toward the first tension anchor; locking the tensioning lock to maintain tension on the first tension member and the second tension member; and trimming excess material of the first tension member and the second tension member.

In some aspects, the techniques described herein relate to a method, wherein locking the tensioning lock includes: adjusting the tensioning lock from a first configuration which can allow tension members to move freely relative to the tensioning lock to a second configuration which prevents the tension members from moving freely relative to the tensioning lock.

In some aspects, the techniques described herein relate to a method, further including advancing a grommet over the first tension member connected to the first ventricular surface anchor; wherein the grommet is positioned against an atrial surface of the heart opposite a ventricular surface anchor attached to the first tension member.

In some aspects, the techniques described herein relate to a method, further including advancing a grommet over the second tension member connected to the first tension anchor; wherein the grommet is positioned against a tissue surface opposite the first tension anchor attached to the second tension member.

In some aspects, the techniques described herein relate to a method, wherein the first tension member and the second tension member are portions of a single tension element.

In some aspects, the techniques described herein relate to a method of tricuspid valve repair including: anchoring a first ventricular surface anchor near an anterior portion of a tricuspid annulus, wherein the first ventricular surface anchor is connected to a first tension member; anchoring a second ventricular surface anchor near a right ventricular surface of a posterior portion of the tricuspid annulus, wherein the second ventricular surface anchor is connected to a second tension member; anchoring a first tension anchor against a left atrial surface of an interatrial septum, wherein the first tension anchor is connected to a third tension member; extending the first tension member connected to the first ventricular surface anchor and the second tension member connected to the second ventricular surface anchor towards the third tension member connected to the first tension anchor; and with the first tension member, the second tension member, and the third tension member, drawing the anterior portion of the tricuspid annulus and the posterior portion of the tricuspid annulus toward the first tension anchor.

In some aspects, the techniques described herein relate to a method, wherein the second ventricular surface anchor is located inferior to a Fossa Ovalis.

In some aspects, the techniques described herein relate to a method, further including trimming excess material from the first tension member, the second tension member, and the third tension member.

In some aspects, the techniques described herein relate to a method, further including: drawing the right ventricular surface toward the first tension anchor further includes: advancing a tensioning lock over the first tension member, the second tension member, and the third tension member to a location proximal the first tension anchor to draw the first ventricular surface anchor and the second ventricular surface anchor toward the first tension anchor; locking the tensioning lock to maintain tension on the first tension member, the second tension member, and the third tension member; and trimming excess material from the first tension member, the second tension member, and the third tension member.

In some aspects, the techniques described herein relate to a tricuspid valve repair system including: two or more surface anchor systems, each surface anchor system including: a surface anchor including a nitinol wire frame defined at its perimeter by a nitinol wire, and including an internal nitinol wire feature within an area defined by a perimeter formed by the nitinol wire frame; wherein the nitinol wire frame includes an austenite state in a deployed configuration when a temperature of the nitinol wire frame is body temperature; a tether assembly connecting the two or more surface anchor systems at a tether connection point; and a tether lock.

In some aspects, the techniques described herein relate to a tricuspid valve repair system, wherein the two or more surface anchor systems and the tether lock are disposed along the tether assembly.

In some aspects, the techniques described herein relate to a tricuspid valve repair system, wherein the surface anchor can rotate laterally relative to the tether assembly.

In some aspects, the techniques described herein relate to a tricuspid valve repair system, further including a grommet and a grommet lock.

In some aspects, the techniques described herein relate to a tricuspid valve repair system, wherein the grommet is a flat grommet including an expandable nitinol frame; wherein the flat grommet is disposed upon the tether assembly through a hole in the flat grommet; and wherein the expandable nitinol frame of the grommet includes an austenite state in a deployed configuration when a temperature of the expandable nitinol frame is a human body temperature.

In some aspects, the techniques described herein relate to a tricuspid valve repair system, wherein the flat grommet additionally includes a covering material providing a planar surface to the expandable nitinol frame.

In some aspects, the techniques described herein relate to a tricuspid valve repair system, wherein the grommet is a T-bar grommet including a singular rigid member with a length along a long axis which is longer than a width along a short axis, wherein the width of the T-bar grommet is configured to accommodate the T-bar grommet within an inner diameter of a delivery catheter; wherein the T-bar grommet is disposed upon the tether assembly through a hole at or near a center of the T-bar grommet; and wherein the T-bar grommet can be pivoted about the tether assembly such that the long axis of the T-bar grommet is approximately parallel to an axis of the tether assembly for insertion into the delivery catheter for deployment; and wherein subsequent to deploying from the delivery catheter, the T-bar grommet can be pivoted about the tether assembly such that a longer axis of the T-bar grommet is at an angle relative to the axis of the tether assembly.

In some aspects, the techniques described herein relate to a tricuspid valve repair system, wherein the grommet is a self-expanding gromet which can expand after deployment to interact with the grommet lock.

In some aspects, the techniques described herein relate to a tricuspid valve repair system, wherein the grommet lock includes a tether hole passing through a distal surface of the grommet lock, a plurality of grommet lock spring arms connected to the distal surface of the grommet lock, a plurality of grommet lock alignment walls, and a grommet lock tether contact surface; wherein the grommet lock contacts the tether assembly by the tether hole and the grommet lock tether contact surface; wherein application of a force on the distal surface of the grommet lock towards a proximal end engages the plurality of grommet lock spring arms by deflecting them at a grommet lock deflection node such that a clamping force is generated at the grommet lock tether contact surface and the grommet is prevented from moving along the tether assembly away from the surface anchor; and wherein the grommet, and the grommet lock are also disposed along the tether assembly.

In some aspects, the techniques described herein relate to a tricuspid valve repair system, wherein the grommet lock includes a first unlocked state which is slidable along the tether assembly and a second locked state which is not slidable along the tether assembly; wherein the second locked state prevents distal translation of the grommet along the tether assembly.

In some aspects, the techniques described herein relate to a tricuspid valve repair system, wherein the grommet lock is a knot formed at the tether connection point; wherein the tether assembly passes through the grommet prior to rejoining the tether assembly at the tether connection point, such that that the knot is proximal to the grommet; and wherein the knot is slidable distally by means of pushing the knot with a pushing catheter; and wherein the knot prevents the grommet from sliding proximally along the tether assembly such that the knot prevents separation of the grommet and the surface anchor.

In some aspects, the techniques described herein relate to a tricuspid valve repair system, wherein the tether assembly is connected to the surface anchor by encircling a nitinol frame internal feature forming a tether loop before rejoining the tether assembly at the tether connection point.

In some aspects, the techniques described herein relate to a tricuspid valve repair system, wherein the surface anchor is covered by a surface anchor outer covering.

In some aspects, the techniques described herein relate to a tricuspid valve repair system, wherein the nitinol wire frame of the surface anchor is formed by laser cutting a nitinol sheet or strip.

In some aspects, the techniques described herein relate to a tricuspid valve repair system, wherein the surface anchor can be mechanically compressed into a first non-deployed state to a size and dimension to be compatible with a catheter having an internal diameter smaller than a width of the surface anchor in its second deployed state.

In some aspects, the techniques described herein relate to a tricuspid valve repair system, wherein the surface anchor is substantially flat, such that a surface anchor length and a surface anchor width are at least 5 times a surface anchor thickness.

In some aspects, the techniques described herein relate to a tricuspid valve repair system, wherein upon release from a surface anchor delivery catheter, the surface anchor transitions from its first non-deployed stated to its second deployed state.

In some aspects, the techniques described herein relate to a tricuspid valve repair system including: an anchor system including a surface anchor including a nitinol frame forming an outer perimeter and a hole; wherein the nitinol frame includes an austenite state in a deployed configuration when a temperature of the nitinol frame is body temperature; a grommet including a distal tubular portion connected to a proximal finger portion; wherein the proximal finger portion is included of a plurality of flexible beams extending radially from the distal tubular portion; a tether for connecting the anchor system, and a surface anchor hub; wherein the anchor system, the grommet, and the surface anchor hub are disposed along the tether.

In some aspects, the techniques described herein relate to a tricuspid valve repair system, wherein the distal tubular portion of the grommet includes a central flexible beam oriented radially inward toward an internal surface of a tube of the grommet.

In some aspects, the techniques described herein relate to a tricuspid valve repair system, wherein the grommet includes nitinol with an austenite state in a deployed configuration when a temperature of the grommet is approximately a temperature of a human body.

In some aspects, the techniques described herein relate to a tricuspid valve repair system, wherein the surface anchor hub includes a distal flange with an outer diameter greater than an inner diameter of the hole within the surface anchor, a midshaft with an outer cross sectional dimension smaller than the inner diameter of the hole within the surface anchor, a proximal nose with an outer diameter smaller than the inner diameter of the hole within the surface anchor and smaller than the inner diameter of the grommet and larger than the outer cross sectional dimension of the midshaft and a hole through a center of the distal flange, and wherein the hole through the center is larger in its internal diameter than the outer diameter of the tether.

In some aspects, the techniques described herein relate to a tricuspid valve repair system, wherein the grommet is disposable from a first position where the grommet is not attached to the surface anchor hub to a second position where the grommet is attached to the surface anchor hub, where the central flexible beam within the distal tubular portion of the grommet is positioned over the midshaft of the surface anchor hub and the central flexible beam of the distal tubular portion of the grommet contacts the proximal nose, such that proximal translation of the grommet relative to the surface anchor hub is limited.

In some aspects, the techniques described herein relate to a tricuspid valve repair system, wherein the plurality of flexible beams of the proximal finger portion of the grommet can be mechanically deflected proximally and radially inward for insertion into a catheter with an inner diameter smaller than a position of the proximal finger portion of the grommet in the deployed configuration.

In some aspects, the techniques described herein relate to a tricuspid valve repair system, wherein deployment of the grommet allows the proximal finger portion of the grommet to transition from its non-deployed configuration to its deployed configuration.

In some aspects, the techniques described herein relate to a tricuspid valve repair system, wherein a distal end of the tether is larger than the inner diameter of the hole through the surface anchor hub such that the tether cannot be pulled through the surface anchor hub in a proximal direction.

In some aspects, the techniques described herein relate to a tricuspid valve repair system, wherein the surface anchor and the grommet can rotate laterally relative to the tether.

In some aspects, the techniques described herein relate to a tricuspid valve repair system, wherein the surface anchor can be mechanically compressed into a first non-deployed state to a size and dimension to be compatible with a catheter having an internal diameter smaller than a width of the surface anchor in its second deployed state.

In some aspects, the techniques described herein relate to a method of implanting a tricuspid valve repair system to repair a heart, the tricuspid valve repair system including a tether and two or more surface anchor systems, each surface anchor system including a surface anchor, a grommet, and a grommet lock, the method including: advancing the tricuspid valve repair system towards the heart, positioning a distal end of a catheter housing a surface anchor system to be adjacent to an implant surface of the heart; piercing the implant surface of the heart with the catheter; pushing the surface anchor of the tricuspid valve repair system from the catheter with a pushing catheter located within the catheter; allowing the surface anchor to transition from a non-deployed configuration to a deployed configuration; partially retracting the catheter such that the catheter no longer pierces the implant surface of the heart; pushing the grommet and the grommet lock of the tricuspid valve repair system from the catheter with the pushing catheter; allowing the grommet to transition from a non-deployed configuration to a deployed configuration; and advancing the grommet lock distally along the tether of the tricuspid valve repair system to a desired distance such that a distance between the surface anchor and the grommet is substantially occupied by a thickness of the implant surface of the heart.

In some aspects, the techniques described herein relate to a method, wherein allowing the surface anchor to transition from the non-deployed configuration to the deployed configuration includes allowing the surface anchor to transition to an austenite state configured to be the deployed configuration.

In some aspects, the techniques described herein relate to a method, wherein allowing the grommet to transition from the non-deployed configuration to the deployed configuration includes allowing the grommet to transition to an austenite state configured to be the deployed configuration.

In some aspects, the techniques described herein relate to a method, further including trimming excess tether from the tricuspid valve repair system.

In some aspects, the techniques described herein relate to a method of implanting a tricuspid valve repair system to repair a heart, the tricuspid valve repair system including a tether and two or more surface anchor systems, each surface anchor system including a surface anchor, a lockable grommet, and a surface anchor hub, the method including: positioning a catheter to be adjacent to an implant surface of the heart; piercing the implant surface of the heart with the catheter; pushing the surface anchor and the surface anchor hub of the tricuspid valve repair system from the catheter with a pushing catheter located within the catheter; allowing the surface anchor to transition from a non-deployed configuration to a deployed configuration; partially retracting the catheter such that the catheter no longer pierces the implant surface of the heart; pushing the lockable grommet of the tricuspid valve repair system from the catheter with the pushing catheter; allowing the lockable grommet to transition from a non-deployed configuration to a deployed configuration; and advancing the lockable grommet distally along the tether of the tricuspid valve repair system over the surface anchor hub to a desired distance such that a distance between the surface anchor and the lockable grommet is substantially occupied by a thickness of the implant surface of the heart, and that the lockable grommet interacts with the surface anchor hub such that the lockable grommet becomes locked from translating proximally relative to the surface anchor hub.

In some aspects, the techniques described herein relate to a method, wherein allowing the surface anchor to transition from the non-deployed configuration to the deployed configuration includes allowing the surface anchor to transition to an austenite state configured to be the deployed configuration.

In some aspects, the techniques described herein relate to a method, wherein allowing the lockable grommet to transition from the non-deployed configuration to the deployed configuration includes allowing the lockable grommet to transition to an austenite state configured to be the deployed configuration.

In some aspects, the techniques described herein relate to a foldable flat implant system for tricuspid valve repair configured to attach to a septal surface anchor, the foldable flat implant system including: a flexible anterior bar anchor non-fixably attached to a delivery catheter; at least one guidewire with a distal tip, the at least one guidewire being passing through a hole in the flexible anterior bar anchor at a rotatable guidewire connection; an anterior bar tether including at least one tether snare configured to pass through a lumen of a snare catheter; wherein the at least one guidewire can non-fixably connect with the at least one tether snare after passing through a treatment tissue and advance through the flexible anterior bar anchor; wherein the at least one guidewire is attached to a tether at a proximal end; wherein pulling the at least one guidewire through the flexible anterior bar anchor by means of the at least one tether snare causes the tether attached to the proximal end of the at least one guidewire to be pulled through the hole in the flexible anterior bar anchor; and wherein the anterior bar tether connects the septal surface anchor with the flexible anterior bar anchor.

In some aspects, the techniques described herein relate to a method for implanting a tricuspid valve repair system to repair a heart of a patient, the method including: advancing into the patient a tricuspid valve repair system including a septal surface anchor attached to a septal surface anchor tether and a foldable flat implant system with a flexible anterior bar anchor, at least one guidewire connected at its proximal end to an anterior anchor tether with a plug end, and at least one tether snare within a steerable anterior anchor delivery catheter, installing the septal surface anchor into a left atrium of the heart via a guidewire and septal surface anchor delivery catheter; inserting the steerable anterior anchor delivery catheter attached to the flexible anterior bar anchor in a non-deployed configuration into a guiding catheter and tracking of the flexible anterior bar anchor to a distal end of the guiding catheter; directing the guiding catheter above a tricuspid valve of the heart; extending the steerable anterior anchor delivery catheter and directing the flexible anterior bar anchor through the tricuspid valve into to a right ventricle; deploying the flexible anterior bar anchor into a deployment configuration; positioning the flexible anterior bar anchor with a distal end of the at least one guidewire to be adjacent to an anterior anchor implant area; piercing the anterior anchor implant area through to an opposite side of the anterior anchor implant area with the distal end of the at least one guidewire; connecting the at least one tether snare to a proximal end of the at least one guidewire; advancing the at least one guidewire through the anterior anchor implant area and through the flexible anterior bar anchor such that the proximal end of the at least one guidewire passes through the flexible anterior bar anchor and that the plug end of the anterior anchor tether is brought into contact with a distal surface of the flexible anterior bar anchor further from the anterior anchor implant area; detaching the flexible anterior bar anchor from the steerable anterior anchor delivery catheter; and removing the steerable anterior anchor delivery catheter from the patient.

In some aspects, the techniques described herein relate to a method, additionally including: positioning the steerable anterior anchor delivery catheter to a secondary position near the anterior anchor implant area, such that a tether passing through the secondary position could still functionally interact with the flexible anterior bar anchor; piercing the secondary position through to an opposite side of the secondary position with the distal end of a second guidewire, wherein the second guidewire is connected at its proximal end to a second anterior anchor tether with a plug end; connecting a second tether snare to a proximal end of the second guidewire; and advancing the second guidewire through the secondary position and through the flexible anterior bar anchor such that the proximal end of the second guidewire passes through the flexible anterior bar anchor and that the plug end of the second anterior anchor tether is brought into contact with the distal surface of the flexible anterior bar anchor further from the anterior anchor implant area.

In some aspects, the techniques described herein relate to a method, additionally including: passing a tether lock over the anterior anchor tether and the septal surface anchor tether via a lock catheter; tensioning the anterior anchor tether in a right atrium to draw a tricuspid annulus along a right ventricular wall toward an interatrial septum and/or a coronary sinus; locking the tether lock to maintain tension on the anterior anchor tether and the septal surface anchor tether; trimming excess tether from the anterior anchor tether and the septal surface anchor tether; and removing all catheters from the patient.

In some aspects, the techniques described herein relate to a method, wherein the anterior anchor implant area is at a right ventricular surface near an anterior tricuspid annulus; wherein the flexible anterior bar anchor spans one to four centimeters of a surface near the anterior tricuspid annulus.

In some aspects, the techniques described herein relate to a method, wherein the flexible anterior bar anchor includes an elongated nitinol frame with a rigid eyelet attached near each end, a covering, and an anchor bar delivery connection near a center of the elongated nitinol frame.

In some aspects, the techniques described herein relate to a method, wherein the covering could be tapered from near the center of the elongated nitinol frame to ends of the elongated nitinol frame.

In some aspects, the techniques described herein relate to a method, wherein the tricuspid valve repair system includes two guidewires and two snare tethers.

In some aspects, the techniques described herein relate to a guidewire delivery system including: a flexible guide catheter with a guide catheter lumen; a stabilizing catheter with a distal tip, a stabilizing catheter lumen, and a flexible region, the stabilizing catheter dimensioned such that the stabilizing catheter can pass through the guide catheter lumen; a helical tip located at the distal tip of the stabilizing catheter; and a guidewire dimensioned such that it can pass through the stabilizing catheter lumen.

In some aspects, the techniques described herein relate to a guidewire delivery system, wherein the helical tip is a laser cut helix with an approximately trapezoidal cross section.

In some aspects, the techniques described herein relate to a guidewire delivery system, wherein the helical tip is a wound wire helix with a circular cross section.

In some aspects, the techniques described herein relate to a guidewire delivery system, wherein the helical tip is two wound helices.

In some aspects, the techniques described herein relate to a guidewire delivery system, wherein the helical tip is a taper wound helix, wherein a radius of curvature of a distal-most end of the helical tip is larger than a radius of curvature of a proximal-most end of the taper wound helix.

In some aspects, the techniques described herein relate to a guidewire delivery system, wherein the helical tip is a taper wound helix, wherein a radius of curvature of a distal-most end of the helical tip is smaller than a radius of curvature of a proximal-most end of the taper wound helix.

In some aspects, the techniques described herein relate to a method for passing a guidewire through a surface of a heart including: advancing a guidewire delivery system towards the heart, the guidewire delivery system including a flexible guide catheter with a guide catheter lumen, a stabilizing catheter with a distal end, a stabilizing catheter lumen, and a flexible region, the stabilizing catheter configured such that the stabilizing catheter can pass through the guide catheter lumen, a helical tip located at the distal end of the stabilizing catheter and a guidewire configured such that it can pass through the stabilizing catheter lumen; positioning the flexible guide catheter within a right atrium of the heart at the surface of the heart; advancing the stabilizing catheter through the flexible guide catheter; positioning the helical tip at the distal end of the stabilizing catheter against the surface of the heart; rotating the helical tip such that the helical tip engages with the surface of the heart; and advancing the guidewire through the stabilizing catheter and through the surface of the heart.

In some aspects, the techniques described herein relate to a method, wherein the surface of the heart through which the guidewire passes is near an anterior tricuspid annulus.

In some aspects, the techniques described herein relate to a method, wherein the surface of the heart through which the guidewire passes is such that the guidewire passes from the right atrium into a right ventricular outflow tract of the heart.

In some aspects, the techniques described herein relate to a method, further including: further rotating the helical tip while the stabilizing catheter is advanced towards the surface of the heart such that the distal end of the stabilizing catheter can completely pass through the surface of the heart.

In some aspects, the techniques described herein relate to a method of tricuspid valve repair including: advancing a guidewire delivery system toward a heart, the guidewire delivery system including a flexible guide catheter with a guide catheter lumen, a stabilizing catheter with a distal tip located on a distal end of the stabilizing catheter, a stabilizing catheter lumen, and a flexible region, the stabilizing catheter configured such that the stabilizing catheter can pass through the guide catheter lumen, a helical tip located at the distal tip of the stabilizing catheter, and a guidewire configured such that it can pass through the stabilizing catheter lumen; preparing at least three surface anchors for deployment, the at least three surface anchors being covered by a surface anchor outer covering and including a nitinol wire frame defined at its perimeter by nitinol wires, an internal nitinol wire feature within an area defined by a perimeter formed by the nitinol wire frame wherein the nitinol wire frame includes an austenite state in a deployed configuration when a temperature of the nitinol wire frame is body temperature; positioning the flexible guide catheter within a right atrium of the heart, near an anterior tricuspid annulus; advancing the stabilizing catheter through the flexible guide catheter; positioning the helical tip at the distal end of the stabilizing catheter against a right atrial surface of the heart, near the anterior tricuspid annulus; rotating the helical tip such that the helical tip engages with the right atrial surface of the heart, near the anterior tricuspid annulus; advancing the guidewire through the stabilizing catheter and through a surface of the heart between the right atrium and a right ventricle; advancing an anchor delivery catheter over the guidewire from the right atrium into the right ventricle; retracting the guidewire back through the anchor delivery catheter; anchoring a first anchor connected to a first tether against a right ventricular surface near an anterior portion of a tricuspid annulus through the anchor delivery catheter; retracting the anchor delivery catheter back through the flexible guide catheter; positioning the flexible guide catheter within the right atrium of the heart, near the anterior tricuspid annulus, approximately adjacent to the first anchor; advancing the stabilizing catheter through the flexible guide catheter; positioning the helical tip at the distal end of the stabilizing catheter against a right atrial surface of the heart, near the anterior tricuspid annulus, adjacent to the first anchor; rotating the helical tip such that the helical tip engages with the right atrial surface of the heart, near the anterior tricuspid annulus; advancing the guidewire through the stabilizing catheter and through the heart between the right atrium and the right ventricle; advancing the anchor delivery catheter over the guidewire from the right atrium into the right ventricle; retracting the guidewire back through the anchor delivery catheter; anchoring a second anchor connected to a second tether against a right ventricular surface near an anterior portion of the tricuspid annulus through the anchor delivery catheter at a distance of 1 to 4 centimeters away from the first anchor; retracting the anchor delivery catheter back through the flexible guide catheter; positioning the flexible guide catheter within the right atrium of the heart near an interatrial septum; advancing the anchor delivery catheter through the flexible guide catheter; positioning a distal tip of the anchor delivery catheter against the interatrial septum inferior to a fossa ovalis; advancing the guidewire through the anchor delivery catheter and through the interatrial septum of the heart; advancing the anchor delivery catheter over the guidewire from the right atrium into a left atrium of the heart; retracting the guidewire back through the anchor delivery catheter; anchoring a third anchor connected to a third tether through the interatrial septum of the heart; retracting the anchor delivery catheter back through the interatrial septum of the heart; passing the first tether, the second tether and the third tether through a tether lock; advancing the tether lock to a location near the third anchor; with the first tether, the second tether, and the third tether, drawing the anterior portion of the tricuspid annulus toward a posterior septal portion of the tricuspid annulus; and actuating the tether lock to clamp the first tether, the second tether, and the third tether and fix a distance between the first anchor, the second anchor, and the third anchor relative to each other.

In some aspects, the techniques described herein relate to a method, further including: advancing a grommet distally along a chosen tether chosen from the first tether, the second tether, or the third tether of the guidewire delivery system; and advancing a grommet lock distally along the chosen tether through which the grommet is passing of the guidewire delivery system to a desired distance such that the distance between an anchor connected to the chosen tether and the grommet is substantially occupied by a thickness of an implant surface of the heart.

In some aspects, the techniques described herein relate to a method, further including: attaching a fourth surface anchor to a delivery catheter, the fourth surface anchor being covered by a surface anchor outer covering and including a nitinol wire frame defined at its perimeter by nitinol wires, an internal nitinol wire feature within an area defined by a perimeter formed by the nitinol wire frame wherein the nitinol wire frame includes an austenite state in a deployed configuration when a temperature of the nitinol wire frame is body temperature; positioning the flexible guide catheter within the right atrium of the heart, near the anterior tricuspid annulus, approximately adjacent to the second anchor; advancing the stabilizing catheter through the flexible guide catheter; positioning the helical tip at the distal end of the stabilizing catheter against a right atrial surface of the heart, near the anterior tricuspid annulus, adjacent to the first anchor; rotating the helical tip such that the helical tip engages with the right atrial surface of the heart, near the anterior tricuspid annulus; advancing the guidewire through the stabilizing catheter and through the heart between the right atrium and the right ventricle; advancing the anchor delivery catheter over the guidewire from the right atrium into the right ventricle; retracting the guidewire back through the anchor delivery catheter; anchoring a fourth anchor connected to a fourth tether against a right ventricular surface near an anterior portion of a tricuspid annulus through the anchor delivery catheter at a distance of 1 to 4 centimeters away from the second anchor; and retracting the anchor delivery catheter back through the flexible guide catheter; wherein the tether lock additionally passes over the fourth tether; wherein drawing the anterior portion of the tricuspid annulus toward a posterior septal portion of the tricuspid annulus further includes the fourth tether; and wherein actuating the tether lock further includes the fourth tether to fix the distance between the first anchor, the second anchor, the third anchor, and the fourth anchor relative to each other.

In some aspects, the techniques described herein relate to a method, wherein a distal tip of the guidewire is configured to transmit a high frequency electrical current to the distal tip; wherein the high frequency electrical current reduces a force required to pass through a portion of the heart.

In some aspects, the techniques described herein relate to a method of tricuspid valve repair including: advancing a guidewire delivery system toward a heart, the guidewire delivery system including a flexible guide catheter with a guide catheter lumen, a stabilizing catheter with a distal tip located on a distal end of the stabilizing catheter, a stabilizing catheter lumen, and a flexible region, the stabilizing catheter configured such that the stabilizing catheter can pass through the guide catheter lumen, a helical tip located at the distal tip of the stabilizing catheter, and a guidewire configured such that it can pass through the stabilizing catheter lumen; preparing at least two surface anchors for deployment, the at least two surface anchors being covered by a surface anchor outer covering and including a nitinol wire frame defined at its perimeter by nitinol wires, an internal nitinol wire feature within an area defined by a perimeter formed by the nitinol wire frame wherein the nitinol wire frame includes an austenite state in a deployed configuration when a temperature of the nitinol wire frame is body temperature; positioning the flexible guide catheter within a right atrium of the heart, near an anterior tricuspid annulus; advancing the stabilizing catheter through the flexible guide catheter; positioning the helical tip at the distal end of the stabilizing catheter against a right atrial surface of the heart, near the anterior tricuspid annulus; rotating the helical tip such that the helical tip engages with the right atrial surface of the heart, near the anterior tricuspid annulus; advancing the guidewire through the stabilizing catheter and through a surface of the heart between the right atrium and a right ventricle; advancing an anchor delivery catheter over the guidewire from the right atrium into the right ventricle; retracting the guidewire back through the anchor delivery catheter; anchoring a first anchor connected to a first tether against a right ventricular surface near an anterior portion of a tricuspid annulus through the anchor delivery catheter; retracting the anchor delivery catheter back through the flexible guide catheter; positioning the flexible guide catheter within the right atrium of the heart, near an interatrial septum; positioning a distal tip of the anchor delivery catheter against the interatrial septum inferior to a fossa ovalis; advancing the guidewire through the anchor delivery catheter and through the interatrial septum of the heart; advancing the anchor delivery catheter over the guidewire from the right atrium into a left atrium of the heart; retracting the guidewire back through the anchor delivery catheter; anchoring a second anchor connected to a second tether through the interatrial septum of the heart; retracting the anchor delivery catheter back through the interatrial septum of the heart; passing the first tether and the second tether through a tether lock; advancing the tether lock to a location near the second anchor; with the first tether and the second tether, drawing the anterior portion of the tricuspid annulus toward a posterior septal portion of the tricuspid annulus; and actuating the tether lock to clamp the first tether and the second tether and fix a distance between the first anchor and the second anchor relative to each other.

In some aspects, the techniques described herein relate to a guidewire delivery system including: a dilator with an internal lumen and an internal lumen shoulder; and a helical guidewire which resides within the internal lumen, wherein the helical guidewire abuts the internal lumen shoulder which prevents axial movement of the helical guidewire through the dilator, wherein the helical guidewire can rotate within the internal lumen; and wherein the helical guidewire has at a distal guidewire end a helical guidewire portion fixably attached to the helical guidewire.

In some aspects, the techniques described herein relate to a method for passing a guidewire through a surface of a heart including: advancing a guidewire delivery system within the heart, the guidewire delivery system including a stabilizing catheter with an internal lumen with an internal lumen shoulder and a helical guidewire which abuts the internal lumen shoulder and can rotate within the internal lumen of the stabilizing catheter, wherein the helical guidewire has at a distal guidewire end a helical guidewire portion fixably attached to the helical guidewire; positioning the guidewire delivery system within a right atrium of the heart; positioning the helical guidewire against the surface of the heart; rotating the helical guidewire such that the helical guidewire engages with the surface of the heart; and advancing the guidewire and the stabilizing catheter through the surface of the heart.

In some aspects, the techniques described herein relate to a lock to be used in a tricuspid valve repair system, including: a lock housing with a pass through hole configured to accommodate at least two tension members through the lock housing; and an adjustable lock tensioner configured to move within the lock housing; wherein the adjustable lock tensioner can constrict the at least two tension members as they pass through the lock housing; and wherein the lock can transition from a first configuration which can allow tension members to move freely relative to the lock to a second configuration which prevents the tension members from moving freely relative to the lock.

In some aspects, the techniques described herein relate to a method of manufacturing a surface anchor, including: activating a laser configured to cut through a nitinol sheet, wherein the nitinol sheet has a thickness and an area configured to accommodate at least a final size of the surface anchor; and displacing the nitinol sheet relative to the laser along a profile within the nitinol sheet; wherein the profile cut from the nitinol sheet is substantially similar to a final shape of the surface anchor.

In some aspects, the techniques described herein relate to a method of tricuspid valve repair including: anchoring a first anchor against a right ventricular surface near an anterior portion of a tricuspid annulus; extending a tension member from the first anchor towards a right atrium surface of an interatrial septum; and with the tension member, drawing the anterior portion of the tricuspid annulus toward a posterior septal portion of the tricuspid annulus.

In some aspects, the techniques described herein relate to a method, wherein drawing the anterior portion of the tricuspid annulus toward the posterior septal portion of the tricuspid annulus includes advancing a lock coupled to the tension member towards the right atrium surface of the interatrial septum.

In some aspects, the techniques described herein relate to a method, including placing a left atrial anchoring element against a left atrial surface of the interatrial septum and coupling the first anchor and the left atrial anchoring element to each other with the tension member.

In some aspects, the techniques described herein relate to a method, further including: anchoring a second anchor against the right ventricular surface of the anterior portion of the tricuspid annulus; extending a second tension member from the second anchor towards the right atrium surface of the interatrial septum; and with the second tension member, drawing the anterior portion of the tricuspid annulus toward the posterior septal portion of the tricuspid annulus.

In some aspects, the techniques described herein relate to a tricuspid valve repair system including one or more features of the foregoing description.

In some aspects, the techniques described herein relate to a method of tricuspid valve repair including implanting one more features of the tricuspid valve repair system of the foregoing description into a patient's heart.

In some aspects, the techniques described herein relate to a method for crossing tissues within a body with a guidewire including: screwing a stabilizing catheter with a helical wire on a distal end into a tissue; passing the guidewire through the stabilizing catheter; and using the stabilizing catheter to support the guidewire while crossing completely through the tissue with the guidewire.

BRIEF DESCRIPTION OF THE DRAWINGS

These and other features, aspects and advantages of the present application are described with reference to drawings of certain embodiments, which are intended to illustrate, but not to limit, the present inventions. It is to be understood that these drawings are for the purpose of illustrating the various concepts disclosed herein and may not be to scale.

FIG. 44A illustrates an embodiment of anchoring element where the anchor is constructed of braided nitinol wire shape set into a disk configuration. An end view of the anchor is shown in which the anchor is depicted substantially round. The anchor can be elongated, which causes the disk to collapse into a long narrow tube for delivery through a catheter. The tensioning band is attached centrally to the distal end of the anchor via an interference knot which causes the anchor to flatten when the tensioning band is tensioned.

FIG. 44B illustrates an embodiment of an anchoring element where the anchor is constructed of braided nitinol wire shape set into a series of disks. Two disks are depicted; however, any number of disks can be constructed. The anchor is shown abutted against a cross section of tissue with a small hole for the tensioning band. Having a plurality of disks increases the amount of material abutted to the tissue which makes the anchor more resistant to pulling through the tissue without increasing the stiffness of the anchor for the purpose of collapsing into the delivery catheter.

FIG. 46A illustrates an anchoring element such as those in FIGS. 35-38, 45, and 50 abutted against tissue with the tensioning band passing through.

FIG. 69A illustrates a surface anchor element to be used as an anchoring element for a tricuspid valve repair system.

FIG. 69B illustrates the surface anchor element from FIG. 69A in its collapsed state within a delivery catheter.

FIG. 70E illustrates one section of the implant system of FIG. 70A while in its pre-deployed state within a delivery catheter.

FIG. 70F illustrates one section of the implant system of FIG. 70A during its installation process to the patient.

FIG. 7I illustrates an implant system with a flat grommet to be used in a tricuspid valve repair system.

FIG. 75A illustrates a grommet lock in its locking configuration to be used within a tricuspid valve repair system.

FIG. 75B illustrates the tether lock in FIG. 75A in its non-locking configuration to be used within a tricuspid valve repair system.

FIG. 80C illustrates a perspective cross-sectional view of the tether lock of FIG. 80A in its non-locking configuration.

FIG. 80D illustrates an exploded view of the tether lock of FIG. 80A.

Figure 81:
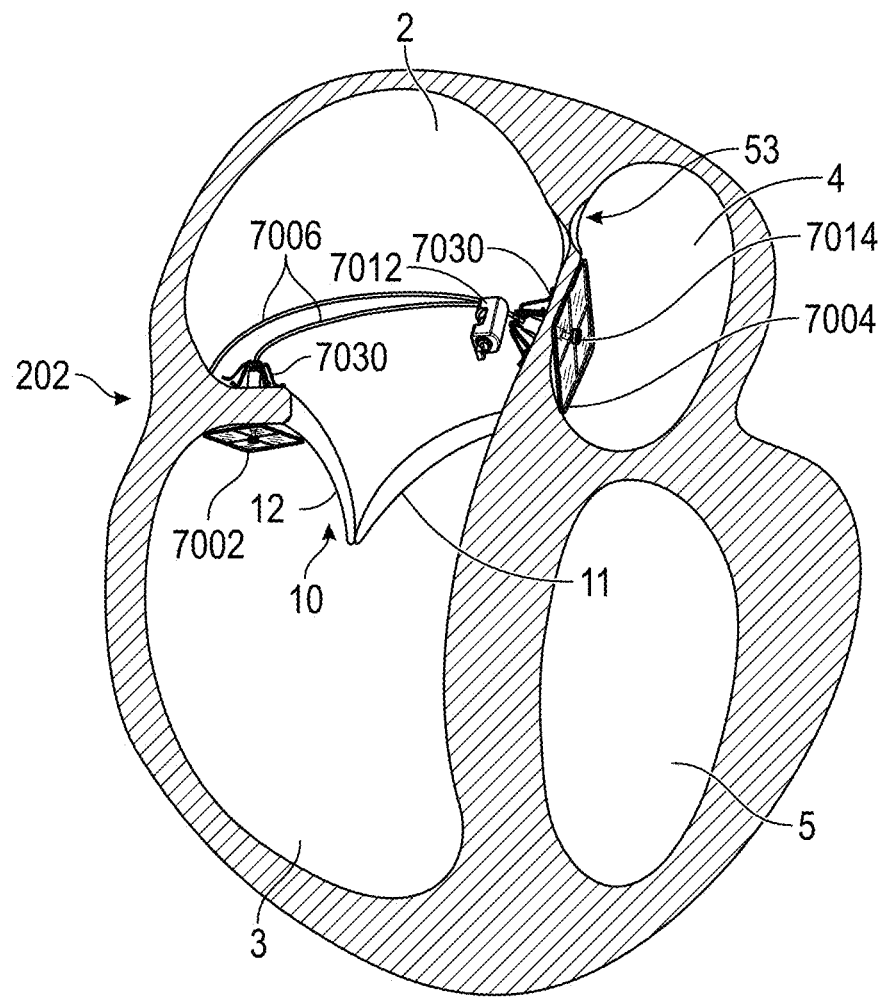

FIG. 81 illustrates a 4-chamber cross section of a heart with an embodiment of treatment comprising an implant system comprising two anterior surface anchors implanted against the right ventricular surface of the anterior tricuspid annulus connected via tensioning bands to one septal surface anchor implanted against the left atrial surface of the interatrial septum, inferior to the fossa ovalis, retained by a lock near the right atrial surface of the interatrial septum to be used as a tricuspid valve repair system.

Figure 82:
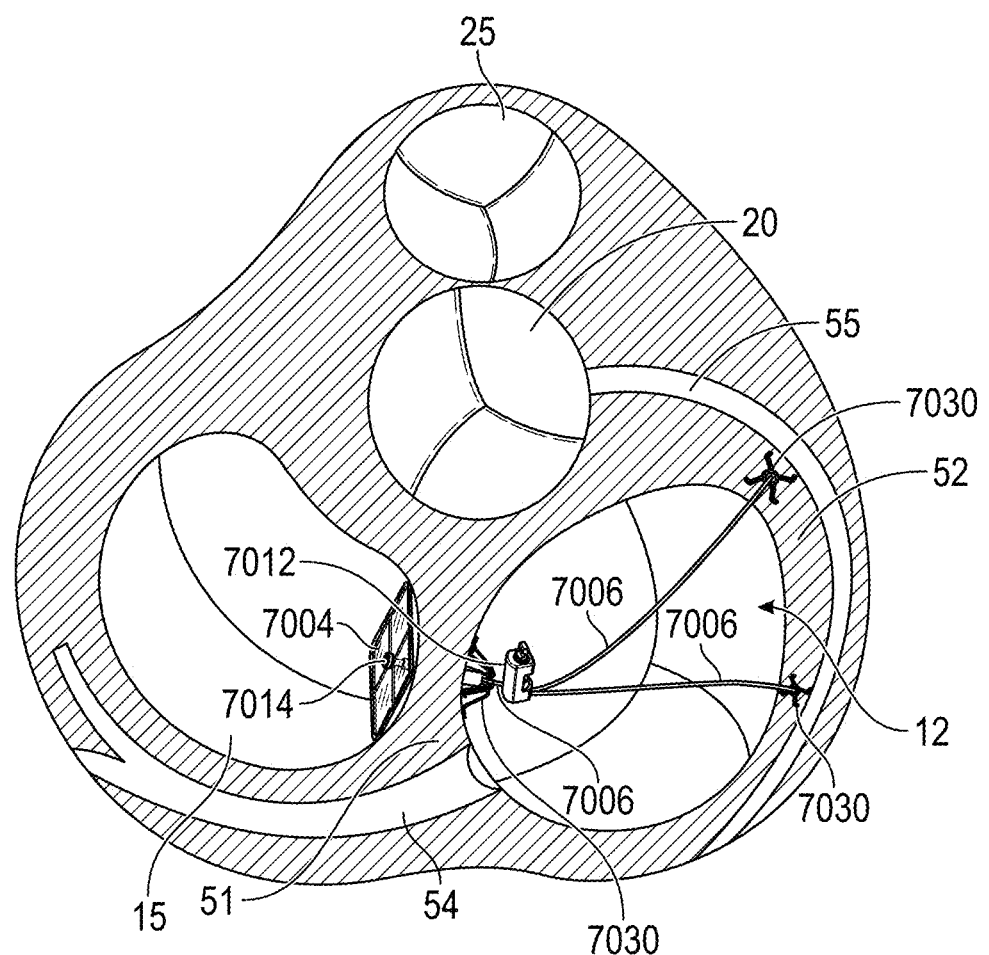

FIG. 82 illustrates a top down (surgeons) view of a heart with an embodiment of treatment according to FIGS. 70A through 70H comprising two anterior surface anchors implanted against the right ventricular surface of the anterior tricuspid annulus connected via tensioning bands to one septal surface anchor implanted against the left atrial surface of the interatrial septum, inferior to the fossa ovalis, retained by a lock near the right atrial surface of the interatrial septum to be used as a tricuspid valve repair system.

DETAILED DESCRIPTION OF EMBODIMENTS

Embodiments of the disclosure will now be described with reference to the accompanying figures. The terminology used in the description presented herein is not intended to be interpreted in any limited or restrictive manner, simply because it is being utilized in conjunction with a detailed description of embodiments of the disclosure. Furthermore, embodiments of the disclosure may include several novel features, no single one of which is solely responsible for its desirable attributes or which is essential to practicing the embodiments of the disclosure herein described. For purposes of this disclosure, certain aspects, advantages, and novel features of various embodiments are described herein. It is to be understood that not necessarily all such advantages may be achieved in accordance with any particular embodiment. Thus, for example, those skilled in the art will recognize that one embodiment may be carried out in a manner that achieves one advantage or group of advantages as taught herein without necessarily achieving other advantages as may be taught or suggested herein.

Figure 1:
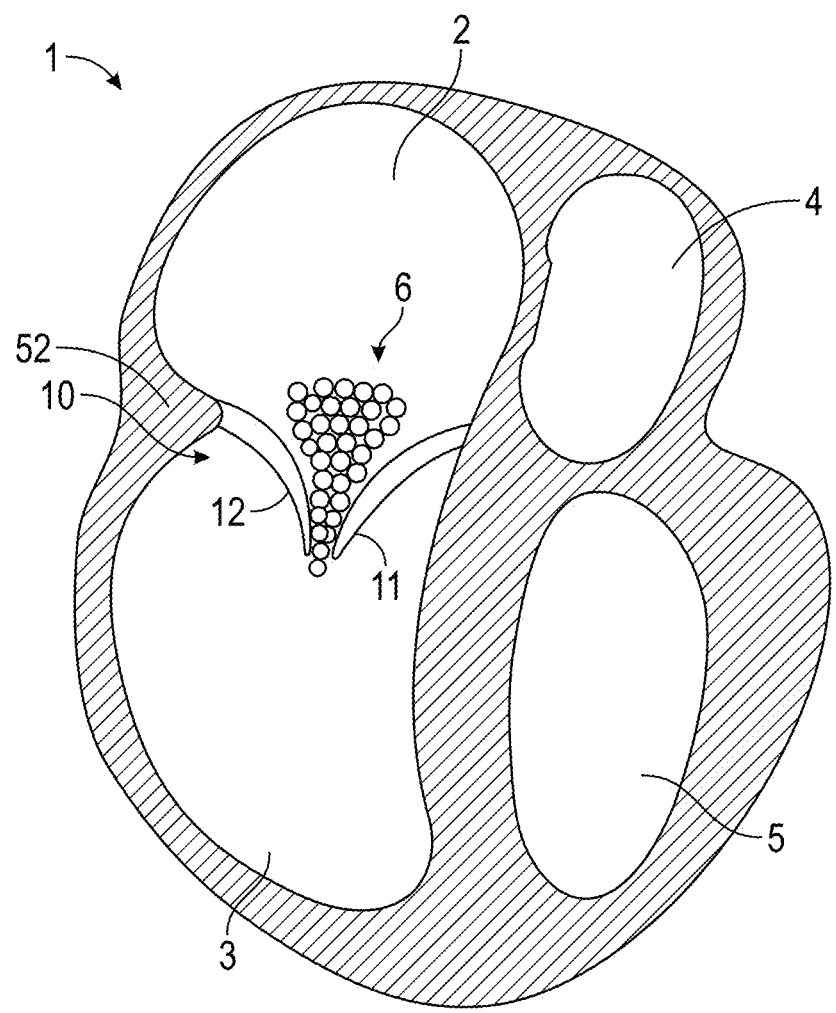
FIG. 1 illustrates a 4-chamber cross section of a heart with a regurgitant jet between the anterior and septal leaflets of the tricuspid valve.
Figure 15:
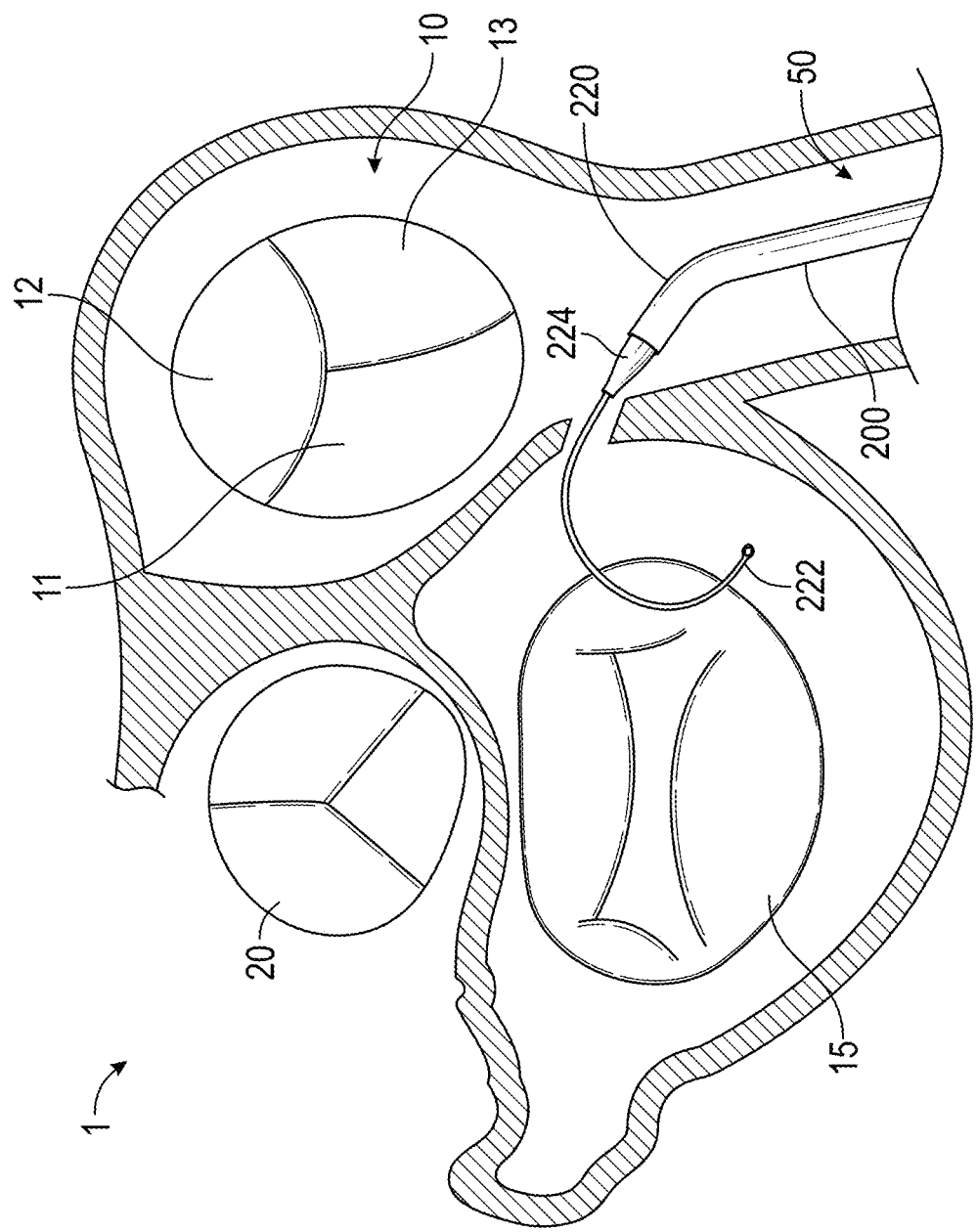
FIG. 15 illustrates the wire crossing the interatrial septum from the right atrium to the left atrium.
Figure 16:
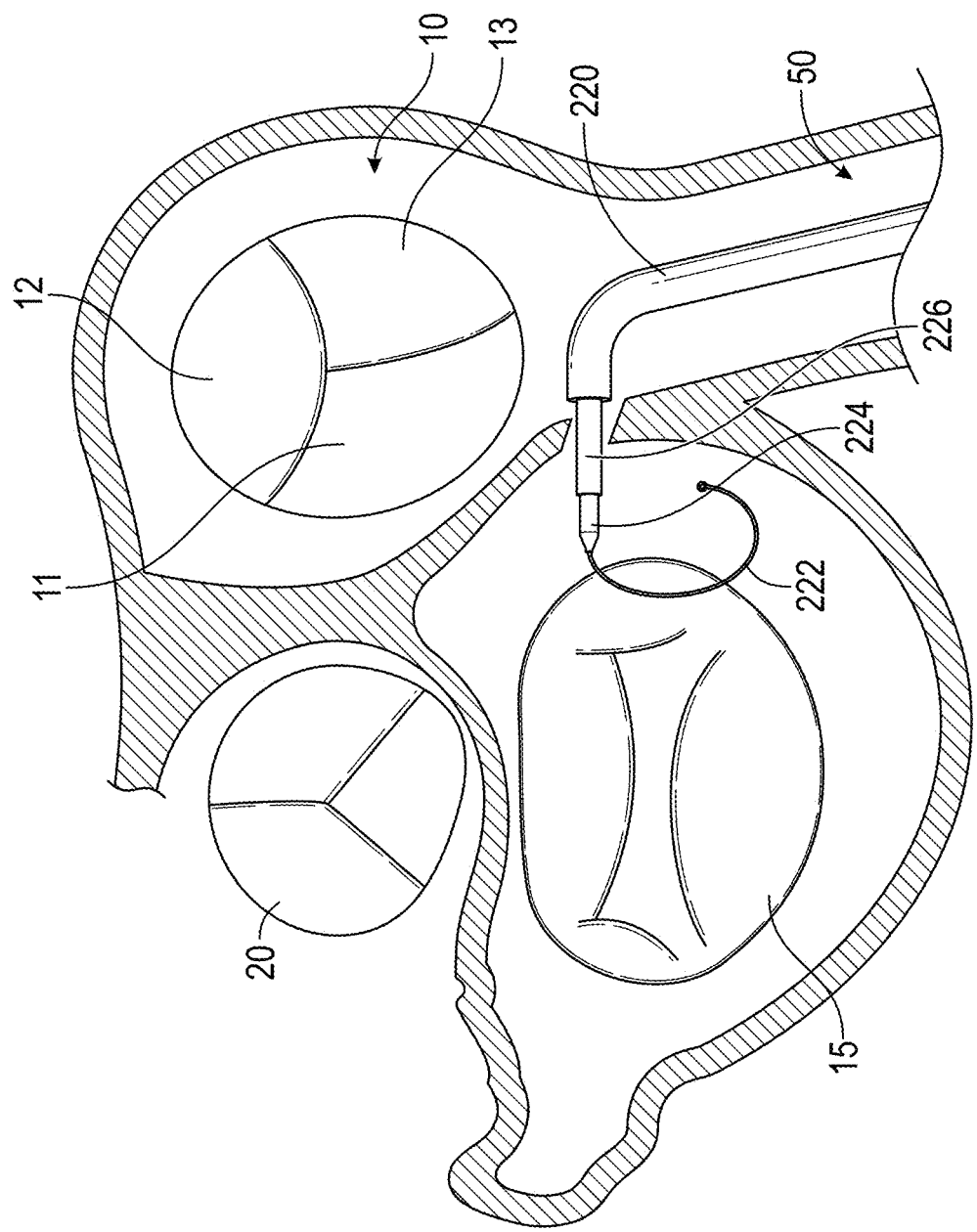
FIG. 16 illustrates the dilator and sheath following the wire across the interatrial septum into the left atrium.
Figure 17:
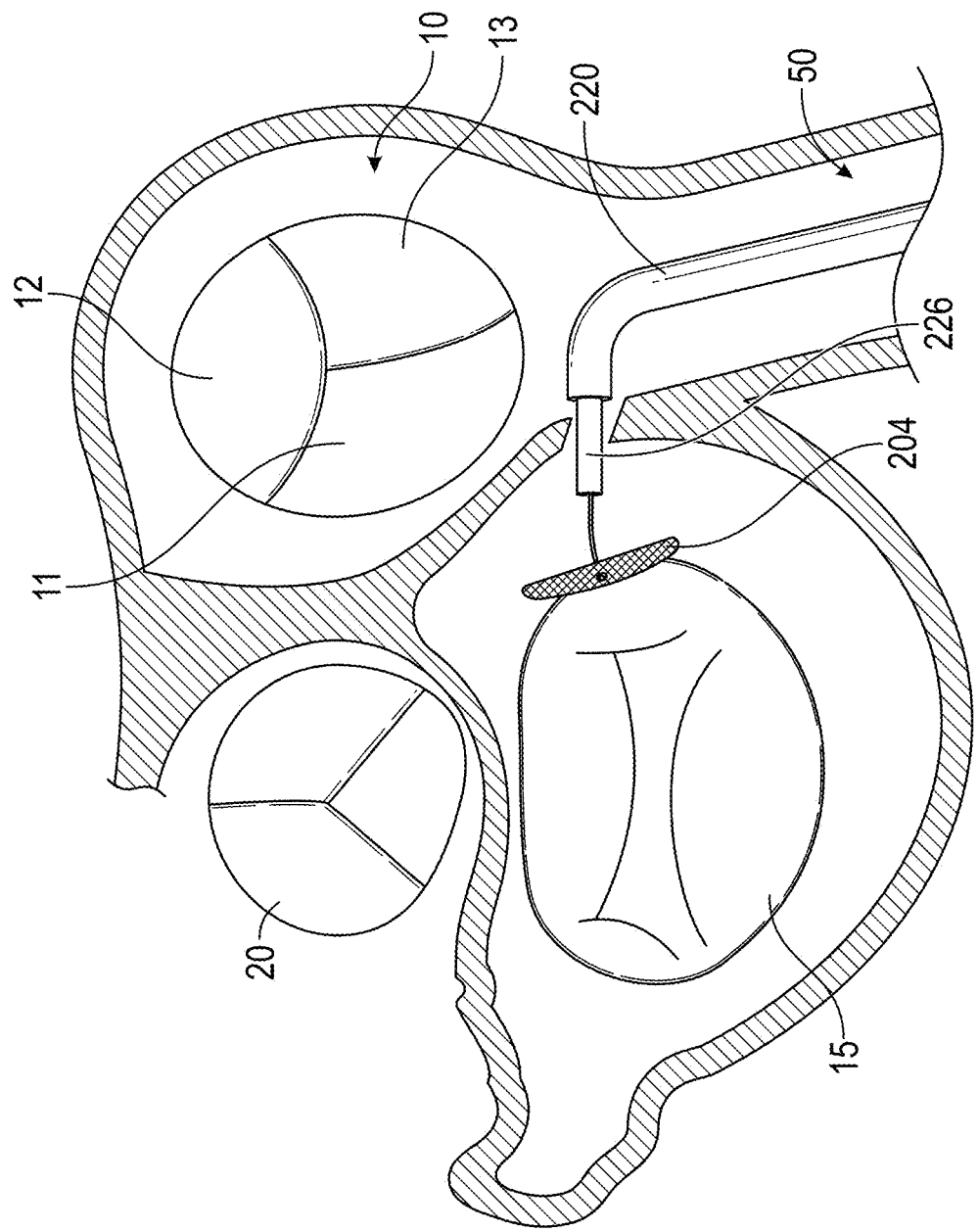
FIG. 17 illustrates a septal anchoring element deployed out of the sheath in the left atrium.
Figure 18:
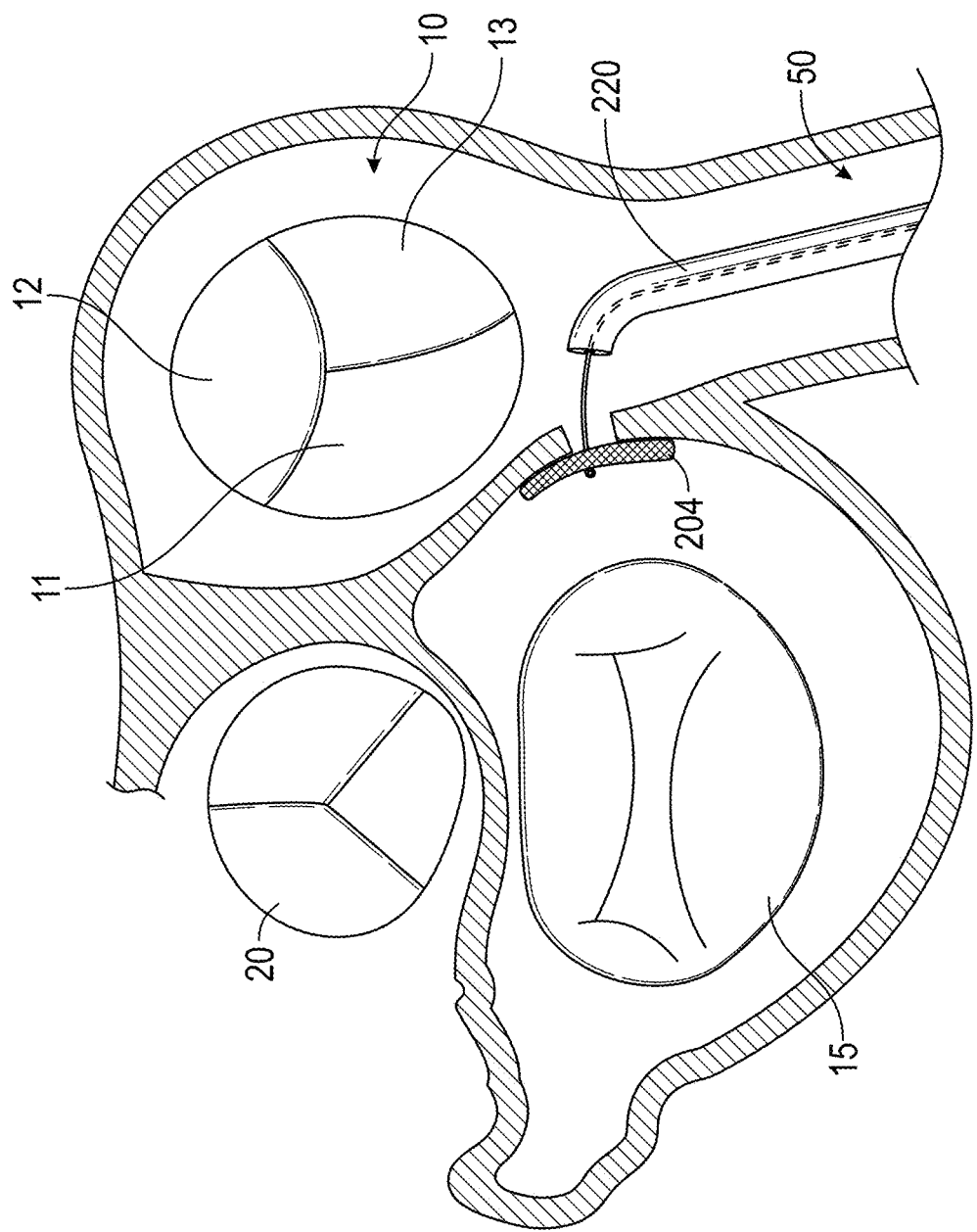
FIG. 18 illustrates the septal anchoring element abutted against the left atrial wall with the anchor deployment catheter or sheath removed and the tension band connected to the anchoring element passing through the guiding catheter.
Figure 19:
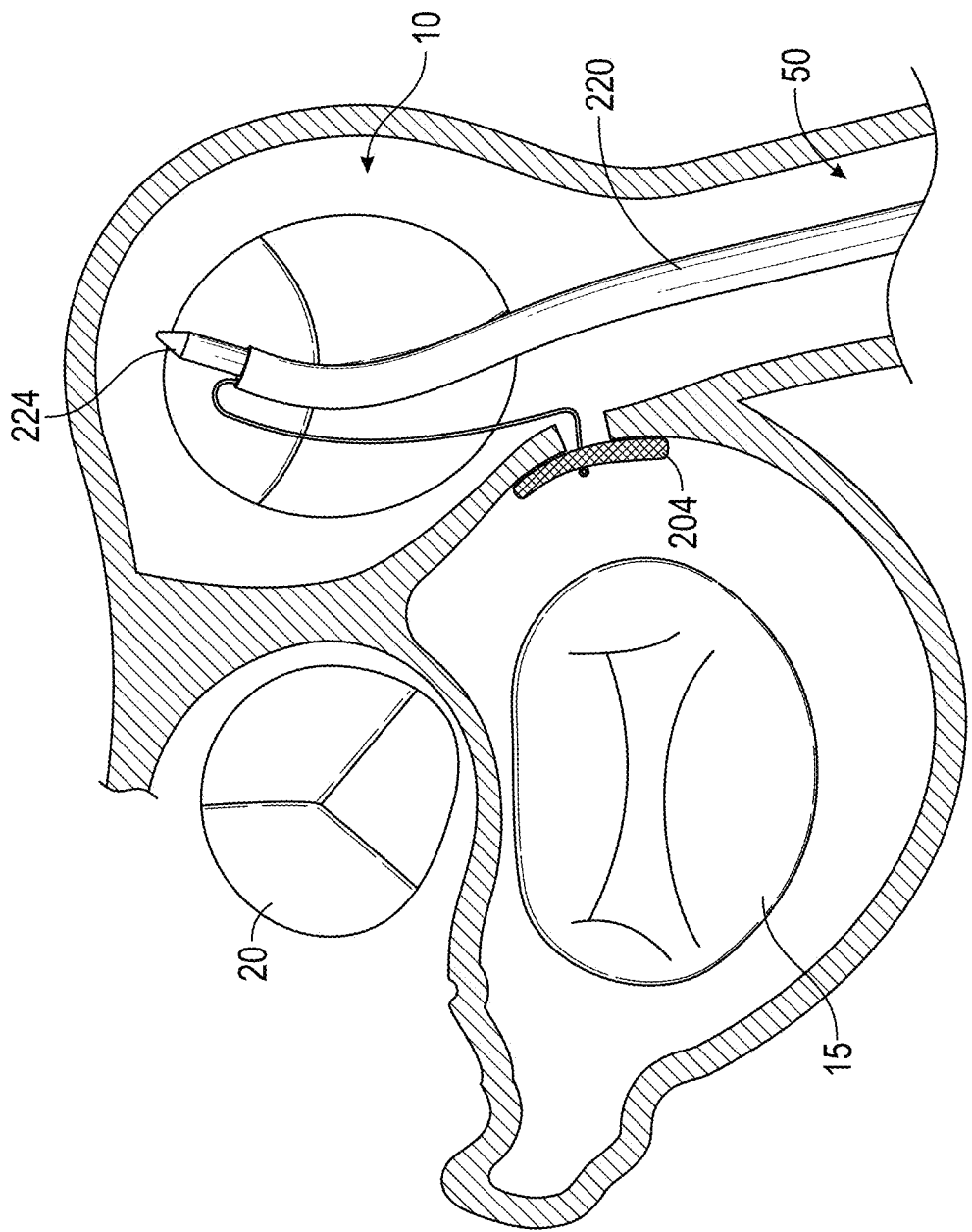
FIG. 19 illustrates the guiding catheter with sheath and dilator directed toward the anterior tricuspid annulus with the septal anchor abutted to the left atrial wall and the tensioning band connected to the septal anchor running through the guiding catheter.
Figure 20:
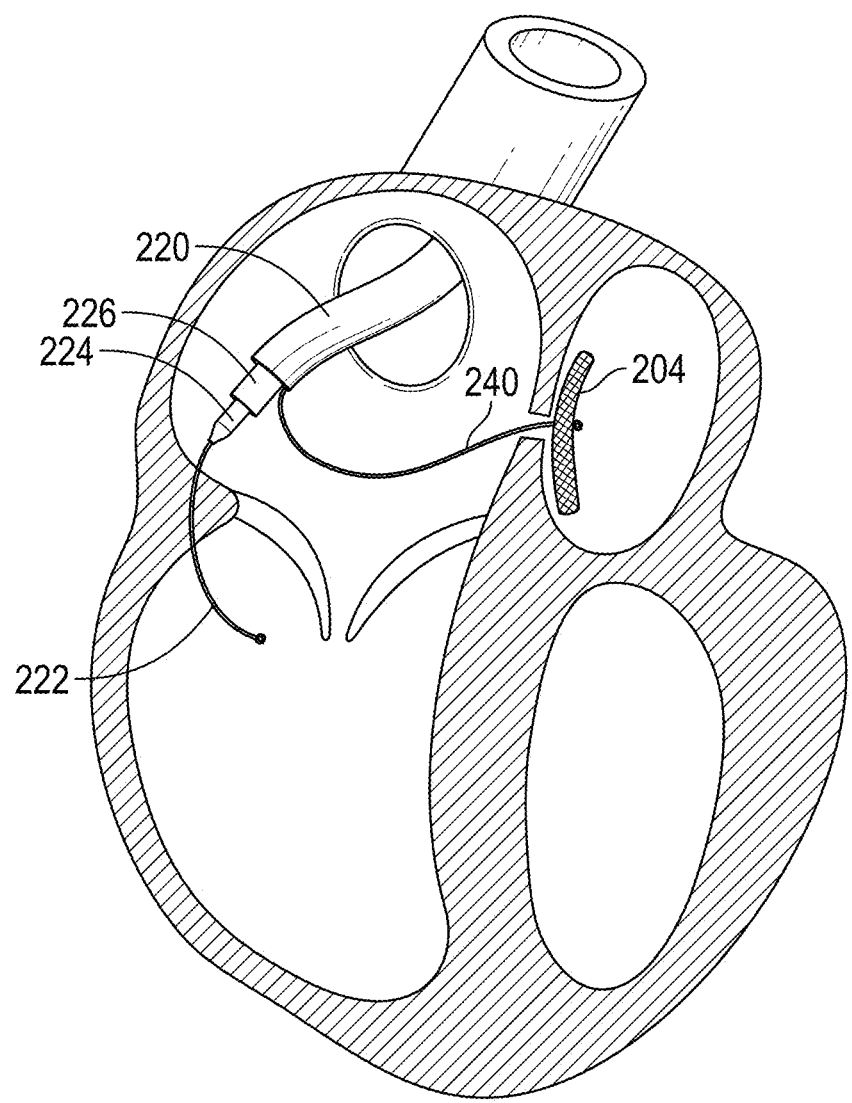
FIG. 20 illustrates a 4-chamber cross section of the heart with the guiding catheter, sheath and dilator directed toward the anterior tricuspid annulus and the wire passing from the right atrial side to the right ventricular side of the anterior tricuspid annulus. The septal anchor is abutted to the left atrial wall with the tension band connected to the septal anchor running through the guiding catheter.
Figure 21:
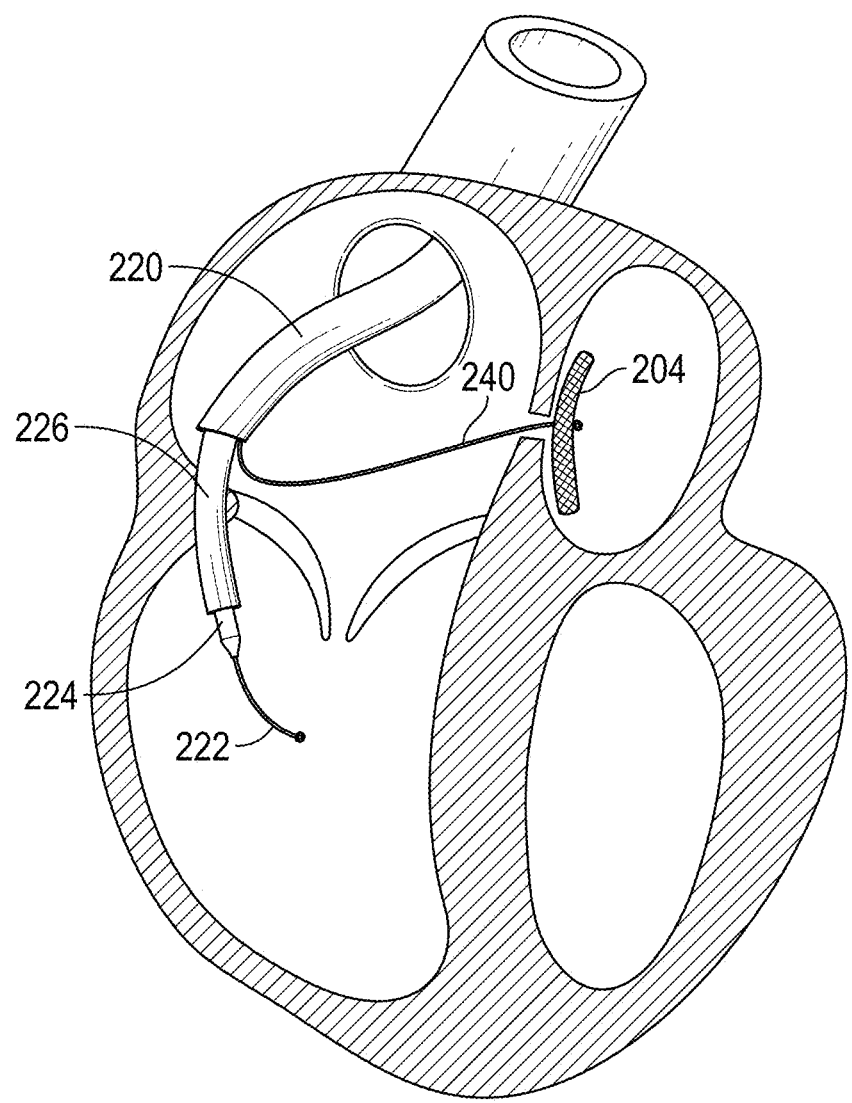
FIG. 21 illustrates the sheath and dilator following the wire across the anterior tricuspid annulus from the right atrium to the right ventricle.
Figure 22:
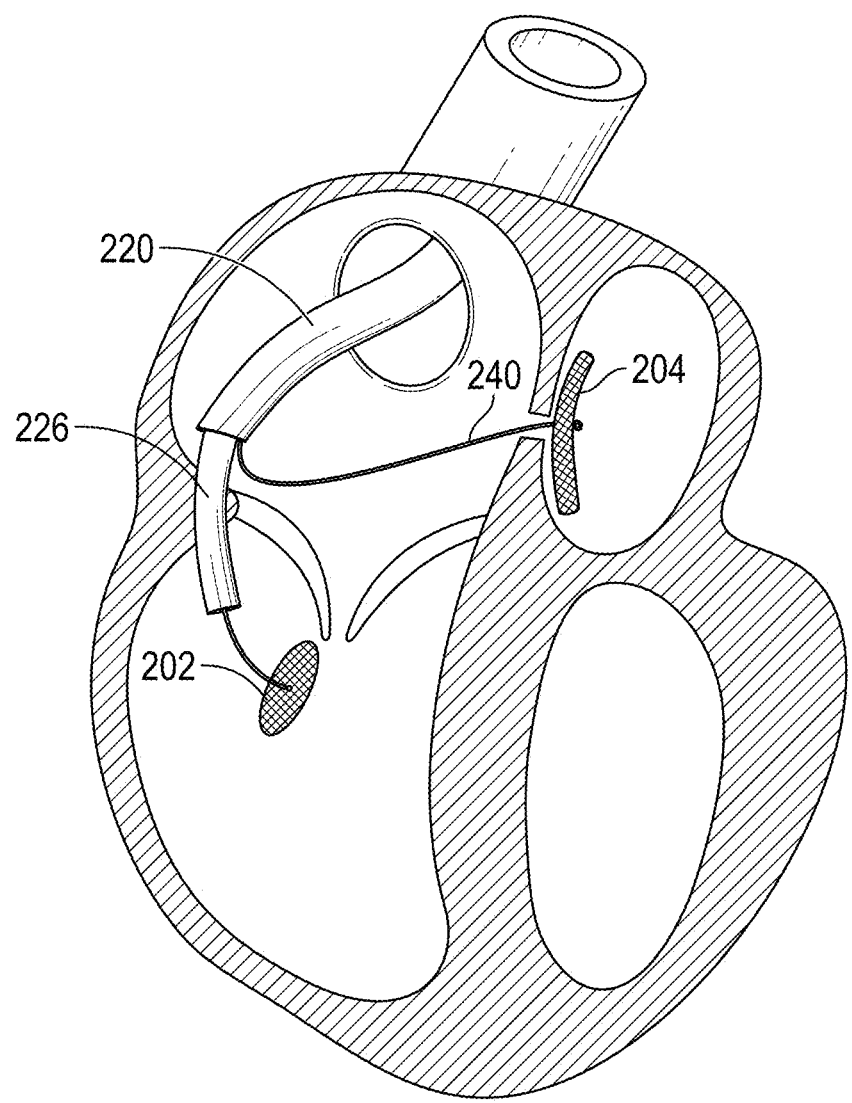
FIG. 22 illustrates the anterior anchoring element deployed out of the sheath into the right ventricle.
Figure 23:
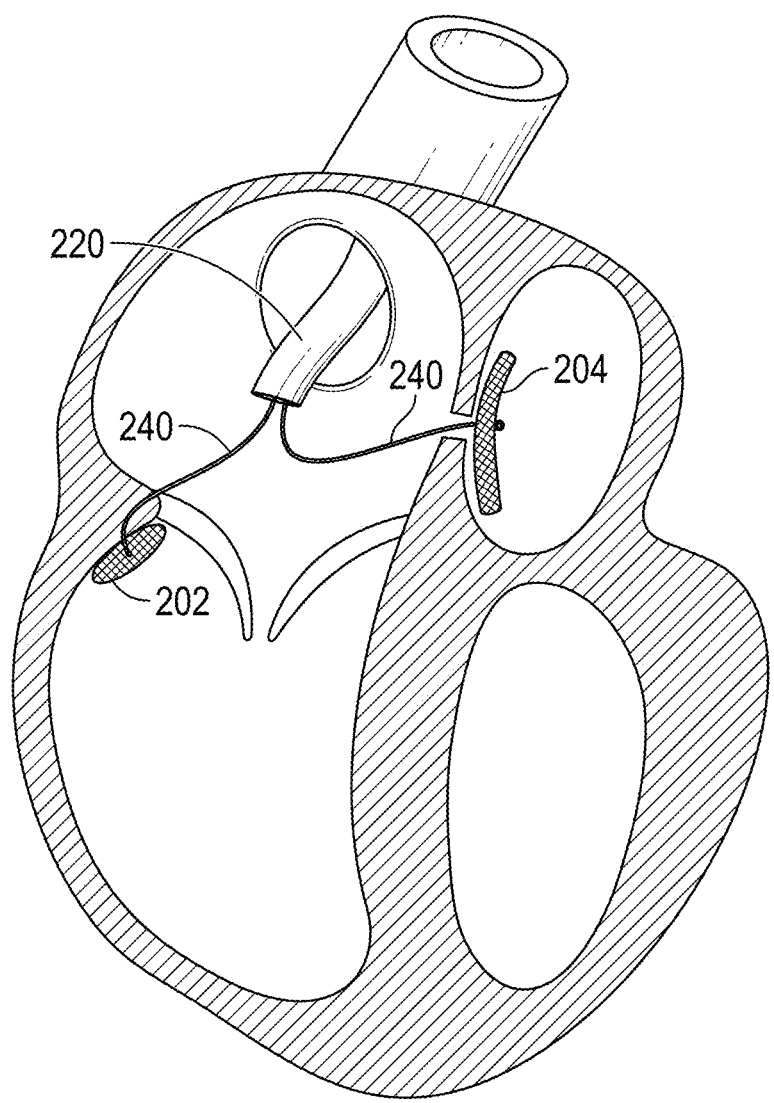
FIG. 23 illustrates the anterior anchoring element abutted to the right ventricular surface of the anterior tricuspid annulus with an attached tensioning band passing from the right ventricle to the right atrium and into the guiding catheter. The septal anchor is abutted to the left atrial wall with an attached tensioning band passing through the interatrial septum from the left atrium to the right atrium and into the guide catheter.
Figure 24:
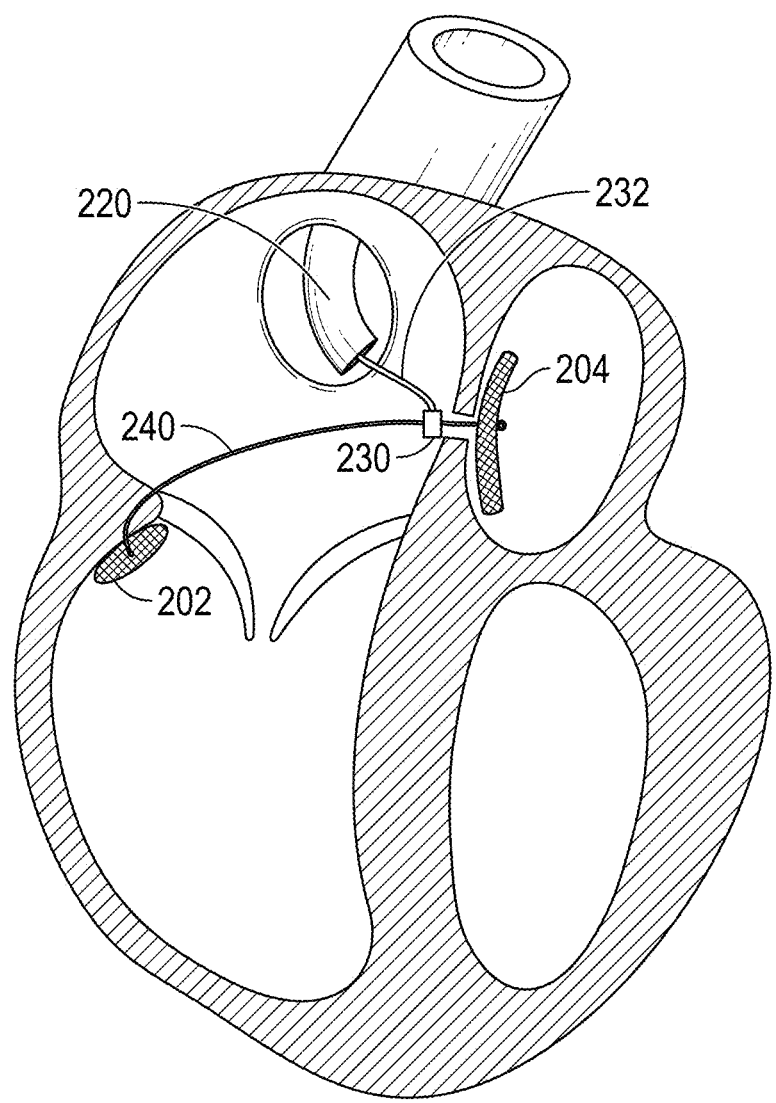
FIG. 24 illustrates locking of the tensioning bands connected to the anterior and septal anchoring elements with a lock placed near the interatrial septum and a lock catheter through the guiding catheter.

FIG. 1 illustrates a 4-chamber cross section of a heart with a regurgitant jet between the anterior and septal leaflets of the tricuspid valve. The heart 1 is divided into four chambers which are responsible for circulating and reoxygenating the blood of a patient. Blood enters the heart in the right atrium 2 and is pumped to the right ventricle 3, separated from the right atrium 2 by the tricuspid valve 10, comprising a septal leaflet 11, anterior leaflet 12, and posterior leaflet 13 (as shown in FIG. 15). Fluid then flows to the lungs to be reoxygenated, and returns to the heart at the left atrium 4, which connects to the left ventricle 5 and then is distributed throughout the body. Important in the healthy operation of the heart are the heart valves between the right atrium 2 and right ventricle 3, and between the left atrium 4 and left ventricle 5. The heart 1 depicted in FIG. 1 depicts a tricuspid valve 10 which is leaking, allowing a regurgitant jet 6 of blood to flow from the right ventricle 3 to the right atrium 2, described as functional tricuspid regurgitation (FTR) herein.

In some applications of the present disclosure techniques are described for repairing a leaking tricuspid valve by pulling the anterior portion of the tricuspid valve annulus toward the septal portion of the tricuspid valve annulus, or that portion of the tricuspid valve annulus in the vicinity of the coronary sinus, via two or more tensioning bands attached via surface anchors near the anterior tricuspid valve annulus, which are connected to a tensioning band attached via a surface anchor to the inferior interatrial septum. Where reference is made to the tricuspid annulus, or to the anterior tricuspid annulus herein, such reference can also include the tissue of the heart near the tricuspid annulus. For example, a location on or near the tricuspid annulus can be defined as within 15 mm from the tricuspid annulus, or areas of the heart whereby imparting a force to such area transmits the force at least partially to the tricuspid annulus. The surface anchors, or tissue anchors, disclosed in certain embodiments can resist forces attempting to withdraw the attached tension member by providing a surface which abuts the endocardial layer of the heart. When surface anchors are placed within a ventricle, the surface anchor can be referred to herein as a ventricular surface anchor. In certain embodiments, the surface anchors can also abut other surfaces of tissues of the heart and/or be also embedded in tissue of the heart. Certain aspects and advantages of the embodiments described herein can also be used with one or more of the anchors being anchors that are embedded within tissue. While two or more tensioning bands are described in many of the embodiments, in certain embodiments a singular tensioning band can be utilized. The tensioning bands (which can also be referred to as tension bands or tensioning elements or tension elements or tension members or tethers) can be part of a tension assembly, wherein the assembly can comprise one or more tension bands/elements. The tension assembly can have multiple individual tension elements/bands that can form a tensioning member (also referred to as a tension member), or a singular tensioning element/band which has portions (e.g., end portions) that form the tension members. For example, a singular tension element (or band) can be looped through a multitude of surface anchors such that the total number of tension elements present in the tether assembly is one (1), where each surface anchor is associated with portions of the tension element to form the tension members. Furthermore, in certain embodiments a surface anchor can be used in place of a tissue anchor as disclosed in embodiments herein, or a tissue anchor can be used in place of a surface anchor as disclosed in embodiments herein. In some embodiments the anterior anchoring elements comprise an anchor that can be 5 millimeters to 30 millimeters long, but in certain embodiments 14 millimeters to 18 millimeters long, and in certain embodiments 2 millimeters to 20 millimeters wide but in certain embodiments 5 millimeters to 10 millimeters wide and in certain embodiments 0.1 millimeters to 5 millimeters thick that are positioned in contact with the right ventricular wall behind the anterior leaflet 12 of the tricuspid valve 52, such as the anchors depicted in FIGS. 2 through 5, 33, 37 through 38, 45, 50, and 69-74. While many embodiments are disclosed in the context of tricuspid valve, it should be appreciated that certain aspects of the methods, systems and apparatus disclosed herein may find utility in other areas of the body including the treatment of other valves of the heart.

Figure 2:
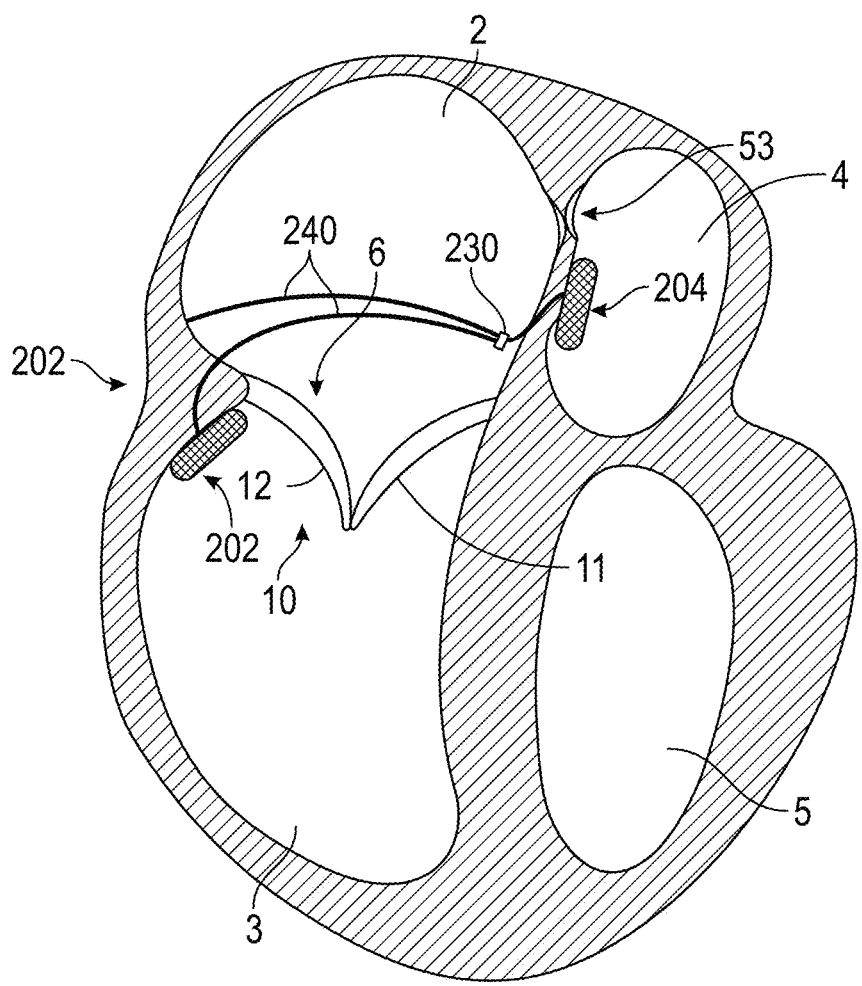
FIG. 2 illustrates a 4-chamber cross section of a heart with an embodiment of treatment comprising an anchoring element implanted against the left atrial surface of the interatrial septum, inferior to the fossa ovalis, and connected via tensioning bands to anchoring elements implanted against the right ventricular surface of the anterior tricuspid annulus by a lock near the right atrial surface of the interatrial septum.

FIG. 2 through 5 depict several possible embodiments of techniques for repairing a leaking tricuspid valve. In FIG. 2, an embodiment of the system comprises three anchoring elements, a first and second anterior anchor 202 implanted against the right ventricular surface of the anterior tricuspid annulus 52, or anterior annulus, in the right ventricle 3 close to the tricuspid valve 10 (the second shown in FIG. 6), and a septal left atrial anchor 204 implanted in the left atrium 4 against the left atrial surface inferior to the fossa ovalis 53. A surface anchor can be referred to with reference to its implant location. As such, the surface anchors implanted near the right ventricular surface of the anterior tricuspid annulus 52 can be referred to as ventricular surface anchors. A surface anchor implanted in the left atrium 4 against the left atrial surface inferior to the fossa ovalis 53, such as the septal left atrial anchor 204, can be referred to as a tension anchor. Implanting multiple tension anchors in or around the same area is also possible. When implanting multiple tension anchors in or around the same area, a center of the second tension anchor should be spaced between 0.5 and 4 centimeters from a center of the first tension anchor, so as to increase efficacy and reduce possible overlap of the anchors on surfaces of the heart. The three anchoring elements are joined by one or more tensioning members 240, or tensioning bands, sutures or tethers, which are positioned closer to effectuate a closing of the tricuspid valve 10 via a lock 230, or tether locks as elaborated in other embodiments disclosed herein.

Figure 3:
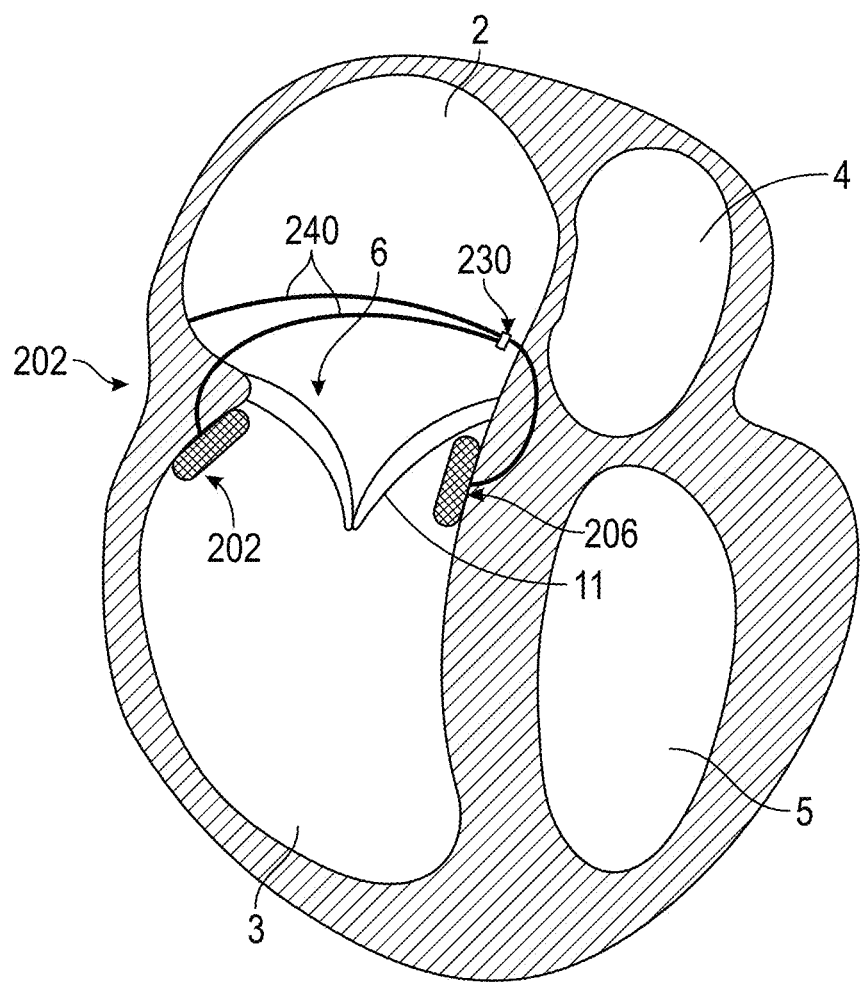
FIG. 3 illustrates a 4-chamber cross section of a heart with an embodiment of treatment comprising an anchoring element implanted against the right ventricular surface of the interventricular septum, inferior to the tricuspid valve leaflet hinge, and connected via tensioning bands to anchoring elements implanted against the right ventricular surface of the anterior tricuspid annulus by a lock near the right atrial surface of the interatrial septum.

In FIG. 3, an embodiment of the system comprises three anchoring elements, a first and second anterior anchor 202 implanted against the right ventricular surface of the anterior tricuspid annulus 52 in the right ventricle 3 close to the tricuspid valve 10, and a septal right ventricular anchor 206 located in the right ventricle 3 on the septal side of the tricuspid valve 10, along the interventricular septum. While the septal right ventricular anchor 206 is not located in the same position as the septal left atrial anchor 204 of FIG. 2, both the septal right ventricular anchor 206 and the septal left atrial anchor 204 act as tension anchors as they connect to the ventricular surface anchors which are surface anchors implanted near the right ventricular surface of the anterior tricuspid annulus 52. The three anchoring elements are similarly joined by one or more tensioning bands which are coupled or attached together with a lock 230 (or tension member lock). In the embodiment of FIG. 3, the lock 230 is located in the right atrium 2. In other embodiments however, the lock 230 can be located elsewhere within the heart, such as within the right ventricle 3, the left atrium 4, or the left ventricle 5. In other embodiments, the lock 230 can be located outside the heart. In other embodiments, the lock 230 can additionally be incorporated into any of the surface anchors or tissue anchors used in the embodiment, such that it is either able to fixably attach to a surface anchor or tissue anchor, or optionally be permanently incorporated into a surface anchor or tissue anchor.

Figure 4:
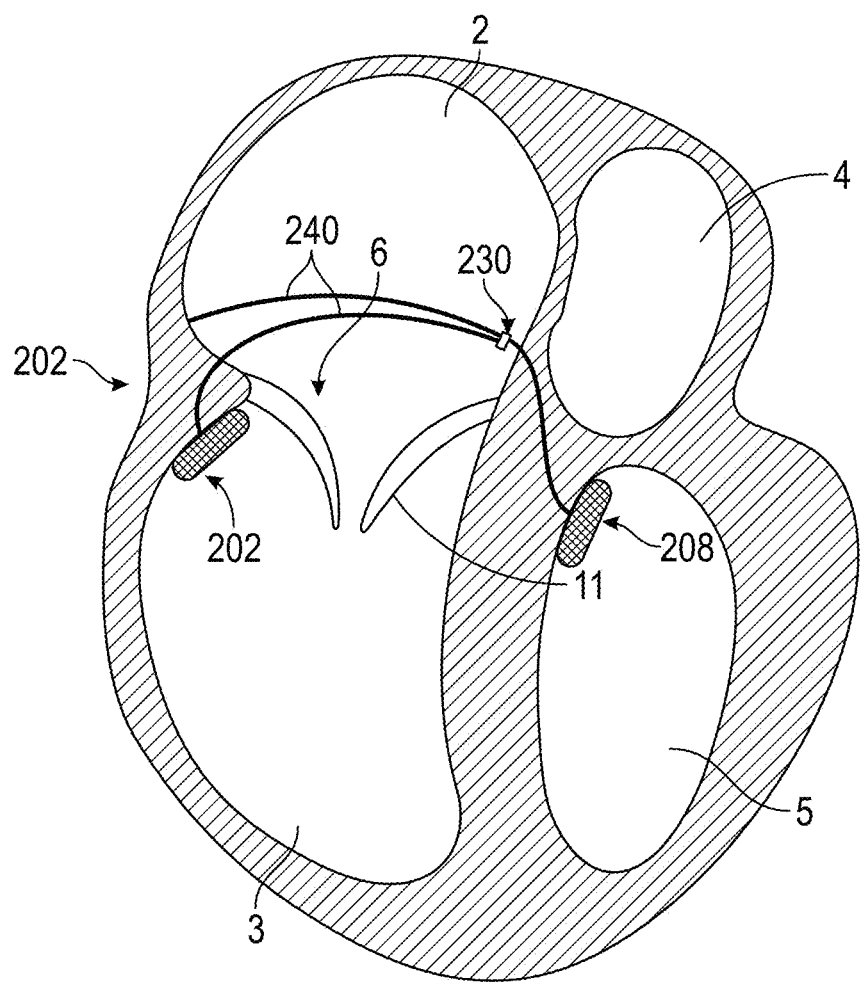
FIG. 4 illustrates a 4-chamber cross section of a heart with an embodiment of treatment comprising an anchoring element implanted against the left ventricular surface of the interventricular septum, inferior to the mitral valve leaflet hinge, and connected via tensioning bands to anchoring elements implanted against the right ventricular surface of the anterior tricuspid annulus by a lock near the right atrial surface of the interatrial septum.

In FIG. 4, an embodiment of the system comprises three anchoring elements, a first and second anterior anchor 202 implanted against the right ventricular surface of the anterior tricuspid annulus 52 in the right ventricle 3 close to the tricuspid valve 10, and a septal left ventricular anchor 208 located in the left ventricle 5. While the septal left ventricular anchor 208 is not located in the same position as the septal left atrial anchor 204 of FIG. 2, both the septal left ventricular anchor 208 and the septal left atrial anchor 204 act as tension anchors as they connect to the ventricular surface anchors which are surface anchors implanted near the right ventricular surface of the anterior tricuspid annulus 52. This principle can refer to other surface anchors disclosed herein. The three anchoring elements are similarly joined by one or more tensioning bands with a lock 230.

Figure 5:
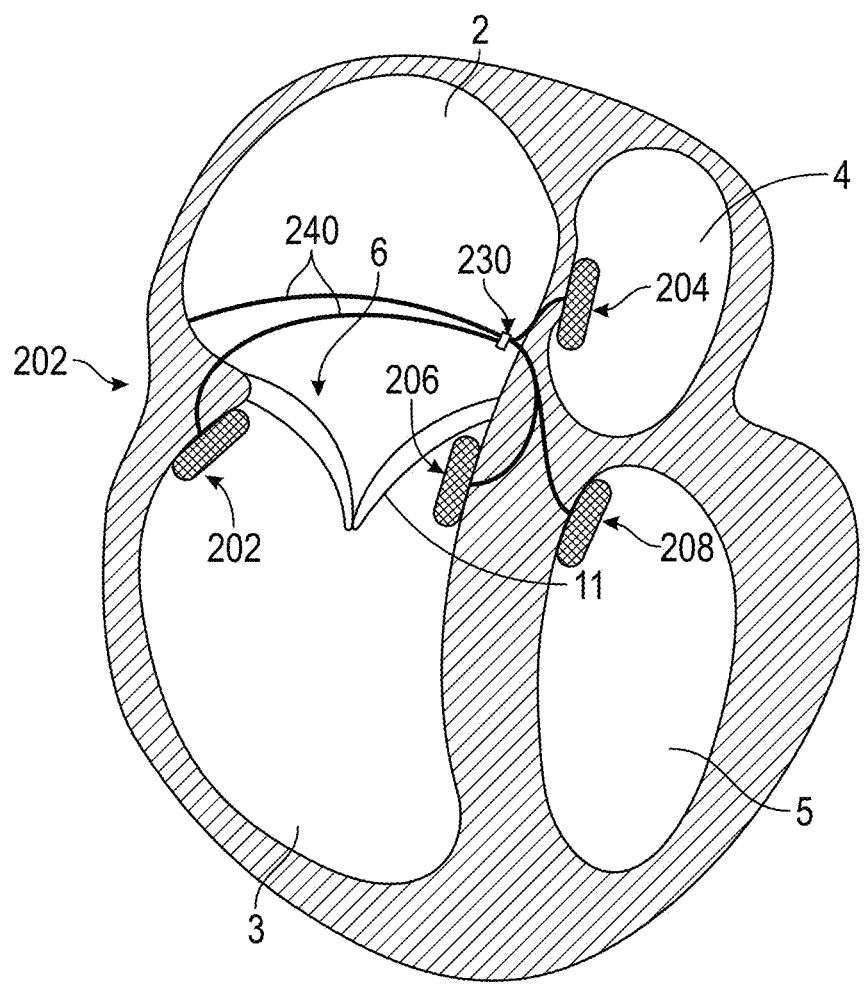
FIG. 5 illustrates a 4-chamber cross section of a heart with an embodiment of treatment comprising an anchoring element implanted in each of the locations illustrated in FIGS. 2 through 4, and connected via tensioning bands to anchoring elements implanted against the right ventricular surface of the anterior tricuspid annulus by a lock near the right atrial surface of the interatrial septum.

In FIG. 5, an embodiment of the system comprises five anchoring elements, a first and second anterior anchor 202 implanted against the right ventricular surface of the anterior tricuspid annulus 52 in the right ventricle 3 close to the tricuspid valve 10, a third septal left atrial anchor 204 located in the left atrium 4, a fourth septal ventricular anchor 206 located in the right ventricle 3 on the septal side of the tricuspid valve 10 along the interventricular septum, and a fifth septal left ventricular anchor 208 located in the left ventricle 5. The three anchoring elements are similarly joined by one or more tensioning bands with a lock 230. FIGS. 6 through 9 depict top down, or short axis, or surgeons', views of implant sites for treatment. The figures generally depict a top down view of the heart, depicting an anterior leaflet 12 of the tricuspid valve 10, the mitral valve 15, the aortic valve 20, and the pulmonary valve 25, as well as the coronary sinus 54 and right coronary artery 55.

Figure 6:
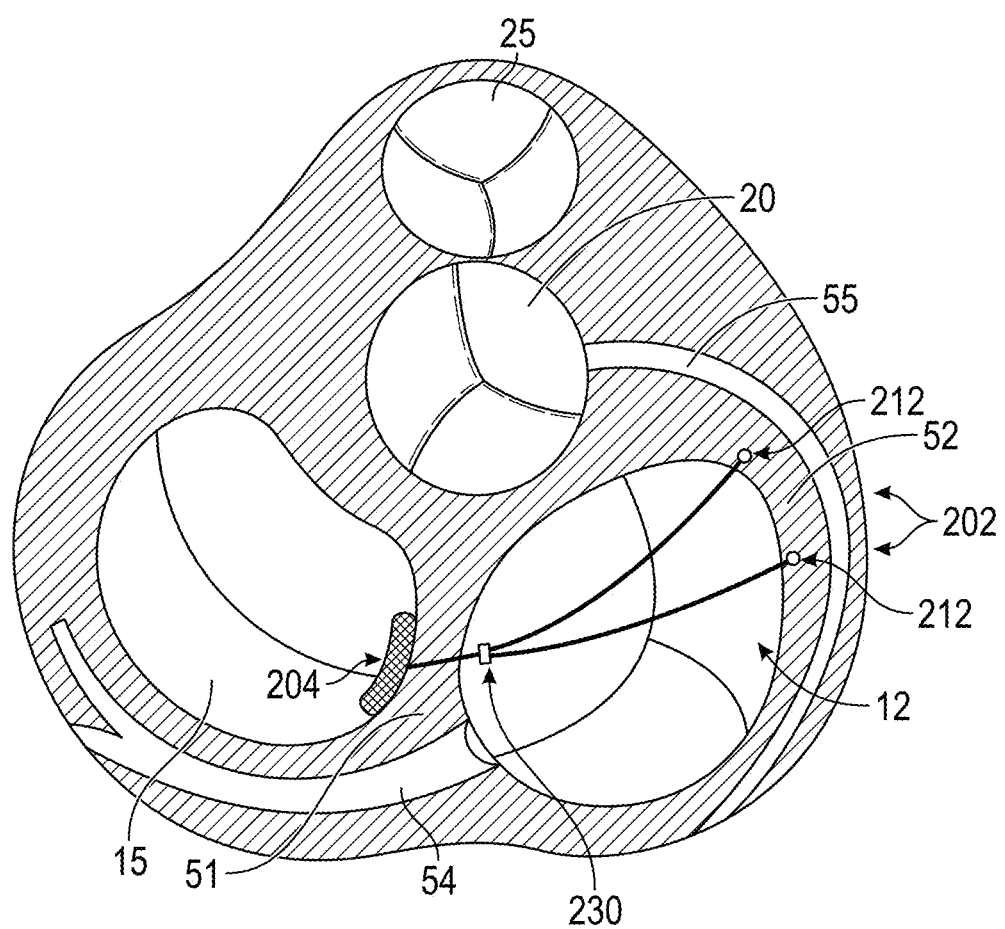
FIG. 6 illustrates a top down (surgeons) view of a heart with an embodiment of treatment according to FIG. 2 comprising an anchoring element implanted against the left atrial surface of the interatrial septum, inferior to the fossa ovalis, and connected via tensioning bands to anchoring elements implanted against the right ventricular surface of the anterior tricuspid annulus by a lock near the right atrial surface of the interatrial septum.

FIG. 6 illustrates a top down (surgeons) view of a heart 1 with an embodiment of treatment comprising an anchoring element 204 implanted against the left atrial surface of the interatrial septum 51, inferior to the fossa ovalis 53 (as shown in FIG. 2), and connected via tensioning bands 240 to anchoring elements 202 implanted against the right ventricular surface of the anterior tricuspid annulus 52 by a lock 230 near the right atrial surface of the interatrial septum, the anterior anchors 202 connected to the tensioning bands 240 through annulus entry points 212.

Figure 7:
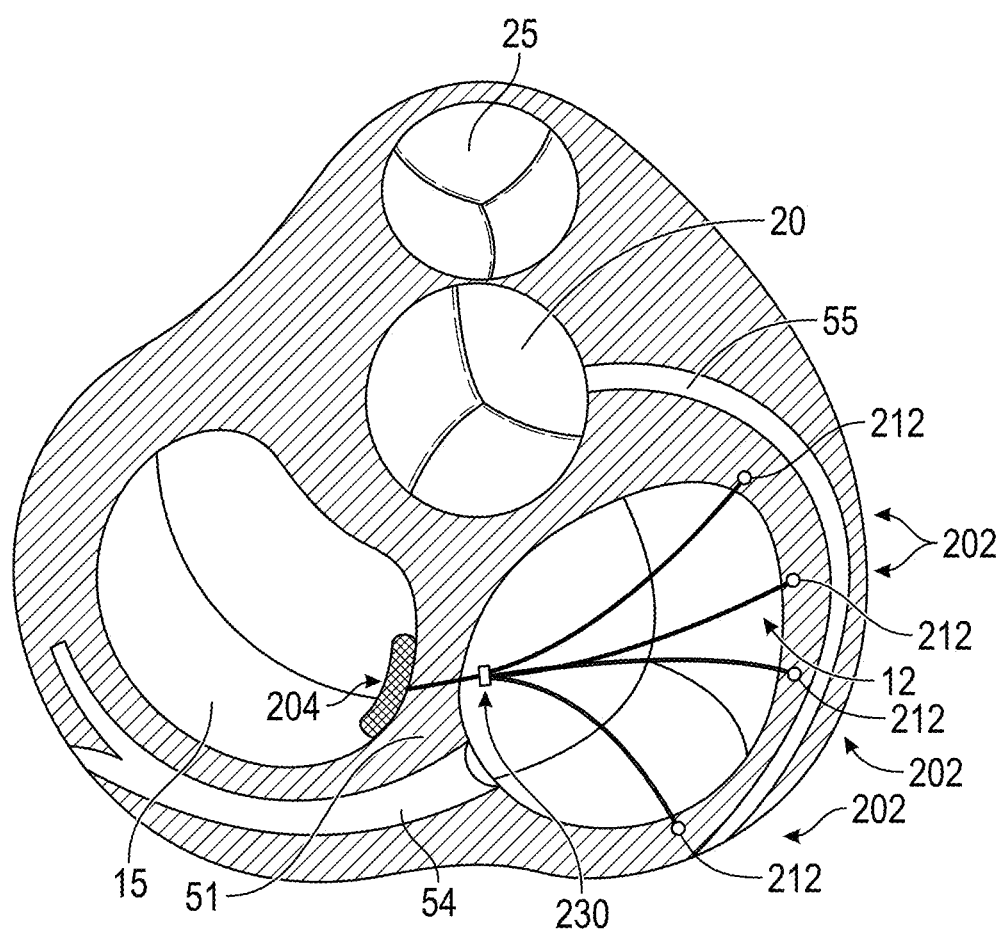
FIG. 7 illustrates a top down (surgeons) view of a heart with an embodiment of treatment comprising an anchoring element implanted against the left atrial surface of the interatrial septum, inferior to the fossa ovalis, and connected via tensioning bands to anchoring elements implanted against the right ventricular surface of the anterior and posterior tricuspid annulus by a lock near the right atrial surface of the interatrial septum.

FIG. 7 illustrates a top down (surgeons) view of a heart 1 with an embodiment of treatment comprising an anchoring element 204 implanted against the left atrial surface of the interatrial septum 51, inferior to the fossa ovalis 53 (as shown in FIG. 2), and connected via tensioning bands 240 to anchoring elements 202 implanted against the right ventricular surface of the anterior and posterior tricuspid annulus 52 by a lock 230 near the right atrial surface of the interatrial septum 51, the anterior anchors 202 connected to the tensioning bands 240 through annulus entry points 212.

Figure 8:
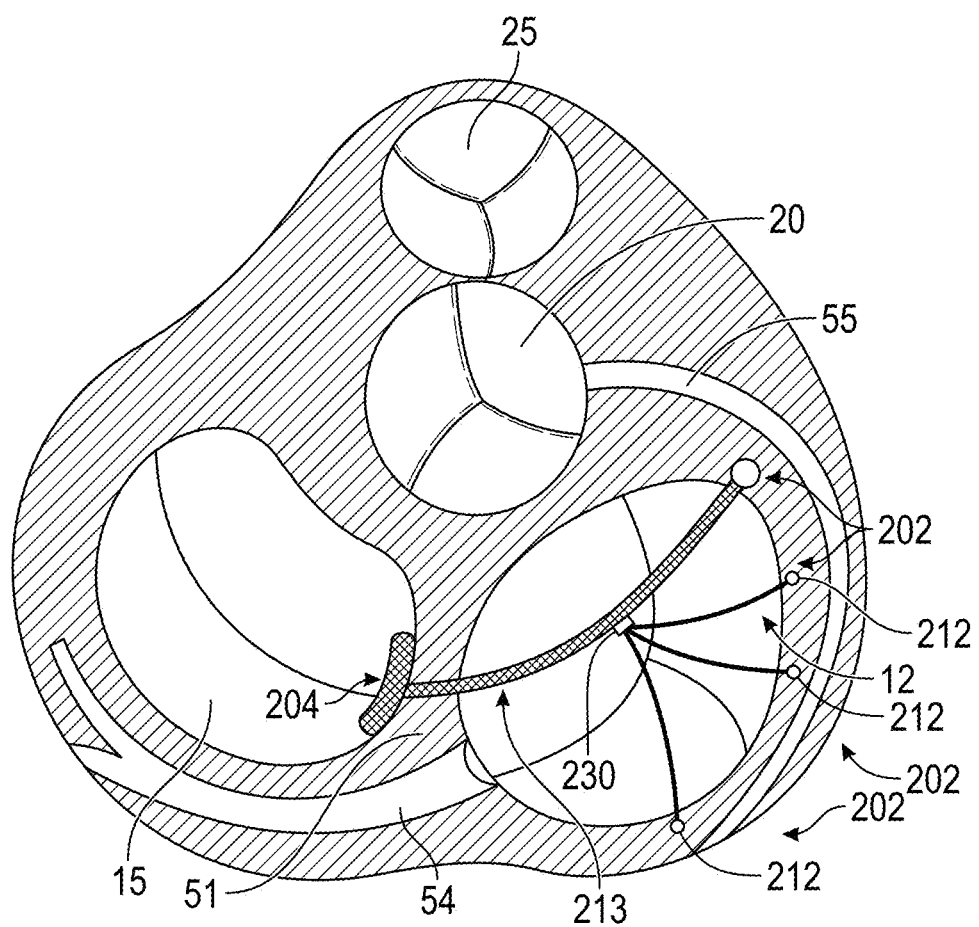
FIG. 8 illustrates a top down (surgeons) view of a heart with an embodiment of treatment comprising anchoring elements and a bar spanning the right atrium from the interatrial septum, inferior to the fossa ovalis, to the RVOT. Anchoring elements implanted on the right ventricular surface of the anterior and posterior tricuspid annulus are attached via tensioning bands to the bar via a lock near the center of the bar and tensioning of the bands draws those portions of the tricuspid annulus in contact with the anchoring elements toward the bar.
Figure 33:
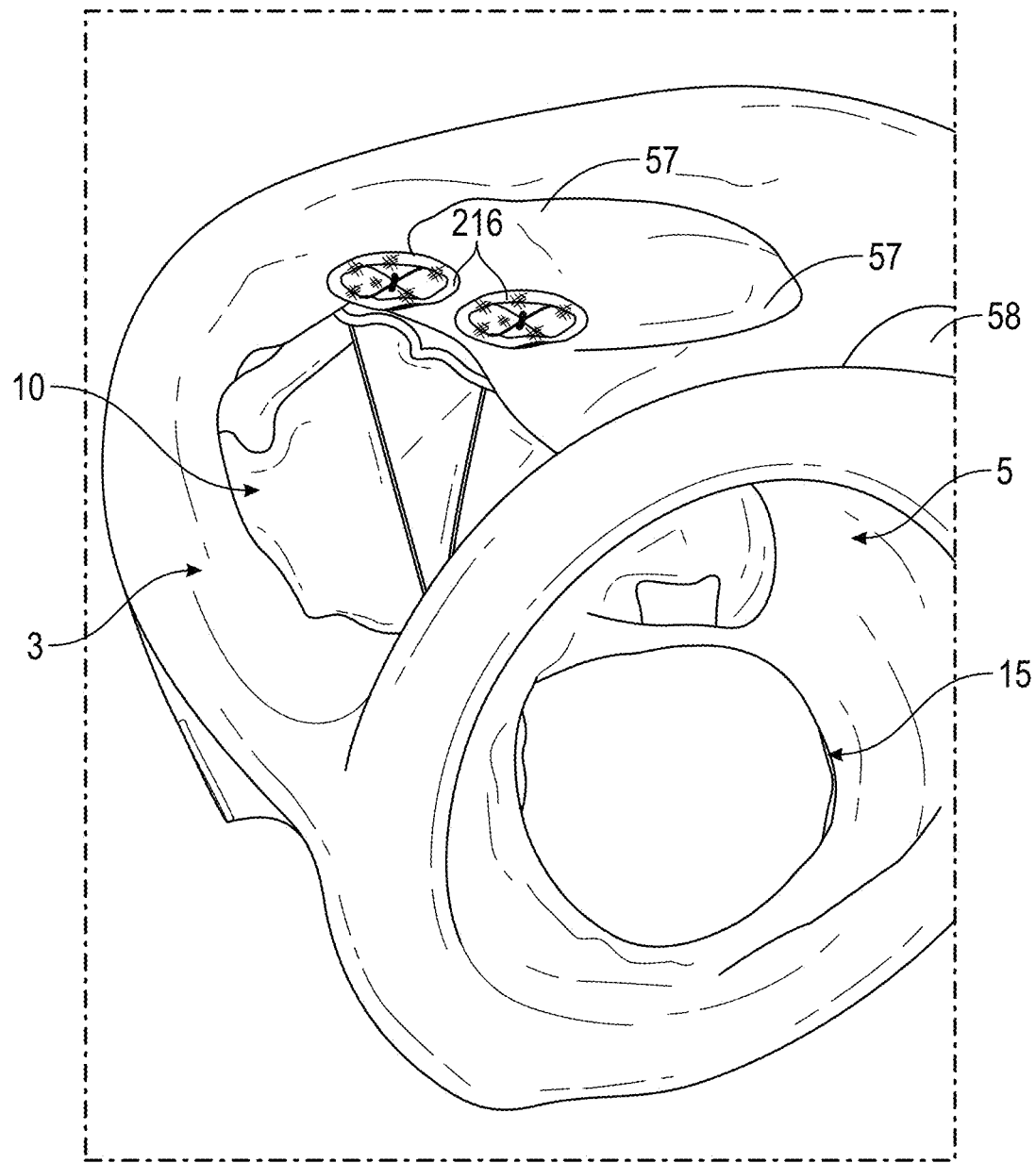
FIG. 33 illustrates the right ventricular view, looking up at the tricuspid valve, of the 2 expandable t-bar anchoring elements positioned against the right ventricular surface of the anterior tricuspid valve annulus in and near the RVOT.

FIG. 8 illustrates a top down (surgeons) view of a heart with an embodiment of treatment comprising anchoring elements 202 and 204 and a bar 213 spanning the right atrium from the interatrial septum 51 connected by a septal left atrial anchor 204, inferior to the fossa ovalis 53 (as shown in FIG. 2), to the right ventricular outflow tract (RVOT) 57 (as shown in FIG. 33). Anchoring elements 202 implanted on the right ventricular surface of the anterior and posterior tricuspid annulus 52 are attached via tensioning bands 240 passing through annulus entry points 212 to the bar 213 via a lock 230 near the center of the bar 213 and tensioning of the bands 240 draws those portions of the tricuspid annulus in contact with the anchoring elements 202 toward the bar 213.

Figure 9:
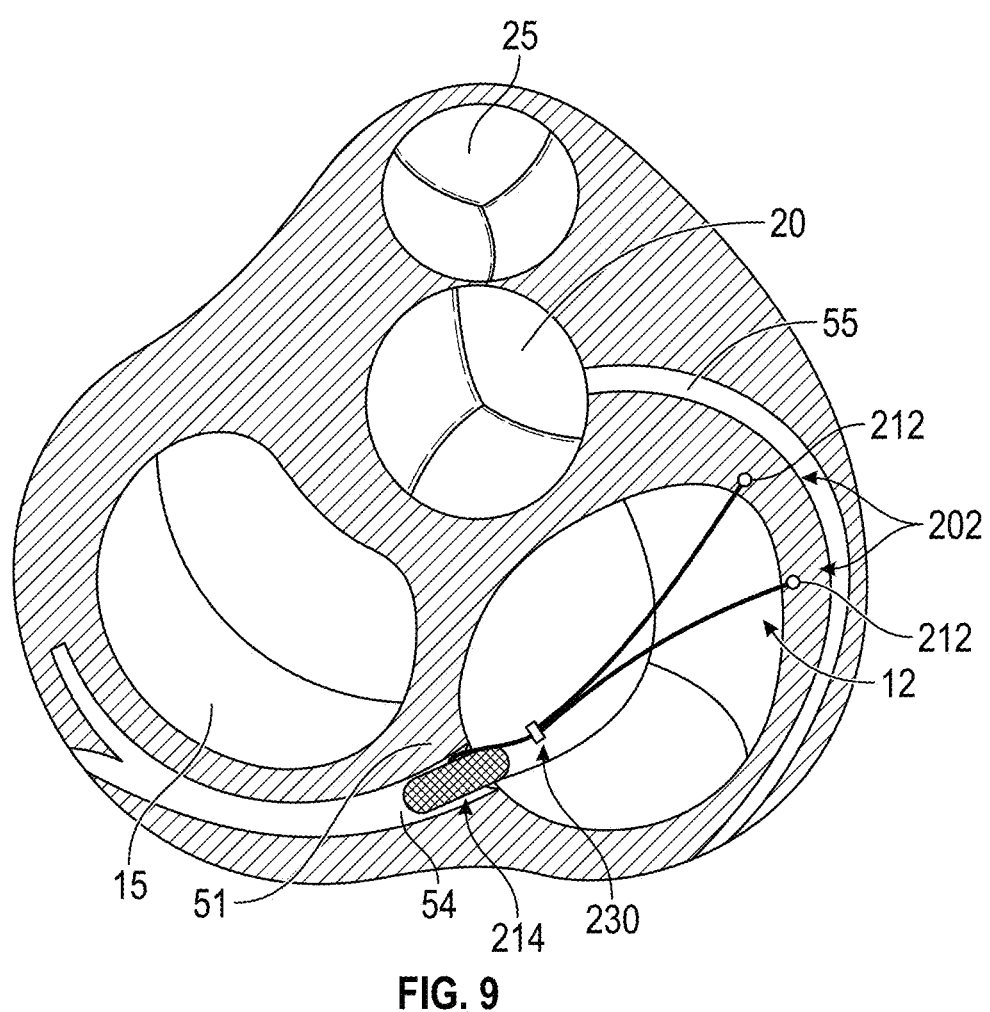
FIG. 9 illustrates a top down (surgeons) view of a heart with an embodiment of treatment comprising an anchoring element implanted against the inferior surface of the coronary sinus, near the ostia, and connected via tensioning bands to anchoring elements implanted against the right ventricular surface of the anterior and posterior tricuspid annulus by a lock near the right atrial surface of the interatrial septum.

FIG. 9 illustrates a top down (surgeons) view of a heart with an embodiment of treatment comprising an anchoring element 214 implanted against the inferior surface of the coronary sinus 52, near the ostia, and connected via tensioning bands 240 to anchoring elements 202 implanted against the right ventricular surface of the anterior and posterior tricuspid annulus 52 by a lock 230 near the right atrial surface of the interatrial septum 53.

FIGS. 10 through 13 illustrate an alternative view of further embodiments of treatment. The figures generally show the right atrium 2 and right ventricle 3 of the heart, with the anterior annulus 52 and coronary sinus 54.

Figure 10:
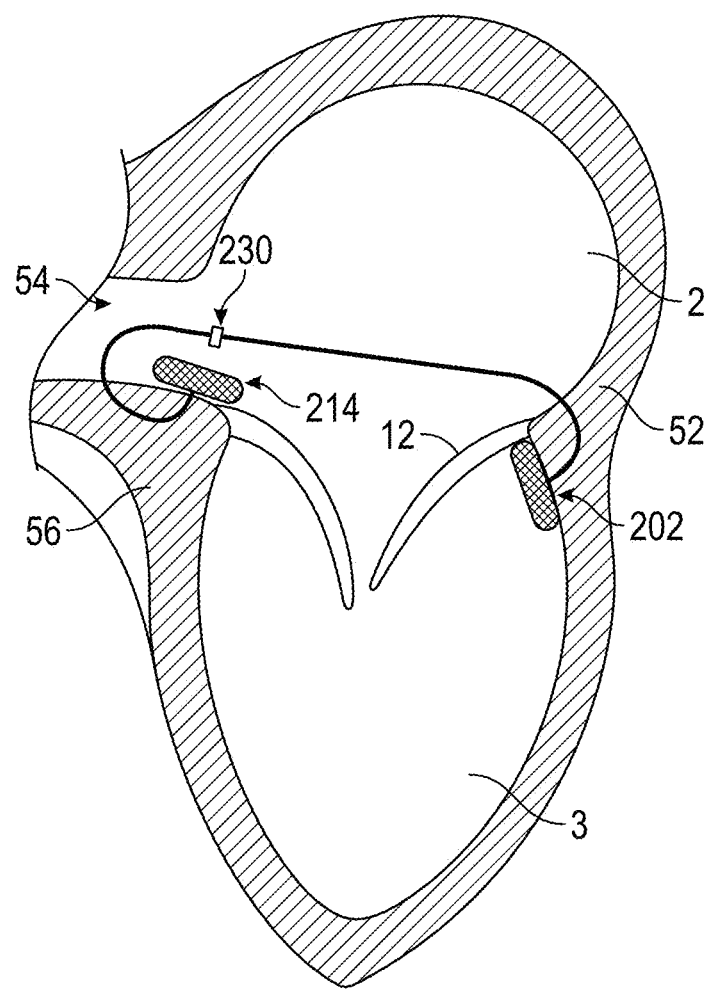
FIG. 10 illustrates a cross section of a heart with an embodiment of treatment comprising an anchoring element implanted on the inferior surface of the coronary sinus, near the ostia of the coronary sinus, with a tensioning band that loops through the left ventricular myocardium inferior to the coronary sinus from within the coronary sinus toward the tricuspid annulus. Another anchoring element is implanted on the right ventricular surface of the anterior tricuspid annulus with a tensioning band traversing through the annulus into the right atrium. The tensioning bands are tensioned and connected together within a lock located near the coronary sinus ostium to pull the anterior tricuspid annulus toward the coronary sinus.

FIG. 10 illustrates a cross section of a heart with an embodiment of treatment comprising an anchoring element 214 implanted on the inferior surface of the coronary sinus 54, near the ostia of the coronary sinus, with a tensioning band 240 that loops through the left ventricular myocardium inferior to the coronary sinus 54 (shown in FIG. 32) from within the coronary sinus toward the tricuspid annulus 52. Another anchoring element 202 is implanted on the right ventricular surface of the anterior tricuspid annulus 52 with a tensioning band 240 traversing through the annulus into the right atrium 2. The tensioning bands are tensioned and connected together within a lock 230 located near the coronary sinus 54 ostium to pull the anterior tricuspid annulus 52 toward the coronary sinus 54.

Figure 11:
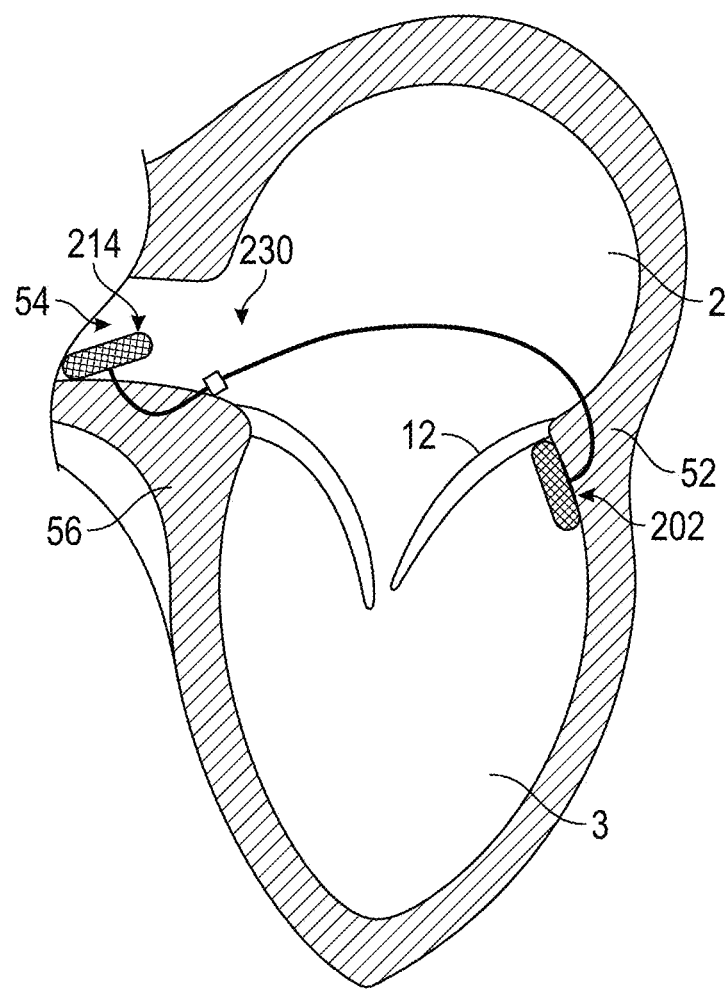
FIG. 11 illustrates a cross section of a heart with an embodiment of treatment comprising an anchoring element implanted on the inferior surface of the coronary sinus, near the ostia of the coronary sinus, with a tensioning band that loops through the left ventricular myocardium inferior to the coronary sinus from near the tricuspid annulus to within the coronary sinus. Another anchoring element is implanted on the right ventricular surface of the anterior tricuspid annulus with a tensioning band traversing through the annulus into the right atrium. The tensioning bands are tensioned and connected together within a lock located near the coronary sinus ostium to pull the anterior tricuspid annulus toward the coronary sinus.

FIG. 11 illustrates a cross section of a heart with an embodiment of treatment comprising an anchoring element 214 implanted on the inferior surface of the coronary sinus 54, near the ostia of the coronary sinus, with a tensioning band 240 that loops through the left ventricular myocardium 56 inferior to the coronary sinus 54 (shown in FIG. 32) from near the tricuspid annulus 52 to within the coronary sinus 54. Another anchoring element 202 is implanted on the right ventricular surface of the anterior tricuspid annulus 52 with a tensioning band 240 traversing through the annulus 52 into the right atrium 2. The tensioning bands 240 are tensioned and connected together within a lock 230 located near the coronary sinus 54 ostium to pull the anterior tricuspid annulus 52 toward the coronary sinus 54.

Figure 12:
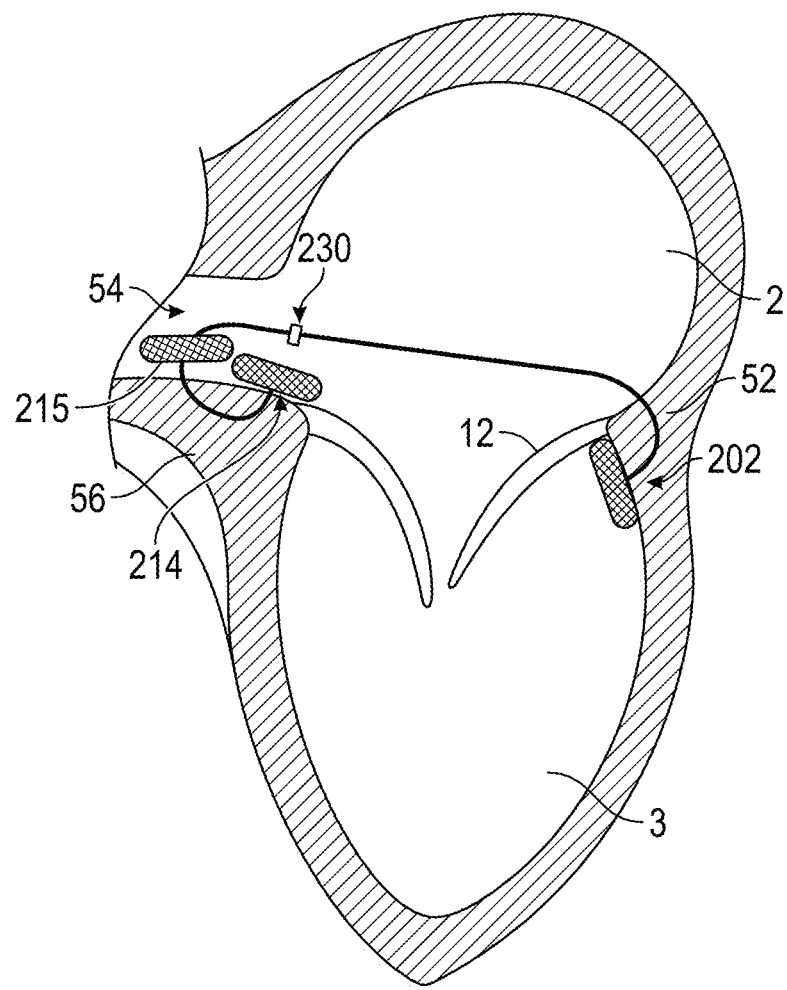
FIG. 12 illustrates a cross section of a heart with an embodiment of treatment comprising anchoring elements implanted similarly to those in FIG. 10 except that a pad is additionally implanted on the inferior surface of the coronary sinus where the tensioning band exits to allow the myocardial tissue to be squeezed between the pad and anchor and prevent the tensioning band from cutting through the myocardial tissue.

FIG. 12 illustrates a cross section of a heart with an embodiment of treatment comprising an anchoring element 214 implanted similarly to FIG. 10, except that a grommet 215 is additionally implanted on the inferior surface of the coronary sinus 54 where the tensioning band exits to allow the myocardial tissue to be squeezed between the grommet 215 and coronary sinus anchor 214 and prevent the tensioning band 240 from cutting through the myocardial tissue.

Figure 13:
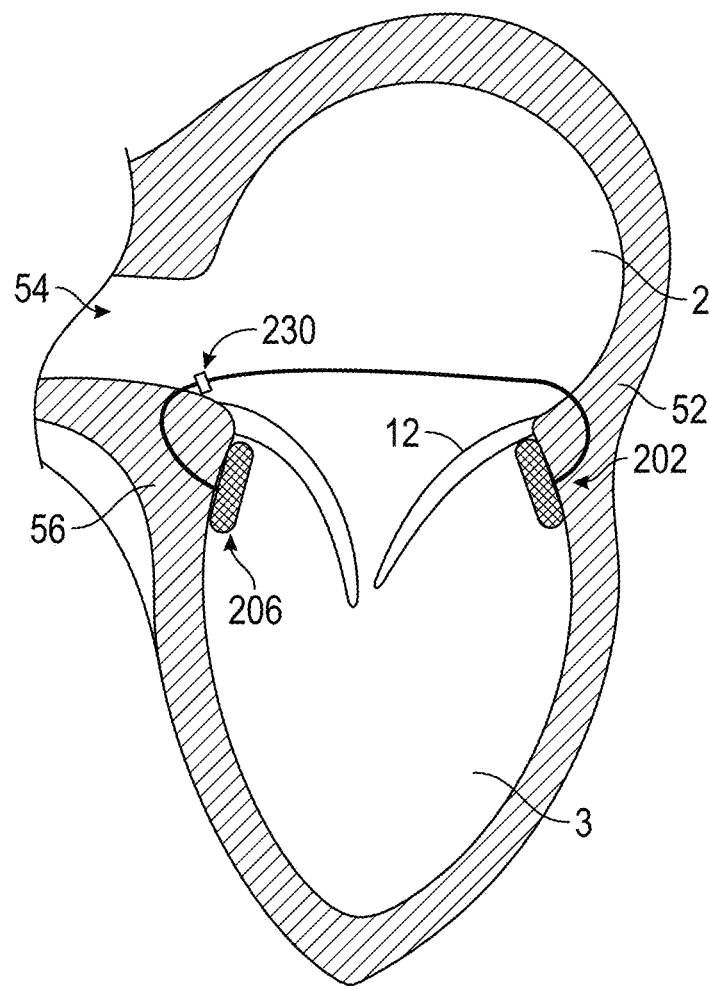
FIG. 13 illustrates a cross section of a heart with an embodiment of treatment comprising an anchoring element implanted against the right ventricular surface of the tricuspid annulus inferior to the coronary sinus ostia (near the septal/posterior tricuspid valve commissure), with a tensioning band that loops through the left ventricular myocardium inferior to the coronary sinus from near the tricuspid annulus to within the coronary sinus. Another anchoring element is implanted on the right ventricular surface of the anterior tricuspid annulus with a tensioning band traversing through the annulus into the right atrium. The tensioning bands are tensioned and connected together within a lock located near the coronary sinus ostium to pull the anterior tricuspid annulus toward the coronary sinus.
Figure 14:
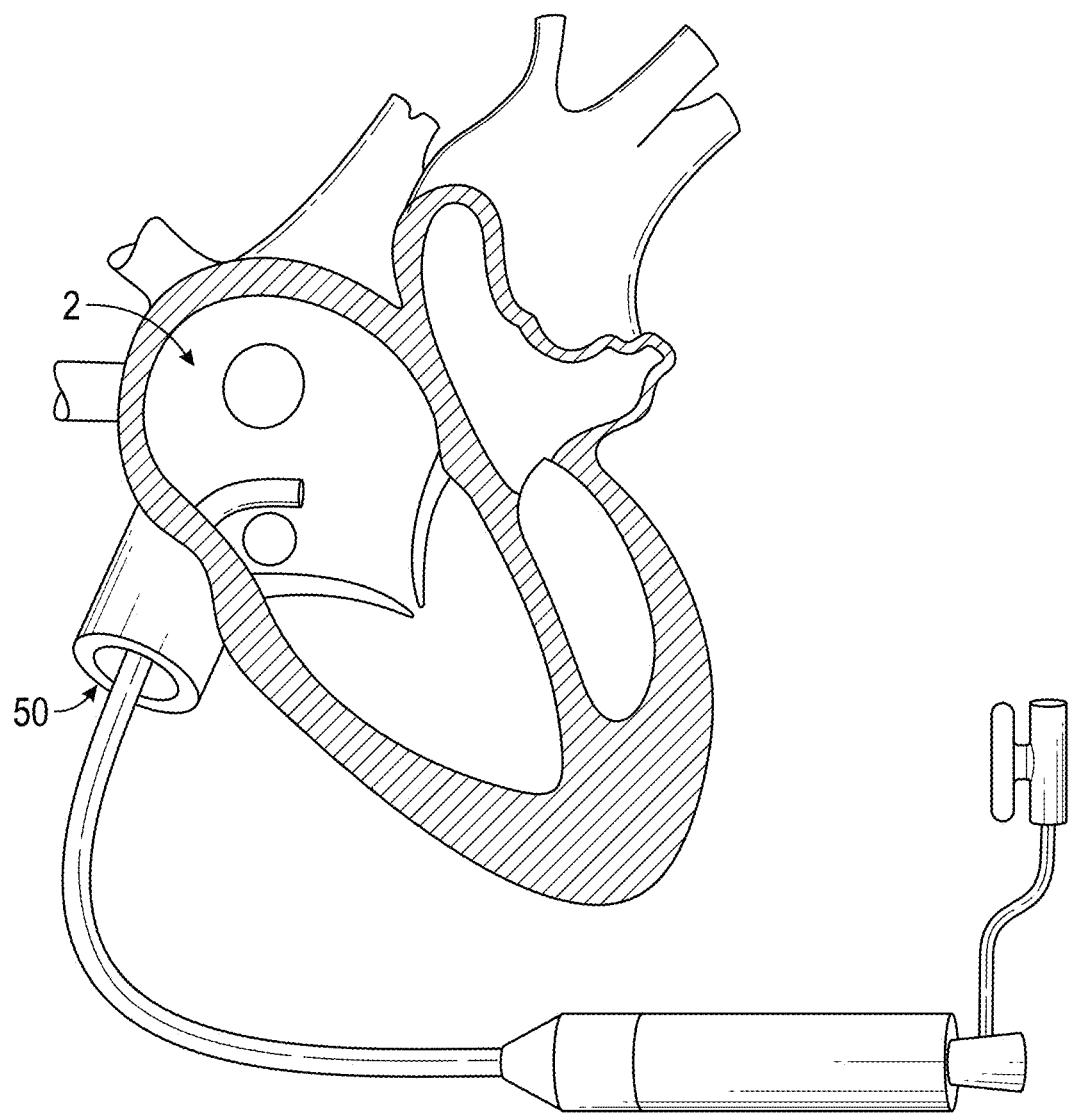
FIG. 14 illustrates catheter entry into the right atrium through the venous circulation system via the femoral vein and the inferior vena cava (IVC) with the distal tip of the catheter positioned inferior to the fossa ovalis and in proximity to the coronary sinus ostia

FIG. 13 illustrates a cross section of a heart with an embodiment of treatment comprising an anchoring element 206 implanted against the right ventricular surface of the tricuspid annulus inferior to the coronary sinus 54 ostia (near the septal/posterior tricuspid valve commissure), with a tensioning band 240 that loops through the left ventricular myocardium inferior to the coronary sinus from near the tricuspid annulus 52 to within the coronary sinus 54. Another anchoring element 202 is implanted on the right ventricular surface of the anterior tricuspid annulus 52 with a tensioning band 240 traversing through the annulus into the right atrium 2. The tensioning bands 240 are tensioned and connected together within a lock 230 located near the coronary sinus ostium to pull the anterior tricuspid annulus toward the coronary sinus.

The anchoring elements (202, 204, 206, 208, 214) can be connected to a flexible tensioning band, or bands, 240 by various mechanisms including a knot, a crimp joint, or other suitable mechanisms and the tensioning band 240 can pass from the anchoring element (202, 204, 206, 208, 214), through one or more tissues within the heart and into the right atrium 2. The tensioning band 240 can pass through various tissues within the heart, as desired or required, such as through the tissue of the right ventricle 3, the tricuspid annulus 52, or the interatrial septum 51. In the embodiments illustrated in, for example, FIGS. 2, 3, 4 and 5, the tensioning band 240 may pass through the tricuspid annulus, or the tissue near the tricuspid valve annulus, at a distance of 0 millimeters to 15 millimeters from the hinge point of the tricuspid valve leaflet 10. The annulus entry point 212 through which the tensioning band 240 passes through the tissue is preferred to be as small as possible such that when the tensioning band is pulled in tension the anchoring element (202, 204, 206, 208) is pulled against the ventricular surface of the tricuspid annulus and is unable to pass through the hole by which the tensioning band 240 passes. Pulling the tensioning band 240 therefore exerts a force upon the tricuspid annulus, that is distributed across the surface area of the anchoring element (202, 204, 206, 208, 214), and acts in the direction of the longitudinal axis of the tensioning band 240. As many anchoring elements as the implanting user desires can be implanted near the tricuspid annulus 52 (within 15 millimeters), behind the anterior 12 or posterior 13 leaflets and/or within the RVOT 57, with at least 1, and in certain embodiments at least 2, anchoring elements spanning a distance of 1 centimeter to 3 centimeters between anchoring elements preferred. In some embodiments the septal anchoring element 204 or any of the anchoring elements can comprise a disk that can be 8 millimeters to 20 millimeters long in certain embodiments, and can be 8 millimeters to 20 millimeters wide in certain embodiments and can be 0.1 millimeters to 5 millimeters thick in certain embodiments and that can be positioned against the left atrial wall superior to the mitral valve 15 and inferior to the fossa ovalis 53, along the posterior interatrial septum 51. The positioning of the septal anchor 204 can be such that it is near the inferior surface of the interatrial septum 51 where the muscle tissue is thicker compared to the interatrial septum or fossa ovalis and is close to (within approximately 20 millimeters in certain embodiments) of the superior surface of the ventricular septum, as the left septal atrial anchor 204 is depicted in FIG. 2. This location may minimize stretching and distortion under tensile loads. The position is also far from the atrioventricular node (AV node) so as to avoid or reduce conduction disturbances and the associated risk of needing to implant a pacemaker as a result of the procedure. The septal anchoring element 204 may be substantially round, oblong, rectangular, square or any other shape suitable for distributing force over a substantial surface area and minimizing interference with the mitral valve 15 and fossa ovalis 53. The position of the anchor 204 inferior to the fossa ovalis 53 may leave that area of the septum accessible for other left sided heart repair or valve replacement procedures. The septal anchor in certain embodiments can be designed to lie flat against the left atrial wall so as not to interfere with mitral valve 15 repair or replacement devices. The septal anchoring element can be connected to a flexible tensioning band 240 by a knot, crimp joint or other suitable device and the tensioning band can pass through the muscle of the interatrial septum 51 into the right atrium1 (see e.g., FIG. 2). The hole through which the tensioning band passes through the tissue is preferred to be as small as possible such that when the tensioning band is pulled in tension the anchoring element is pulled against the left atrial muscular surface and is unable to pass through the hole by which the tensioning band passes. Pulling the tensioning band 240 therefore exerts a force on the muscle of the interatrial septum 51, which is distributed across the surface area of the anchoring element 204 and acts in the direction of the longitudinal axis of the tensioning band. When the tensioning band(s) 240 connected to the anterior anchoring element(s) 202 and the tensioning band(s) 240 connected to the septal anchoring element 204 are routed through a common orifice in a locking mechanism 230 and are simultaneously tensioned, the anterior tricuspid annulus 52 is pulled toward the septal anchor 204 on the interatrial septum 51, reducing the distance between the anterior leaflet hinge point 12 and septal leaflet hinge point 11 and increasing the overlap of the tricuspid valve leaflets at their point of coaptation.

Figure 35:
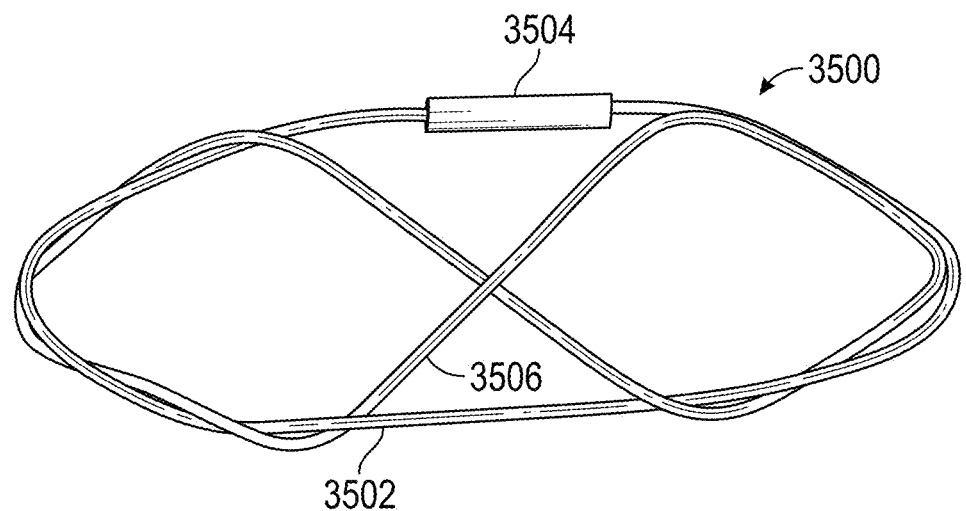
FIG. 35 illustrates an anchoring element embodiment where the anchor is constructed of a nitinol wire form that is heat-set into an elliptical perimeter, with triangular ends, and a cross in the center. The perimeter is constructed of 2 layers of nitinol wire that are spiral wrapped around each other to lock the wire together and distribute force from the center cross to the perimeter or vice-versa. A stainless steel sleeve connects the free ends of the wire.

The anchoring elements (202, 204, 206, 208, 214) in certain embodiments are constructed of expanding form such that the anchoring elements (202, 204, 206, 208, 214) can be compressed, flattened, elongated, or squeezed into a catheter or sheath 220 of between 1 millimeter and 3 millimeters internal diameter and then expand into their implantation configuration upon exiting the catheter. Expansion can be achieved via passive mechanism, for instance via the stored potential energy of the anchoring element materials as a result of being strained into the catheter 220, or via active mechanism whereby the anchoring element (202, 204, 206, 208, 214) is expanded by an externally controlled mechanism such as by a screw that translates a proximal element relative to a distal element with a set of linkages between the proximal and distal elements such that when the proximal and distal elements are brought closer together the anchor expands. Additionally, expansion can be achieved by rotating the anchoring element longitudinally with respect to the attached tensioning band, such that the long axis of the anchoring element is aligned with the longitudinal axis of the tensioning band 240, for passage through the catheter 220, and when the anchoring element (202, 204, 206, 208, 214) exits the catheter 220 it is allowed to rotate relative to the tensioning band such that the plane approximated by the anchoring element (202, 204, 206, 208, 214) is normal to the longitudinal axis of the tensioning band 240. The anchoring elements' construction is of implantable grade materials and could use metallic materials such as stainless steel, cobalt-chrome or nitinol or polymeric materials such as peek, or nylon or a composite of polymeric and metallic materials. The preferred materials in certain embodiments will have a high degree of recoverable strain (>1%) such that the anchor is not plastically deformed when compressed into the delivery catheter. Some embodiments disclosed herein include an anchoring element (202, 204, 206, 208, 214) with a metallic frame or scaffold (such as the anchoring element 3500 as depicted in FIG. 35) that is covered in a thin material (such as the covering 3708 of covered anchoring element 3700 in FIG. 37) of biologic, such as bovine or porcine pericardium, or synthetic, such as polyethylene terephthalate (PET) or expanded polytetrafluoroethylene (ePTFE), origin. The frame gives the anchoring elements increased bending stiffness, to distribute force from the tensioning bands over a greater surface area, and passive or self-expanding properties. The anchoring elements can in some embodiments be substantially flat, such that its length and width are at least 5 times its thickness. In some embodiments, the anchoring element can have its length and width at least 10 times its thickness. The covering 3708 promotes tissue healing and ingrowth, sealing of the hole by which the tensioning bands 240 pass and can also transfer load between disconnected portions of the metallic frame. When constructed of nitinol or other shape memory materials the frame could be heat set into a preferred deployment configuration such that when heated to body temperature and deployed from a catheter inside the body the frame assumes the heat set shape.

The tensioning bands 240 can be sutures, cables, wires, threads, filaments or similar devices which are flexible in bending and compression while retaining a high degree of tensile strength and stiffness. The tensioning bands 240 can also be rods, brackets, struts, supports, or similar devices which resist bending and compressive forces as well as tensile forces. The tension band 240 construction can be of implant grade materials and could use polymeric materials such as PET, polyethylene, ultra high molecular weight polyethylene (UHMWPE), ePTFE, PTFE or other suitable polymers or could use metallic materials such as stainless steel, nitinol, or cobalt-chromium or could use a combination of such materials. Construction of the tensioning bands could be monofilament or multifilament with the filaments arranged axially, twisted, woven, or braided. The cross-sectional dimension of the tension bands could be in the range of 0.075 millimeters to 0.76 millimeters but and in certain embodiments be in the range of 0.13 millimeters to 0.38 millimeters to provide an optimal balance of tensile strength, flexibility, profile and abrasion resistance. The cross section of the tensioning bands could be substantially round, elliptical, or flat and the materials could contain radiopaque coatings, or be compounded with radiopaque materials or have a filament of radiopaque material woven or extruded through the cross section to facilitate observation under fluoroscopy. Examples of radiopaque materials could include platinum, platinum iridium, bismuth, barium sulfate or tungsten. In some embodiments, the ultimate tensile strength of the tensioning bands or tethers can be greater than 2 pound-force but, in certain embodiments, can be greater than 8 pound-force. In some embodiments, tensile stiffness can be greater than 0.045 mm/mm/N. In some embodiments, the ultimate tensile stiffness of the tensioning bands or tethers can be greater than 0.45 mm/mm/N. The tensioning band 240 can in some embodiments be a rigid or semi-rigid member which can resist compressive forces. In some embodiments, the tensioning band 240 can be a flexible or semi-flexible member. A flexible or semi-flexible member may have a compressive strength much less than the rigid or semi-rigid member, such that the flexible or semi-flexible member would buckle or deform under any significant compressive force. For example, a flexible member may buckle or bend at a force less than 10% or less than 1% of the force resisted by the flexible member in tension.

The locking element 230 could be constructed with a hole parallel the long axis of the lock through which all tensioning members 240 are able to freely pass, and can be used to connect or attach the tension members of the tensioning assembly. The lock 230 used within the treatment could be any embodiment of tether lock disclosed in FIGS. 75 through 80, other locks disclosed herein such as lock 4850, or other suitable lock, as desired or required. When the tensioning bands 240 are pulled within the lock it causes the portion of the tensioning members 240 between the lock 230 and anchoring members (202, 204, 206, 208, 214) to shorten relative to the lock 230 which therefore pulls the anchoring elements (202, 204, 206, 208, 214) together. FIG. 48B discloses an embodiment of a lock 4850 which has a second hole 4856 exiting the side of the lock so that the tensioning members 240 could enter the hole running through the lock from the distal end 4854 and exit the lock through the side hole 4856. A screw 4852 could be threaded into the proximal end of the hole running through the lock as depicted in FIG. 48b. When the screw 4852 is threaded into the lock 4850, the lock 4850 transitions from its non-clamping configuration to its clamping configuration to clamp the tensioning bands 240 between the hole running parallel the axis of the lock 4854 and the hole exiting the side of the lock 4856, locking the tensioning bands 240 in place. Alternatively, the screw could be incorporated into the locking mechanism, such as in tether locks 7600 and 7900 disclosed herein. The lock could be of metallic construction such as stainless steel or titanium or of rigid polymer construction suck as PEEK. Another way to construct the lock would be to make it from thin walled metallic tubular construction with a central hole through which the tensioning bands can freely pass. Once the tensioning bands have been tensioned, the lock can be crimped against the tensioning bands 240 by flattening and bending the lock with an externally controlled sliding pin, or by compressing a set of opposing pins or anvils within the lock catheter. Suitable implantable materials could include stainless steel or titanium.

FIGS. 14 through 24 depict an example method for implanting an embodiment of the treatment in the heart of a patient. In certain embodiments, the steps for implantation can include one or more of the following steps: first preparing an implant system 200 to include, two or more anchors (as depicted in FIGS. 14 through 24, an anterior anchor 202 and a left septal atrial anchor 204), two or more tensioning bands 240, and a lock 230, a guide catheter system, an implant catheter system and a locking catheter system for entry into the venous system at the groin.

Then, tracking of the guide catheter 200 through the IVC 50 to the right atrium 2.

Then, tenting of the interatrial septum 51 with a sheath 226 and dilator 224 assembly through the catheter 220.

Then, crossing of the interatrial septum 51, into the left atrium 4, with a wire 222, followed by the dilator 224 and sheath 226.

Then, removal of the dilator 224 and wire 222, leaving the sheath 226 in the left atrium 4.

Then, tracking the septal anchor 204 through the sheath 226 into the left atrium 4.

Then, release of the septal anchor 204 in the left atrium 4.

Then, removal of the sheath 226 from the guiding catheter 220, leaving the septal anchor 204 in the left atrium 4 and septal anchor 204 tensioning member(s) 240 externalized through the guiding catheter 220.

Then, insertion of the dilator 224 and sheath 226 through the guiding catheter 220, beside the septal anchor suture 240.

Then, directing the guide catheter to the anterior annulus 52.

Then, tenting of the tricuspid annulus 52 with the sheath 226 and dilator 224 through the guiding catheter 220.

Then, crossing of the annulus 52, into the right ventricle 3 and/or the RVOT, with a wire 222, followed by the dilator 224 and sheath 226.

Then, removal of the dilator 226 and wire 222, leaving the sheath 226 in the right ventricle and/or the RVOT.

Then, tracking the anterior anchor 202 through the sheath 226 into the right ventricle 3 and/or the RVOT.

Then, release of the anterior anchor 202 in the right ventricle 3 and/or the RVOT.

Then, removal of the sheath 226 from the guiding catheter 220, leaving the anterior anchor 202 against the right ventricular surface of the tricuspid annulus and the anterior anchor 202 tensioning member 240 externalized through the guiding catheter.

Then, implantation of additional anterior anchors 202 in the same manner as the first anterior anchor 202.

Then, tracking of a lock 230 over the externalized sutures 240 connected to the implants, within the guiding catheter 220, via a lock catheter 232.

Then, tensioning of the sutures 240 in the right atrium 2 to draw the tricuspid annulus 52 along the right ventricular free wall toward the interatrial septum 51 and/or the coronary sinus 54.

Then, locking of the lock 230 to maintain tension on the sutures 240 and cutting of the free end of the sutures 240 adjacent the lock.

Then finally, removal of all catheters from the body.

In another embodiment, a method similar to the method described above for implanting an embodiment of the treatment in the heart of a patient can be performed, using a substantially similar system, except that the anterior anchor(s) 202 are implanted prior to the septal anchor(s) 204.

The methods above can also further include advancing of grommets 219 along the tension members 240 on a surface adjacent to any embodiment of a surface anchor and on the opposite side of the surface of the heart adjacent to the surface anchor. The grommet 219 acts to retain the embodiment of the surface anchor against the skin such that the section of the heart adjacent the surface anchor is pinched between the anchor and grommet and the anchor is unable to move from its location.

The procedure could be performed under ultrasound imaging guidance, for example transesophageal echocardiography (TEE) or intracardiac echocardiography (ICE), and fluoroscopic imaging guidance. The steps for implantation can be performed in a different order from those described, for instance, the anterior anchor(s) 202 may be implanted prior to the septal anchor(s) 204. The number of anchors implanted may be up to the discretion of the implanting user. The guiding catheter 220 may be of steerable construction through, for example, the use of pull cables affixed to a point or points in the distal 5 centimeters of the guiding catheter 220 which are controlled external to the body by rotating a knob or pulling a lever on the guide catheter handle that tensions and shortens the pull cable relative to the catheter shaft. The pull cable can be biased to one side of the catheter shaft such that shortening the pull cable causes shortening of the catheter shaft on the side that the pull cable is biased toward resulting in the catheter shaft articulating in the direction of the pull cable. Alternatively, a central slidable lumen can be pulled relative to a fixed outer lumen of construction whereby the materials of the outer lumen are such that the flexural modulus is higher on one side of the outer lumen relative to another side of the outer lumen in a region or regions of the outer lumen within the distal 5 centimeters. Pulling the inner lumen exerts a compressive force on the outer lumen which causes the catheter to articulate in the direction where the flexural modulus of the outer lumen is lower. The advantage to this construction is that the pulling member is substantially along the neutral axis of the catheter which does not cause the catheter to bend or bow along the proximal region, where the flexural modulus of the outer lumen is uniform around the circumference, and where bending or bowing might not be desirable. The guiding catheter 220 can be 1, 2 3 or 4 way steerable and in the case of more than 1 steering plane the articulation points can be in the same location or separated by a distance of 0.5 centimeters to 4 centimeters along the length of the catheter such that the catheter articulates in different directions at 2 or more distinct regions.

The wire 222 used to cross the septum 51 and the tricuspid annulus 52 can optionally be powered by alternating current in the radio frequency range such that the wire forms an electrode whereby the sudden change in impedance at the distal end of the wire results in an arc, causing the tip of the wire to heat and cross the tissue more easily. Alternatively, the tip of the wire 222 can be sharpened to increase the stress concentration on the tissue when the wire is pushed against the tissue, causing the wire to more easily puncture and cross the tissue. The distal end of the wire 222 can be straight such that when extended out of the dilator 224 it travels in a direction substantially the same as the direction the tip of the dilator is pointing or the distal end of the wire 222 can be curved such that it will travel in a curved path relative to the dilator in order to take a more advantageous path through the tissue or avoid various structures when the wire exits into a chamber of the heart. The curvature of the wire 222 can be variable and can be configured into a spiraled or pigtail configuration proximal to a straight or less tightly curved section such that when the wire is extended from the dilator it curls into a loop or multiple loops making it atraumatic if contacting heart tissues distal to those being crossed. Additionally, the curvature of the wire can be configured such that the distal tip curves in a direction different (or the same) from a more proximal section such that the curvature of the more proximal section will align with the curvature of the guide catheter (due to the wire taking the path that results in the lowest strain energy within the wire) and the distal section will curve in a predictable and controllable direction when exiting the dilator.

Where reference is made to the anterior annulus 52 or the anterior implant(s) or anterior anchor(s) 202, it is in reference to locations substantially across the tricuspid valve 10 from the interatrial septum 51 and may include the region from the septal commissure of the anterior leaflet 12 to approximately the center of the posterior tricuspid leaflet. Reference to the right ventricle 3 or right ventricular surface of the anterior tricuspid annulus 52 may also include those portions of the RVOT 57 within close proximity (within 10 millimeters or within 15 millimeters or within 20 millimeters) of the tricuspid annulus. Utilizing that the portion of the RVOT behind the anterior tricuspid valve leaflet 12 and/or anterior tricuspid valve annulus offers the unique advantage of being a large space to safely pass a wire into (or from) and place a surface anchor while also having a relatively large tissue thickness between the right ventricle and right atrium which can contribute to a robust anchoring location. Optionally, after delivery of each anchoring element (202, 204, 206, 208, 214), a grommet, such as 215, 219, 4710, 4802, 7030, 7102, 7220, 7302 or 7402 with a lock 230, either attached to the grommet or separate from the grommet, may be tracked over the suture(s) attached to the anchoring element and abutted against the tissue on the heart chamber adjacent to the chamber by which the anchoring element is abutted (for instance against the right atrial septum for the left atrial anchoring element or against the right atrial annular surface for the anterior anchoring element(s)). The lock will then be used to clamp the suture such that the tissue is between the anchoring element and grommet with the grommet and lock retaining the anchoring element against or within close proximity of the tissue during the remainder of the procedure, or if the suture is cut or breaks. Hence the anchoring element would not be able to migrate or embolize in the absence of tension on its attached tether. The grommet as used here could be the grommets disclosed herein and depicted in FIG. 71, 72A, 73, or 74, or other grommets available, as desired or required.

Tensioning of the tension members 240 affixed to the septal and anterior anchoring elements (202, 204, 206, 208, 214) can be performed under ultrasound and fluoroscopic guidance at the user's discretion to reduce or eliminate the tricuspid regurgitation 6 and increase the coaptation between the tricuspid leaflets.

An alternative embodiment herein disclosed includes an anchoring element(s) placed against the left ventricular wall inferior to the mitral valve 15 on the interventricular septum (such as the left ventricular septal anchor 208 of FIG. 5) with an attached suture 240 passing from the left ventricular chamber 5 to the right atrium 2. Yet another embodiment herein disclosed includes an anchoring element(s) placed against the right ventricular surface inferior to the tricuspid valve 10 (such as the right ventricular septal anchor 206 of FIG. 5), near the interventricular septum, with an attached tether(s) 240 passing through the tricuspid annulus 52 and/or ventricular myocardium into the right atrium 2 and/or coronary sinus 54. Yet another embodiment herein disclosed includes an anchoring element abutted against the inferior surface of the coronary sinus 54 (such as the coronary sinus anchor 214 of FIGS. 10, 11 and 12) with an attached tension members 240 traversing through the left ventricular myocardium 56 inferior to the coronary sinus 54. As the tether passes through the left ventricular myocardium 56 it can form a loop, as in FIGS. 10 and 12, or make a curved path with the anchor at the distal end, as in FIG. 11. The steps for implantation for any of the alternate embodiments are substantially the same as already described, except that the guiding catheter will be directed to facilitate implantation of the anchoring element to the alternate anatomical location. Any embodiment herein disclosed can be utilized singularly or in combination with any of the other embodiments. Any of the anchor embodiments herein disclosed can be used in any one of, or all of, the anatomical locations herein disclosed.

FIGS. 25 through 31 depict the steps for implantation of another embodiment herein disclosed. The figures generally represent an embodiment of a foldable flat implant system 4000 comprising a guiding catheter 4001, a flexible steerable delivery catheter 4002 non-fixedly connected to an anchor bar 4040, a septal anchor 4020, and a snare catheter 4070. The anchor bar 4040 can incorporate holes or slots for passage of one or multiple guidewires 4060 which can pierce anatomical locations within the heart in a substantially similar fashion as the guidewire 222 disclosed herein. The snare catheter 4070 can be comprised of one or multiple snare guide catheters 4072 which guide one or multiple snare wires 4074 to be used during the method of implantation of another embodiment herein. The septal anchor 4020 disclosed herein can be substantially similar to the anchor 204 as disclosed in FIGS. 17 through 24.

The steps for implantation of the embodiment of the foldable flat implant system 4000 as disclosed in FIGS. 25 through 31 can include one or more of the following steps: first, guiding catheter 4001 entry into the venous system at the groin.

Then, tracking of the catheter through the IVC 50 to the right atrium 2.

Then, tenting of the interatrial septum 51 with a sheath and dilator assembly through the catheter, such as the sheath 226 and the dilator 224 disclosed herein.

Then, crossing of the interatrial septum 51, into the left atrium 4, with a guidewire, such as the guidewire 222 disclosed herein, followed by the dilator and sheath.

Then, removal of the dilator and wire, leaving the sheath in the left atrium.

Then, tracking the septal anchor 4020 through the sheath into the left atrium.

Then, release of the septal anchor 4020 in the left atrium.

Then, removal of the sheath from the guiding catheter, leaving the septal anchor in the left atrium and septal anchor suture(s) externalized through the guiding catheter.

Then, insertion of a steerable anterior anchor delivery catheter 4002, with attached anterior anchor 4040 in a folded or compressed configuration, into the guiding catheter 4001 and tracking of the anchor to the distal end of the guiding catheter.

Then, directing the guide catheter 4002 above the tricuspid valve 10.

Then, extending the anterior anchor delivery catheter 4002 and directing the anterior anchor 4040 through the tricuspid valve, into to the right ventricle 3 and or RVOT.

Figure 25:
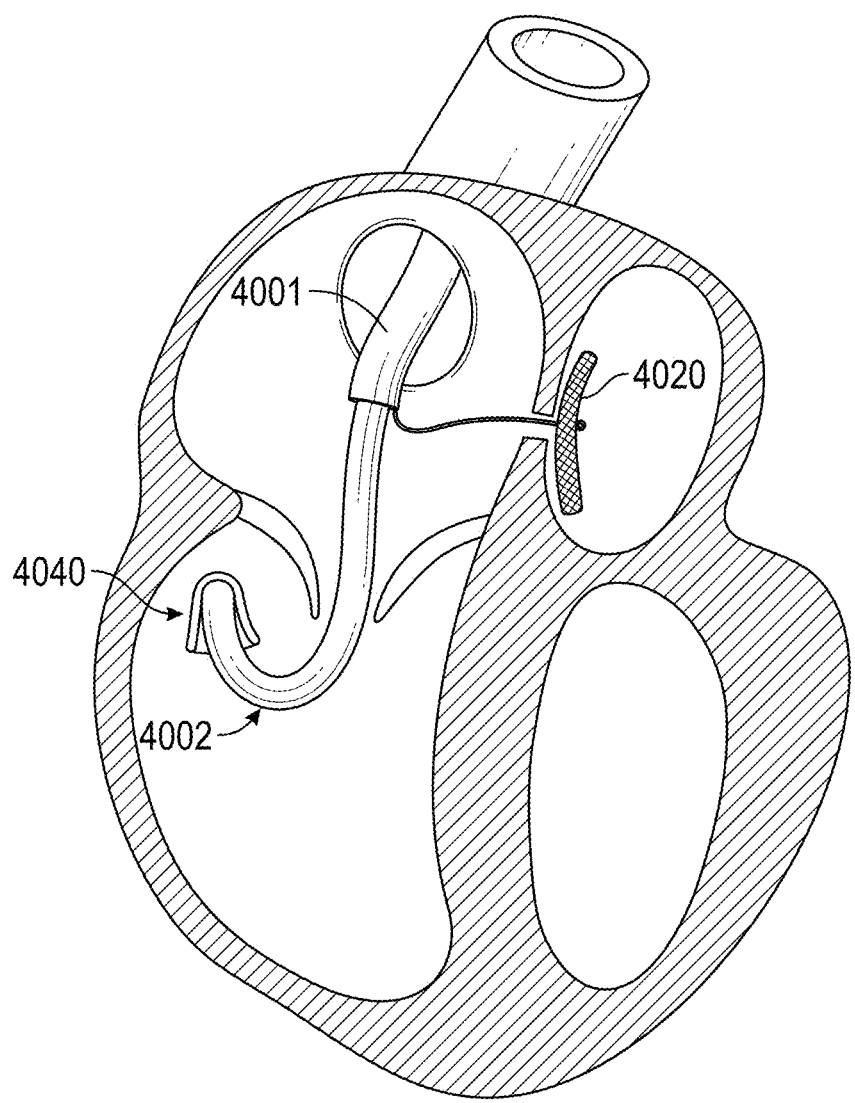
FIG. 25 illustrates the guiding catheter in the right atrium above the tricuspid valve with the anterior anchor delivery catheter through the tricuspid valve and hooked under the anterior tricuspid valve leaflet in the right ventricle. The anterior anchor is illustrated mounted to the distal end of the catheter in a folded configuration. A septal anchor is abutted against the left atrial wall with an attached tensioning band passing through the interatrial septum into the guiding catheter.

Then, articulating the anterior anchor delivery catheter 4002 to form a "J" shape within the right ventricular outflow tract 57 such that the anterior anchor 4040 is hooked behind the anterior tricuspid valve leaflet 12 within the right ventricle 3, such as in FIG. 25. FIG. 25 illustrates the guiding catheter 4001 in the right atrium 2 above the tricuspid valve 10 with the anterior anchor delivery catheter 4002 through the tricuspid valve 10 and hooked under the anterior tricuspid valve leaflet 12 in the right ventricle 3. The anterior anchor 4040 is illustrated mounted to the distal end of the catheter 4002 in a folded configuration. A septal anchor 4020 is abutted against the left atrial wall with an attached tensioning band 4074 passing through the interatrial septum 51 into the guiding catheter 4001.

Then, unfolding or expanding the anterior anchor 4040 into a deployment configuration that is approximately planar and has a length of 1-4 centimeters, but in certain embodiments 1.5-2.5 centimeters.

Then, pulling the anterior delivery catheter 4002 such that the anterior anchor abuts against the right ventricular surface of the anterior tricuspid annulus 52 with the anterior anchor spanning a distance of 1 centimeters to 4 centimeters of the anterior tricuspid annulus 52.

Figure 26:
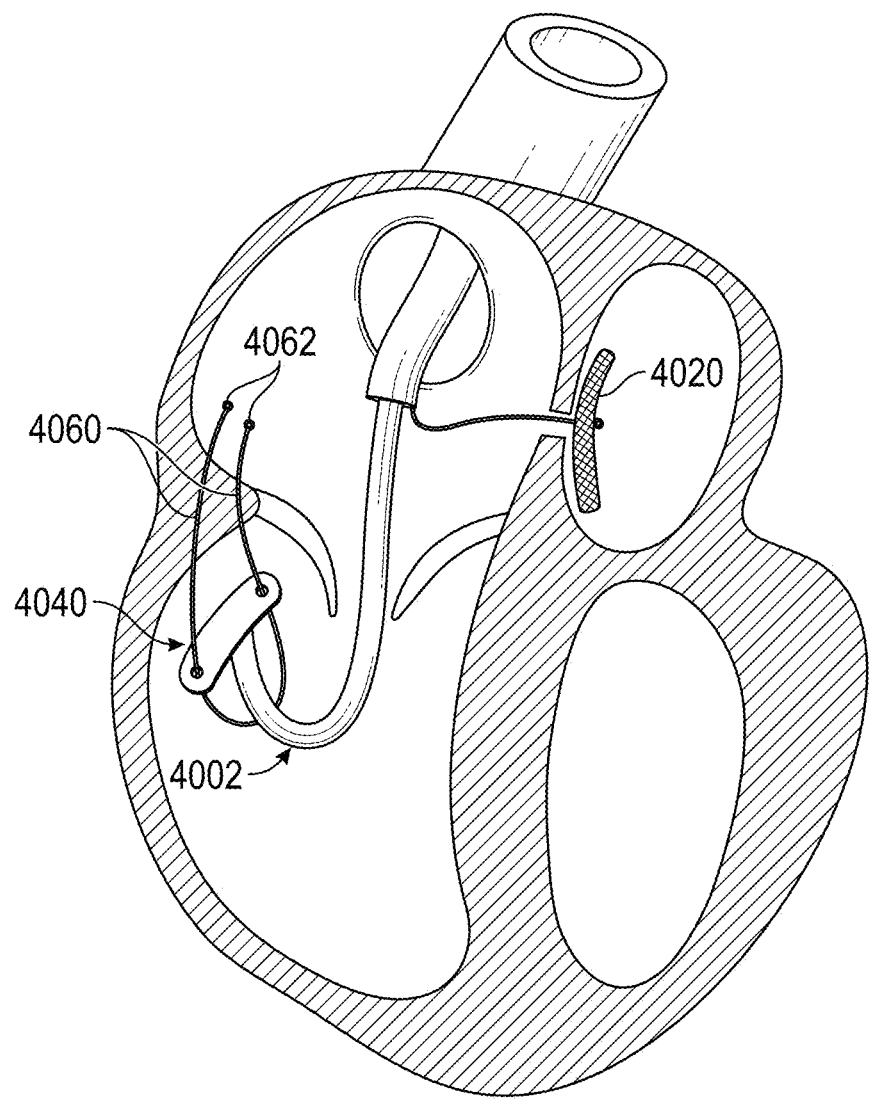
FIG. 26 illustrates the anterior anchor in its expanded or deployment configuration in the right ventricle behind the anterior tricuspid valve leaflet with wires through each end of the anterior anchor traversing through the anterior tricuspid valve annulus from the right ventricle to the right atrium.

Then, crossing the annulus with 2 or more guidewires 4060, through the anterior anchor, with the outermost wires 1 centimeter to 4 centimeters apart, such that the wires exit into the right atrium, as shown in FIG. 26. FIG. 26 illustrates the anterior anchor 4040 in its expanded or deployment configuration in the right ventricle 3 behind the anterior tricuspid valve leaflet 12 with wires 4060 through each end of the anterior anchor traversing through the anterior tricuspid valve annulus 52 from the right ventricle 3 to the right atrium 2.

Then, snaring the 2 or more guidewires 4060 within the right atrium with a same number of snare catheters 4070, the snare catheters 4070 traveling through a snare guide catheter 4072.

Figure 27:
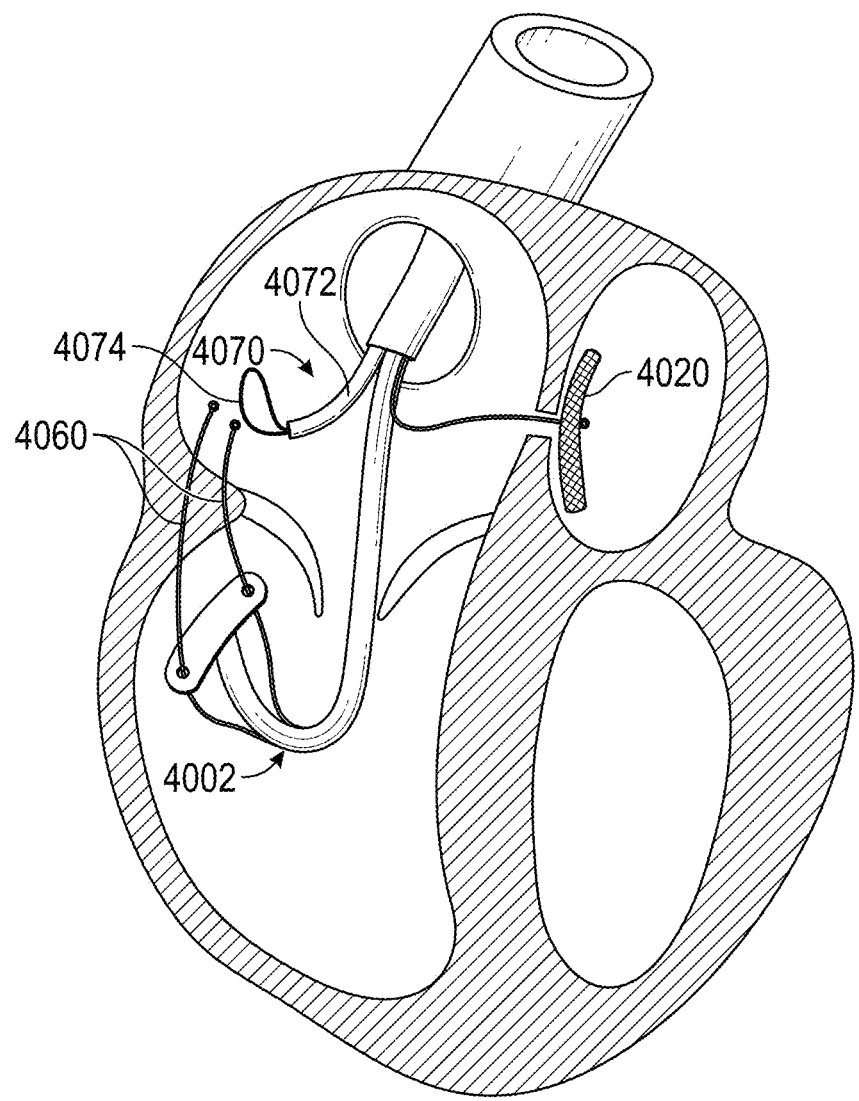
FIG. 27 illustrates a snaring catheter exiting the guide catheter into the right atrium and positioned to capture one of the wires across the anterior tricuspid valve annulus.
Figure 28:
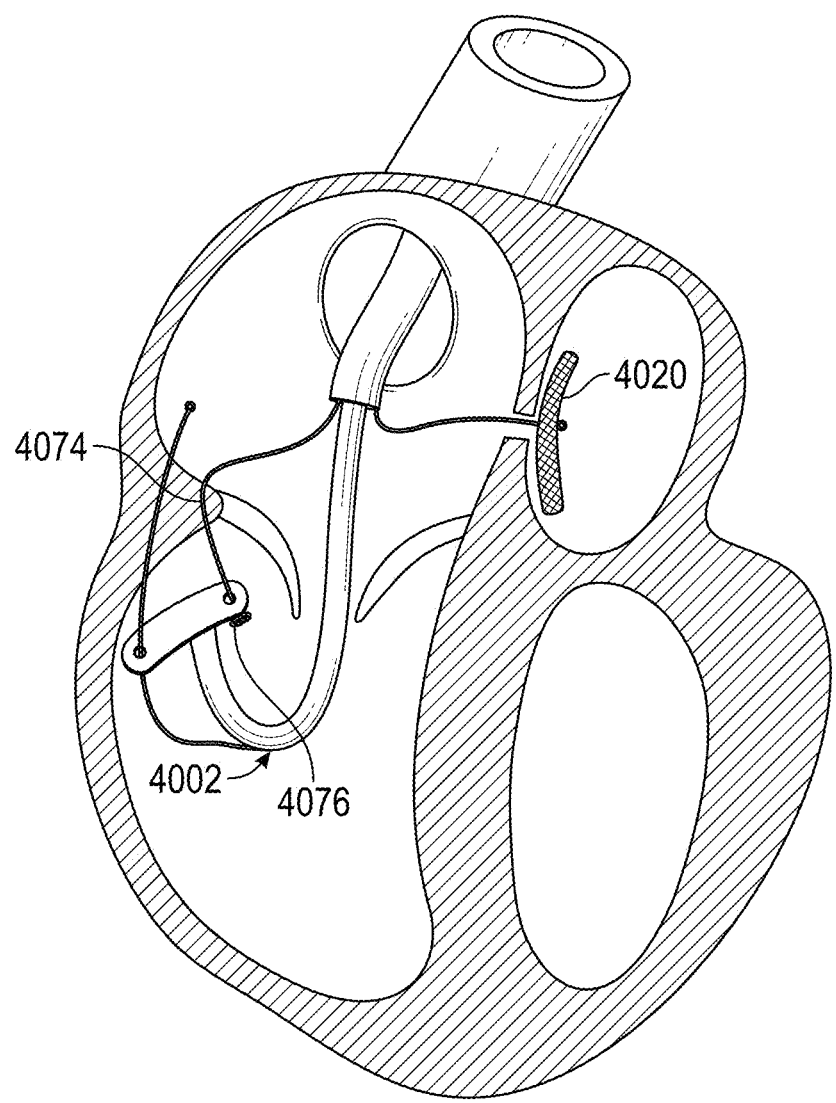
FIG. 28 illustrates the first tensioning member of the anterior anchor snared through the guiding catheter with the plug at the end of the tensioning band abutted against the anterior anchor.
Figure 29:
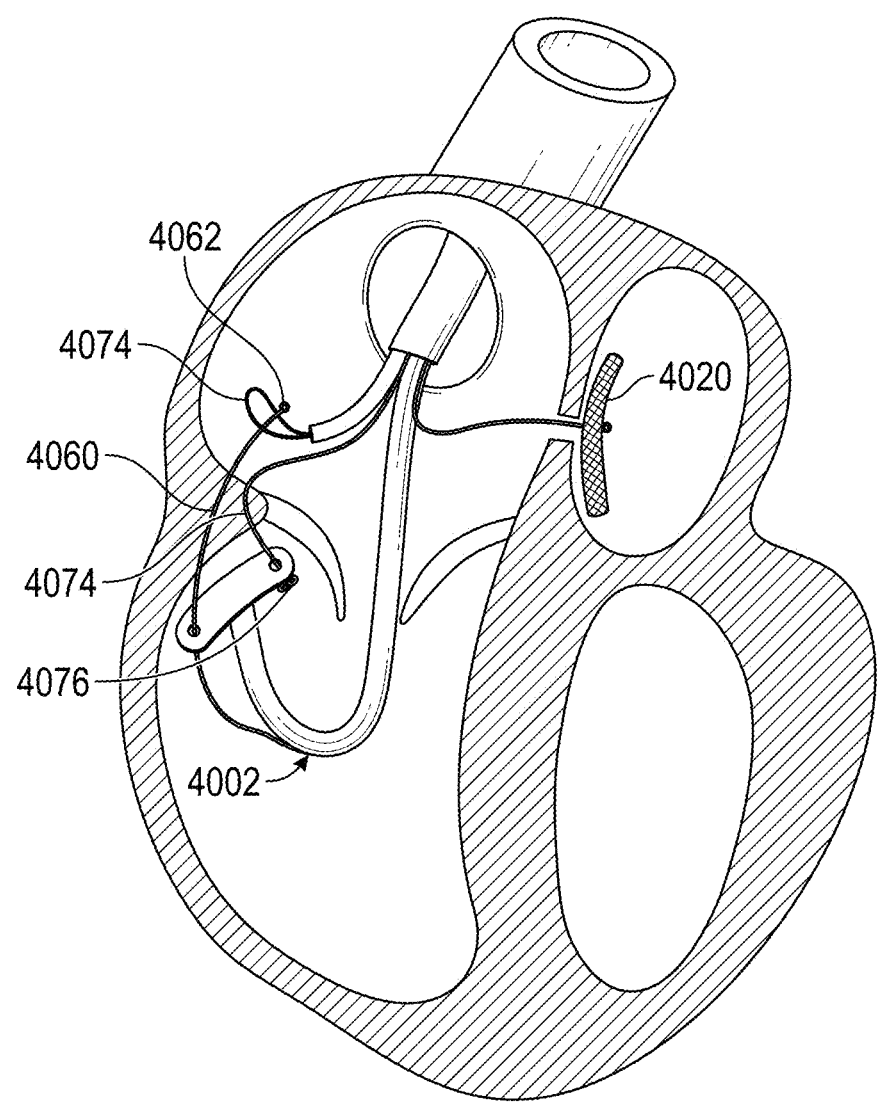
FIG. 29 illustrates a snaring catheter exiting the guiding catheter into the right atrium and positioned to capture the second wire across the anterior tricuspid valve annulus.

Then, pulling the wires 4060, which are attached to sutures 4074 with plugs 4076 at the ends, through the guiding catheter 4001 and in a direction external to the patient until the plug 4076 ends of the sutures abut against the anterior anchor, as depicted in FIGS. 27 through 29. FIG. 27 illustrates a snaring catheter 4072 exiting the guide catheter 4001 into the right atrium 2 and positioned to capture one of the wires 4060 across the anterior tricuspid valve annulus 52. FIG. 28 illustrates the first tensioning member 4074 of the anterior anchor 4040 snared through the guiding catheter 4001 with the plug 4076 at the end of the tensioning band 4074 abutting the anterior anchor 4040. FIG. 29 illustrates a second snaring catheter 4072 exiting the guiding catheter into the right atrium 2 and positioned to capture the second wire 4060 across the anterior tricuspid valve annulus 52.

Figure 30:
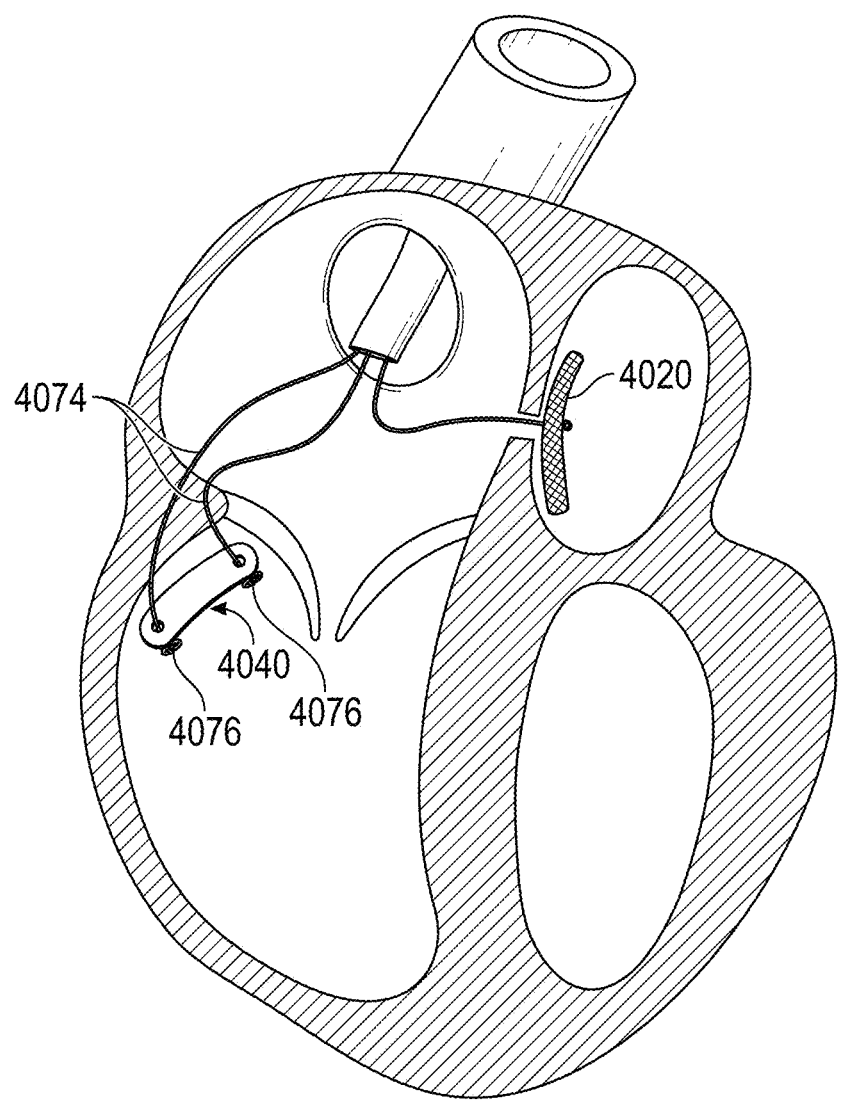
FIG. 30 illustrates both tensioning bands connected to the anterior anchor snared through the guiding catheter with the plugs at the ends of the tensioning bands abutted against the anterior anchor and the anterior anchor delivery catheter removed.

Then, detaching of the anterior anchor 4040 from the anterior anchor delivery catheter 4002 and removal of the anterior anchor delivery catheter 4002, as in FIG. 30. FIG. 30 illustrates both tensioning bands 4074 connected to the anterior anchor 4040 snared through the guiding catheter 4001 with the plugs 4076 at the ends of the tensioning bands 4074 abutting the anterior anchor 4040, with the anterior anchor delivery catheter 4002 removed.

Figure 31:
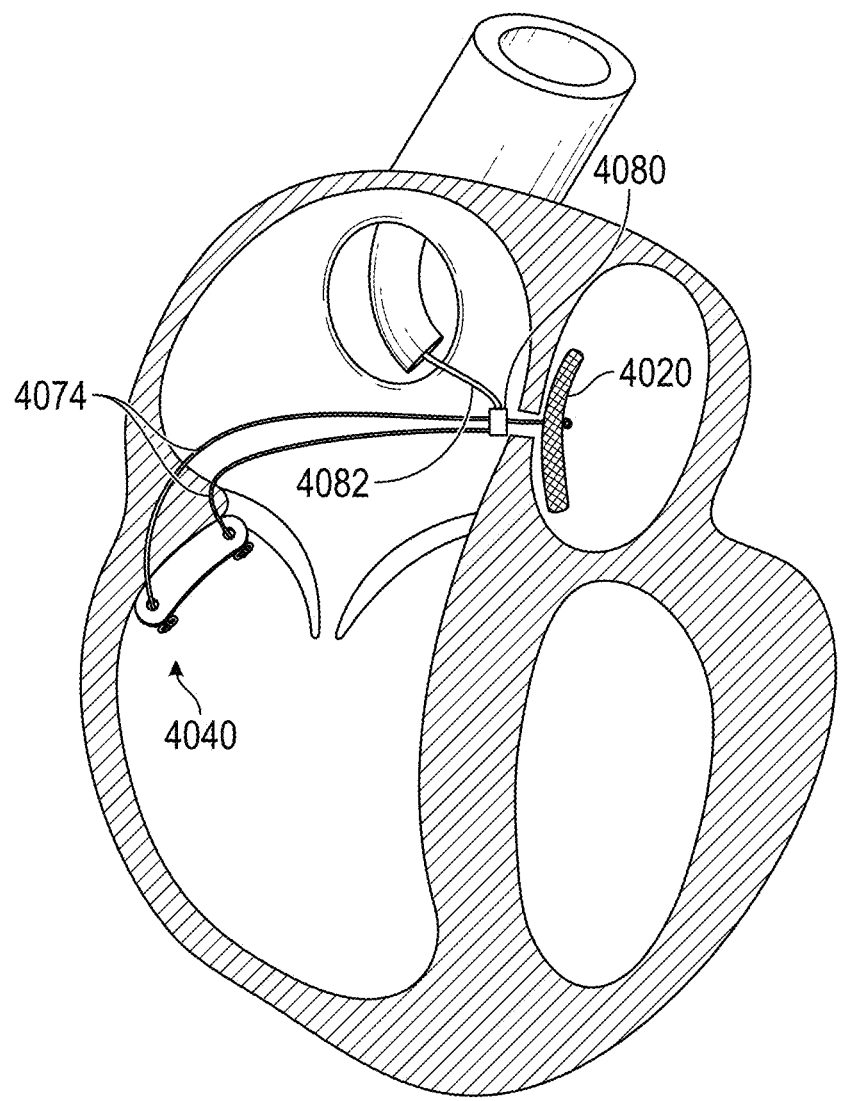
FIG. 31 illustrates the anterior anchor abutted to the ventricular surface of the anterior tricuspid valve annulus with the attached tensioning bands routed to a lock near the interatrial septum. The septal anchor is illustrated abutted against the left atrial wall with the attached tensioning band routed to the lock. A lock catheter is extending out of the guide catheter and connected to the lock.

Then, tracking of a suture lock 4080 over the externalized sutures 4074 connected to the implants, within the guiding catheter, via a lock catheter 4082, as depicted in FIG. 31. In this figure, the anterior anchor is abutted to the ventricular surface of the anterior tricuspid valve annulus 52 with the attached tensioning bands 4074 routed to a lock 4080 near the interatrial septum 51. The septal anchor 4020 is illustrated abutted against the left atrial wall with the attached tensioning band 4074 routed to the lock 4080. A lock catheter 4082 is extending out of the guide catheter and connected to the lock 4080.

Then, tensioning of the sutures 4074 in the right atrium 3 to draw the tricuspid annulus 52 along the right ventricular free wall toward the interatrial septum 51 and/or the coronary sinus 54.

Then, locking of the suture lock 4080 to maintain tension on the sutures and cutting of the free end of the sutures adjacent the lock.

Then finally, removal of all catheters from the body.

Figure 41:
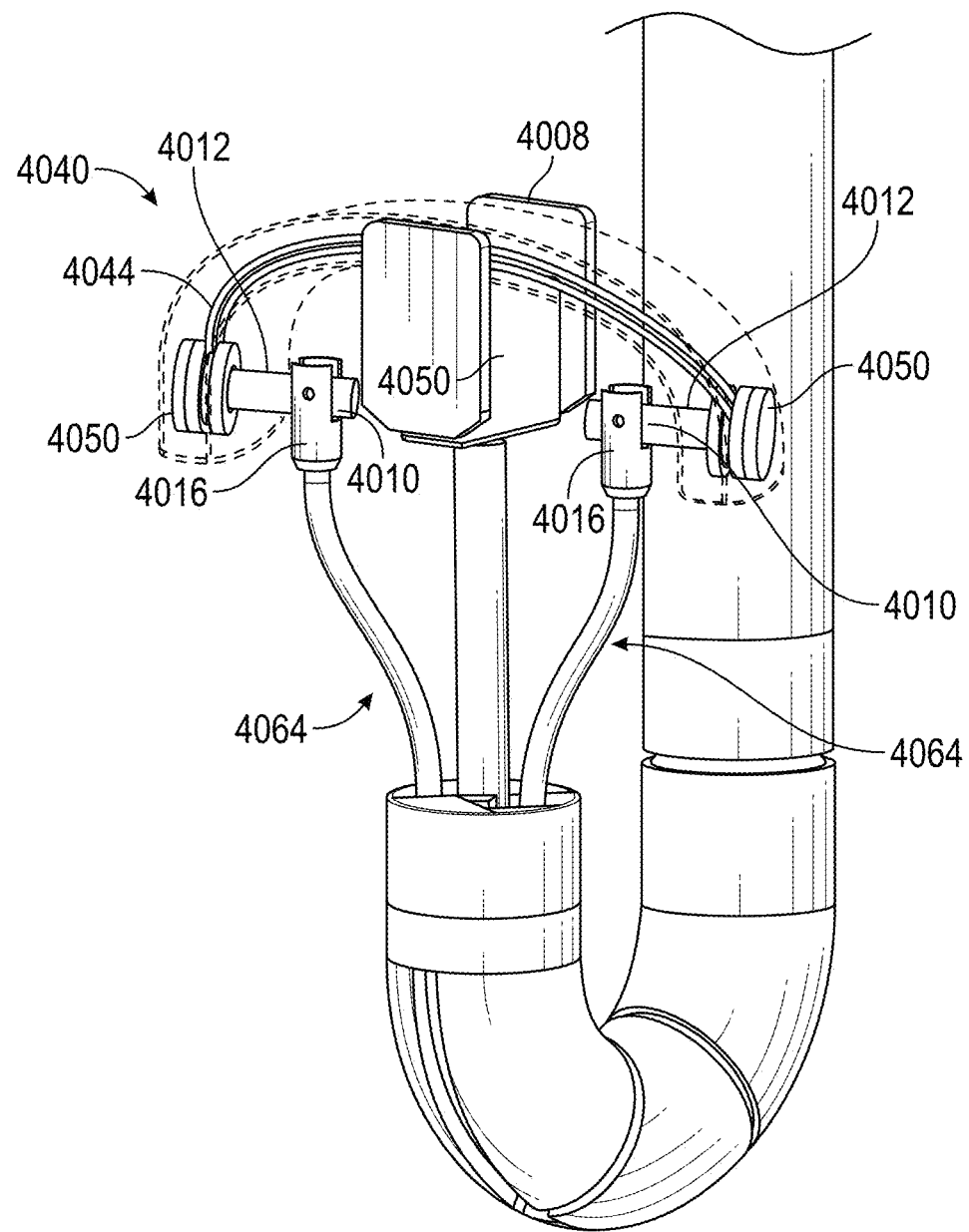
FIG. 41 illustrates the anterior anchor illustrated in FIG. 40 in a folded configuration where the anchor is folded by tensioning the flexible hollow tubes connected to each end of the anchor.
Figure 42A:
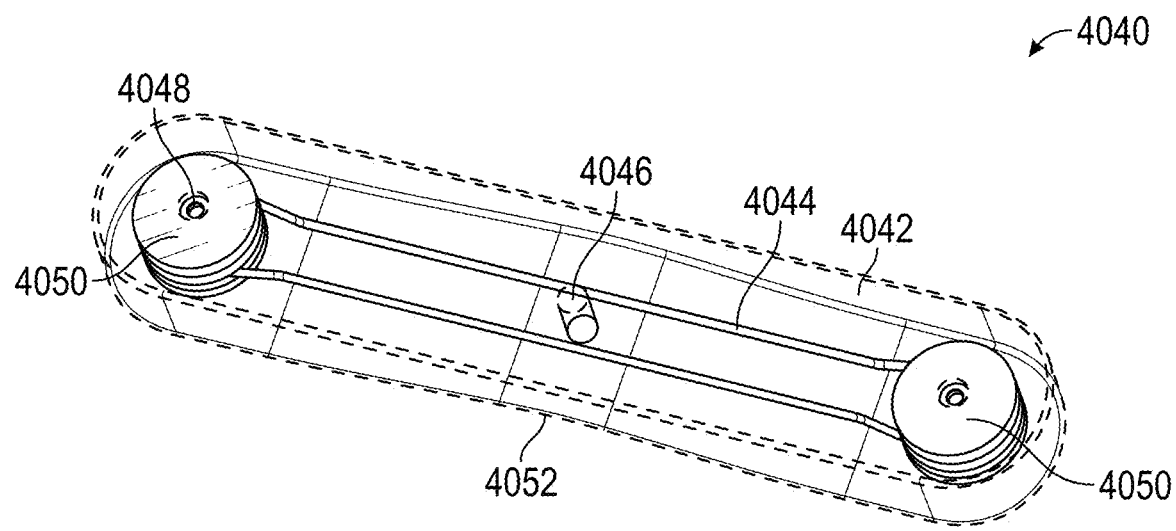
FIG. 42A illustrate an isometric view of the anterior anchor "bar" illustrated in FIGS. 40 and 41 with a transparent polymeric covering. The internal metallic frame made from nitinol can be seen with two threaded stainless steel hubs with through holes interference fit into each end of the frame. A central hole is shown for attachment to the delivery catheter. The hubs are threaded to attach to the swivels of the delivery catheter and the through holes are sized to allow passage of the wires and tensioning bands but block passage of the plugs at the ends of the tensioning bands. The covering could be injection molded or compression molded over the frame and hub from flexible and elastic materials such as silicone elastomer, Pellethane® or other suitable materials or could be a sewn-on or heat bonded fabric covering of PET, PTFE felt or other suitable materials.
Figure 42B:
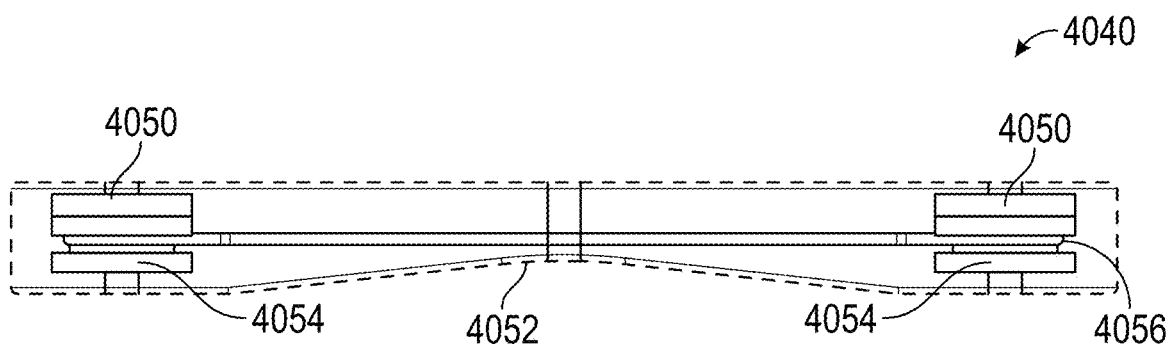
FIG. 42B illustrates a side view of the anterior anchor "bar" shown in FIG. 42B showing the frame and hubs encapsulated within the covering. The covering tapers to a thinner profile toward the center to reduce the bending stiffness at the center and cause the anchor to preferentially fold about the center when the hub ends are pulled with the center fixed to a catheter.
Figure 43:
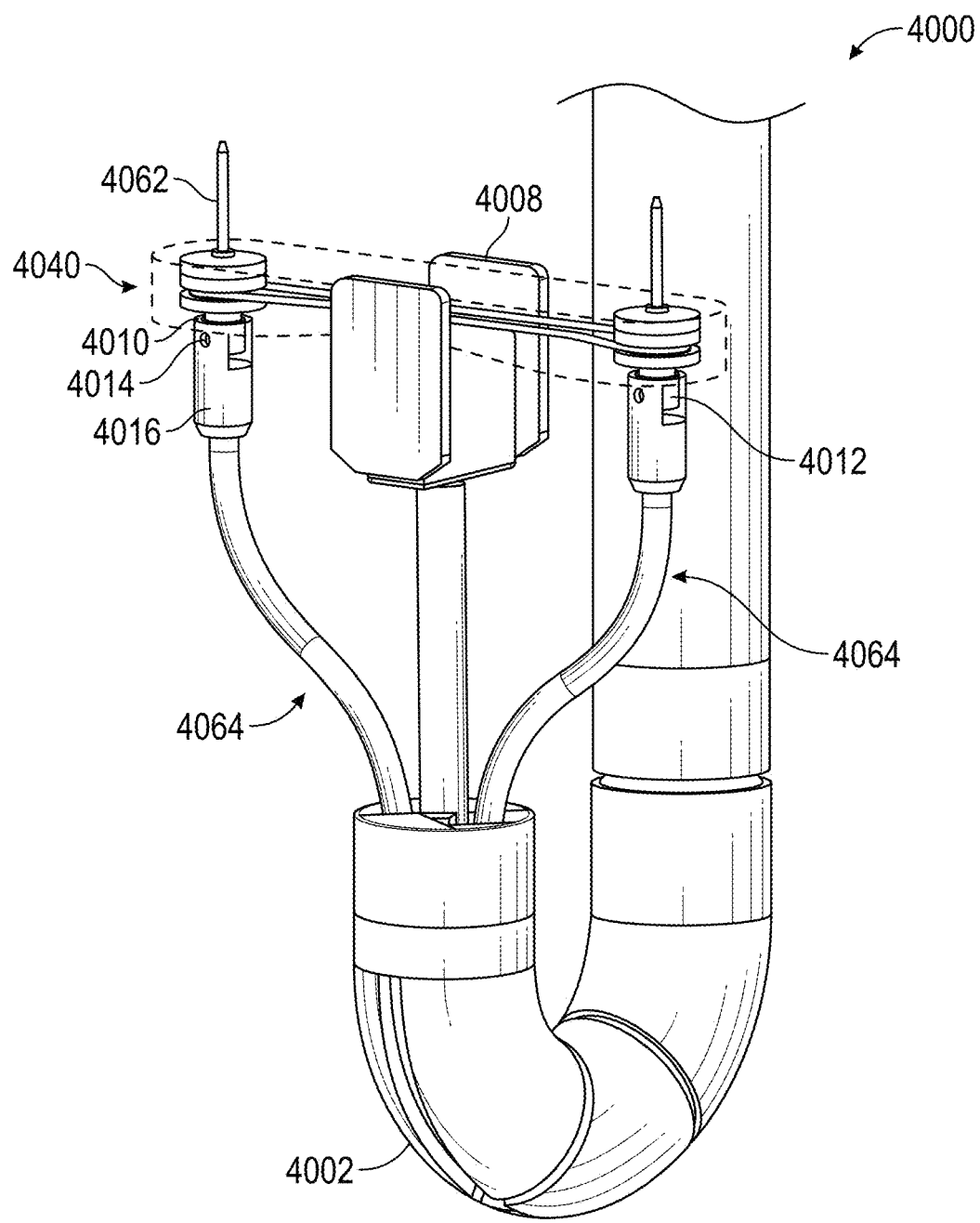
FIG. 43 illustrates the anterior anchor "bar" shown in FIGS. 40-42 attached to a delivery catheter in an articulated configuration. The swivels can be seen attached to the hubs of the anchor and connected to flexible hollow tubes of laser cut metallic or twisted metallic strand construction. The swivels allow the anchor to transition from a first folded configuration in which the axes of the hubs are substantially perpendicular to the catheter tip axis to a second deployed configuration in which the axis of the anchor hubs are substantially parallel to the axis of the catheter tip. The wires can be seen extending from the anchor hubs. The swivels can be detached from the anchor by rotation of the flexible hollow tubes.

The foldable flat implant system 4000 used in the above method is further depicted in FIGS. 40A through 43. The anterior anchor 4040 could be constructed using a superelastic frame made of nitinol wire or laser cut nitinol sheet or strip with a length of approximately 10 millimeters to 35 millimeters and a width of approximately 3 millimeters to 7 millimeters, such as the anchor bar structural member 4044 in FIG. 42A. The frame could be attached to stainless steel, titanium, or polymeric hubs 4050 (such as polyetheretherketone (PEEK) or polyphenylsulfone) by providing a snap fit where the frame expands over the hub and snaps into a groove 4056 on the hub 4050. The hubs could be threaded and have a hole 4054 running through the center, such that the threads can be attached to a guidewire catheter connection 4010 which can swivel during deployment, the guidewire catheter connection 4010 being connected to guidewire catheters 4064 on a delivery catheter 4002, and such that the holes 4054 allow passage of wires 4062 and sutures 4074. Advantageously, the holes 4054 through the hubs 4050 are sized such that the wires 4062 and sutures 4074 are a close fit so that they may pass freely but a plug, sleeve or knot attached to the ends of the sutures will get caught such that when caught the sutures transfer tensile force to the anchor. The hub 4050 could alternatively take the form of a rigid eyelet or similar rigid feature which has a passthrough hole to allow the guidewire 4062 through the anterior anchor 4040. The anchor could be covered in a compliant material 4042, for example silicone elastomer, thermoplastic elastomer such as Pellethane®, PTFE felt, or other suitable implantable grade materials to minimize stress concentrations on the tissue and seal the holes through the tissue by which the sutures 4074 pass. The covering could be molded over the frame (injection or compression molded) or sewn to the frame with thread or sutures or thermally bonded to the frame. The covering and/or frame could be tapered in cross section, as shown by 4052 in FIG. 42B, such that it is thinner in the center, resulting in less bending stiffness in the center, such that when the ends of the anchor are tensioned (through the hubs 4050) and the center of the anchor 4040 is held fixed, the anchor preferentially folds about it's center to facilitate tracking through the guide catheter 4001 and navigation into the RVOT and behind the anterior tricuspid valve leaflet 12 without entangling chordae tendineae. When the tension applied to the hubs 4050 is released, the superelastic properties of the frame allow it to recover back to a flat deployment configuration without plastic deformation of the frame. The center of the anchor could have a threaded hole, or a molded in L-latch, for attachment to the delivery catheter. The delivery catheter 4002 could include flexible guidewire catheters 4064 affixed to guidewire catheter connections 4010 that are threaded on the distal end for attachment to the anchor hubs, as shown in FIG. 41. The guidewire catheter connections 4010 would have a hole through the center to allow passage of wires 4060 and tensioning bands 4074 and could swivel between 0 degrees and 90 degrees between the distal and proximal ends such that in a first folded configuration the axis of the anchor hubs could be substantially perpendicular to the axis of the delivery catheter and in a second deployed configuration the axis of the anchor hubs could be substantially parallel to the axis of the delivery catheter. The flexible guidewire catheters 4064 could be of laser cut stainless steel construction where discontinuous slots are cut around the circumference of the tube to provide flexibility while retaining torsional stiffness or could be of multi-fillar helically twisted stainless steel cable construction. The guidewire catheters 4064 could be jacketed with a polymer, such as Pebax or fluorinated ethylene propylene (FEP) to enhance lubricity. Alternatively, the guidewire catheters 4064 could be of braid re-enforced polymer construction such as Pebax, nylon or polyimide. The anterior anchor delivery catheter 4002 can be steerable in a similar manner as the guiding catheter herein disclosed.

Figure 32:
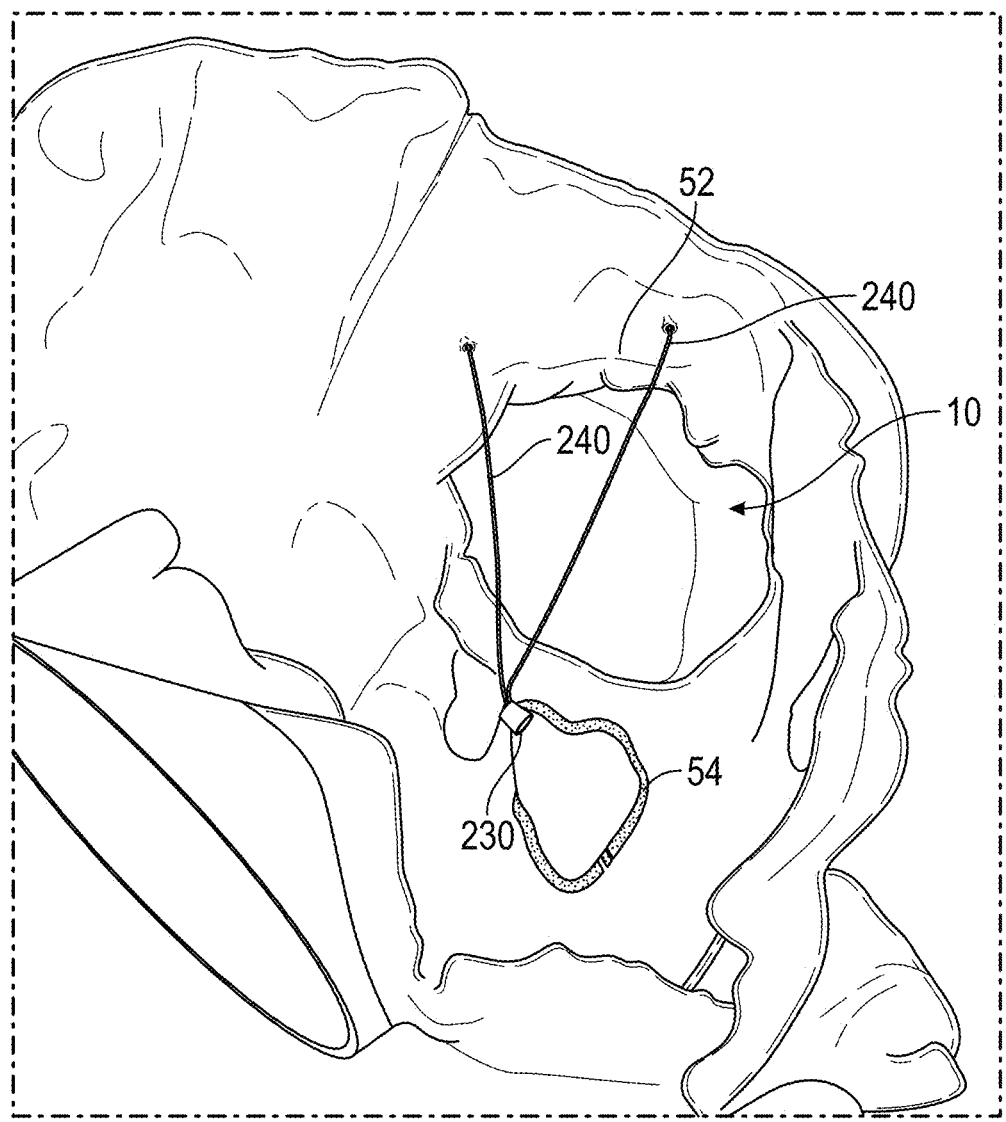
FIG. 32 illustrates the view from the right atrium, looking down on the tricuspid valve, of the tensioning bands passing through the anterior tricuspid valve annulus and connected to a lock near the interatrial septum and coronary sinus ostium.

FIG. 32 depicts an embodiment of the device, as viewed from the right atrium 2, whereby two flexible bands 240 traverse from a location in the right ventricle 3 in or around the right ventricular surface of the anterior tricuspid annulus 52 (that portion of the tricuspid annulus attached to the anterior tricuspid valve leaflet), through the annular tissue into the right atrium 2 and to a locking hub or lock 230 located near the inferior and posterior surface of the interatrial septum 51, on the right atrial side. Each tension member 240 is connected to a right ventricular surface anchor 202 (such as the anchors shown in FIGS. 2 through 13) located on the anterior annulus 52 of the tricuspid valve 10 through a knot, crimp connector or cam-lock mechanism. Applying tension to the flexible bands 240 pulls the surface anchors 202 against the right ventricular surface of the anterior tricuspid annulus 52 which therefore pulls the anterior tricuspid annulus 52 toward the suture lock, decreasing the distance between the anterior tricuspid annulus 52 and the interatrial septum 51. A unique aspect of the location of the right ventricular anchors 202 illustrated in FIG. 32 is 1) that the anchors are substantially in or near the space forming the right ventricular outflow tract 57 which provides a large surface area on the ventricular side of the tricuspid annulus for safely traversing the tricuspid annulus (without risk of puncturing the right coronary artery of damaging the tricuspid leaflet), for opposing the tensioning forces on the tricuspid annulus and for placement of a large surface area anchor(s) 202 (which distribute the force over a larger surface area and therefore reduce stresses on the tissue) and 2) that the line of force application created by spanning the anterior tricuspid annulus 52 with two or more tensioning members substantially reduces the tricuspid annular dimension at the region of the tricuspid valve 10 that most often shows a regurgitant jet 6 in functional tricuspid regurgitation.

Figure 34:
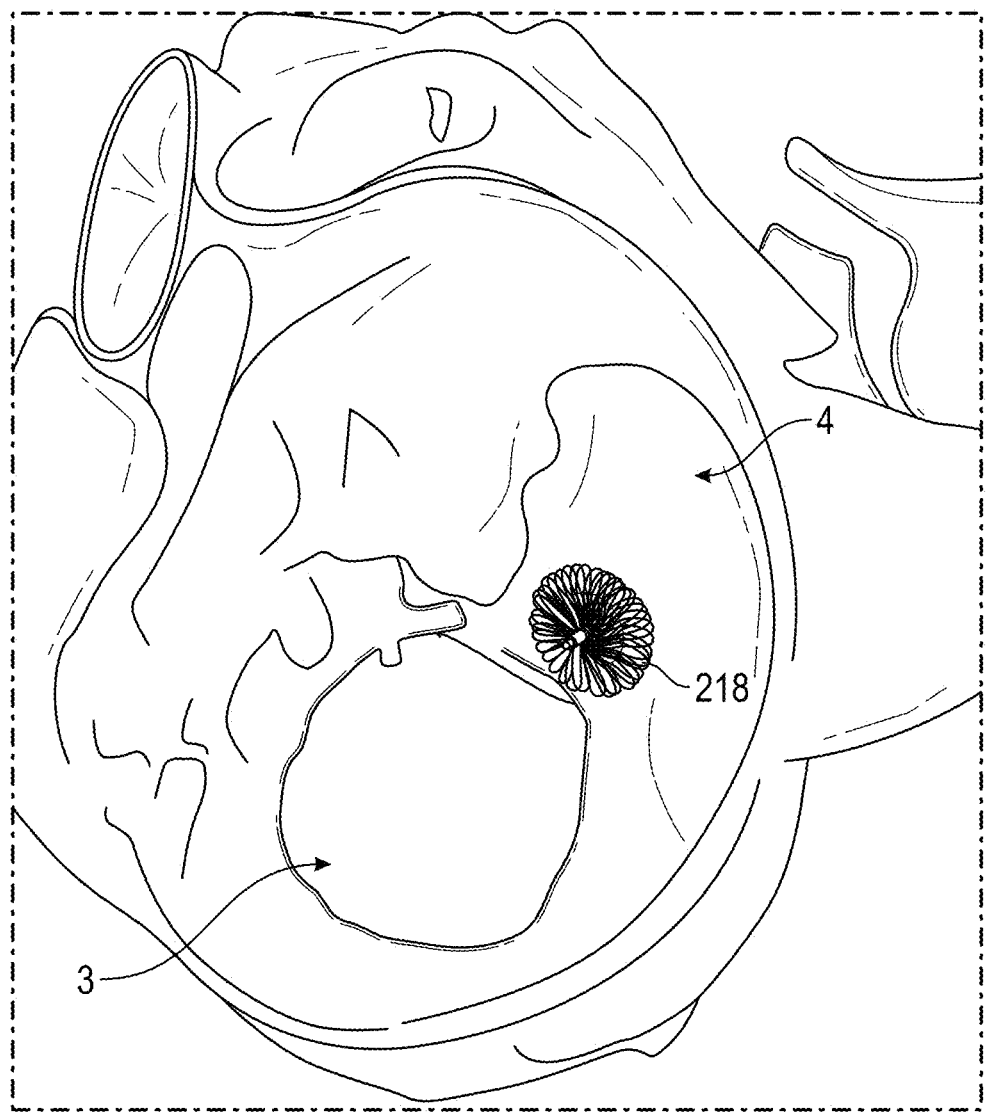
FIG. 34 illustrates a braided nitinol anchor in the left atrium, abutted against the left atrial wall of the interatrial septum, superior to the mitral valve.

FIG. 34 shows the septal portion of the nitinol mesh anchor 218 depicted in FIG. 32. The septal portion of the device is located in the left atrium 4 inferior to the fossa ovalis 53 and superior to the mitral valve 15. The septal device can be constructed of a septal anchor 218 that lies substantially flat against the left atrium (to prevent interference with common mitral valve 15 interventions and minimize the risk of thrombosis) and is connected to a flexible band 240 that traverses through the interatrial septum 51 and is connected to the lock 230. This location is significant in that it is thick and muscular and in close proximity to the superior surface of the left ventricular myocardium which makes it relatively immobile compared to the anterior tricuspid annulus 52. When the tensioning members 240 connected to the anterior tissue anchors 202 and the band connected to the septal tissue anchor 218 are tensioned within the lock 230 by a catheter 232 inserted in the left or right femoral vein, a force vector is created which pulls the anterior tricuspid annulus 52 toward the interatrial septum 51. The lock 230 can be activated via a catheter 232 to clamp the flexible tensioning members 240 and maintain the tensile force on the bands. The catheter 232 can then be used to trim the tensioning members 240 proximal to the suture lock such that any excess material can be removed or trimmed, and only minimal material is left permanently in the patient. Trimming excess material from a tensioning member would be beneficial in limiting unwanted interference in operations of the heart or an unwanted thrombogenic response. An alternative angle of this installation can be shown in FIG. 33, which illustrates the right ventricular view, looking up at the tricuspid valve 10, of the 2 expandable anchoring elements 202 positioned against the right ventricular surface of the anterior tricuspid valve annulus 52 in and near the RVOT 57.

Figure 36:
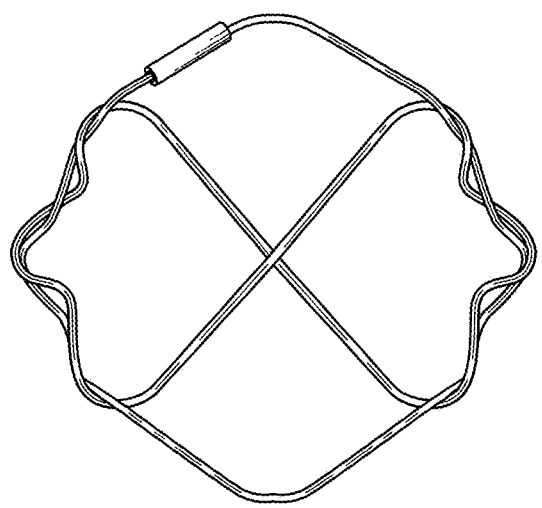
FIG. 36 illustrates an alternate configuration of the wire form from FIG. 35 where the wire form is heat-set into a more rounded perimeter profile.
Figure 37:
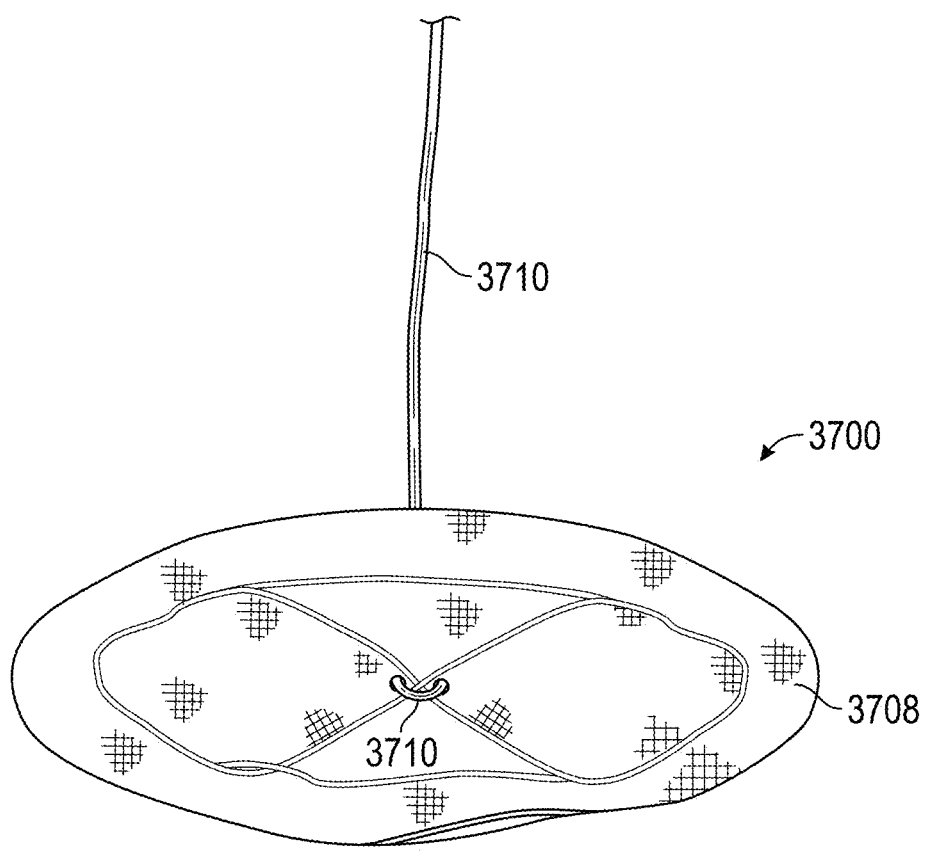
FIG. 37 illustrates the anchoring element of FIG. 35 with a polymeric or fabric covering over the wire form and a tensioning band attached to the center cross with a knot.
Figure 38:
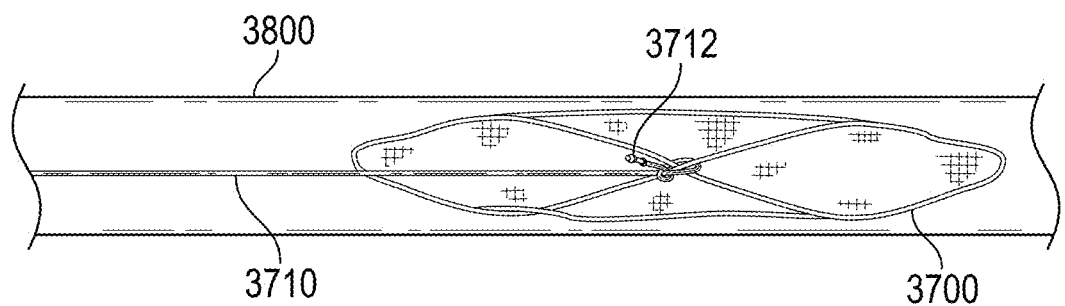
FIG. 38 illustrates the anchoring element of FIG. 37 elongated and compressed into a deployment catheter or sheath.

Several embodiments of the tissue anchors are herein disclosed. In one embodiment, depicted in FIGS. 33 and 35 through 38, the anchoring element 3500 is constructed from a nitinol wire forming a perimeter 3502 and an interior region where the wire makes one or more crosses 3506. The wire can be spiral wrapped around itself around the perimeter in 2 or more layers such that the layers are locked together, such that force applied to one layer, or to the center cross 3506, is transmitted to all layers simultaneously. The nitinol wire can be heat set such that it will maintain its form when in an austenitic state and the free ends of the wire can be connected by a sleeve that can be crimped or otherwise bonded to the nitinol wire such as with the sleeve 3504 depicted in FIG. 35, or the ends of the wire can be fused together via welding. The austenite finish temperature (Af) of the nitinol can be such that when heated to body temperature (37° C. or approximately 37° C.) the nitinol material is of austenitic structure. Body temperature can normally range from 97° F. (36.1° C.) to 99° F. (37.2° C.), though it can also be slightly above the range or slightly below the range, depending on a variety of factors and in certain embodiments the austenite finish temperature (Af) can be from 97° F. (36.1° C.) to 99° F. or from approximately 97° F. (36.1° C.) to approximately 99° F. The anchor perimeter can be constructed to be substantially oblong, such as the anchoring element depicted in FIG. 35, to be substantially round such as the embodiment depicted within FIG. 36, or any other shape, as desired or required. The anchor can be bare wire, such as in FIG. 35, or can be covered with a covering 3708 of synthetic (PET, ePTFE, or similar) or biological (pericardial tissue) origin, such as the optional covering 3708 as depicted in FIG. 37. The covering 3708 can be tightly adhered to the wire form, or it can be loose (allowing relative movement between the covering and wire form). The covering serves to form the interactive layer between the anchor and tissue, promote tissue healing and incorporation of the anchor into the tissue (ingrowth), provide sealing of the hole through which the flexible tensioning bands pass through the tissue and lock the wire form together across its surface area. Suitable techniques of attaching the covering to the frame could include suturing or sowing the cover to the frame, thermally bonding the covering to the frame, molding the covering around the frame, or other suitable attachment processes, as required. A flexible tensioning band 3710, substantially similar to other tensioning bands disclosed herein such as tensioning band 240, can be connected at or near the center of the wire form (as demonstrated in FIG. 37 with the flexible band 3710 being connected to the wire cross 3506 for the covered anchoring element 3700 with an optional covering 3708) such that when the flexible band 3710 is pulled upon it transfers tensile force substantially to the center of the wire form via its connection to the covered anchoring element 3700 at the knot 3712. In this manner, when the flexible band 3710 is pulled through a hole, and the anchor contacts the orifice to that hole, the entire perimeter 3502 of the anchor opposes entry into the hole in a similar fashion to other anchors disclosed herein, such as a T-bar. The construction of the wire form of the anchoring element 3500 and the superelastic properties of the nitinol in which it is made allow the anchor to be compressed along its length, which elongates and narrows its form substantially, facilitating entry into and traversal through a catheter 3800 with an internal diameter substantially smaller than the length or width of the unconstrained anchor as demonstrated within FIG. 38, illustrating the anchoring element 3700 of FIG. 37 elongated and compressed into a clear tube simulating a deployment catheter 3800. When the constraint of the catheter 3800 is released, such as by the anchor exiting the catheter, the anchor expands back into its pre-configured form, creating a large surface area by which force can be transmitted to tissue. The anchor 3700 is rotatable relative to the flexible band 3710 such that when the anchor 3700 is compressed and elongated as depicted in FIG. 38 within its first non-deployed configuration, it may also be rotated relative to the flexible band 3710 into a first pre-deployed state where the axis of the flexible band 3710 and the plane formed by the anchor 3700 in its pre-deployed state are relatively parallel to each other in order to facilitate translation into and through a catheter. Once the anchor 3700 is deployed from, and is no longer constrained by, a catheter, any force applied to the anchor 3700 along an axis from the attachment location on the anchor 3700 to the flexible band 3710 causes the anchor 3700 to rotate relative to the band to where the plan formed by the anchor 3700 is more perpendicular than parallel to the axis of the flexible band 3710. When the flexible band 3710 is pulled through an orifice, such as through a passage through tissue, with the anchor 3700 on one side of the orifice and the free end of the flexible band 3710 on the opposite side of the orifice, contact between the anchor 3700 and the material, such as a cardiac tissue, through which the orifice causes the anchor to rotate relative to the flexible band until the side of the anchor opposite to the side that originally contacted the material also contacts the material. Once the anchor is in contact with the material, the anchor will achieve its second deployed configuration where the moments on the anchor relative to the attachment point of the flexible band 3710 are in equilibrium and the plane of the anchor is more perpendicular than parallel to the axis of the flexible band, or at some angle relative to the axis of the flexible band other than parallel which causes the anchor to achieve rotational equilibrium. Thus, in this second deployed configuration, the anchor lays flat against the material through which the orifice passes and resists entry into the orifice.

Figure 39:
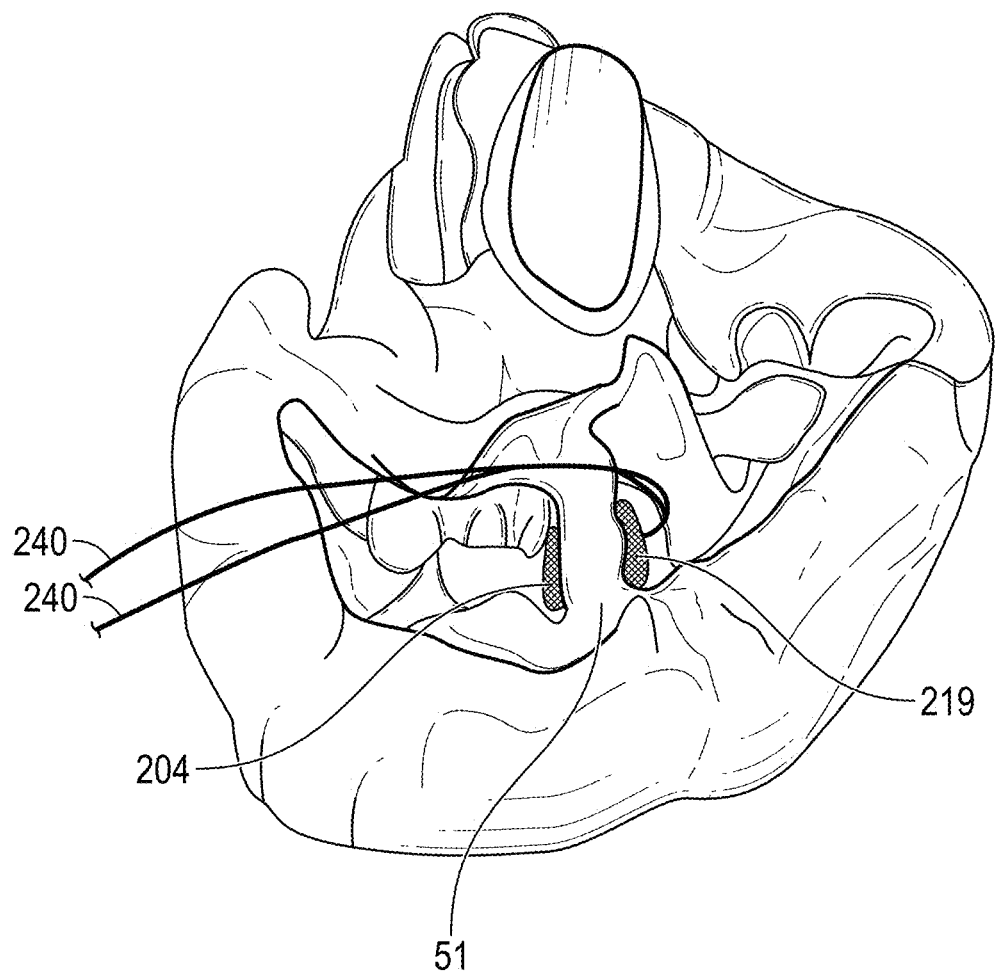
FIG. 39 illustrates a braided nitinol septal anchor abutted against the left atrial wall of a heart with a grommet affixed to the tensioning band at the right atrial exit of the tensioning band such that the septum is pinched between the anchor and grommet and the anchor is unable to move from its location.
Figure 40A:
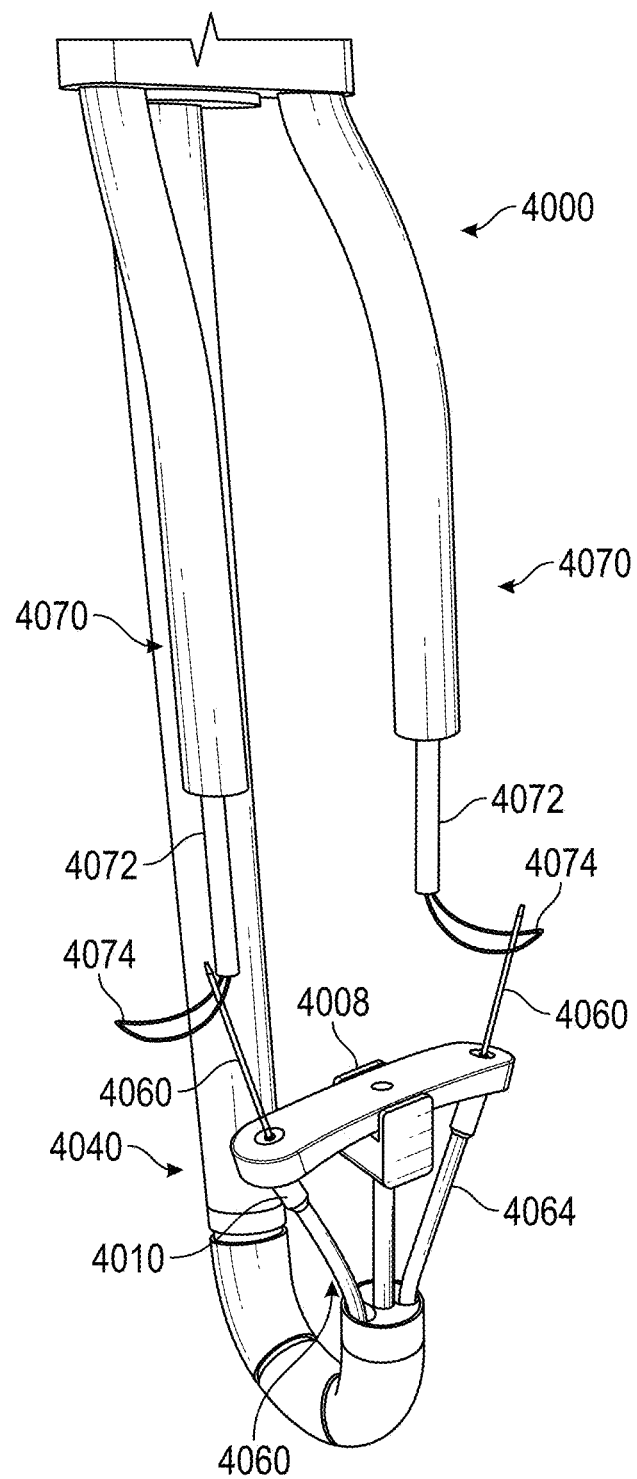
FIG. 40A illustrates an embodiment of the anterior anchor "bar" and delivery catheter where the anchor is attached to the delivery catheter in the center and the ends of the anchor are attached to hollow flexible tubes with a threaded swivel joint on the distal ends. Wires are passing through the hollow tubes, through the anchor and through the loops of snare catheters that are positioned near the wire exit points.
Figure 40B:
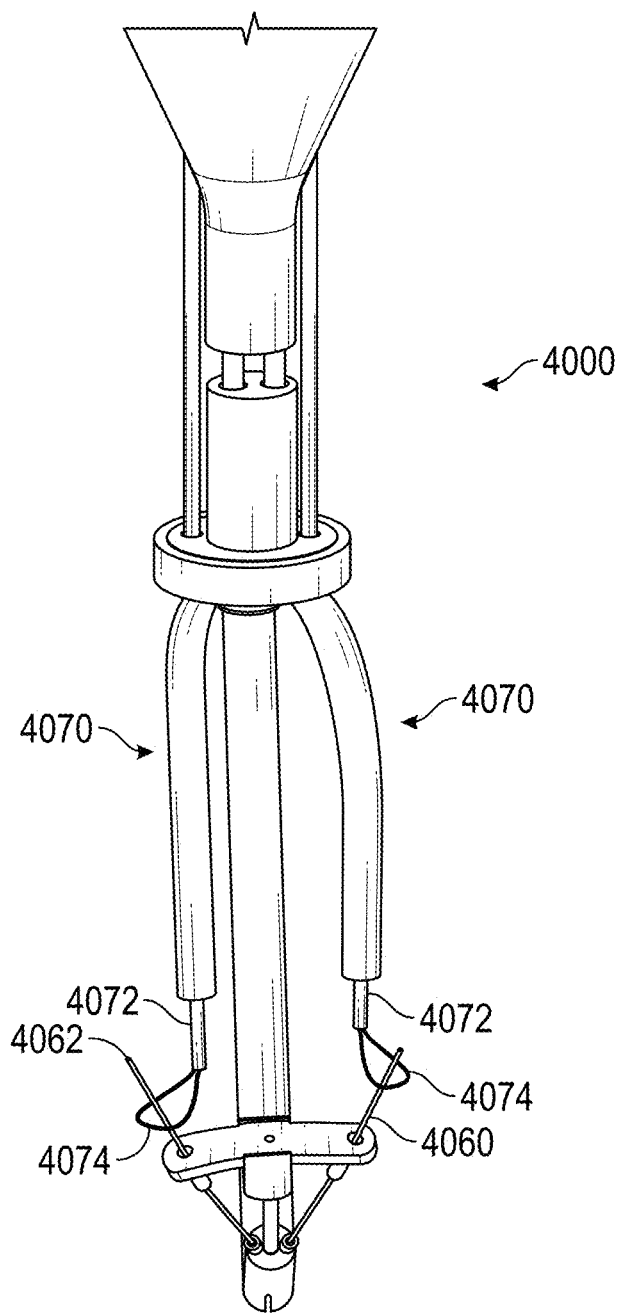
FIG. 40B shows an alternative view of the embodiment of FIG. 40A.

FIG. 39 illustrates a braided nitinol septal anchor 204 abutted against the left atrial wall of a heart with a grommet 219 (similar in function to the coronary sinus grommet or pad 215 of FIG. 12) affixed to the tensioning band 240 at the right atrial exit of the tensioning band such that the septum 51 is pinched between the anchor and grommet and the anchor is unable to move from its location.

Figure 45:
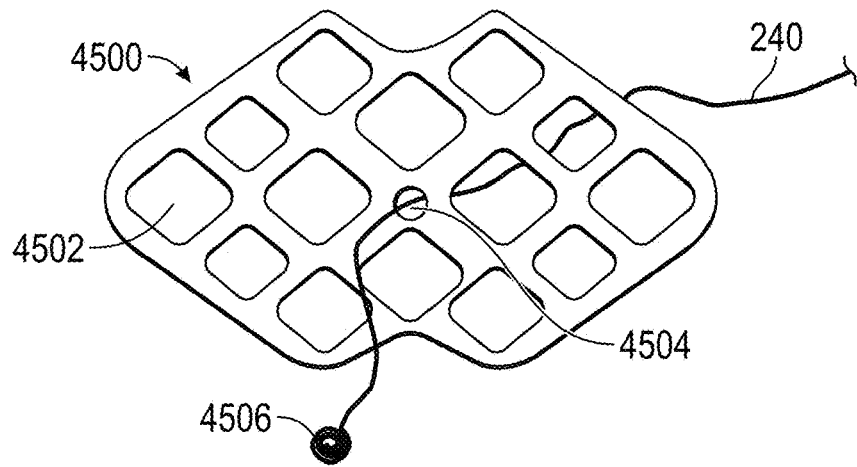
FIG. 45 illustrates an anchor embodiment where the anchor is constructed from a laser cut nitinol sheet or strip with a diamond pattern. The laser cut pattern allows the anchor to be compressed and elongated into a narrow profile for delivery through a catheter and then allows it to passively return to the deployed configuration shown when exiting the catheter. A central hole does not allow the knot in the tensioning band to pass such that when the tensioning band is pulled it will pull the anchor from the center and cause it to lie flat against any surface the anchor contacts.

In other embodiments of the tissue anchor the anchor frame can be laser cut from nitinol sheet material with a central hole, or cross, and various diamond shaped elements such as the anchoring frames illustrated in FIGS. 45, 50 and the frame 7020 of the anterior surface anchor 7002 illustrated in FIGS. 69 and 70. The diamond shaped elements allow compression and elongation of the anchor such that it can be reduced in cross sectional area for delivery through a catheter and is able to expand into its deployment configuration upon exiting the catheter. The anchor can be covered with a polymeric or biological covering as previously disclosed. The central hole would be sized to allow free passage of the tensioning band but so as not to allow passage of a knot at the distal end of the tensioning band so that when the tensioning band is pulled the knot will transfer force to the anchor.

Figure 44C:
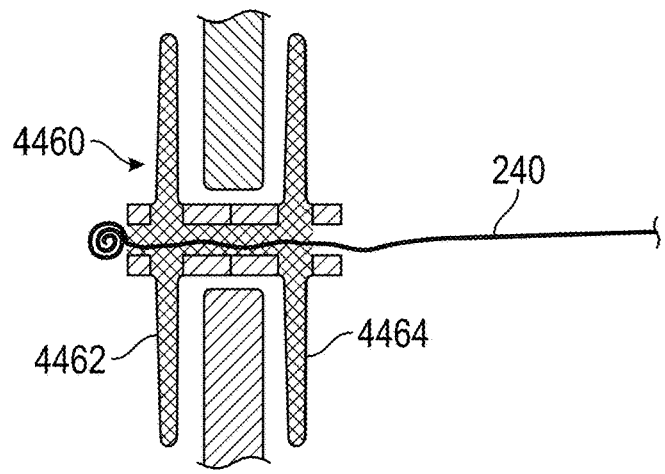
FIG. 44C illustrates an embodiment of an anchoring element where the anchor is constructed of braided nitinol wire shape-set into two disks such that a distal disk is abutted to the tissue and resists pulling through when the tensioning band is tensioned and a proximal disk is configured to slide over the tensioning band and retain the anchor in place while the tensioning band is slack or if it is cut or breaks.
Figure 44D:
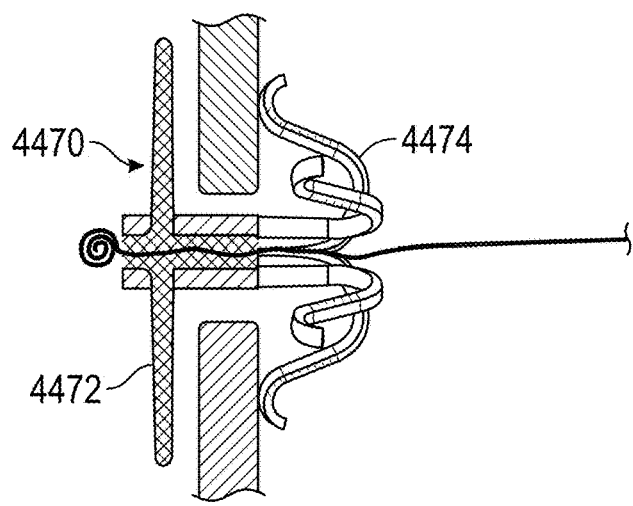
FIG. 44D illustrates an embodiment of an anchoring element similar to FIG. 44C except that the anchor is retained in place on the proximal end by shape set nitinol fingers. The fingers can be laser cut from a tube or be individual wire elements attached to the proximal hub of the anchor and can straightened out for tracking through a delivery catheter. 4 fingers are depicted in a cross configuration, however; any number of fingers can be used in the construction.

In other embodiments of the tissue anchor, such as those illustrated in FIG. 44, the anchor is constructed from braided nitinol wire with the proximal and distal ends fused to hollow hubs which allow free passage of the tensioning bands. The anchor could be heat-set into a round, elliptical, or oblong disk, or a plurality of disks (for example anchor 4450 in FIG. 44b), to give a large flat surface area for force transmission to the tissue. The tensioning band could pass freely through the center of the anchor and be affixed to the distal hub or have a knot on the distal end that interferes with the hole through the distal hub of the anchor such that when the tensioning band is pulled it causes force to be applied to the distal hub of the anchor which causes the anchor to flatten against any surface it is abutted to as illustrated in FIGS. 44A through D. The anchor could be pulled from the proximal end, or the distal and proximal ends of the anchor could be pulled apart relative to each other which causes the anchor to elongate and shrink in diameter, such as the catheter 4408 when in its non-deployed configuration 4408, so that it can be loaded into and deployed from a catheter. Constructing the anchor from a plurality of disks increases the amount of material in contact with tissue which increases the force required to pull the anchor through tissue without increasing the force necessary to elongate the anchor for delivery through a catheter.

1, 2, 3 or more tissue anchors, each connected to a flexible band, can be placed at the right ventricular surface of the anterior tricuspid annulus 52. Additional anchors (as many as the operator chooses), each connected to a flexible band, can be implanted around the tricuspid annulus in any location along the anterior or posterior annulus. All flexible bands can be routed to a central lock, located near the interatrial septum, or anywhere over the tricuspid valve orifice, and the bands can be tensioned either simultaneously, individually, or any combination in-between to pull each tissue anchor toward the interatrial septum.

In another embodiment, 2 or more bands can be connected to a single tissue anchor spanning the ventricular surface of the anterior tricuspid annulus 52, such as with the foldable flat implant system 4000 disclosed in FIGS. 40 through 43. In the case of a single anchor with two or more flexible bands attached, at least two of the flexible bands 4072 will be located near either end of the anchor 4040 such that the portion of the anchor between the flexible bands spans from 1-4 centimeters of the anterior tricuspid annulus 52, with the bands traversing from the right ventricle 3, through the annular muscle 52, and into the right atrium 2 at locations on the anterior annulus 52 from 1 to 3 centimeters, or more, apart. In the instance of a single anchor 4040 with multiple attached flexible bands 4072, the anchor may be foldable, such as in FIG. 41, by providing a flexible internal frame 4044 or by providing linkages such that the anchor may be folded into a slim profile for introduction into the RVOT and for minimizing any interaction with native chordae tendinea and then expanded once in the RVOT at or near the ventricular surface of the tricuspid annulus.

The embodiment of a system to install multiple bands to a single tissue anchor as depicted in FIGS. 40 through 43 comprises a foldable flat implant system 4000 with a flexible delivery catheter 4002 to deliver an anchor bar 4040 non-fixably attached to a delivery catheter anchor interface 4008, the anchor bar 4040 having guidewire hubs 4050 with tether holes 4048 allowing passage of at least two anchor bar guidewires 4060, the anchor bar guidewire 4060 interacting with the snare wire 4074 guided by the snare guide catheter 4072 housed within the snare catheter 4070. The process demonstrating its installation is depicted in FIGS. 25 through 31.

The anchor bar 4040 can be made of a flexible biocompatible material and is depicted in dashed lines in FIGS. 40A through 43 to show internal components. The anchor bar 4040 comprises an anchor bar structural member 4044, which can be comprised of nitinol or some other semi-rigid material to provide structure to the anchor bar 4040. Connected to the anchor bar structural member 4044 are anchor bar guidewire hubs 4050 which can connect to the guidewire catheters 4064 supporting anchor bar guidewires 4060 during use via a guidewire hub threading 4054 connected to the guidewire catheter connection 4010. The anchor bar 4040 has an anchor bar delivery connection 4046 to non-fixably connect to the flexible delivery catheter 4002 at the delivery catheter anchor interface 4008. The anchor bar 4040 is covered by an anchor bar covering 4042 made of biocompatible material. The anchor bar 4040 is flexible, as shown in FIG. 41, such that it can be bent for ease of use while inserting the foldable flat implant system 4000 into the patient.

The anchor bar guidewires 4060 pass through the anchor bar 4040, which is connected to a guidewire catheter connection 4010 housing the guidewires, the guidewire catheter connection 4010 being a flexible hinge to accommodate the flexible nature of the anchor bar 4040. The guidewire catheter connections 4010 are constructed of a distal element 4012 with a thread on the distal end configured for attachment to the guidewire hub threads 4054, a proximal element 4016 with a rotation slot point passing through its distal end through which the proximal element 4016 interfaces with the distal element 4012 via a pin 4014 slotting through the proximal element 4016 and the distal element 4012. The pin allows the proximal element 4016 to pivot relative to the distal element 4012, from parallel to perpendicular, while transferring torsional, tensile and compressive forces between the distal and proximal elements. This hinged connection assists in reducing angular strain on the anchor bar guidewire 4060. The anchor bar guidewires 4060 pass through the anchor bar guidewire lumen 4048 surrounded by the anchor bar guidewire hubs 4050 and terminate at anchor bar guidewire distal tips 4062 which are pointed to facilitate entry into the heart tissue.

During deployment, the anchor bar guidewire distal tips 4062 pass through the tissue of the patient to interact with snare wires 4074 provided by snare guide catheters 4072 delivered via a snare catheter 4070 connected to the foldable flat implant system 4000. The anchor bar guidewires 4060 can connect to the snare guide catheters 4072 and recede through the tissue and through the snare catheter until externalized from the patient. The anchor bar guidewires 4060 can have flexible tethers (such as sutures) attached to their distal end so that when the anchor bar guidewires are pulled completely through the snare catheter the tethers are pulled through the guidewire hubs 4050 of the anchor bar 4040 until knots or other suitable end terminations on the tethers interfere with the hole 4048 of the guidewire hubs 4050.

FIGS. 44A through 51C depict alternative embodiments of tissue anchors.

In other embodiments of the tissue anchor the anchor can be laser cut from nitinol sheet material with a central hole, or cross, and various diamond shaped elements, such as the anchor 4400 depicted in FIG. 44A. The anchor 4400 is shape set into a disk configuration. An end view of the anchor is shown in which the anchor is depicted substantially round. The anchor can be elongated, which causes the disk to collapse into a long narrow tube for delivery through a catheter. The tensioning band 240 is attached centrally to the distal end of the anchor via an interference knot 4404 which causes the anchor to flatten when the tensioning band is tensioned. The diamond shaped elements 4402 allow compression and elongation of the anchor such that it can be reduced in cross sectional area for delivery through a catheter and is able to expand into its deployment configuration upon exiting the catheter. The anchor can be covered with a polymeric or biological covering as previously disclosed. The central hole 4406 would be sized to allow free passage of the tensioning band but so as not to allow passage of a knot at the distal end of the tensioning band so that when the tensioning band is pulled the knot will transfer force to the anchor.

FIG. 44B illustrates an embodiment of an anchoring element where the anchor 4450 is constructed of braided nitinol wire shape set into a series of disks. Two disks are depicted; however, any number of disks can be constructed. The anchor is shown abutted against a cross section of tissue with a small hole for the tensioning band 240. Having a plurality of disks increases the amount of material abutted to the tissue which makes the anchor more resistant to pulling through the tissue without increasing the stiffness of the anchor for the purpose of collapsing into the delivery catheter.

FIG. 44C illustrates an embodiment of an anchoring element 4460 where the anchor is constructed of braided nitinol wire shape-set into two disks such that a distal disk 4462 is abutted to the tissue and resists pulling through when the tensioning band 240 is tensioned and a proximal disk 4464 is configured to slide over the tensioning band and retain the anchor in place while the tensioning band is slack or if it is cut or breaks.

FIG. 44D illustrates an embodiment of an anchoring element 4470 similar to the embodiment depicted in FIG. 44C except that the anchor 4470 is retained in place on the proximal end by shape set nitinol fingers 4474. The anchor 4470 has a distal disk 4472 substantially similar to the distal disk 4462 of FIG. 44C. The fingers can be laser cut from a tube or be individual wire elements attached to the proximal hub of the anchor and can straightened out for tracking through a delivery catheter. 4 fingers are depicted in a cross configuration, however; any number of fingers can be used in the construction.

FIG. 45 illustrates an anchor embodiment 4500 where the anchor is constructed from a laser cut nitinol sheet with a diamond pattern 4502. The laser cut pattern allows the anchor to be compressed and elongated into a narrow profile for delivery through a catheter and then allows it to passively return to the deployed configuration shown when exiting the catheter. A central hole 4504 does not allow the knot 4506 in the tensioning band 240 to pass such that when the tensioning band is pulled it will pull the anchor from the center and cause it to lie flat against any surface the anchor contacts.

Figure 46A:
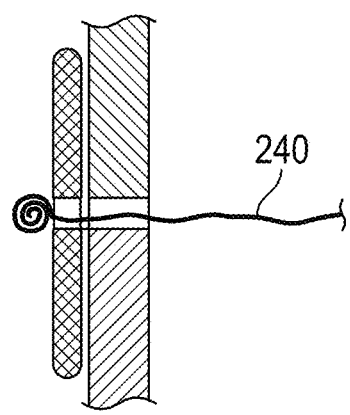
Figure 46B:
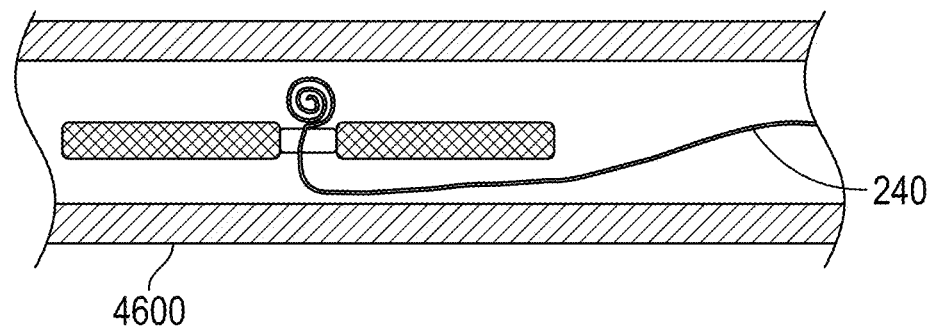
FIG. 46B illustrates the anchor illustrated in FIG. 46A inserted into a catheter.
Figure 46C:
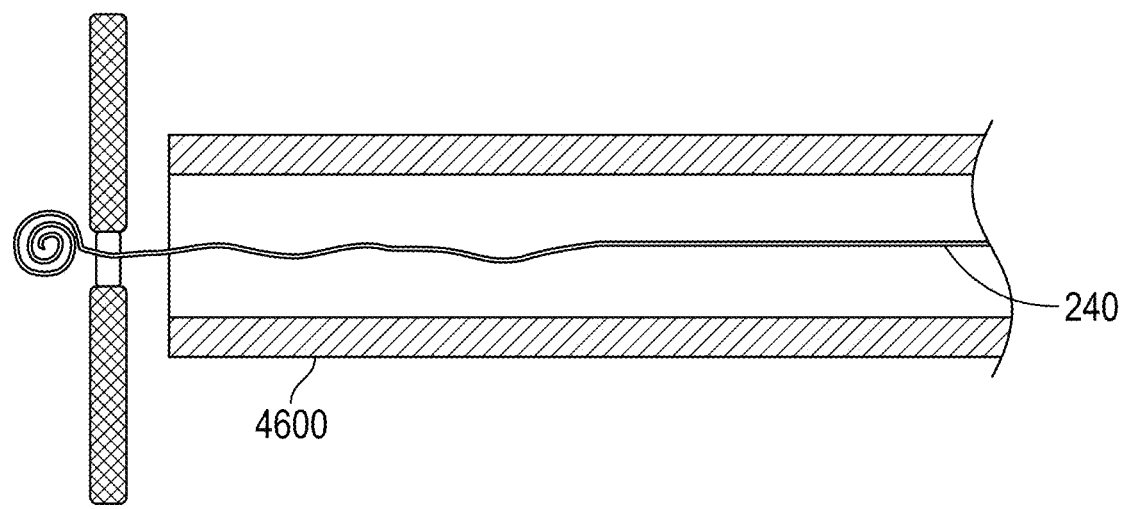
FIG. 46C illustrates the anchor illustrated in FIG. 46B deployed from the catheter wherein it assumes a "t-bar" configuration when the tensioning band is pulled and the anchor comes into contact with any structure.

FIGS. 46A through 46C illustrate how the embodiments of anchors disclosed herein, such as the anchors from FIGS. 35 through 38, 45, 50, and 69 through 74, can be deployed into a patient. FIG. 46A illustrates a side bisected view of an example anchoring element abutted against tissue with the tensioning band 240 passing through. FIG. 46B illustrates the anchor illustrated in FIG. 46A inserted into a catheter 4600, which can be substantially similar to other delivery catheters disclosed herein, such as catheter 220. FIG. 46C illustrates the anchor illustrated in FIG. 46B deployed from the catheter 4600 wherein it assumes a deployed configuration when the tensioning band is pulled and the anchor comes into contact with any structure.

Figure 47A:
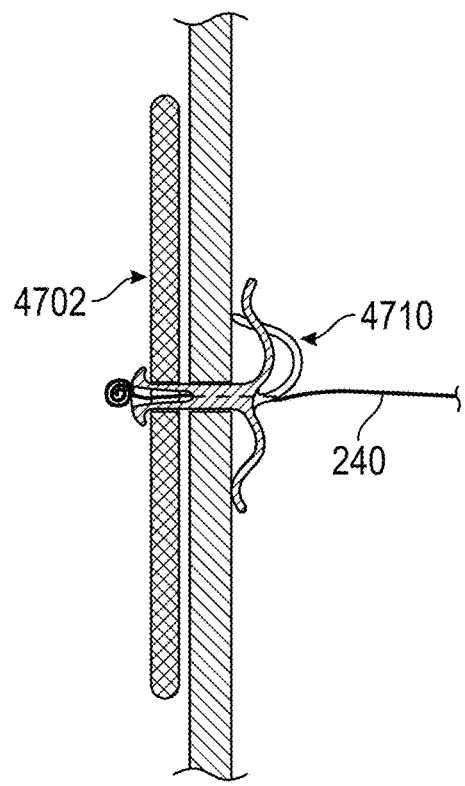
FIG. 47A illustrates an anchor such as those illustrated in FIGS. 45 and 50a-c with a proximal grommet constructed from a laser cut nitinol tube snap fit into the center hole of the anchor. The grommet comprises a plurality of laser cut nitinol fingers that are shape set into a configuration in which they are curved and spread out radially from the tube axis such that the fingers may retain the anchor in place on the tissue while the tensioning band is slack or if the tensioning band is broken or cut. The distal end of the nitinol tube is constructed with a raised step and taper with slots cut to form cantilever beam sections. When the anchor is tensioned against the tube the taper at the distal end of the tube causes the beams to deflect toward the centerline allowing the raised step to pass through the hole in the anchor. Once the raised step is through the hole the stored potential energy in the beams causes them to straighten and the raised end of the tube becomes locked to the anchor.
Figure 47B:
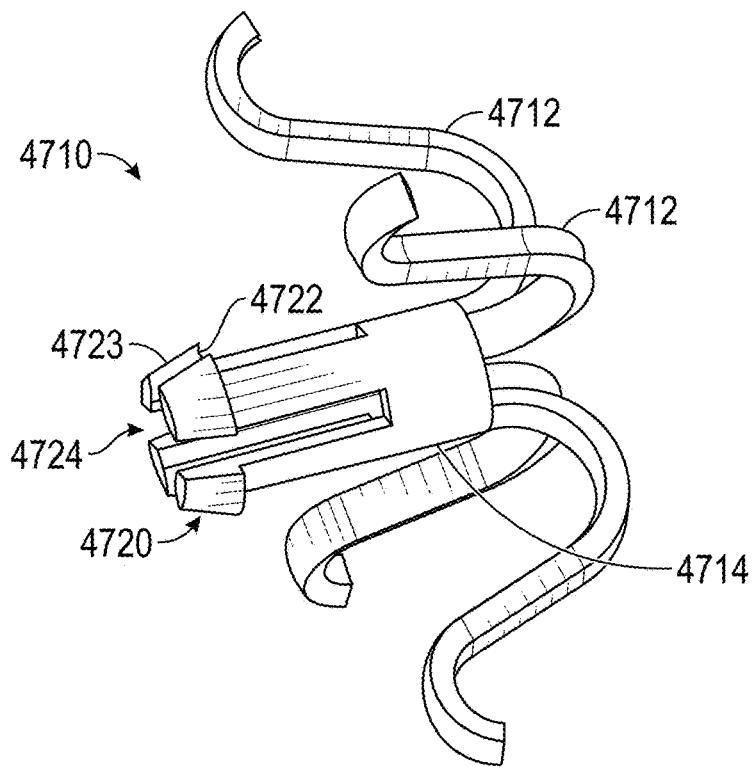
FIG. 47B illustrates an isometric rendering of the grommet element illustrated in FIG. 47A.

FIG. 47A illustrates an anchor such as those illustrated in FIGS. 45 and 50A-C with a proximal grommet 4710 constructed from a laser cut nitinol tube snap fit into the center hole of the anchor. FIG. 47B illustrates an isometric rendering of the grommet element illustrated in FIG. 47A. The grommet 4710 comprises a plurality of laser cut nitinol fingers 4712 that are shape set into a configuration in which they are curved and spread out radially from the tube axis such that the fingers may retain the anchor 4702 in place on the tissue while the tensioning band is slack or if the tensioning band 240 is broken or cut. The distal end 4720 of the nitinol tube 4714 is constructed with a raised step 4722 and taper 4723 with slots 4724 cut to form cantilever beam sections. When the anchor 4702 is tensioned against the tube 4714 the taper 4723 at the distal end of the tube causes the beams to deflect toward the centerline allowing the raised step 4722 to pass through the hole in the anchor 4702. Once the raised step 4722 is through the hole the stored potential energy in the beams causes them to straighten and the raised distal end 4720 of the tube becomes locked to the anchor.

Figure 48A:
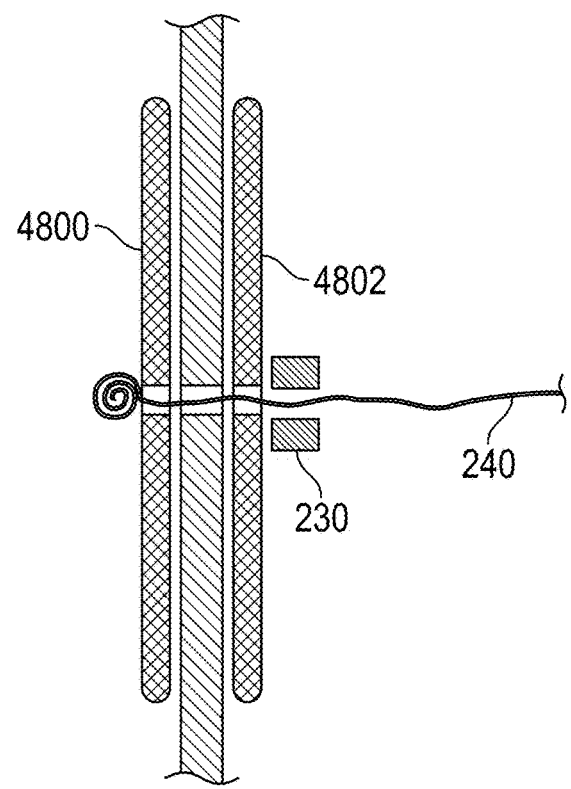
FIG. 48A illustrates an alternative configuration for retaining the anchor in place in the absence of tension on the tensioning band whereby the tissue is compressed between an anchor on the distal end and a flat grommet on the proximal end that slips over the tensioning band. A lock is crimped to the tensioning band to lock the distance between the anchor and grommet. The grommet can be of a similar construction to any of the anchoring elements disclosed herein.
Figure 48B:
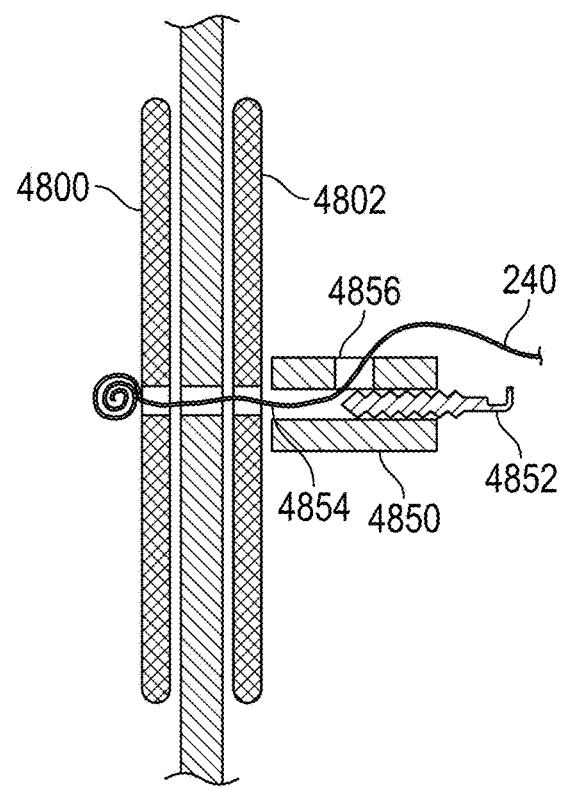
FIG. 48B illustrates a similar configuration as FIG. 48A except that the grommet is locked relative to the anchor with a locking mechanism that utilizes a screw that when rotated clamps the tensioning band between a central hole and a side exit hole.
Figure 49A:
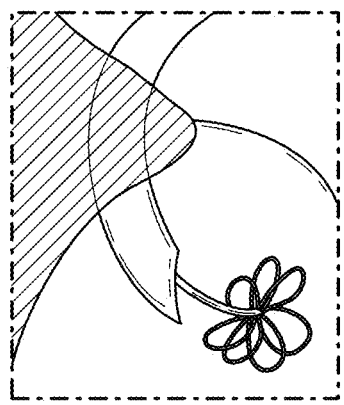
FIGS. 49A-49F illustrate various alternative anchor concepts; 49A depicts a braided nitinol anchor similar in function to an Amplatzer device; 49B depicts an S-hook anchor; 49C depicts a T-Bar anchor; 49D depicts a ship anchor; 49E depicts a suture into bar anchor; 49F depicts a rigid hook into a bar, and can include an additional barb.
Figure 49B:
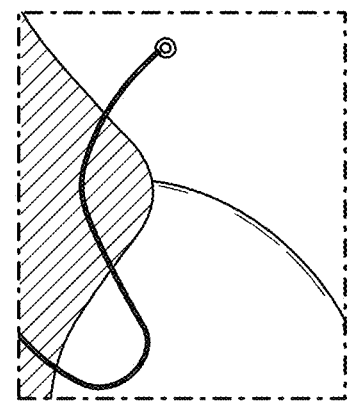
Figure 49C:
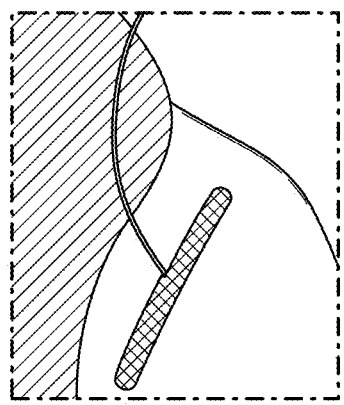
Figure 49D:
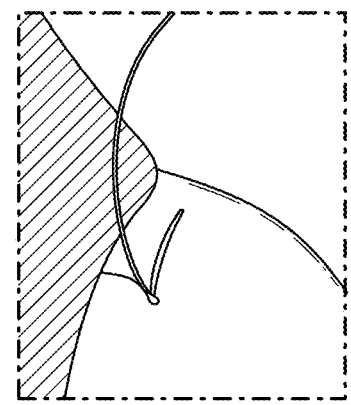
Figure 49E:
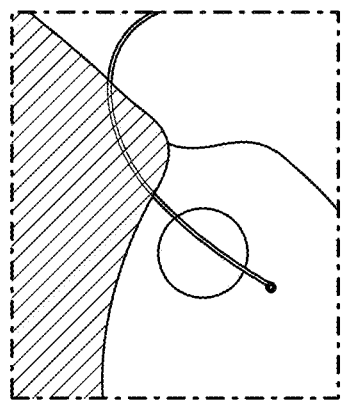
Figure 49F:
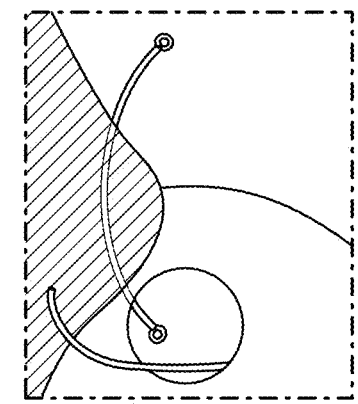

FIG. 48A illustrates an alternative configuration for retaining the anchor 4800 in place in the absence of tension on the tensioning band whereby the tissue is compressed between an anchor 4800 on the distal end and a flat grommet 4802 on the proximal end that slips over the tensioning band 240. A lock 230 is crimped to the tensioning band 240 to lock the distance between the anchor 4800 and grommet 4802. The grommet can be of a similar construction to any of the anchoring elements or grommet elements disclosed herein.

FIG. 48B illustrates a similar configuration as FIG. 48A except that the grommet 4802 is locked relative to the anchor 4800 with a locking mechanism 4850 that utilizes a screw 4852 that when rotated clamps the tensioning band between a central hole 4854 and a side exit hole 4856.

FIGS. 49A-49F illustrate various alternative anchor concepts; 49A depicts a braided nitinol anchor similar in function to an Amplatzer device; 49B depicts an S-hook anchor; 49C depicts a T-Bar anchor; 49D depicts a ship anchor; 49E depicts a suture into bar anchor; 49F depicts a rigid hook into a bar, and can include an additional barb.

Figure 50A:
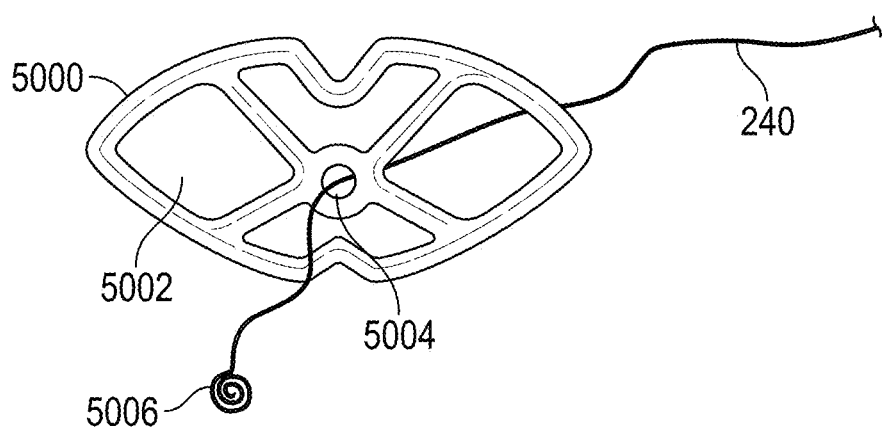
FIG. 50A illustrates an anchor embodiment where the anchor is constructed from laser cut nitinol sheet or strip with a diamond pattern that allows the anchor to compress and elongate into a narrow profile for delivery through a catheter and then passively return to the deployed configuration shown when exiting the catheter. A central hole does not allow the knot in the tensioning band to pass such that when the tensioning band is pulled it will pull the anchor from the center and cause it to lie flat against any surface the anchor contacts.

FIG. 50A illustrates an anchor embodiment 5000 where the anchor is constructed from laser cut nitinol sheet with a diamond pattern 5002 that allows the anchor to compress and elongate into a narrow profile for delivery through a catheter and then passively return to the deployed configuration shown when exiting the catheter. A central hole 5004 does not allow the knot 5006 in the tensioning band 240 to pass such that when the tensioning band 240 is pulled it will pull the anchor from the center and cause it to lie flat against any surface the anchor contacts.

Figure 50B:
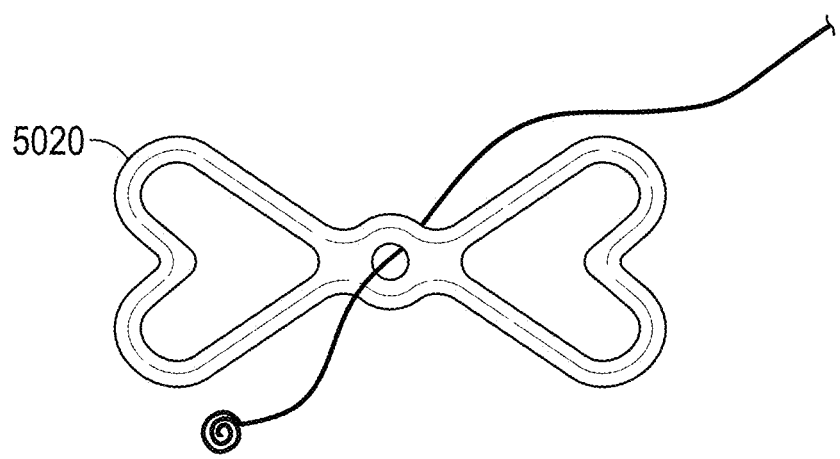
FIG. 50B illustrates an alternative cut configuration 5020 of the anchor in FIG. 50A.

FIG. 50B illustrates an alternative cut configuration for an anchor 5020 which is substantially similar to the anchor 5000 in FIG. 50A.

Figure 50C:
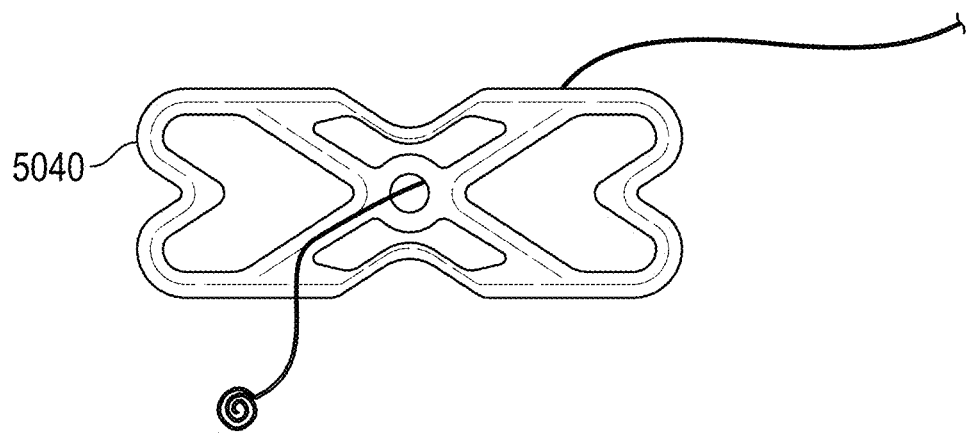
FIG. 50C illustrates an alternative cut configuration 5040 of the anchor in FIGS. 50A and 50B.

FIG. 50C illustrates an alternative cut configuration for an anchor 5040 which is substantially similar to the anchor 5000 in FIG. 50A and the anchor 5020 in FIG. 50B.

Figure 51A:
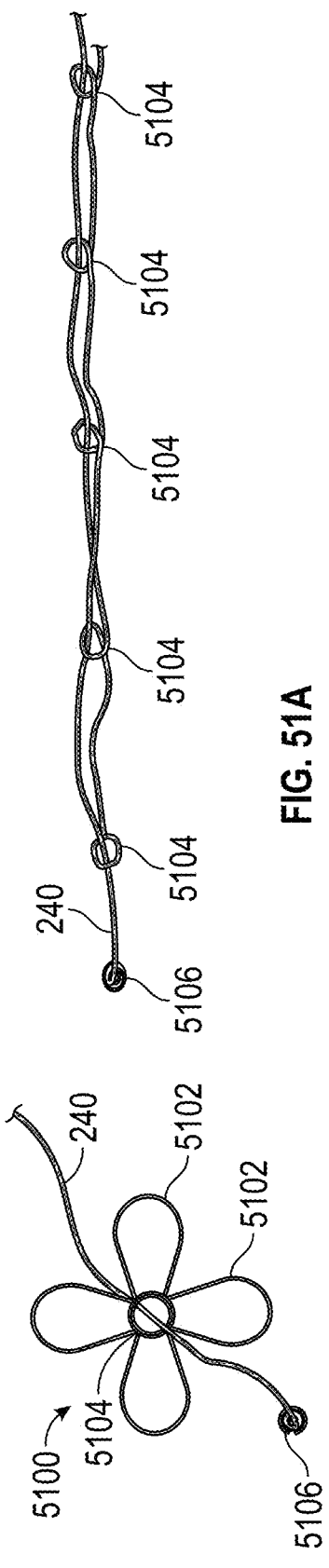
FIG. 51A illustrates an anchor embodiment where the anchor is constructed from a shape set nitinol wire to form a series of lobes. The wire is wrapped into a tight loop between each lobe such that a center hole is approximated through the anchor. The tensioning band passes through the center hole which constrains the lobes from displacing radially relative to each other. The tensioning band has a knot formed at the distal end that cannot passthrough the central hole such that when the tensioning band is pulled the knot contacts the center of the anchor and pulls the anchor from the center. The anchor can be elongated to facilitate delivery through a catheter and upon exiting the catheter returns to the shape set configuration due to the stored potential energy in the wire from the straightening process

FIG. 51A illustrates an anchor embodiment 5100 where the anchor is constructed from a shape set nitinol wire to form a series of lobes 5102. The wire is wrapped into a tight loop 5104 between each lobe such that a center hole is formed through the anchor. The tensioning band 240 passes through the center hole which constrains the lobes from displacing radially relative to each other. The tensioning band 240 has a knot 5106 formed at the distal end that cannot passthrough the central hole formed by the tight loops 5104 such that when the tensioning band 240 is pulled the knot 5106 contacts the center of the anchor 5100 and pulls the anchor 5100 at its center. The anchor 5100 can be elongated to facilitate delivery through a catheter and upon exiting the catheter returns to the shape set configuration due to the stored potential energy in the wire from the straightening process.

Figure 51B:
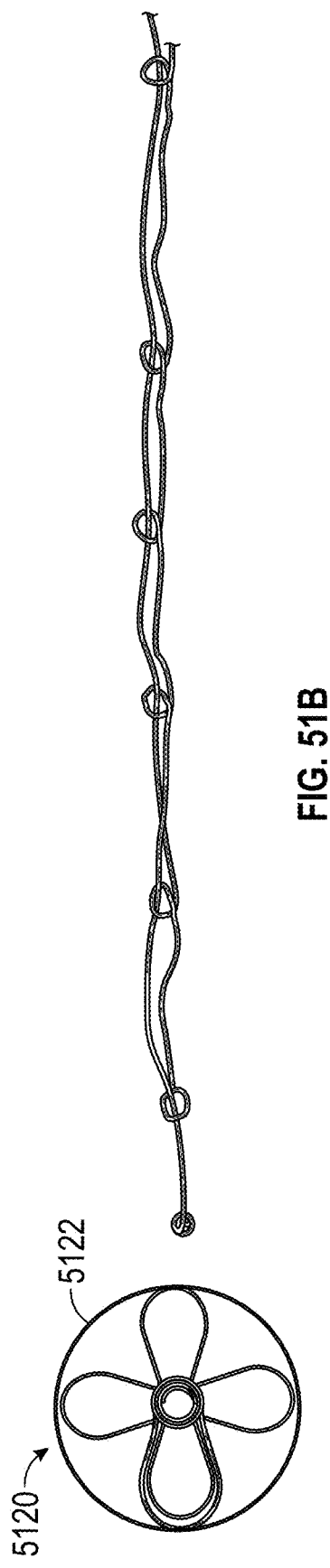
FIG. 51B illustrates an anchor embodiment similar to FIG. 51A except that in addition to the lobes the wire is also formed into a perimeter circle.

FIG. 51B illustrates an anchor embodiment 5120 substantially similar to the anchor 5100 of FIG. 51A, except that in addition to the lobes 5102 the wire is also formed into a perimeter circle 5122.

Figure 51C:
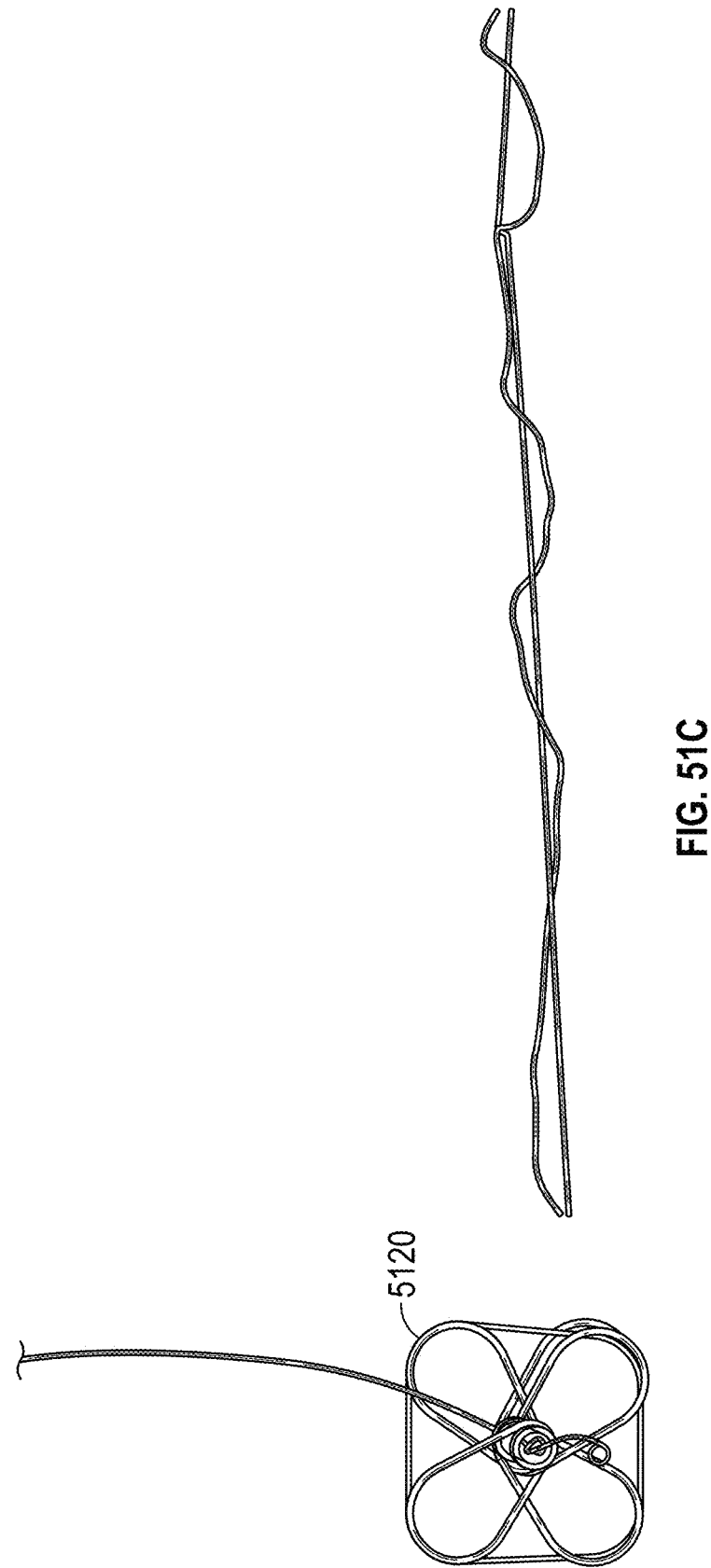
FIG. 51C illustrates an alternative perspective of the anchor illustrated in FIG. 51B. The anchor can be straightened to facilitate delivery through a catheter. The anchor can be pulled into a catheter by simply pulling the distal end and can be pushed back out of the catheter by pushing either the distal or the proximal end. Pushing the distal end causes the anchor to elongate as it is pushed due to the counteracting friction against the catheter walls proximal to the point of force application which lowers deployment forces compared to pushing from the proximal end.

FIG. 51C illustrates an alternative embodiment of the anchor 5120 illustrated in FIG. 51B. The anchor can be straightened to facilitate delivery through a catheter. The anchor can be pulled into a catheter by simply pulling the distal end of the arch wire forming the anchor 5120 and can be pushed back out of the catheter by pushing either the distal or the proximal end of the arch wire. Pushing the distal end causes the anchor to elongate as it is pushed due to the counteracting friction against the catheter walls proximal to the point of force application which lowers deployment forces compared to pushing from the proximal end.

Any of the anchor embodiments herein disclosed could also include a grommet on the wall of tissue opposite of where the anchor is abutted. The grommet holds the anchor in place in the absence of tension on the tensioning band or if the tensioning band is cut or broken. The grommet could be permanently affixed to the anchor, affixed to the anchor after deployment by providing a snap fit connection, or a separate component that is slipped over the tensioning band and locked in position relative to the anchor with a separate lock that pushes the grommet against the tissue wall and clamps the tensioning band. The grommet could be of braided nitinol construction or of laser cut nitinol tube construction with fingers shape set radially outward from the central axis to grip the tissue. The grommet can be of a similar construction to any of the anchoring elements disclosed herein, such as grommet 7030 of FIG. 70, frame 7104 of FIG. 71, grommet 7220 of FIG. 72, and expanding grommet 7402 of FIG. 74, can be another applicable grommet, or any other grommet, as desired or required.

Figure 59:
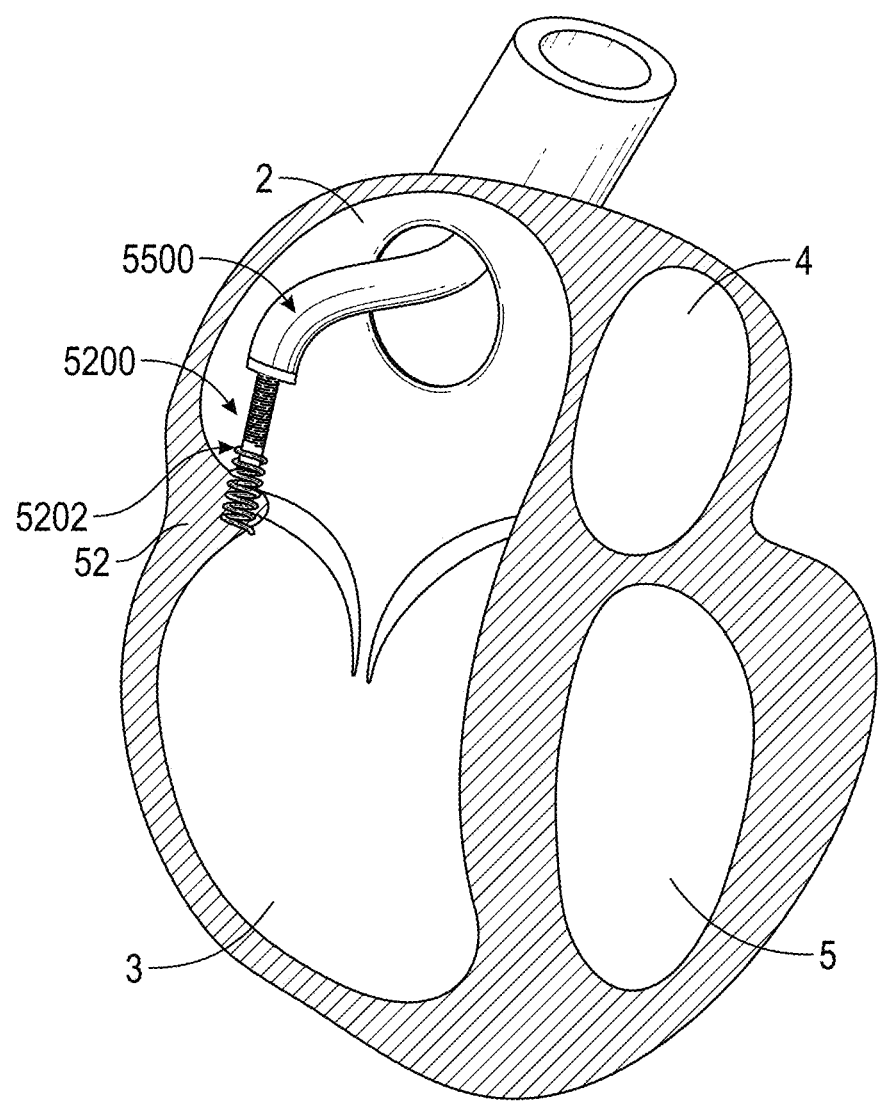
FIG. 59 illustrates a 4-chamber cross section of the heart with a guide catheter in the right atrium and a stabilizing catheter with a distal helix being directed by the guide catheter to a location near the anterior tricuspid valve annulus. The helix is being screwed into the tissue by applying torque to the stabilizing catheter.
Figure 60:
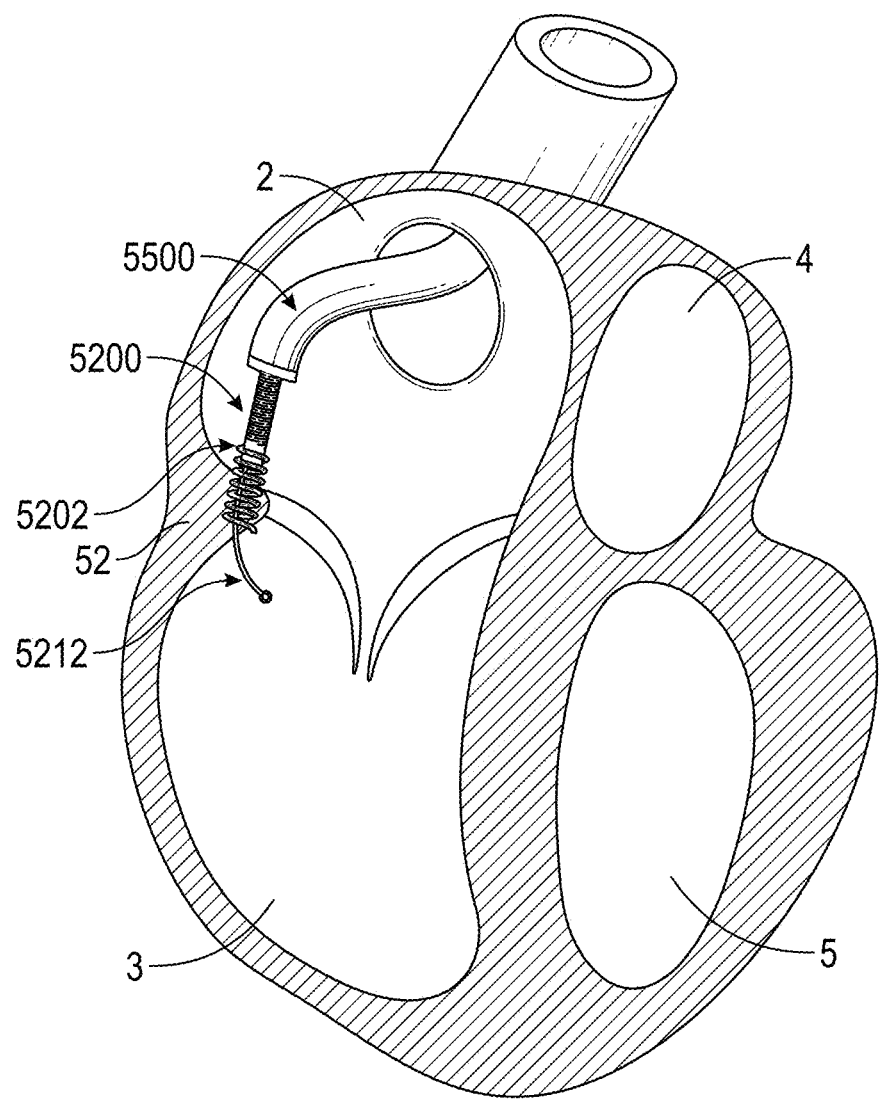
FIG. 60 illustrates a 4-chamber cross section for the heart with the guide catheter and stabilizing catheter illustrated in FIG. 59 and a guidewire passing through the stabilizing catheter and through the tissue into the right ventricle.

In some applications of the present disclosure techniques are described for crossing the tissue at or near (within 15 millimeters) a tricuspid valve annulus, from the right atrium into the right ventricle, by first attaching or embedding the distal end of a stabilizing catheter in the tissue at or near the tricuspid valve annulus from the right atrial side and second passing a guidewire through the stabilizing catheter which will exit the distal end of the stabilizing catheter and pass through tissue at or near the tricuspid valve annulus from the right atrium into the right ventricle, as illustrated for example, in FIGS. 59 and 60. The guidewire can then be left in place, across the tricuspid valve annulus, or the tissue near the tricuspid valve annulus, while the stabilizing catheter is retracted or removed from the tissue, leaving the guidewire in place across the tissue. See example illustrated in FIG. 61. The guidewire can then be used as a rail for passing additional catheters or devices across the tissue from the right atrium into the right ventricle, such as for the deployment of surface anchors embodiments as disclosed herein. This method and apparatus for crossing tissue with the guidewire can be incorporated into the procedures illustrated in FIGS. 14 through 24 to more easily facilitate crossing the tricuspid annulus, or the interatrial septum, with the anchor delivery catheter 226 and dilator 224.

In some applications the stabilizing catheter features a helical wire coil on the distal end of the stabilizing catheter to facilitate screwing the distal end of the stabilizing catheter into the tissue, examples of which are illustrated in FIGS. 52 through 57, 59 through 60, and 62 through 65. The stabilizing catheter can provide, but is not limited to providing, the following unique advantages: 1) By using a rotational motion and applying torque to the stabilizing catheter to pierce the tissue at the target location, significant force (force is approximately proportional to torque applied divided by the radius of the catheter's distal helix) can be generated at a sharpened tip of the stabilizing catheter to quickly penetrate the tissue 2) By rotating a helical wire coil into the tissue the resultant force vector at the tip of the stabilizing catheter is acute with respect to the axis of the stabilizing catheter which can minimize deflection of the tissue and stabilizing catheter relative to each other when penetrating the tissue since there is minimal compressive force applied along the axis of the stabilizing catheter 3) Once the distal helical coil of the stabilizing catheter penetrates tissue, continued rotation of the stabilizing catheter generates a normal force on the surface of the helical coil with a force component in the direction of the stabilizing catheter axis that drives the helix deeper into the tissue 4) Once the distal helix of the stabilizing catheter is embedded in the tissue it's location relative to the tissue is fixed and it is able to resist translational forces and shear forces in any direction 5) Once the distal helix of the stabilizing catheter is embedded in the tissue the stabilizing catheter provides a conduit which can direct a guidewire to the distal tip of the stabilizing catheter and support the guidewire from bending, buckling, skiving or deflecting off course when passing through the tissue. 6) The stabilizing catheter can be easily removed by rotation in the direction opposite to the direction for rotation. 7) The use of a helical wound wire at the distal end of the stabilizing catheter minimizes trauma to the tissue, leaving only a small puncture the diameter of the wire. These advantages, discretely or in combination with each other, make it easier to pass a guidewire through a precise location in moving tissues of a beating heart.

The present disclosure is not limited to crossing the tricuspid valve annulus 52 from the right atrium 2 to the right ventricle 3 but can be used as a technique for crossing between any two adjacent chambers of the heart which can include from the right atrium 2 to the left atrium 3, the right ventricle 3 to the left ventricle 5, the right ventricle 3 to the right atrium 2, the left atrium 4 to the right atrium 2, the left ventricle 5 to the right ventricle 3, the left atrium 4 to the left ventricle 3 (near or across the mitral valve annulus 15), the left ventricle 5 to the right ventricle 3 (near or across the mitral valve annulus 15) or the heart ventricles or atriums to the pericardial space. The present disclosure can furthermore be incorporated as a technique for crossing other tissues within the body outside of the heart.

In certain embodiments the steps for passing a guidewire through a treatment area can include one or more of the following steps:

First, guiding a guide catheter 5500 into the venous system at the groin.

Then, tracking of the guiding catheter 5500 through the IVC 50 to the right atrium 2.

Figure 58:
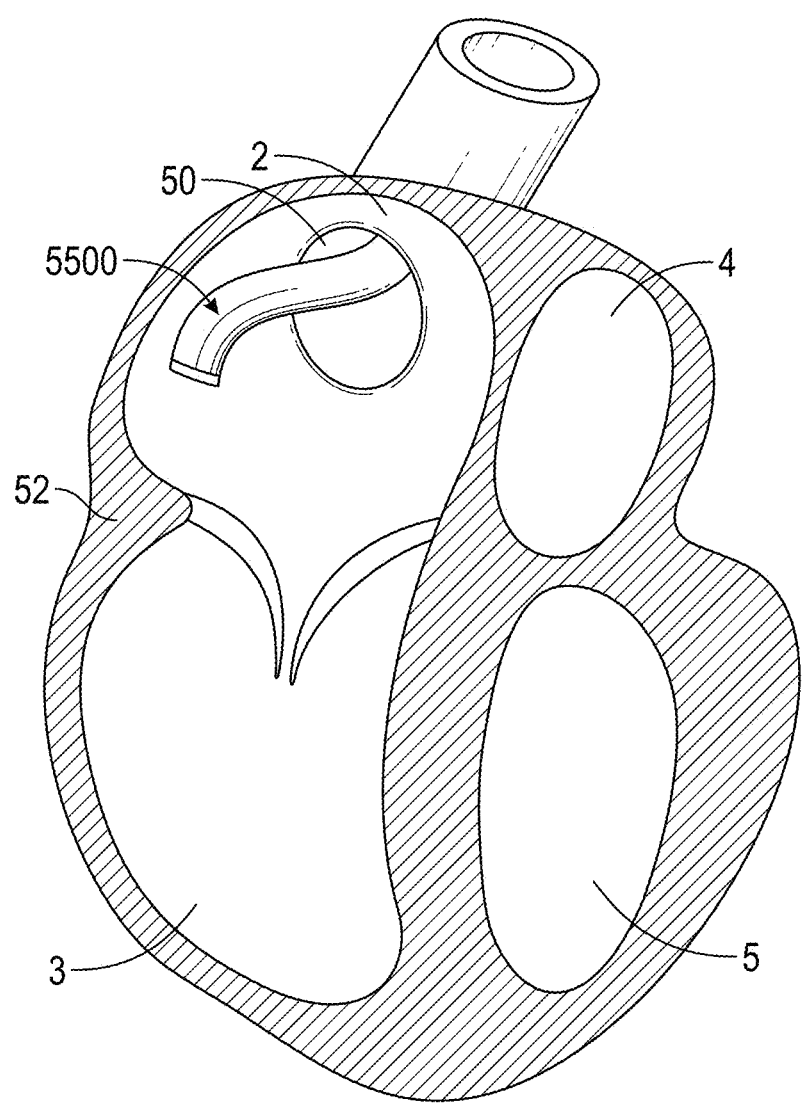
FIG. 58 illustrates a 4-chamber cross section of the heart with a guide catheter entering the right atrium from the IVC. The guide catheter is directed toward the anterior tricuspid valve annulus.

Then, positioning of the distal end of the guiding catheter 5500 at or near the tricuspid valve annulus 52, directed toward the intended treatment area as illustrated in FIG. 58.

The position of the guiding catheter 5500 can be within 30 millimeters of the tricuspid valve annulus 52.

Then, passing of a stabilizing catheter 5200 through the guiding catheter 5500, or extension of a stabilizing element out of the distal end of the guiding catheter 5500, until the helical distal end 5202 of the stabilizing catheter 5200 exits the guiding catheter 5500 and contacts the tissue at or near (within 20 millimeters) the tricuspid valve annulus 52 at the treatment area.

Then, applying forward pressure while rotating the stabilizing catheter to screw the distal end 5202 of the stabilizing catheter 5200 into the tissue at the treatment area as illustrated in FIG. 59. FIG. 59 illustrates a 4-chamber cross section of the heart 1 with a guide catheter 5500 in the right atrium 2 and a stabilizing catheter 5200 with a distal helix 5202 being directed by the guide catheter 5500 to a location near the anterior tricuspid valve annulus 52, where the helix 5202 is being screwed into the tissue by applying torque to the stabilizing catheter 5200.

Then, once the stabilizing catheter 5200 is securely attached to the tissue, passing a guidewire 5212 through the stabilizing catheter 5200 until the distal tip of the guidewire 5212 contacts the tissue where the stabilizing catheter 5200 is imbedded.

Then, pushing the guidewire 5212 through the tissue until it exits the tissue into the right ventricle 3 as illustrated in FIG. 60. FIG. 60 illustrates a 4-chamber cross section for the heart 1 with the guide catheter 5200 and stabilizing catheter 5500 illustrated in FIG. 59 and a guidewire 5212 passing through the stabilizing catheter 5500 and through the tissue near the anterior tricuspid valve annulus 52 into the right ventricle 3. In some embodiments, an alternating current is passed through the guidewire 5212 at this step to heat the distal tip and reduce the force to pass the guidewire through the tissue.

Then, removing the stabilizing catheter 5200 from the tissue by rotating the stabilizing catheter 5200 in the direction opposite to that used for insertion into the tissue.

Figure 61:
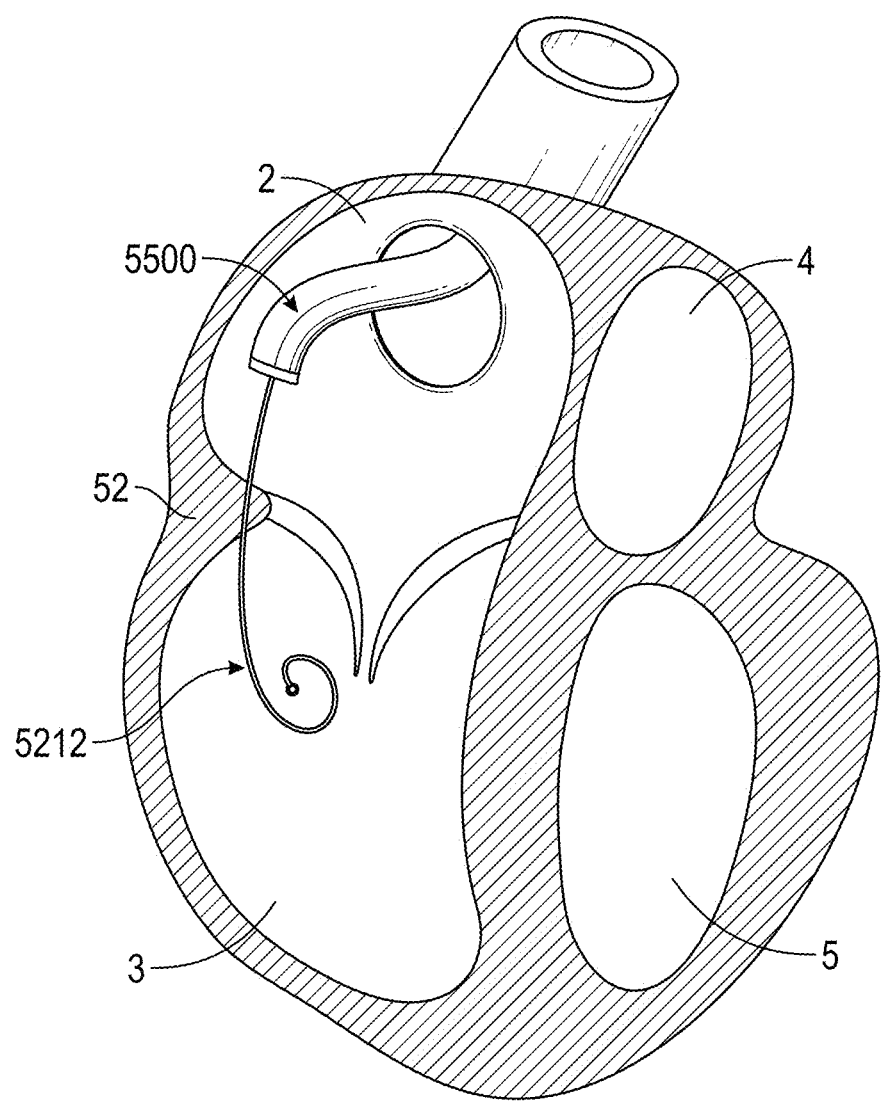
FIG. 61 illustrates a 4-chamber cross section of the heart with a guide catheter in the right atrium and a guidewire passing through the tissue at or near the anterior tricuspid valve annulus, from the right atrium to the right ventricle. The stabilizing catheter illustrated in FIGS. 59 and 60 has been withdrawn.
Figure 62:
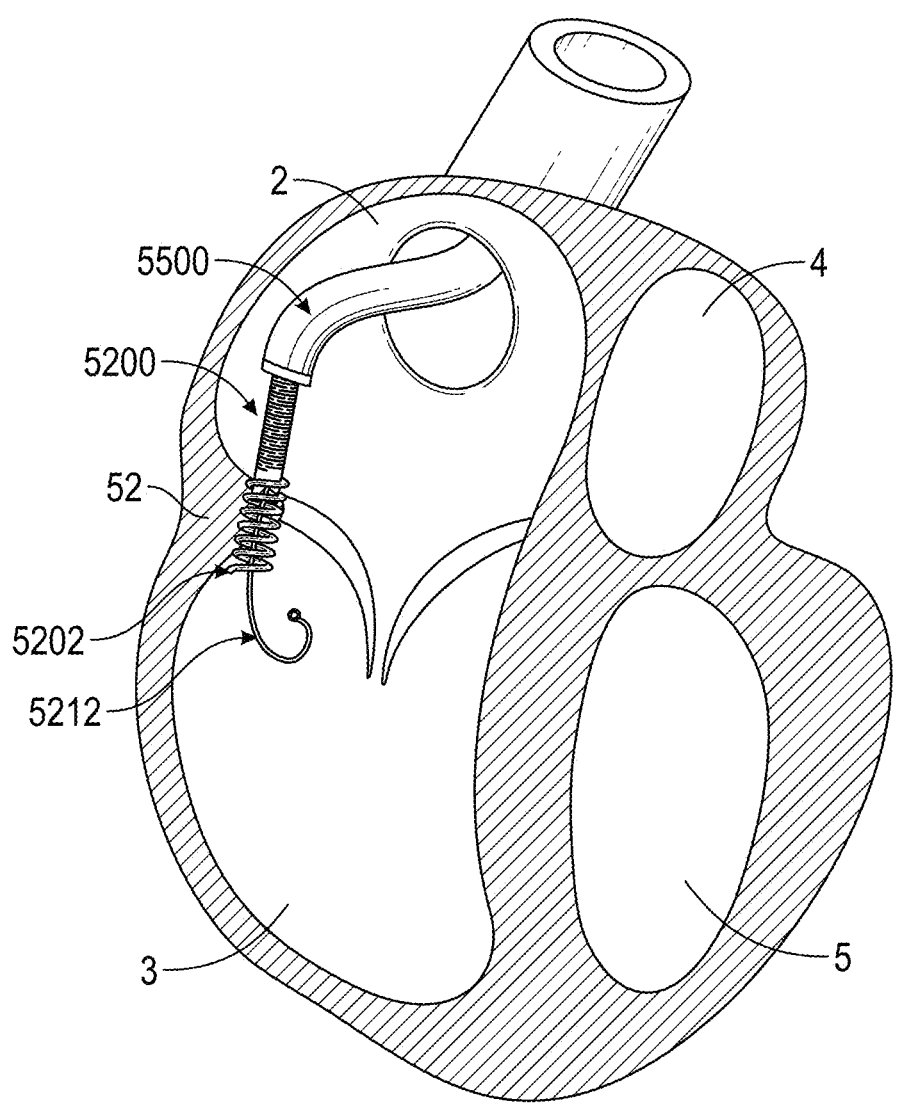
FIG. 62 illustrates a 4-chamber cross section of the heart with a guide catheter in the right atrium directing a stabilizing catheter to a location at or near the anterior tricuspid valve annulus. The distal helix of the stabilizing catheter has been screwed through the tissue such that it exits into the right ventricle and a guidewire is illustrated passing through the stabilizing catheter into the right ventricle.

Then finally, removal or retraction of the stabilizing catheter 5200 while leaving the guidewire in place across the tissue from the right atrium 2 to the right ventricle 3 as illustrated in FIG. 61. FIG. 61 illustrates a 4-chamber cross section of the heart 1 with a guide catheter 5500 in the right atrium 2 and a guidewire 5212 passing through the tissue at or near the anterior tricuspid valve annulus 52, from the right atrium 2 to the right ventricle 3. The stabilizing catheter illustrated in FIGS. 59 and 60 has been withdrawn.

Figure 52:
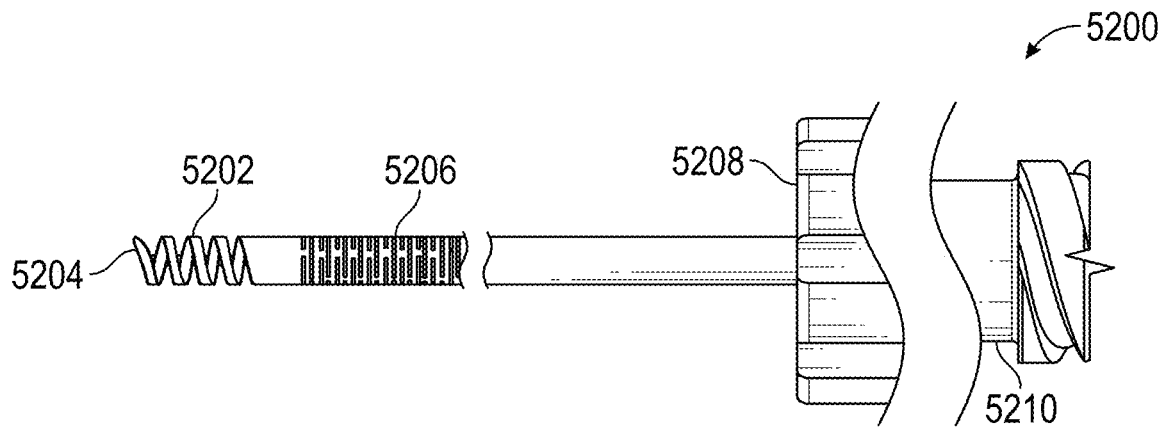
FIG. 52 illustrates a stabilizing catheter having a distal helix with a pointed tip that is laser cut from a solid tube. Immediately proximal to the helix is a flexible region created by laser cutting interrupted slots into the tube. The most proximal region of the catheter is shown with a handle to apply torque and/or translation and a hub to accept a hemostasis valve or other accessories.
Figure 53:
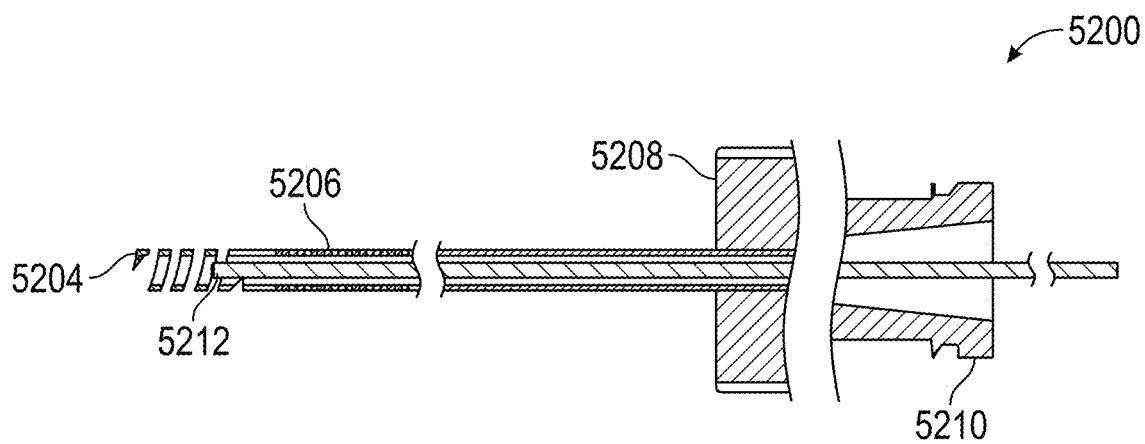
FIG. 53 illustrates a cross sectional view of the stabilizing catheter illustrated in FIG. 1 showing a guidewire through the ID of the stabilizing catheter.

In some embodiments of the present disclosure a stabilizing catheter comprises a catheter with a distal tip constructed of a helical shaped wire attached to or transitioning to a substantially tubular catheter with an inner diameter and an outer diameter, such as the embodiment depicted in FIGS. 52 through 56. A handle 5208 could be attached near the proximal end of the stabilizing catheter 5200 to provide an area for a user to grip the catheter and apply torque or translation to the catheter as illustrated in FIGS. 52 and 53. The distal helical wire 5202 can be between 2 millimeters and 10 millimeters in length, but could be any length suitable for screwing into the desired tissue. The pitch of the helix 5202 could be between 10 and 40 revolutions per inch and the wire diameter could be from 10 to 30 thousandths of an inch. The outer diameter of the helix could be from 40 to 156 thousandths of an inch. The distal tip 5204 of the helical wire 5202 can be sharpened into a point in order to more easily penetrate tissue when the tip is pressed against tissue due to the increased contact stress exerted from the reduced surface area of the tip. When the tip 5204 of the distal helix 5202 of the catheter is pressed against tissue and a torque is applied to the catheter a force is imparted between the tip 5204 of the helix 5202 and the tissue that is approximately proportional to the torque applied divided by the radius of the helix. This force causes the helix to penetrate the surface of the tissue (the endocardial layer) and to continue penetrating the tissue (through the myocardium) in front of the helix tip. Continuing to rotate the catheter once the helix tip has penetrated the tissue imparts a force along the axis of the helix that pulls the helix further into the tissue. Thus, the helical end of the catheter screws into the tissue.

Figure 54:
FIG. 54 illustrates the distal end of a stabilizing catheter having a helical wire with sharpened tip welded to a catheter main body of tubular construction with interrupted laser cut slots to provide flexibility while maintaining torsional stiffness.
Figure 55:
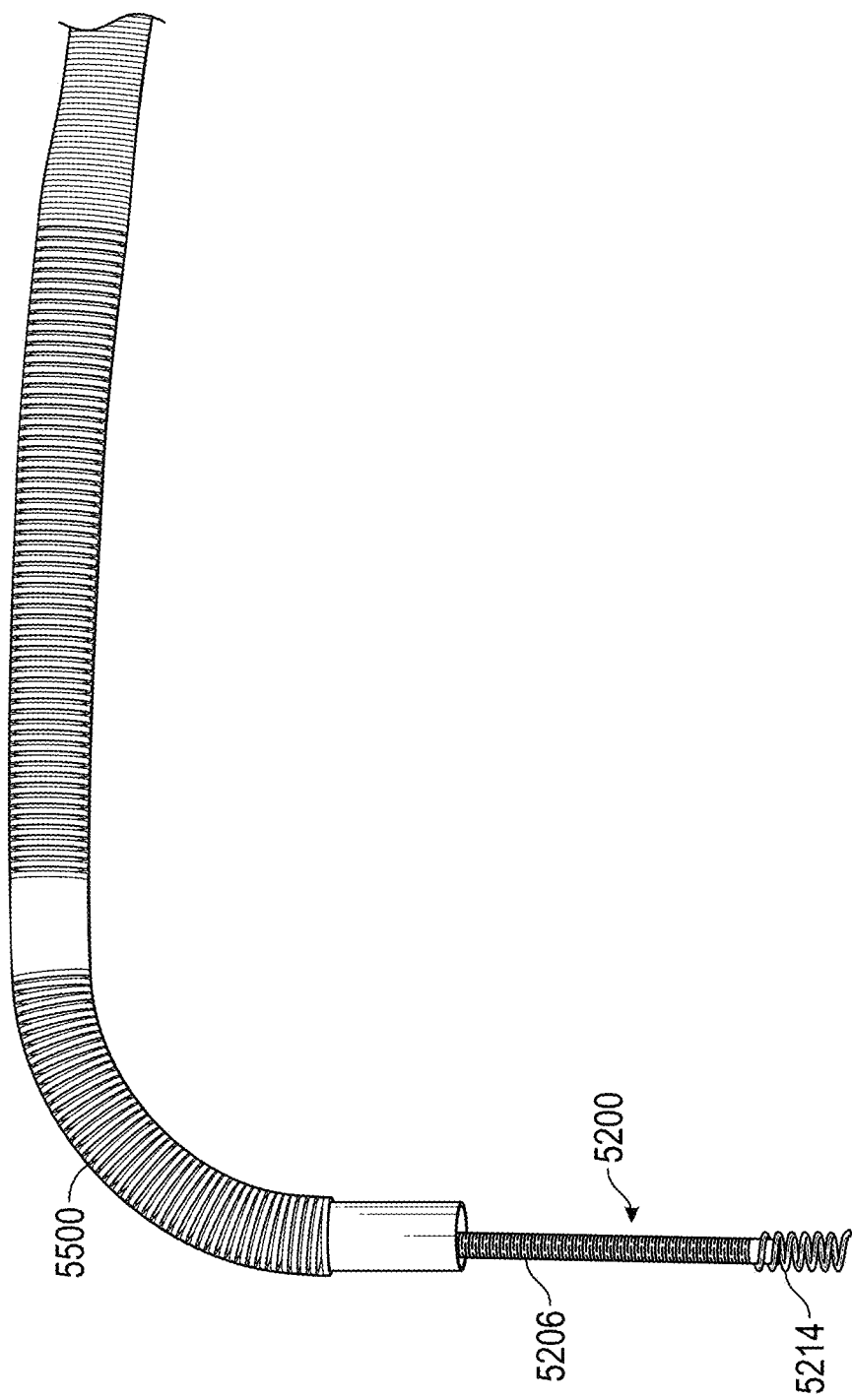
FIG. 55 illustrates the stabilizing catheter illustrated in FIG. 54, passing through a guiding catheter.
Figure 56:
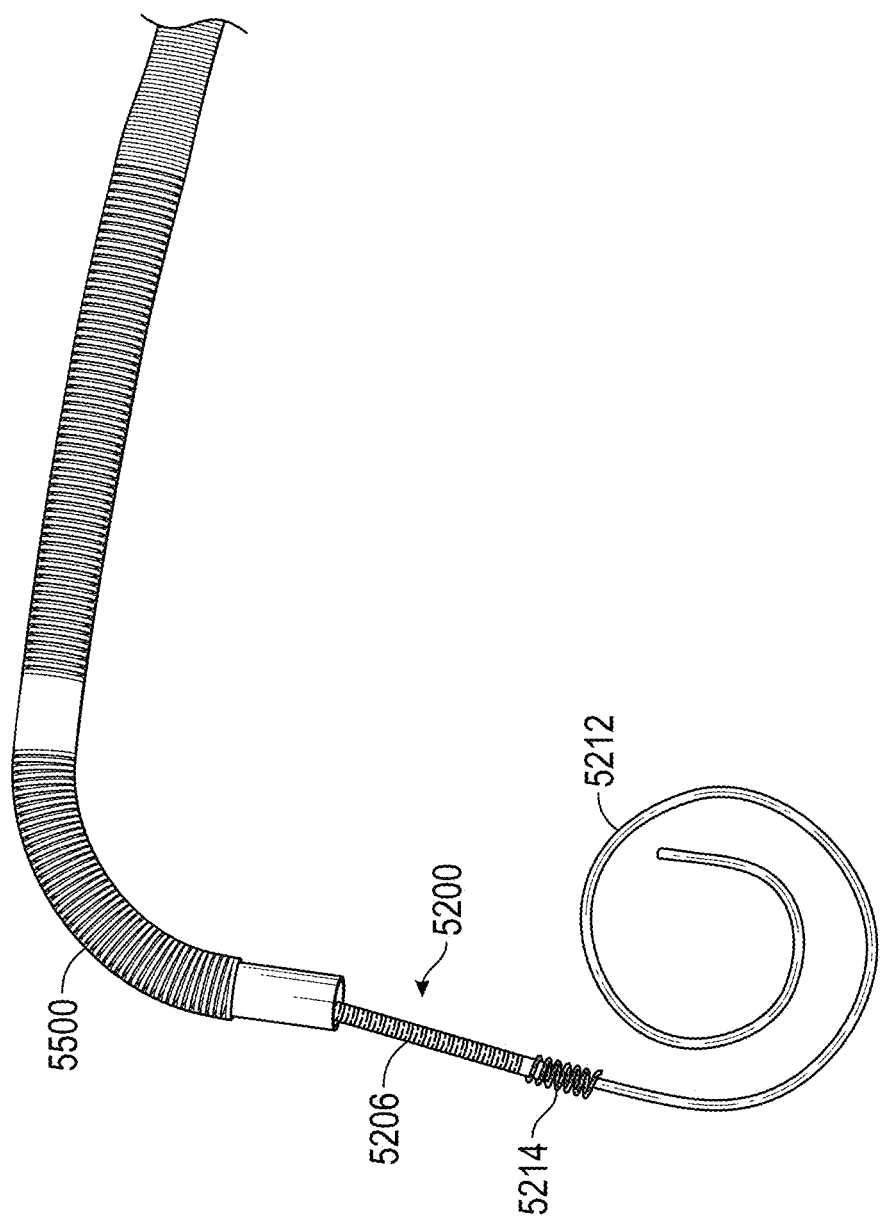
FIG. 56 illustrates the stabilizing catheter and guide catheter illustrated in FIG. 55 with a guidewire extended out the distal end.

The helical wire 5202 forming the distal end of the stabilizing catheter could be constructed from metal suitable for direct contact with the blood stream within the human body. Examples include stainless steel, titanium, nitinol, and tungsten. The inner diameter of the helix is sufficient for a guidewire to pass through. The helical wire can be of substantially round, circular, square, rectangular, or trapezoidal construction or any cross-sectional shape suitable for the manufacture of the helix. Alternatively, the helical wire could be constructed from rigid plastic, such as peek, composite material such as carbon fiber or ceramic material. The wound wire helix 5214 can be constructed as a separate component that is attached to the distal end of the stabilizing catheter by welding (as illustrated in FIG. 54), soldering, crimping, mechanical interlock connection, adhesives, or other processes as desired or required. Alternatively, the helical wire could be laser cut from the stabilizer catheter tubing as illustrated in FIG. 52. The helix 5202 can form an outer diameter that is approximately equal to the outer diameter of the stabilizing catheter shaft, as illustrated by example in FIGS. 52 and 53, or it can form an outer diameter that is larger (see example illustrated in FIG. 54) or smaller than the shaft of the stabilizing catheter. Constructing the stabilizing catheter with a helical coil larger than the diameter of the main catheter shaft can help to reduce the torque to pass the stabilizing catheter main shaft completely through the tissue as illustrated by example in FIG. 63. In some embodiments disclosed within the helix can comprise 2 or more helically wound wires, such as the double helix 6400 within FIG. 64, to increase the lead of the helix without changing the surface area of the wire relative to a single wire helix of equivalent pitch. In other embodiments disclosed within, the helix can taper outward, such as the taper helix 6500 in FIG. 65, or inward to create a squeezing effect as the helix is screwed into tissue which could enhance retention of the tissue. In some embodiments, all or a portion of the guidewire or the helix can have a circular cross section; in other embodiments, the cross section could be rectangular or trapezoidal. An outward tapered helix can provide more clearance for the guidewire as it advances through tissue in the center of the helix.

Figure 57:
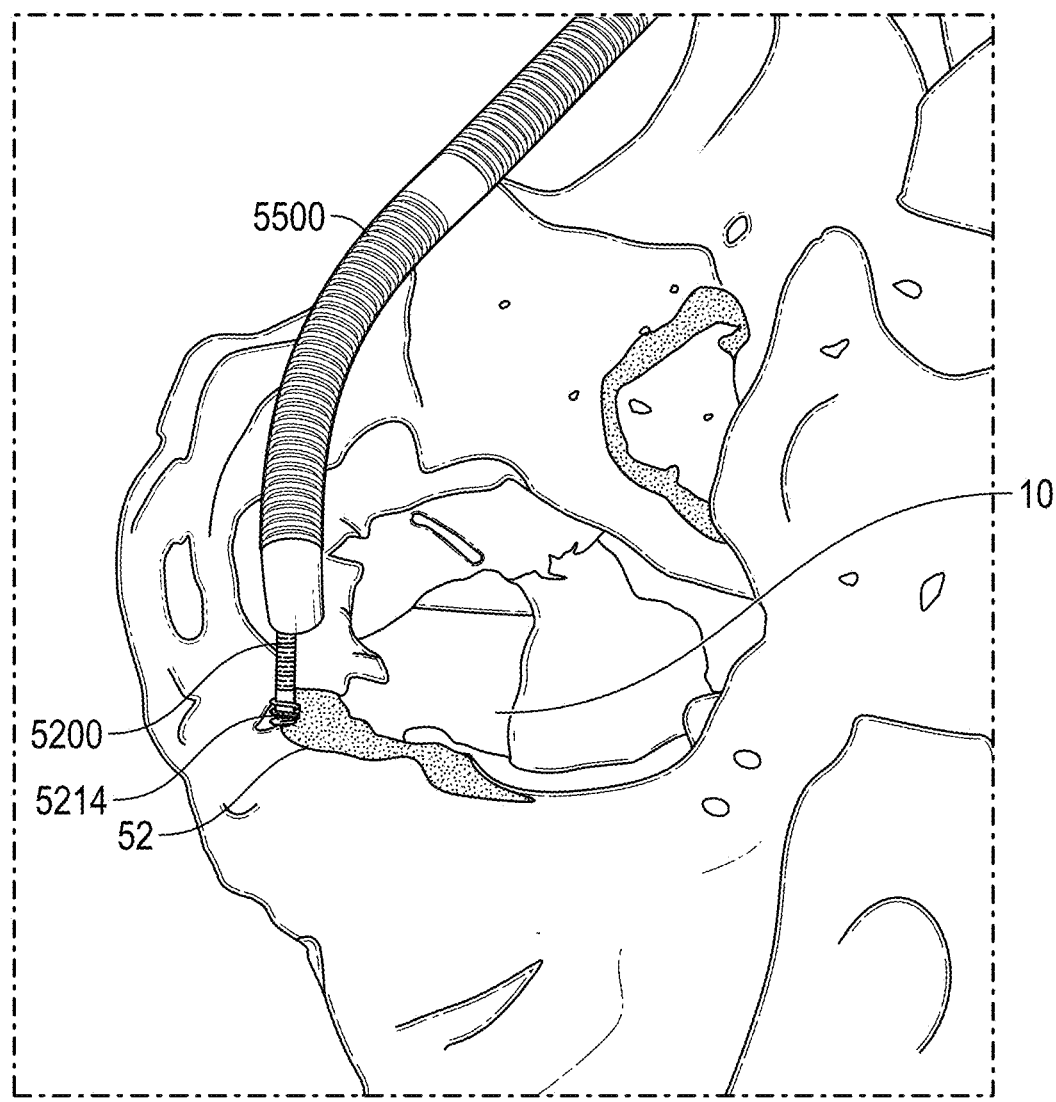
FIG. 57 illustrates the stabilizing catheter and guide catheter illustrated in FIG. 56 in the right atrium of a human heart model. The helix of the stabilizing catheter is screwed into the model near the anterior tricuspid annulus from the right atrial side.

FIG. 57 illustrates a stabilizing catheter such as the stabilizing catheter 5200 and guide catheter 5500 disclosed herein in the right atrium 3 of a human heart 1. The helix 5202 of the stabilizing catheter 5200 is screwed into the heart near the anterior tricuspid annulus 52 from the right atrial side.

The shaft of the stabilizing catheter 5200 can be constructed to be flexible in bending with relatively high torsional stiffness. Examples of suitable constructions are laser cut metallic tubing, multiple fillar hollow helical stranded wire or cable and braid wire re-enforced polymer. This type of construction allows the stabilizing catheter to navigate tortuous pathways and to transmit torque through curved or tortuous pathways. The internal diameter of the stabilizing catheter is such that it is slightly larger than the outside diameter of the intended guidewire in order to allow unrestricted movement of the guidewire through the stabilizing catheter. When the shaft of the stabilizing catheter is constructed of metal, the outside diameter of the stabilizing catheter can be covered with polymer such as polyether block amide (PEBA), polyamide (Nylon), polyimide, polytetraflouroethylene (PTFE), fluorinated ethylene propylene (FEP) or any other polymer suitable for direct contact with the bloodstream. The polymer outer covering can be implemented to reduce friction, provide a hemostatic seal between the inner diameter and the outer diameter of the catheter or provide electrical isolation. When the shaft of the stabilizing catheter is constructed of metal, the inner diameter can also be constructed from a polymer layer in order to reduce friction, provide a hemostatic seal between the inner diameter and the outer diameter or provide electrical isolation.

In some embodiments of the present disclosure the stabilizing catheter 5200 can be designed as a permanent component of a guiding catheter 5500 that telescopes in and out the distal tip of the guiding catheter. In other embodiments the stabilizing catheter 5200 is a separate component that can be inserted through the guiding catheter and removed completely from the guiding catheter, such as in FIGS. 55 through 57.

Figure 63:
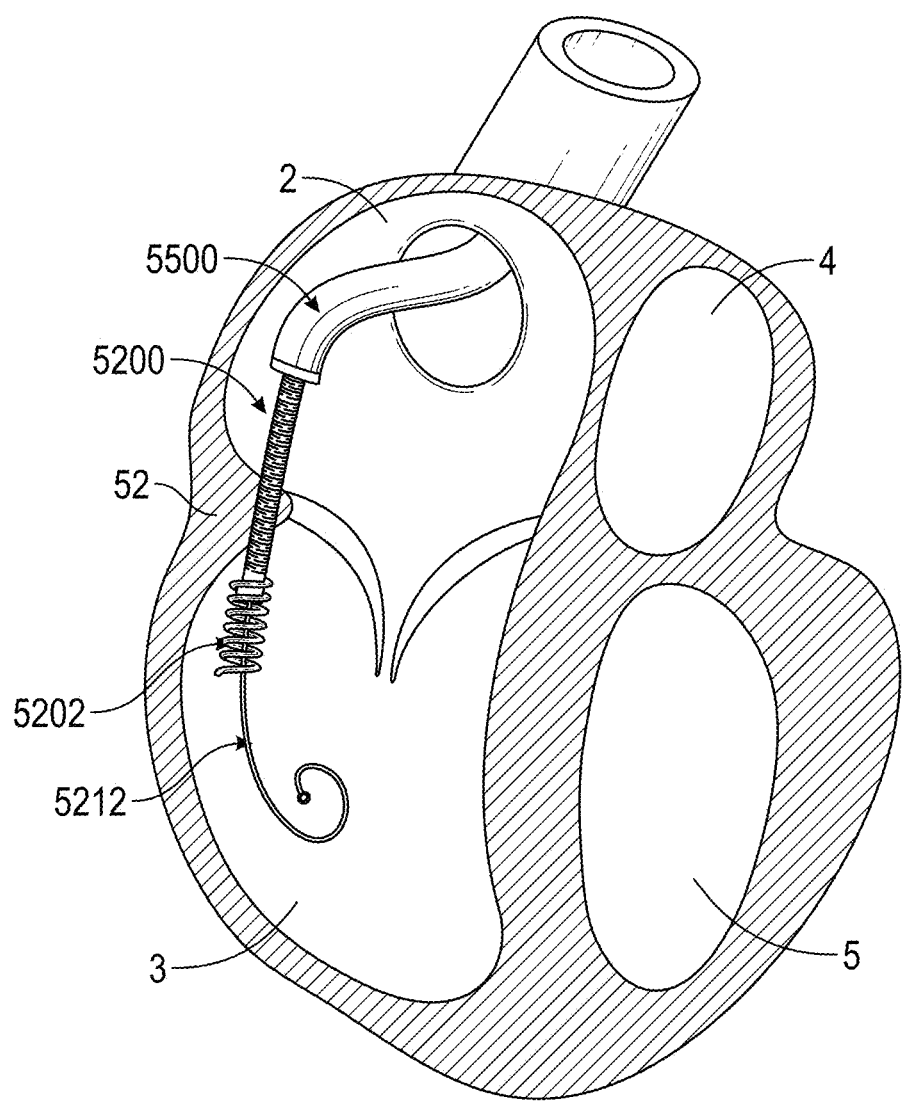
FIG. 63 illustrates a 4-chamber cross section of the heart with the guide catheter, stabilizing catheter and guidewire illustrated in FIG. 62 except that the distal helix of the stabilizing catheter has been screwed completely through the tissue such that the main shaft of the stabilizing catheter exits into the right ventricle.
Figure 64:
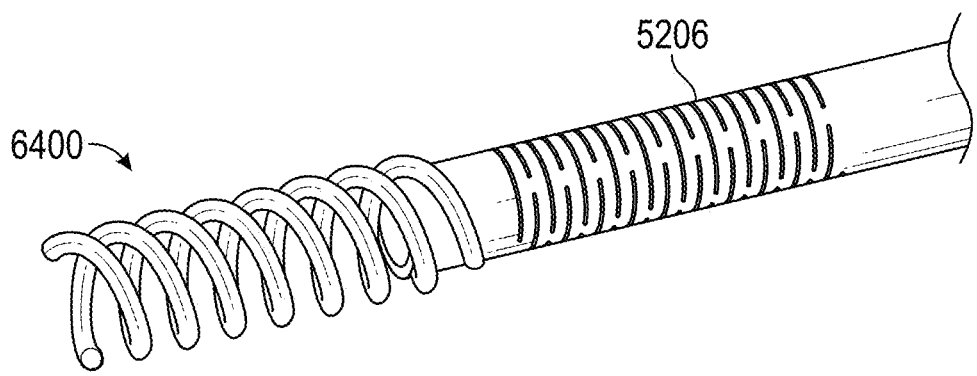
FIG. 64 illustrates a stabilizing catheter having a distal helix constructed of 2 helical wound wires 180 degrees apart.
Figure 65:
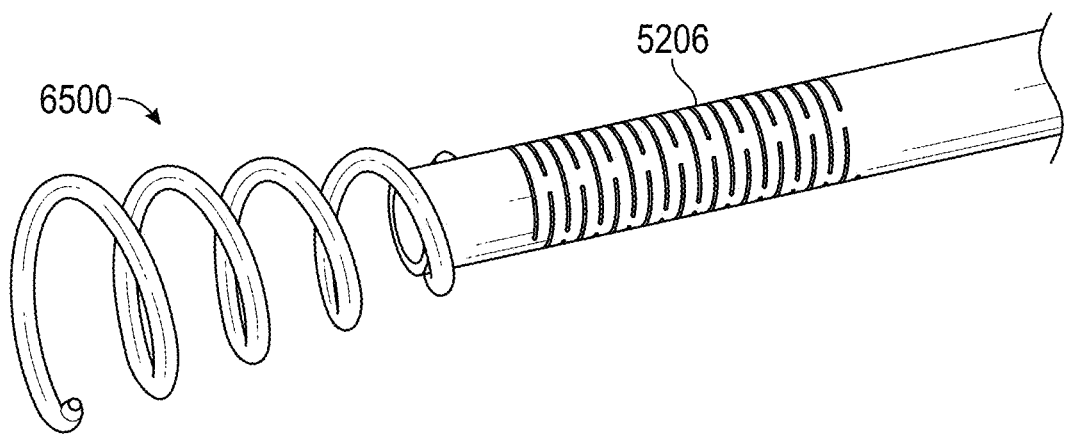
FIG. 65 illustrates a stabilizing catheter having a distal helix that tapers outward from a smaller outer and inner diameter at the junction to the catheter main body to a larger inner and outer diameter near the tip.

In some embodiments of the present disclosure the helix 5202 of the stabilizing catheter can be screwed completely through the tissue that is being crossed such that the stabilizing catheter enters one side of the tissue and exits the opposite side of the tissue and the guidewire can henceforth be passed unobstructed through the stabilizing catheter from one side of the tissue to the other, as in FIG. 63. This step can be performed after the step performed in FIG. 59, as disclosed herein. For example, when crossing the tricuspid valve annulus, the helix 5202 can be screwed from the right atrium 2, through the tissue at or near the tricuspid valve annulus 52 and into the right ventricle 3. In other embodiments, the helix 5202 is only screwed partially through the tissue and the guidewire 5212 must be pushed through the remaining tissue in order to cross the tissue, as in FIG. 60. In such instances, the stabilizing catheter 5200 provides a conduit through which the guidewire 5212 passes that can counteract the force exerted by the tissue on the wire and prevent the tissue from pushing away from the wire. The stabilizing catheter 5500 also prevents the guidewire 5212 from buckling, bending, bowing, or skiving under the compressive force required to cross the tissue due to a combination of the additional bending stiffness provided by the stabilizing catheter and due to the ability of the stabilizing catheter 5200 to be pulled in tension to offset the compressive load on the guidewire.

In some embodiments of the present disclosure, the guidewire 5212 can be constructed of electrically conductive material, such as stainless steel, titanium, nitinol, or tungsten and insulated with an electrically insulative polymer such as PTFE, FEP, polyimide or PEBA. The distal tip of the guidewire can be uninsulated, thus forming an electrode. When a high frequency electrical current is applied to the guidewire 5212 from a signal generator with a return path through the patient's body, an electrical discharge is generated at the uninsulated tip which causes the tip of the guidewire to heat rapidly and pass through tissue with less force. Voltage is typically applied to the wire in the radiofrequency range. Commercially available guidewires such as those manufactured by Baylis Medical Inc. are available for such use. Alternatively, the distal tip of the guidewire 5212 can be shaped to assist in mechanically penetrating through tissue, under force alone. The tip of the guidewire can be sharpened into a point to reduce the force necessary to cross the tissue.

Figure 66:
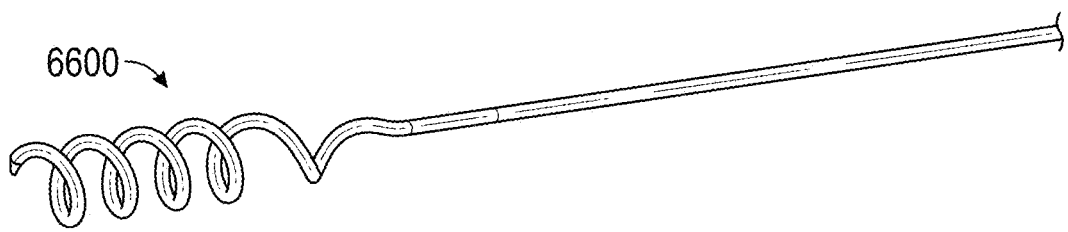
FIG. 66 illustrates a guidewire having the distal end wound into a helix and transitioning to a straight wire.

In another embodiment of the present disclosure the guidewire itself can be constructed with a helical wound wire at the distal tip, as depicted in FIG. 66. This guidewire 6600 can be screwed into tissue in the same manner as a stabilizing catheter 5200 with helical distal end already described and offers the same advantages for engaging tissue within a beating heart. The helical end of the wire 6600 could be formed by mechanically winding the wire itself or by attaching a separate helical wound wire to the guidewire by, for example, welding, soldering, mechanical interlock or adhesive bonding. The guidewire with helically wound tip 6600 can be screwed completely through the tissue and once the helix exits the tissue into the chamber adjacent to the where it originates, it can be pushed freely into such chamber and act as a rail for passing additional devices. Suitable materials of construction are metals suitable for contact with the blood stream. Examples include stainless steel, titanium, nitinol, and tungsten. An advantage of forming a helix on the guidewire is elimination of extra steps for introducing and removing a stabilizing catheter such as stabilizing catheter 5200.

Figure 67:
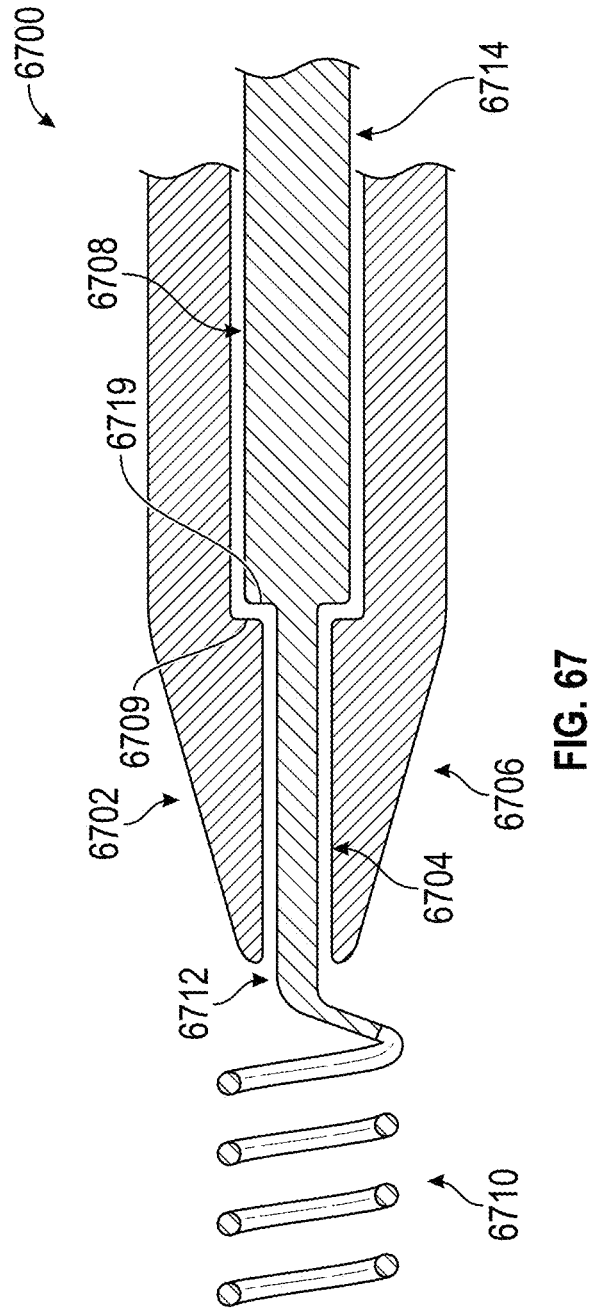
FIG. 67 illustrates a cross section of a dilator having a smaller distal inner diameter and a larger proximal inner diameter with a guidewire inside the dilator having a distal end wound into a helix, a section immediately proximal the distal end of a smaller diameter and a more proximal section of a larger diameter. The guidewire is hence captured in the dilator.

FIG. 67 depicts a cross-sectional view of a dilation system 6700 comprising a dilator 6702 and helical guidewire 6710 similar to the helical guidewire 6600 of FIG. 66. The guidewire 6710 can have a relatively smaller diameter 6712 which is followed by a straight section of relatively larger diameter 6708. Such a guidewire can be assembled into a dilator 6702 which has a tapered distal end 6706 with a smaller internal diameter 6704 that transitions to a larger internal diameter 6708 proximal to the distal tip such that the smaller diameter straight section of the guidewire is captured in the smaller inner diameter of the dilator by a dilator shoulder 6709 as illustrated in FIG. 67. As the guidewire 6710 is screwed into tissue the shoulder 6719 formed at the transition from smaller diameter 6712 to larger diameter 6714 of the guidewire will push against the corresponding shoulder 6709 between the smaller internal diameter 6704 and larger internal diameter 6708 of the dilator which will in turn push the dilator 6702 through the tissue following the guidewire 6710. In an alternative construction, the dilator can be permanently bonded or fixed to the guidewire such that the dilator and guidewire act as a single component and rotation of the dilator causes rotation of the guidewire, hence by rotating the dilator it can be screwed through tissue.

Figure 68:
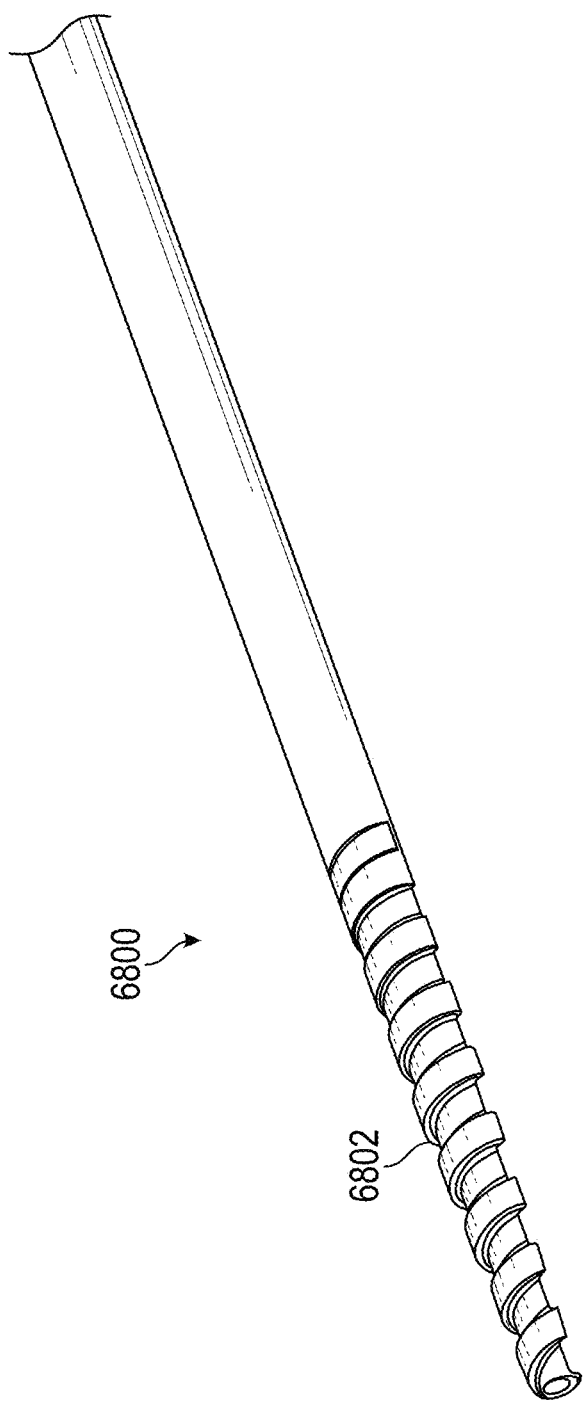
FIG. 68 illustrates a dilator having a thread formed in the distal tapered section.

In another embodiment of the present disclosure a dilator 6800 is constructed with a helical thread 6802 cut into the distal taper of the dilator as illustrated in FIG. 68. When passing the dilator through tissue, rotation of the dilator generates a force imparted against the lead of the thread acting in the direction of the dilator axis that pulls the dilator through the tissue, thus making passage through the tissue easier than pushing alone. The dilator could be constructed from polymeric material such as PEBA, high or low density polyethylene, nylon or other suitable polymers and could be re-enforced with metallic or polymer braid, laser cut metallic tubing or other suitable materials to increase torsional stiffness.

In some applications of the present disclosure systems are described for facilitating the implant of anchors in tissue at or near (within 15 millimeters) a tricuspid valve annulus, from the right atrium into the right ventricle, by first attaching or embedding the distal end of a stabilizing catheter in the tissue at or near the tricuspid valve annulus from the right atrial side and second passing a guidewire through the stabilizing catheter which will exit the distal end of the stabilizing catheter and pass through tissue at or near the tricuspid valve annulus from the right atrium into the right ventricle. The systems vary as desired or required, and can include a multitude of anchors, a multitude of tethers, and a multitude of tether locks.

Figure 69C:
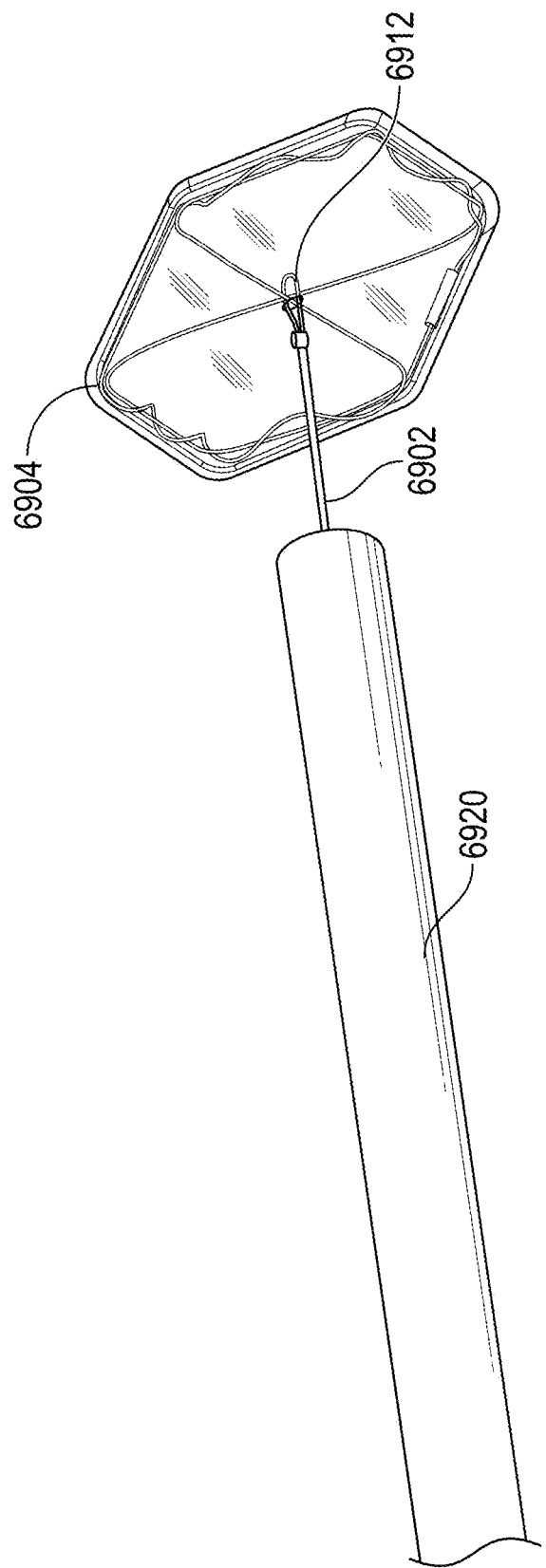
FIG. 69C illustrates the surface anchor element from FIG. 69B after it has been deployed from its delivery catheter.

FIGS. 69A through 69C illustrate an embodiment of a surface anchor system 6900 usable in a method for tricuspid valve repair. Referencing FIG. 69A, the surface anchor system 6900 is composed of a nitinol wire frame 6904 forming a perimeter and having a nitinol frame internal feature 6916 inside the perimeter, a surface anchor outer covering 6906 and a tether 6902 that is attached to the nitinol wire frame 6904 at the nitinol frame internal feature 6916 via a tether loop 6912 of the tether 6902 which is secured with a tether knot 6914. The nitinol frame internal feature 6916 is can be near the center of the area formed by the perimeter but could be at any location within the perimeter. The nitinol frame internal feature 6916 as depicted within FIG. 69A-C is shown as a cross-shape. The nitinol wire frame 6904 wraps around itself at a helical section 6910 along the perimeter of the frame formed by the nitinol wire such that when a force is applied to the nitinol frame, or a portion of the frame, the force is distributed throughout the frame. The surface anchor 6901 can be substantially similar to the anchor 3700 as described herein. The surface anchor 6901 is flexible such that it can assume a non-deployed configuration whereby it can be elongated and compressed for insertion into catheter 6920 with an inner diameter much smaller than the than the width of the unconstrained anchor as shown in FIG. 69B. When the surface anchor is pushed off the catheter and is no longer constrained, the strain energy of the nitinol frame is released and surface anchor 6901 converts from its non-deployed configuration as shown in FIG. 69B to its deployed configuration as shown in FIGS. 69A and 69C. Where the tether 6902 connects to the surface anchor 6901, the tether 6902 can pivot as the tether loop 6912 is connected to the surface anchor 6901 by a tether knot 6914. This allows the surface anchor 6901 to transition from its non-deployed configuration as shown in FIG. 69B where the tether axis is substantially parallel to the plane of the anchor to its deployed configuration as shown in FIGS. 69A and 69C where the tether axis is substantially perpendicular to the plane of the surface anchor, or at some angle other than parallel. If the surface anchor 6901 is passed through an orifice, such as passage or hole through body tissue, while attached to the tether 6902, then pulling the free end of the tether on the other side of the orifice will cause the surface anchor 6901 to be pulled against the opening of the orifice. The nitinol wire frame 6904 of the surface anchor 6901 can be heat set in its deployed state such that it will maintain its form when in an austenitic state. The austenite finish temperature (Af) of the nitinol can be such that when heated to body temperature (approximately 37° C.) the nitinol material transitions to an austenite crystal structure and returns to its deployed state. This can be heat-set into the deployed configuration as shown in FIGS. 69A and 69C such that when heated above its austenite finish temperature it naturally assumes the perimeter shape unless constrained. The free ends of nitinol wire frame 6904 can be joined with a surface anchor wire connector 6908 (e.g., a crimp connector). Alternatively, the free ends can be joined by other means, such as by welding. The surface anchor 6901 can be deployed from the catheter 6920 via a pushing catheter 122 that fits inside the catheter 6920 and when translated toward the distal end of the catheter 6920 contacts the surface anchor and pushes it out of the catheter 6920.

Figure 70A:
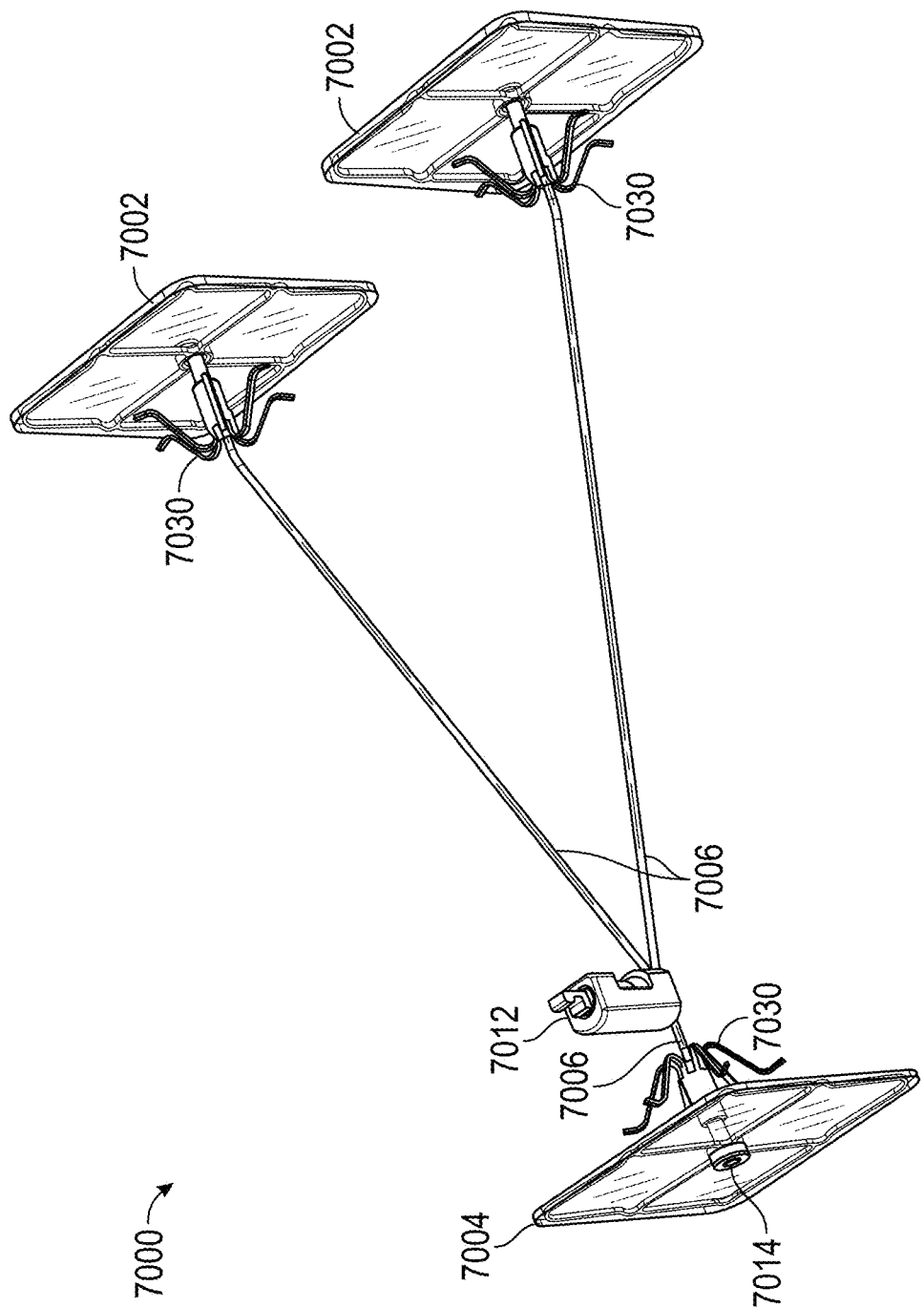
FIG. 70A illustrates an implant system comprising two anterior surface anchors and one septal surface anchor to be used as a tricuspid valve repair system.
Figure 70C:
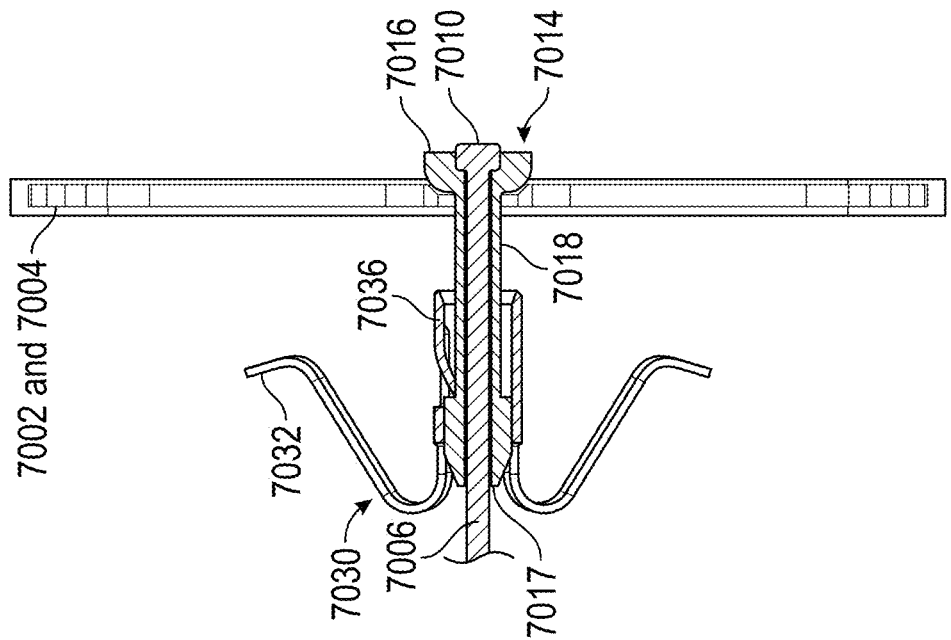
FIG. 70C illustrates a side cross-sectional view of the surface anchors including the grommet and anchor hub to retain the surface anchors to a patient.
Figure 70B:
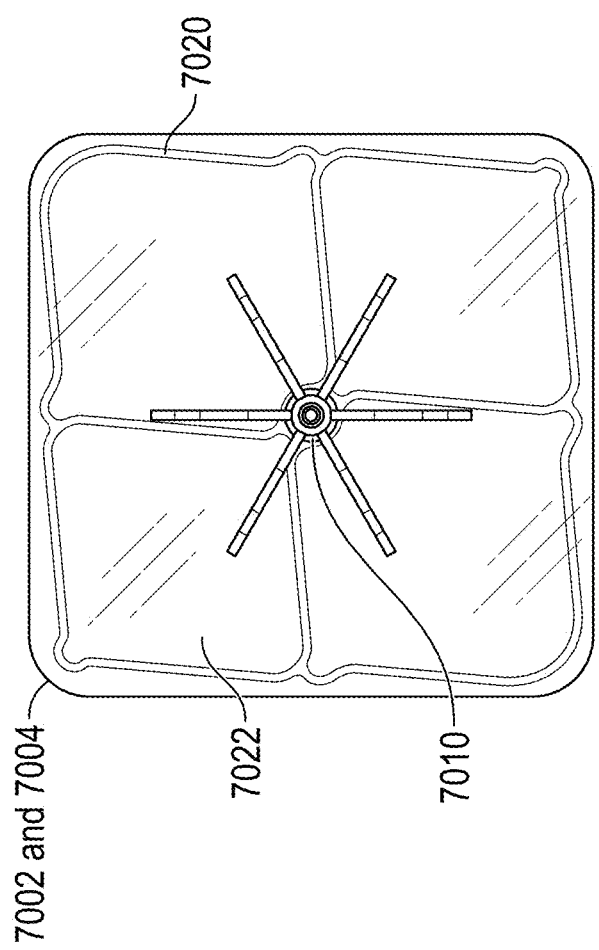
FIG. 70B illustrates the surface anchors from FIG. 70A to be used in the tricuspid valve repair system.
Figure 70D:
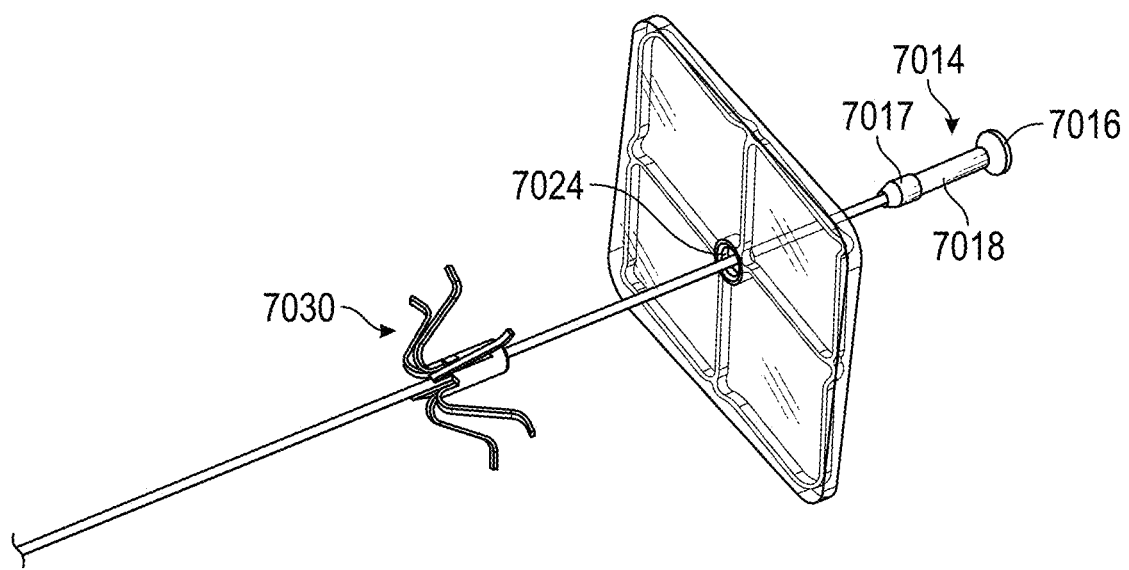
FIG. 70D illustrates one section of the implant system of FIG. 70A demonstrating the order of elements as the system is being deployed.
Figure 70G:
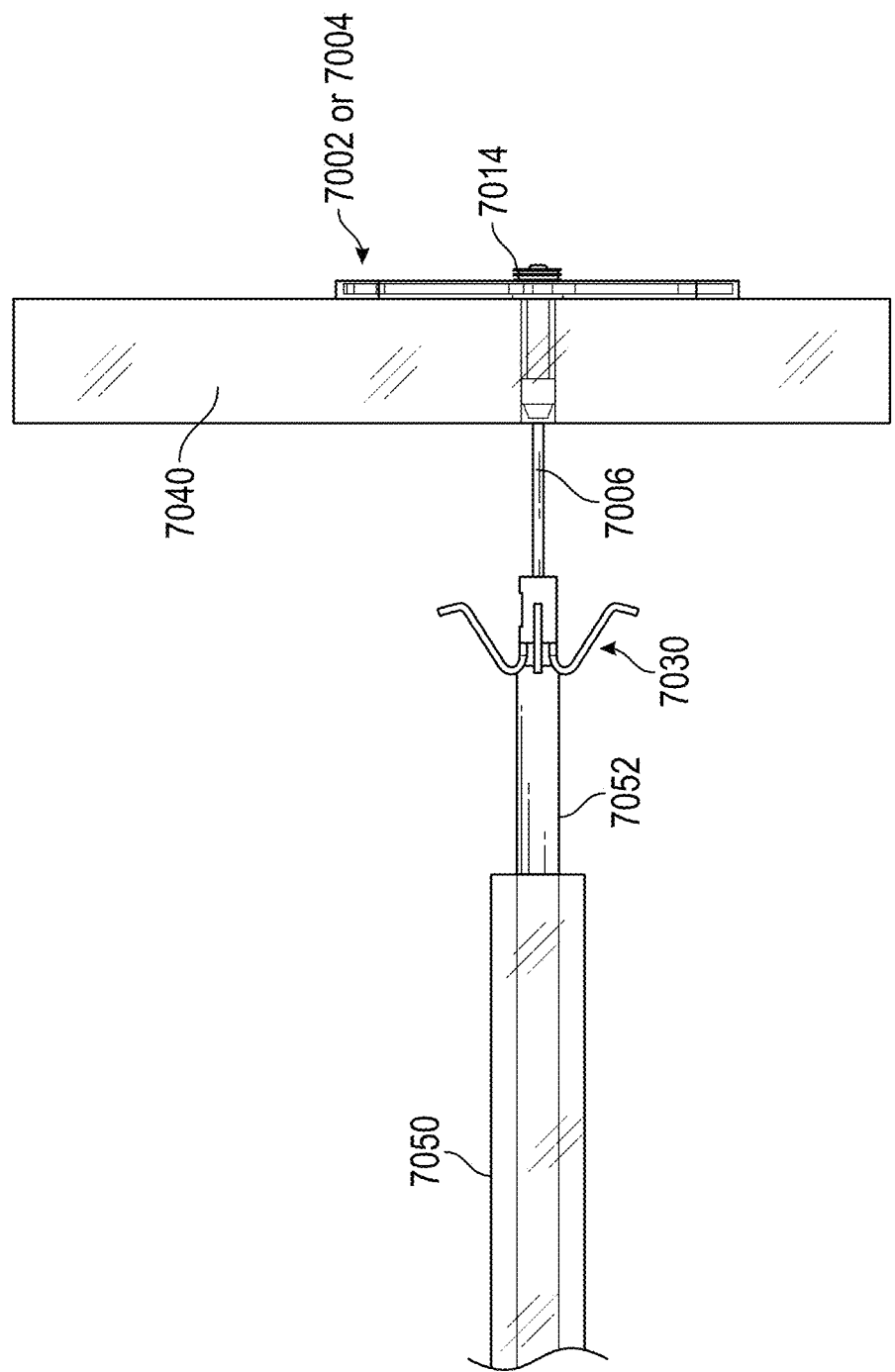
FIG. 70G illustrates one section of the implant system of FIG. 70A during its installation process to the patient after the step depicted in FIG. 70F.
Figure 70H:
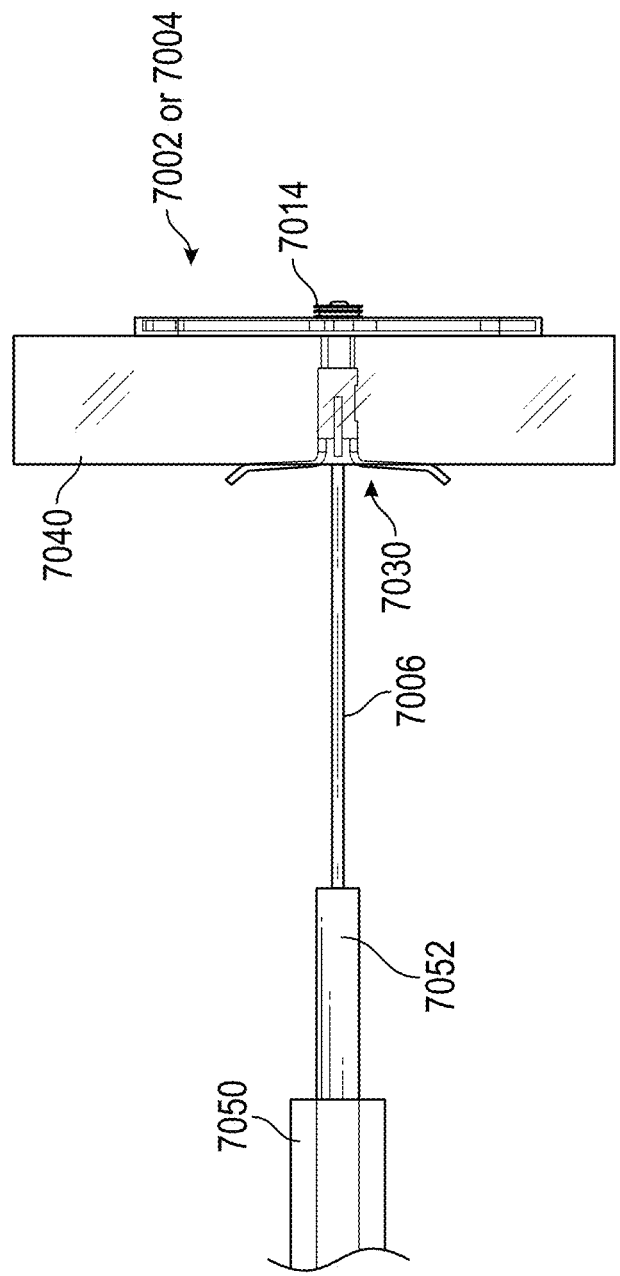
FIG. 70H illustrates one section of the implant system of FIG. 70A during its installation process to the patient after the step depicted in FIG. 70G.

FIG. 70A-70H illustrates an implant system 7000 comprising a plurality (2 shown) of anterior surface anchors 7002 connected to a septal surface anchor 7004 via tethers 7006 that engage each surface anchor with an attached surface anchor hub 7014. The tethers 7006 can be tensioned through the tether lock 7012, which pulls the anterior surface anchors 7002 toward the septal surface anchor 7004. When the surface anchors are engaged with tissue on either side of an annulus of a heart valve, such as the anterior surface anchors 7002 being engaged with the right ventricular surface of the anterior tricuspid valve annulus and the septal surface anchor 7004 being engaged with the left atrial septum, the tethers can be tensioned to decrease the distance between the anterior surface anchors 7002 and septal surface anchor 7004, which reduces the distance across the heart valve annulus and improves coaptation of the heart valve leaflets. FIG. 70A illustrates lockable tissue grommets 7030 which may be positioned on the surface of the tissue opposite to the surface where the anterior surface anchors 7002 and septal surface anchor 7004 are abutted and effectively lock the surface anchors 7002 and 7004 in place such that they cannot migrate in the absence of tension on the tethers. Thus, the tissue may be sandwiched between the surface anchor 7002 or 7004 and the lockable tissue grommets 7030 as illustrated in FIG. 70H and elaborated herein.

FIG. 70B illustrates a frontal view of the surface anchor of the anterior surface anchors 7002 and the septal surface anchor 7004. The surface anchor of 7002 and 7004 is composed of a nitinol frame 7020 which can be laser cut into a series of flexible struts which allow the surface anchor to be elongated and compressed, as described herein and illustrated in FIGS. 70E and 72C. The nitinol frame 7020 and be covered with a surface anchor outer covering 7022 which could comprise a fabric or solid elastic covering to promote sealing, healing and tissue ingrowth into the surface anchor. The anterior surface anchors 7002 and the septal surface anchor 7004 additionally comprise a hole 7024 located within the perimeter defined by the nitinol frame 7020, as depicted in FIG. 70D.

With reference to FIGS. 70C and 70D, the lockable tissue grommet 7030 non-fixably attaches, or locks, with the surface anchor hub 7014 to retain the anterior surface anchor 7002 or septal surface anchor 7004 against a surface of the heart. As shown in FIG. 70C, the tether 7006 may be passed through a central lumen passing through a central distal tubular portion of the tissue grommet 7030, an anterior surface anchor 7002 or septal surface anchor 7004 and the surface anchor hub 7014, then tied to form a tether knot 7010. Alternatively, the tether 7006 can be passed through those members then have a mechanical fastener placed at the end of the tether 7006 such that when the tether is tensioned the tether knot 7010 or attached fastener cannot pull through the lumen of the surface anchor hub 7014. The surface anchor hub 7014 can be constructed such that the distal end forms a surface anchor hub bell 7016 with a major diameter such that the surface anchor hub 7014 cannot pass through a hole 7024 in surface anchor 7002 or 7004. The surface anchor hub 7014 has a surface anchor hub nose or distal flange 7017 at its proximal end with a diameter smaller than the surface anchor hub bell 7016, but larger than the surface anchor hub midshaft 7018. The surface anchor hub nose or flange 7017 is sized such that when the surface anchor hub 7014 interacts with the tissue grommet 7030, a tissue grommet flexible retaining finger or central flexible beam 7036 which is located centrally on the tissue grommet 7030 oriented radially inward, and the surface anchor hub nose or flange 7017 interfere and substantially prevents the tissue grommet 7030 from moving longitudinally in the proximal direction, as elaborated herein. The surface anchor hub midshaft 7018 has a diameter smaller than the surface anchor hub bell 7016 or the surface anchor hub nose 7017 such that the central flexible beam 7036 can interact with a face of the surface anchor hub nose 7017 at a surface formed due to the difference in diameter between the dimension of the surface anchor hub nose 7017 and the dimension of the surface anchor hub midshaft 7018, thus retaining the tissue grommet 7030 and preventing proximal translation of the tissue grommet 7030 relative to the surface anchor hub 7014. The surface anchor tissue grommet 7030 can incorporate a tissue grommet central flexible beam 7036 that is pre-disposed into the internal diameter of the grommet. The tissue grommet flexible retaining finger or central flexible beam 7036 is dimensioned in such a way that the tip of the tissue grommet flexible retaining finger 7036 naturally rests behind a latitudinal surface of the surface anchor hub nose 7017 and can deflect outward allowing the grommet to pass over the hub, such that the nose would interfere with the finger if forces affecting the implant system 7000 would separate the surface anchor hub 7014 and tissue grommet 7030 after they interfaced. Thus, the grommet becomes locked to the hub and the distance between the grommet and the surface anchor becomes fixed. In some embodiments of the present disclosure the tissue grommet 7030 is depicted with one tissue grommet central flexible beam 7036, however; in other embodiment the tissue grommet can be constructed with a plurality of central flexible beams 7036 which together provide the same function as a singular central flexible beam 7036 described wherein.

The surface anchor tissue grommet 7030 can be constructed with a proximal finger portion comprising a multitude of flexible tissue grommet flexible arms or beams 7032 extending radially from the distal tubular portion that can be deflected into a pre-deployed configuration to allow insertion into a catheter 7050 as shown in FIGS. 70E and 70F. When released from the catheter 7050 the stored strain energy in the tissue grommet flexible arms or beams 7032 can cause the arms to move back into the deployed configuration. Suitable materials of construction for the tissue grommet flexible arms can have a high degree of recoverable strain, such as being able to recover more than 1%, more than 5%, or other percentages, as desired or required. As such, materials such as nitinol are suited for use, or other materials as elaborated herein or known to one having skill in the relevant art.

FIGS. 70E through 70H depict an example method for implanting an embodiment of the treatment system 7000 in the heart of a patient. In certain embodiments, the steps for implantation can include one or more of the following steps:

First, the surface anchor tissue grommet 7030 and surface anchors 7002 or 7004 are crimped into their respective pre-deployment configurations and the tissue grommet 7030, anterior surface anchor 7002 or septal surface anchor 7004, tether 7006 and surface anchor hub 7014 are constrained within a catheter 7050 which houses an outer pushing catheter 7052 and inner pushing catheter 7054. The grommet, surface anchor and hub are spaced out axially from each other. This is depicted in FIG. 70E.

Then, the catheter assembly with implant assembly are advanced through a heart tissue 7040 until the catheter exits the opposite side of the tissue from which it entered.

Then, the inner pushing catheter 7054 is translated distally to slidably displace the surface anchor 7002 or 7004 and surface anchor hub 7014 distally until they exit the distal end of the catheter. The surface anchor expands upon exiting the catheter into its deployed configuration. This step is depicted in FIG. 70F.

Then, the inner pusher is withdrawn distally into the catheter.

Then, the catheter is retracted distally out of the tissue.

Then, the outer pushing catheter 7052 is used to push the tissue grommet 7030 out the distal end of the catheter. Once the grommet exits the catheter it assumes it's deployed configuration. This step is depicted in FIG. 70G.

Then, while pulling tension on the tether 7006, the outer pushing catheter 7052 is used to push the tissue grommet 7030 over the surface anchor hub 7014 as previously described until the grommet is locked to the hub.

Then, as the grommet is pushed against the distal surface of the tissue (in the process of pushing over the hub) the tissue grommet flexible arm 7032 deflect distally. Once the grommet is locked to the hub, the tissue grommet flexible arm 7032 apply compression to the heart tissue 7040 sandwiching the heart tissue 7040 between the tissue grommet 7030 and the surface anchor 7002 or 7004. Thus, the space between the grommet and the surface anchor is substantially occupied by the thickness of the surface to which the implant is affixed. This fixes the surface anchor in place. This step is depicted in FIG. 70H.

Figure 71:
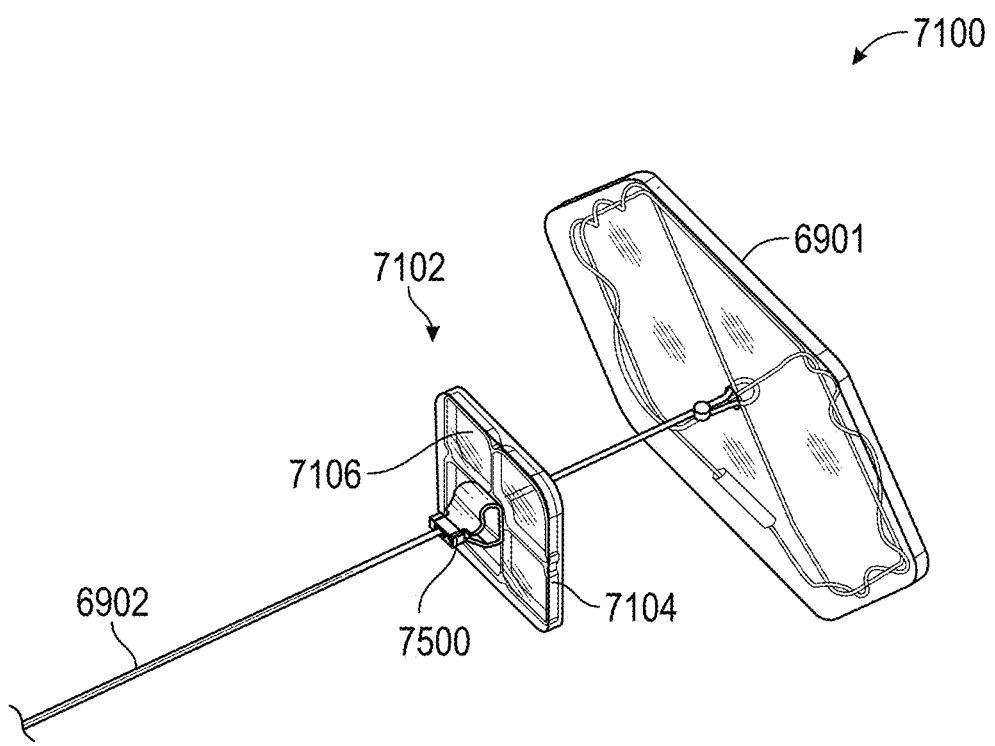

FIG. 71 illustrates an alternative embodiment of an implant system 7100 featuring a surface anchor 6901 as previously described attached to a tether 6902 as previously described and featuring another embodiment of a grommet hereafter referred to as a flat grommet 7102 which is fixed from translating proximally by a tether lock 7500, as described herein. In one embodiment of the present disclosure the flat grommet 7102 can be constructed similarly to the surface anchors 6901, 7002, and 7004 as shown and described in FIGS. 69A and 70B, with an expandable metallic frame 7104 and optionally a covering material 7106. The flat grommet 7102 features a hole through which the tether passes and is able to translate along the tether. The flat grommet 7102 may be elongated, compressed, and pivoted about the axis of the tether 6902 similar to the surface anchors 6901, 7002, and 7004 previously described. The tether lock 7500 can be constructed as illustrated in FIGS. 75A-D such that it is slidable along the tether 6902 when pushed distally but grips the tether 6902 and prevents sliding when pushed with a force in the proximal direction. The implant system 7100 can use any other embodiment of a tether lock described herein, or any other tether lock suitable for implant, as desired or required. The function of the flat grommet 7102 with the tether lock 7500 whereby it sandwiches the tissue between the grommet and surface anchor and prevents migration of the surface anchor is substantially the same as the function of the tissue grommet 7030 and surface anchor hub 7014.

Figure 72A:
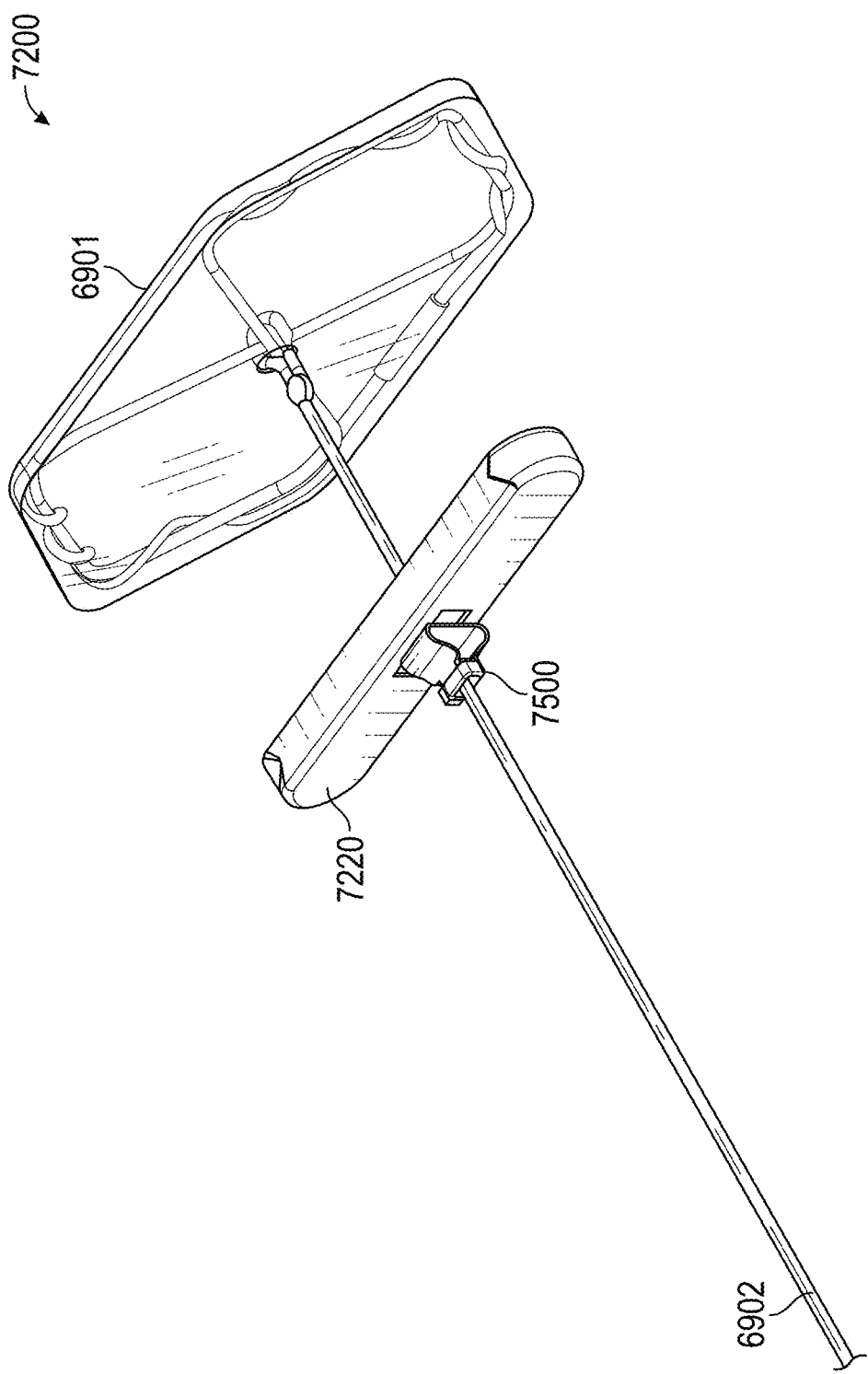
FIG. 72A illustrates an implant system with a T-bar grommet to be used in a tricuspid valve repair system.
Figure 72B:
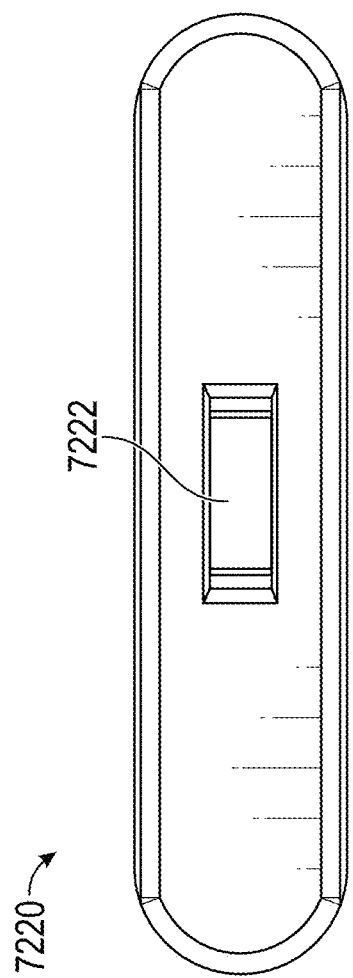
FIG. 72B illustrates a front view of the T-bar grommet depicted in FIG. 72A.
Figure 72C:
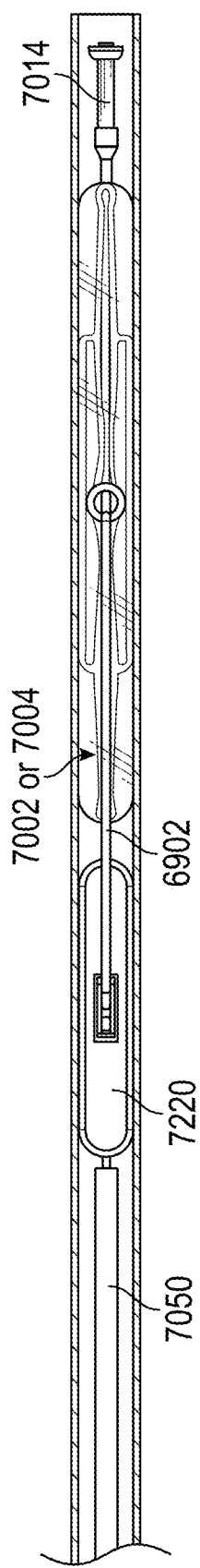
FIG. 72C illustrates the implant system of FIG. 72A while in its pre-deployed state.

FIGS. 72A-72C illustrates an alternative embodiment of an implant system 7200. The implant system 7200 is substantially similar to the implant system 7100 as depicted in FIG. 7100, except that instead of a flat grommet 7102, the implant system 7200 utilizes a T-bar grommet 7220. The T-bar grommet 7220 is a rigid, non-expanding form and has a length significantly greater than its width. The T-bar grommet 7220 can comprise a singular rigid member. The T-bar grommet 7220 has a hole or T-bar slot 7222 at or near the center through which a tether 6902 can pass and the grommet can be slidably translated along the axis of the tether. The width of the T-bar grommet is less than the inner diameter of a catheter 7050 and the T-bar grommet can be pivoted about the tether such that the long axis of the T-bar grommet is approximately parallel to the axis of the tether for insertion into a catheter for deployment, as illustrated in FIG. 72C. When the T-bar grommet 7220 is not constrained by the catheter and experiences a load applied to its surface at any distance away from the tether 6902, such as when contacting tissue, the T-bar grommet 7220 pivots relative to the tether 6902 such that its long axis is approximately perpendicular to the axis of the tether, as illustrated in FIG. 72A. The T-bar grommet 7220 can be constrained from translating proximally along the tether 6902 with a tether lock 7500 as previously described. Any of the locks herein disclosed can be used as a tether lock.

Figure 73:
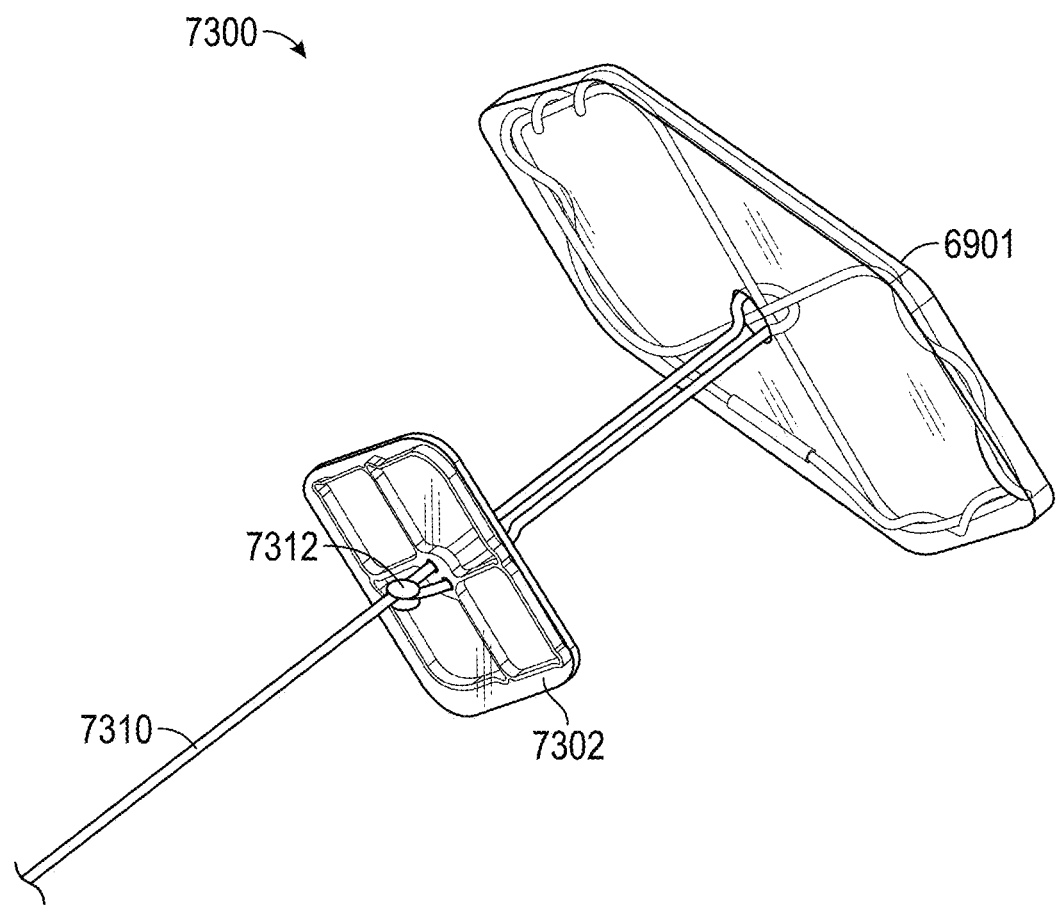
FIG. 73 illustrates an implant system with a flat grommet with slidable tether connection point to be used in a tricuspid valve repair system.

FIG. 73 illustrates an alternative embodiment of an implant system 7300 for securing grommets as previously described, such as a flat grommet 7102. In this embodiment a tether 7310 is formed into a loop which passes through a flat grommet 7302 a first time, passes through a surface anchor 6901 a first time, passes back through the surface anchor 6901 a second time thus encircling the surface anchor 6901, passes through the flat grommet 7302 a second time, and terminates by rejoining with the tether at a sliding connection point 7312 at a position before the tether 7310 first passed through the flat grommet 7302, such that pulling on the tether 7310 draws the surface anchor 6901 toward the flat grommet 7302 by advancing the connection point 7312 distally along the tether. The grommet used within the implant system 7300 can be the flat grommet 7302, the T-bar grommet 7220, or any other compatible grommet with the tether 7310 system as desired or required. As depicted in FIG. 73, a flat grommet 7302 is used. The tether connection point 7312 can be a slidable knot, or other similar connection point, such that the tether connection point 7312 can slide along the first portion of the tether 7310 before it is first passed through the flat grommet 7302. The function of the grommet is similar to those previously described, however, rather than being fixed from translating proximally along the tether by a tether lock 7500 it is fixed from translating proximally by the tether connection point 7312, which can be a slidable knot. The implant system 7300 can be deployed in a substantially similar method as previous implant system 7200. The gap between the flat grommet 7302 and surface anchor 6901 is initially set to be greater than the thickness of the tissue that will be sandwiched between the grommet and anchor. Once the surface anchor 6901 is deployed on one side of the tissue and the flat grommet 7302 is deployed on the opposite side of the tissue, the slidable knot 7312 can be moved distally with a pushing catheter like 7050 while applying tension to the free end of the tether 6902 which causes tether connection point 7312 to slide distally and reduce the distance between the flat grommet 7302 and surface anchor system 6900 until the tissue is adequately compressed between the flat grommet 7302 and surface anchor system 6900. The tether connection point 7312 resists sliding proximally, maintaining compression of the tissue.

Figure 74A:
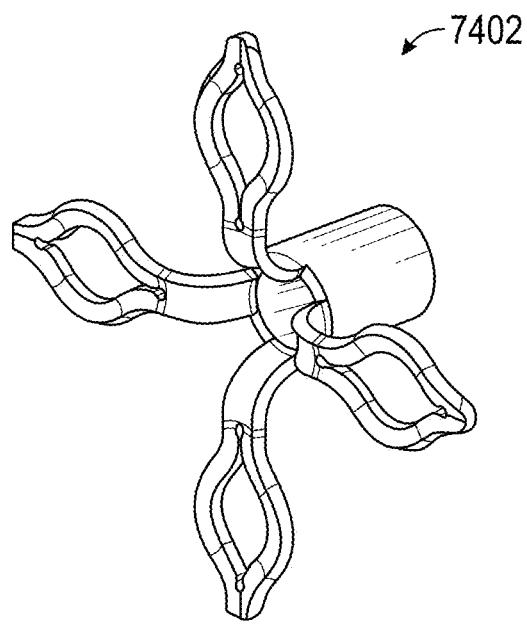
FIG. 74A illustrates a self-expanding grommet to be used within a tricuspid valve repair system.
Figure 74B:
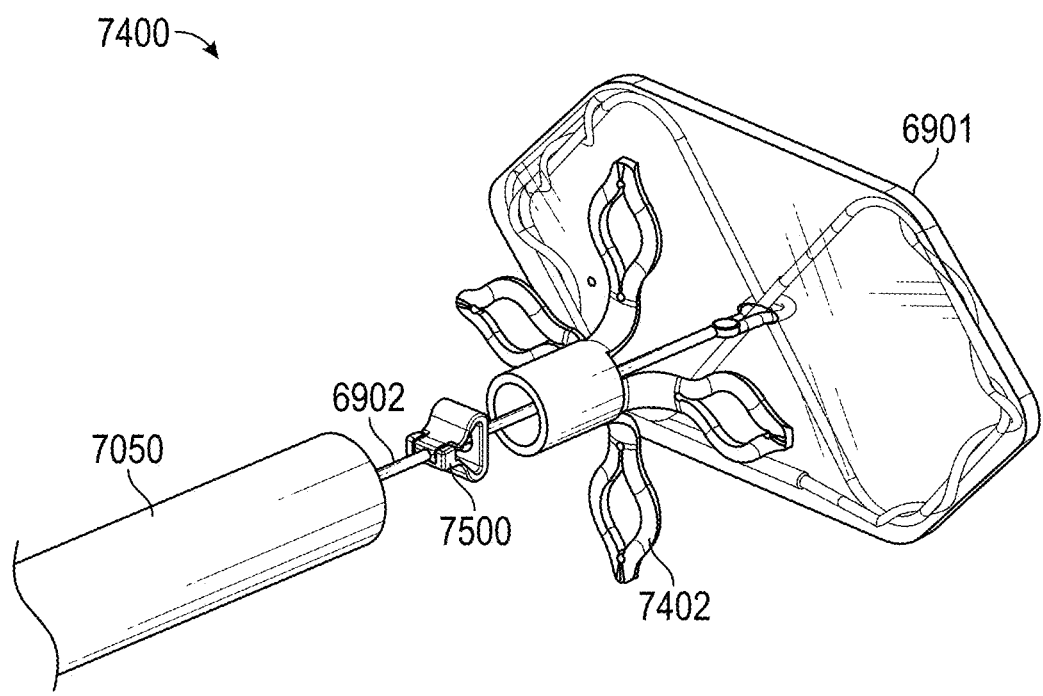
FIG. 74B illustrates an implant system with the self-expanding grommet in FIG. 74A to be used within a tricuspid valve repair system.

FIGS. 74A and 74B illustrates an alternative embodiment of an implant system 7400 for securing grommets as previously described, such as a flat grommet 7102. In this embodiment, the grommet used to retain the surface anchor 6901 to the treatment area is a self-expanding grommet 7402. FIG. 74A displays the self-expanding grommet 7402 in a deployed state, after the grommet has expanded. FIG. 74B displays the self-expanding grommet 7402 in an implant system 7400, utilizing a surface anchor 6901, a tether lock 7500, a tether 6902, and a catheter 7050. The self-expanding grommet 7402 can be deployed in a similar method to the other grommets disclosed herein. While within a delivery catheter, the self-expanding grommet 7402 is in a collapsed state where its arms have not yet expanded. Upon being forced out of the deployment catheter 7050, the arms of the self-expanding grommet 7402 are configured to return to its deployed state, as shown in FIGS. 74A and 74B. The flat grommet 7402 is can be constructed of Nitinol, or other similar materials, with shape-memory and high recoverable strain properties that allow the flat grommet 7402 to be heat-set into a first expanded or deployed configuration, as shown in FIGS. 74A and 74B, then be constrained into a second collapsed configuration for translation through a catheter in such a way so that after deployment the flat grommet 7402 can recover to the expanded configuration when released from the catheter.

Figure 75C:
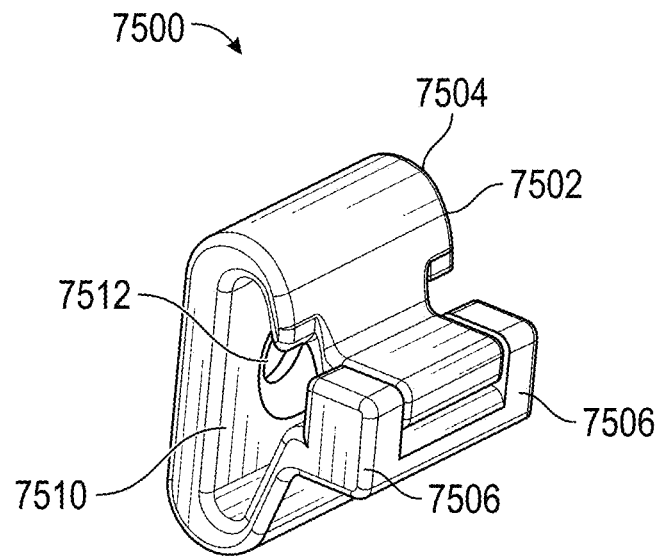
FIG. 75C illustrates an alternative view of the tether lock in FIG. 75A in its locking configuration to be used within a tricuspid valve repair system.
Figure 75D:
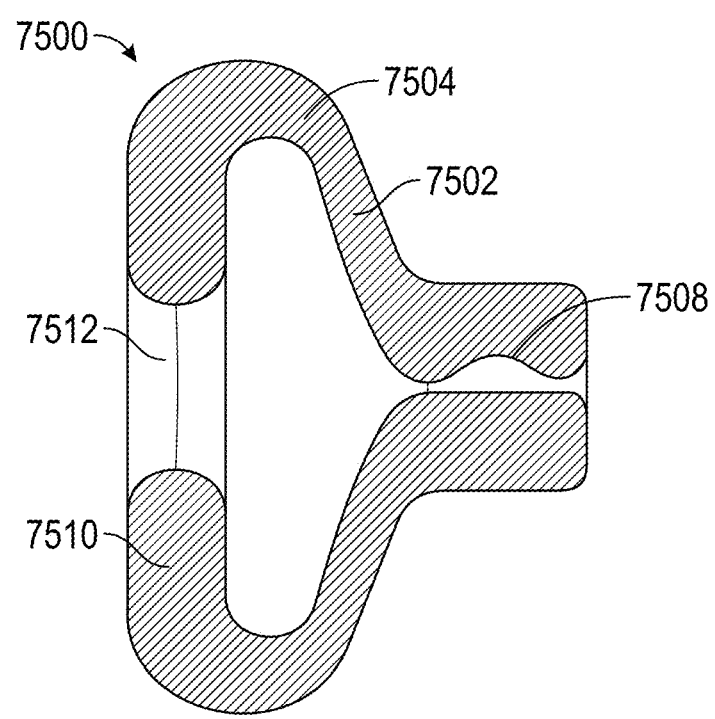
FIG. 75D illustrates a cross-sectional side view of the tether lock in FIG. 75A.

FIGS. 75A through 75D illustrate an embodiment of a tether lock 7500. FIG. 75A depicts the tether lock 7500 in a closed configuration, wherein the tether lock spring arms 7502 are elastically bent at the tether lock deflection nodes 7504 to close the tether lock 7500 on the tether 6902 and prevent its sliding in the lateral direction. The tether lock 7500 can have one or more tether lock deflection nodes 7504 for one or more tether lock spring arms 7502. FIG. 75B depicts the tether lock 7500 in an open configuration which allows the tether lock 7500 to slide laterally along the tether 6902. FIG. 75C depicts the tether lock 7500 in a closed position from another angle. The tether lock 7500 additionally has a tether lock tether hole 7512 on the tether lock's distal end 7510 through which the tether 6902 can pass. The tether lock 7500 additionally comprises at least one tether lock alignment wall 7506 located on the proximal end of the tether lock 7500 which can keep the tether 6902 aligned with the closing member of the tether lock 7500. The tether 6902 continues passing between the tether lock tether contact surface 7508 such that it is pinched between the spring arms. When a force is applied to the tether lock moving from the tether lock's proximal side to the tether lock distal end 7510, the friction force between the tether 6902 and the tether lock tether contact surface 7508 induces a moment on the spring arms that causes them to pinch together, effectively clamping onto the tether as illustrated in FIG. 75A. If a force is applied to the tether lock moving from the tether lock's distal side to the tether lock's proximal side, the friction between the tether 6902 and tether lock tether contact surface 7508 induces a moment on the spring arms that causes them to spread apart, allowing the tether lock to slide along the tether. Thus, the tether lock can be pushed distally and will slide along the tether with minimal force but when the tether lock encounters a proximally directed force, such as the resistive force of compressing tissue between a surface anchor and grommet, the tether lock automatically clamps down onto the tether and prevents movement. The greater the proximally directed force on the tether lock, the greater the clamping force on the tether. The tether lock can be of metallic construction such as stainless steel, titanium or nitinol or polymeric construction such as PEEK or Nylon. The tether lock tether contact surface 7508 of the spring arms can have a toothed geometry as shown to increase friction on the tether.

FIGS. 76A through 80D depict several alternative embodiments of tether locks to be used with various tethers (e.g., tether 6902, tether 7006, etc.) usable instead of the depicted tether locks disclosed herein, such as lock 230 from FIGS. 2 through 13, lock 4080 from FIG. 31, lock 7012 from FIG. 70A, lock 7500 from FIGS. 71 through 72, and 74 through 75, or other embodiments of implant systems as disclosed herein. The various lock embodiments disclosed herein can accommodate an adjustable lock tensioner which disposes within the main body of the lock, such that the adjustable lock tensioner can constrict one or more tension members which pass at least partially through the lock housing.

Figure 76A:
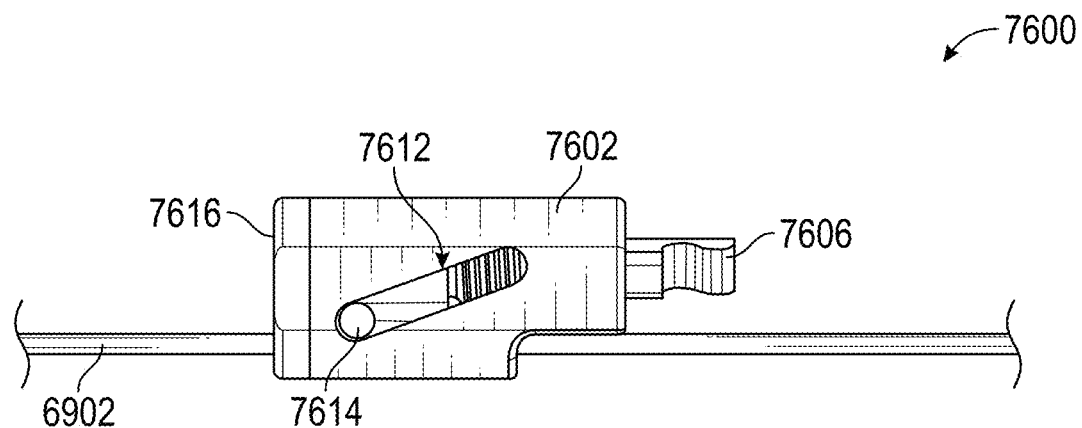
FIG. 76A illustrates an alternative embodiment of a tether lock in its locking configuration to be used within a tricuspid valve repair system.
Figure 76B:
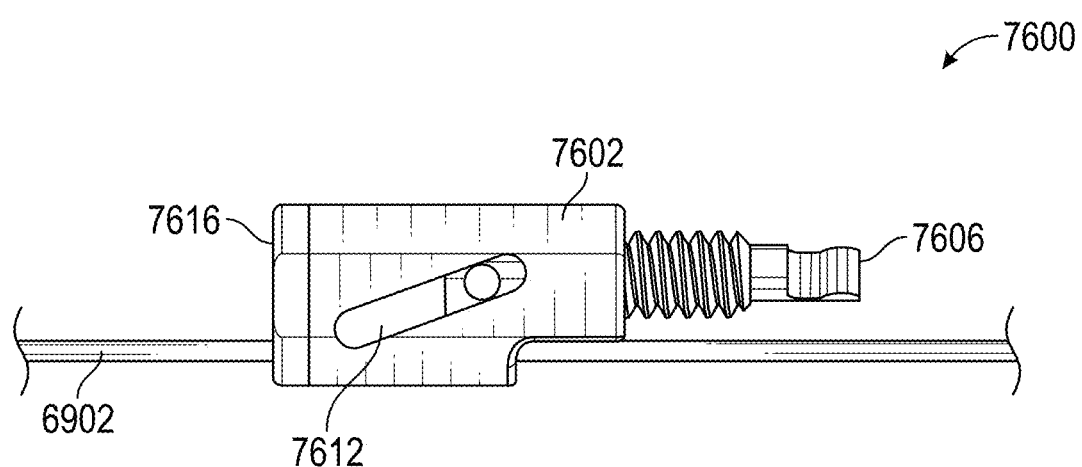
FIG. 76B illustrates the tether lock of FIG. 76A in its non-locking configuration to be used within a tricuspid valve repair system.
Figure 76C:
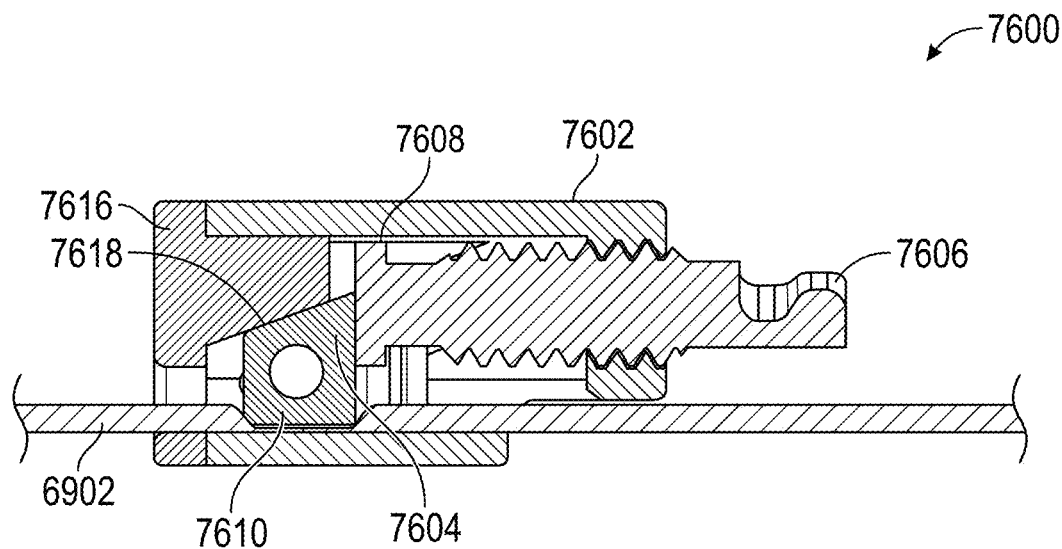
FIG. 76C illustrates a cross-sectional view of the tether lock of FIG. 76A in its locking configuration to be used within a tricuspid valve repair system.
Figure 76D:
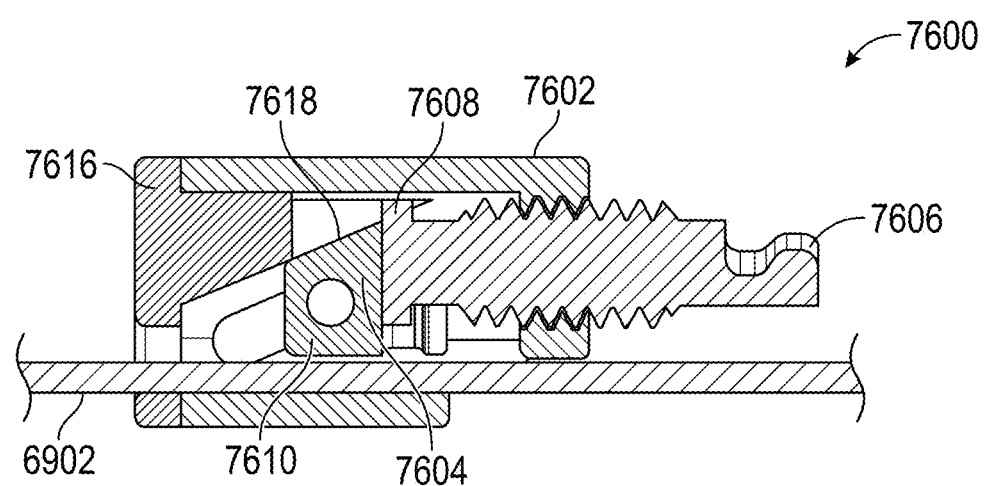
FIG. 76D illustrates a cross-sectional view of the tether lock of FIG. 76A in its non-locking configuration to be used within a tricuspid valve repair system.
Figure 76E:
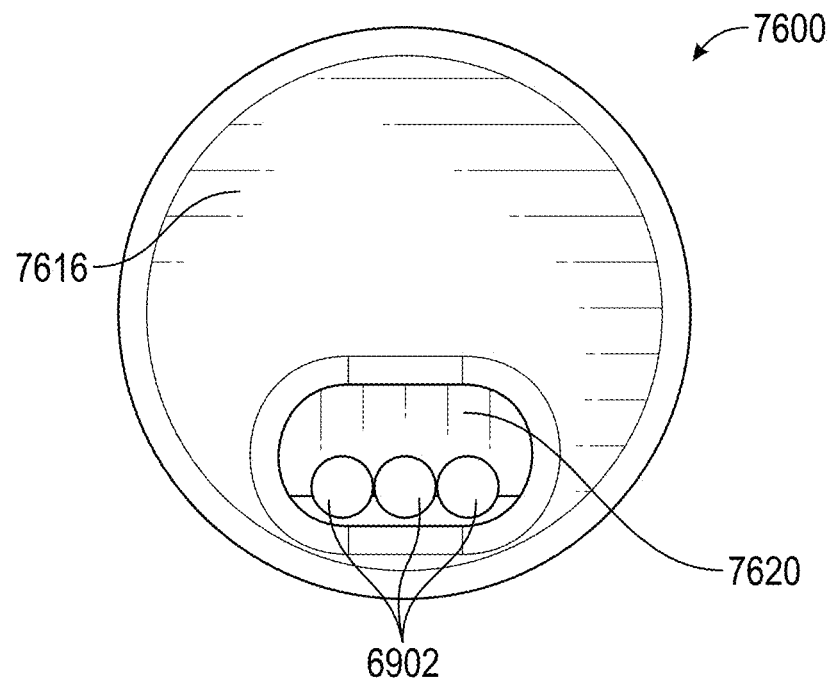
FIG. 76E illustrates a front view of the tether lock of FIG. 76A to be used within a tricuspid valve repair system.
Figure 76F:
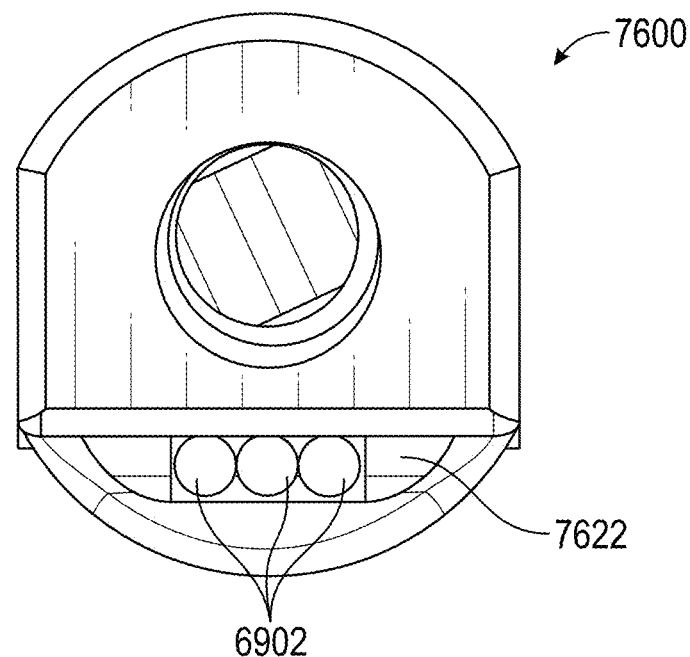
FIG. 76F illustrates a rear view of the tether lock of FIG. 76A to be used within a tricuspid valve repair system.

FIGS. 76A through 76F illustrate an embodiment of a tether lock 7600 with a slidable wedge 7604 driven by a lead screw 7606 that clamps onto one or more tethers 6902, hereinafter referred to as a slidable wedge tether lock 7600. The lock is shown in the locked configuration in FIGS. 76A and 76C, which shows a cross-sectional view of the slidable wedge tether lock 7600. The lock is shown in an unlocked configuration in FIGS. 76B and 76D, which shows a cross-sectional view of the slidable wedge tether lock 7600. The screw can have a flange 7608 that is captive in a slot 7610 of the slidable wedge 7604 such that translation of the lead screw 7606 in either direction along its axis exerts a force onto the wedge causing it to translate in the direction of the lead screw 7606. The lock can be constructed with a tether lock housing 7602 with a housing slot 7612 at an angle relative to the axis of the housing. The housing slot 7612 can engage a pin 7614 which passes through the slidable wedge 7604 such that when the wedge is translated proximally the housing slot 7612 exerts an upward force on the pin 7614 causing the wedge to rise in the housing (into an unlocked configuration). Translation of the wedge distally has the opposite effect where the slot will cause the wedge to be driven downward in the housing, ultimately clamping the tether into a locked configuration. Optionally or in addition to the above locking configuration system, the slidable wedge 7604 can interact with a housing tip 7616 along a housing tip angled surface 7618 relative to the axis of the tether lock housing 7602 such that distal translation of the wedge causes a downward force on the wedge due to the reaction force at the housing tip angled surface 7618. Thus, screwing the lead screw 7606 into the tether lock housing 7602 in this embodiment causes the slidable wedge 7604 to clamp the tethers. The more acute the angle between the slot 7610 and/or housing tip angled surface 7618 and the tether axis, the greater the downward clamping force. Tension on the tether, directed distally relative to the lock, causes a frictional force between the tether 7006 and the slidable wedge 7604 which causes the wedge to translate distally and the resulting reaction force between the housing slot 7612 and pin 7614 or slidable wedge 7604 and housing tip 7616 further causes the wedge to clamp down on the tether, thus, increasing tension on the suture causes increased clamping force on the tether even if the screw were to loosen over time. Thus, the mechanism is self-locking in the presence of tension on the tether, mitigating the potential for loosening over time. FIG. 76E illustrates the passage of the tethers into a housing tip opening 7620 at the distal end of the lock and FIG. 76F illustrates the tether lock housing opening 7622 with the tethers exiting from the proximal end of the lock.

Figure 77A:
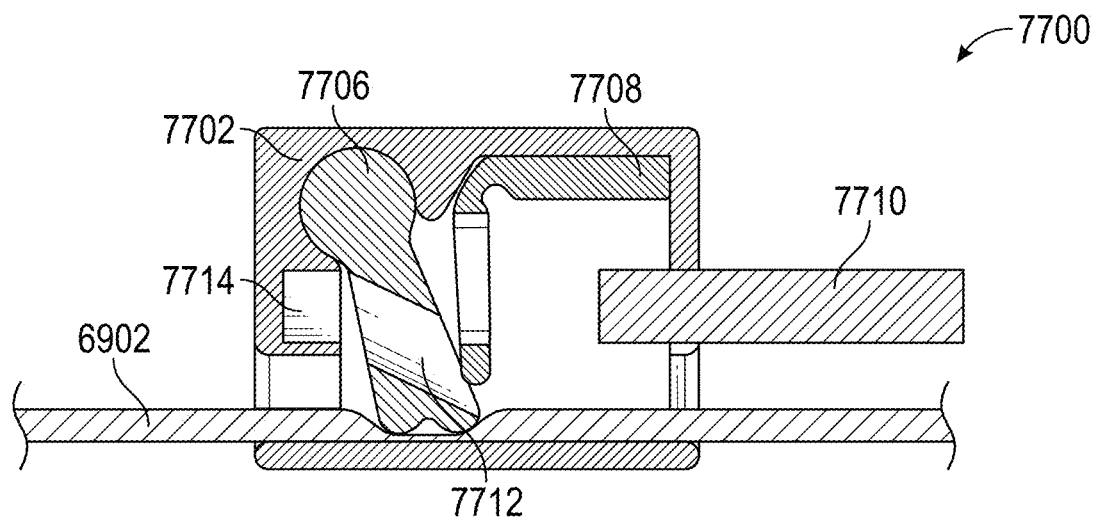
FIG. 77A illustrates a cross-sectional view of an alternative embodiment of a tether lock to be used in a tricuspid valve repair system in its locking configuration.
Figure 77B:
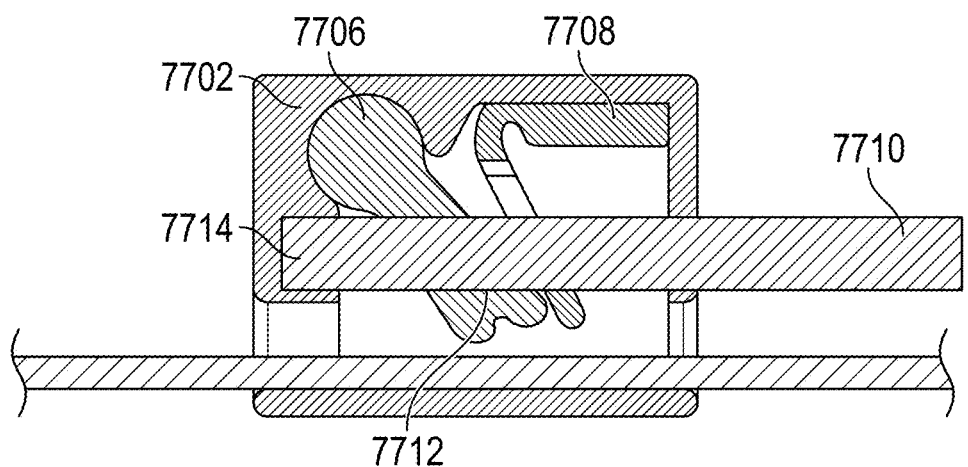
FIG. 77B illustrates a cross-sectional view of the tether lock of FIG. 77A in its non-locking configuration.
Figure 77C:
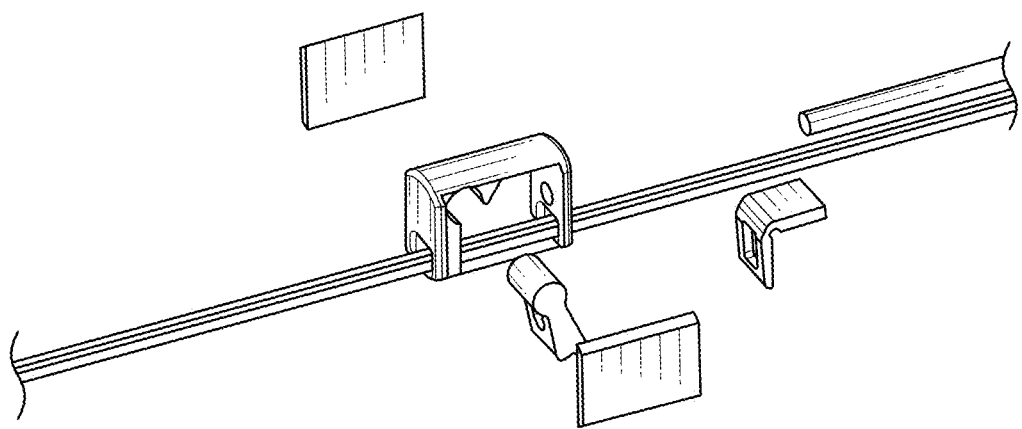
FIG. 77C illustrates an exploded view of the tether lock of FIG. 77A.
Figure 78A:
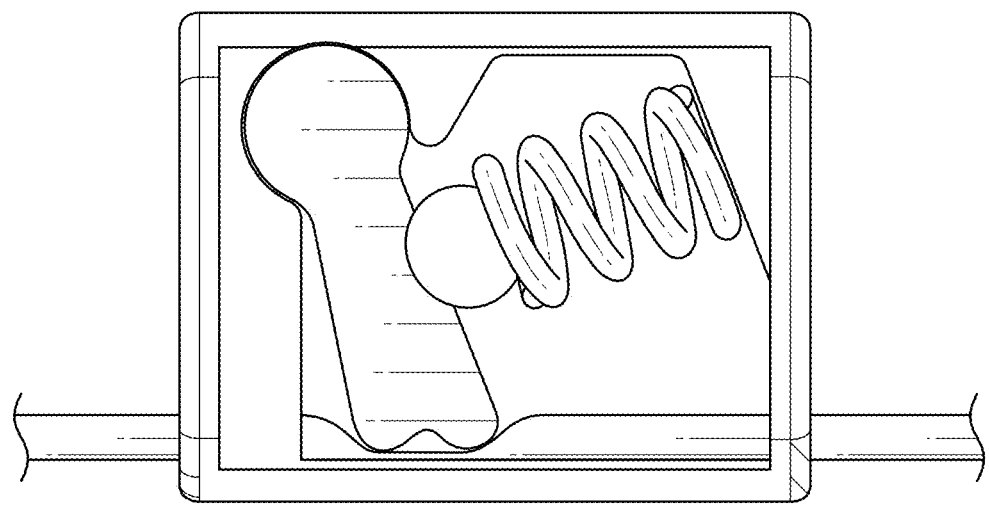
FIG. 78A illustrates a cross-sectional view of an alternative embodiment of a tether lock to be used in a tricuspid valve repair system in its locking configuration.
Figure 78B:
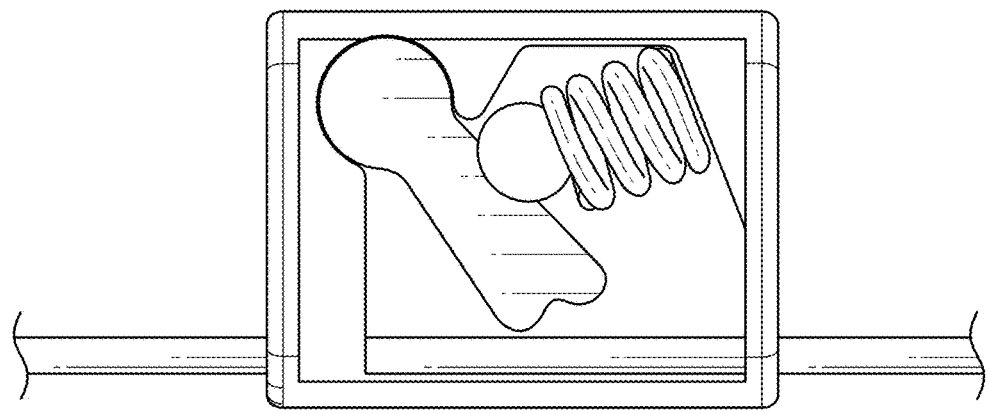
FIG. 78B illustrates a cross-sectional view of the tether lock of FIG. 78A in its non-locking configuration.
Figure 78C:
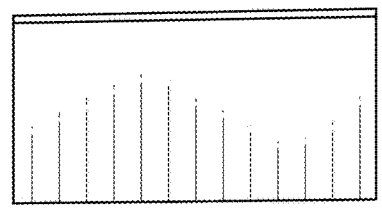
FIG. 78C illustrates an exploded view of the tether lock of FIG. 78A.
Figure 78C:
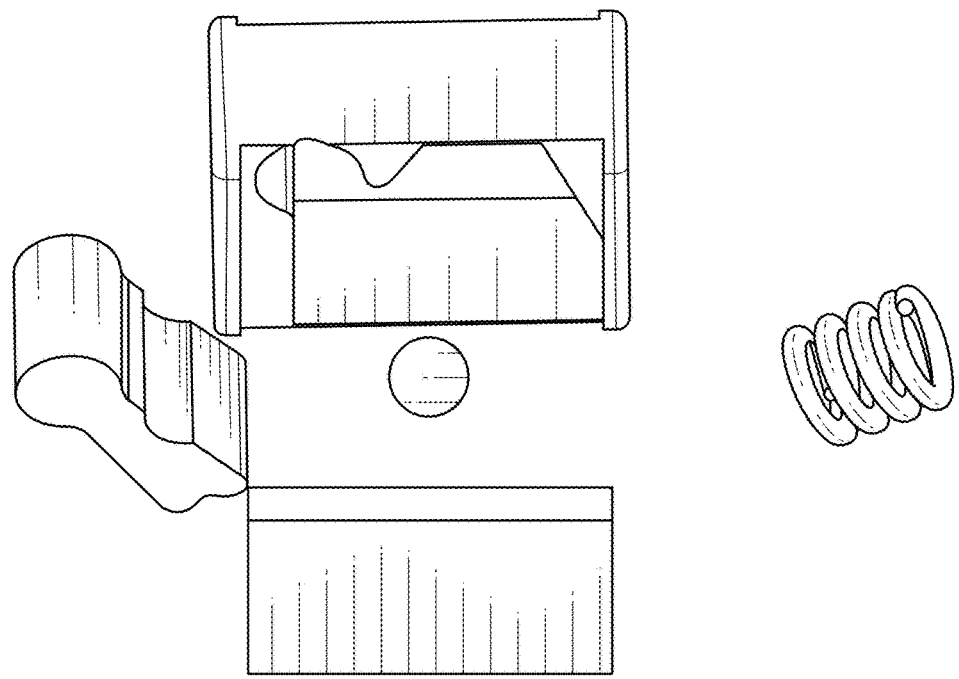

FIGS. 77A through 77C illustrate an embodiment of a tether lock with a rotatable pawl that clamps one or more tethers, hereinafter referred to as a rotatable pawl tether lock 7700. A cross section of the lock is shown in the closed configuration in FIG. 77A and in its open configuration in FIG. 77B. FIG. 77C is an exploded view of the components. When the tether 6902 is in contact with the pawl contact surface 7706 and tether 6902 is pulled distally in tension, a friction force is applied to the pawl in the direction the tether is being pulled which causes a moment about the rounded end of the pawl where it is constrained in a matching round groove in the tether lock housing 7702. The moment causes the pawl contact surface 7706 to rotate in the direction the tether 6902 is being pulled. If the tether is pulled distally, such as due to the tensile force on the tether when reducing a heart valve annulus, the arc path of the pawl causes the end of the pawl to drive downward and clamp the suture. Thus, the lock is self-locking when tension is applied in a distal direction to the tether and increasing tension results in an increasing clamping force. The lock could house a spring clip 7708 which exerts a moment on the pawl contact surface 7706 causing it to be in the closed position. To hold the pawl contact surface 7706 in an open position, which is desirable to smoothly advance the lock over the tethers through a patients anatomy to its intended location and to fine tune tension on the tethers when reducing a heart valve annulus without obstruction, a pull pin 7710 can be inserted through a pawl pass through hole 7712 to counteract the spring clip 7708 force and hold the pawl open. The end of the pull pin could reside in a pawl recess hole 7714 to provide additional support on the pull pin. Removal of the pull pin will cause the rotatable pawl 7704 to spring into its locked configuration. During assembly, the pawl and spring can be inserted into the housing from the side and two tether lock side housings 7703 can be welded or otherwise attached to the housing to hold everything in place. FIGS. 78A through 78C illustrates an alternative embodiment of a spring clip 7808 that could be used to disposition the pawl 7804 into a primary locked configuration. A pawl ball 7816 could be positioned between the spring clip 7808 and pawl 7804 to ensure a smooth contact surface and prevent binding between the pawl and spring. The spring could be manufactured as a typical coil spring in this embodiment.

Figure 79A:
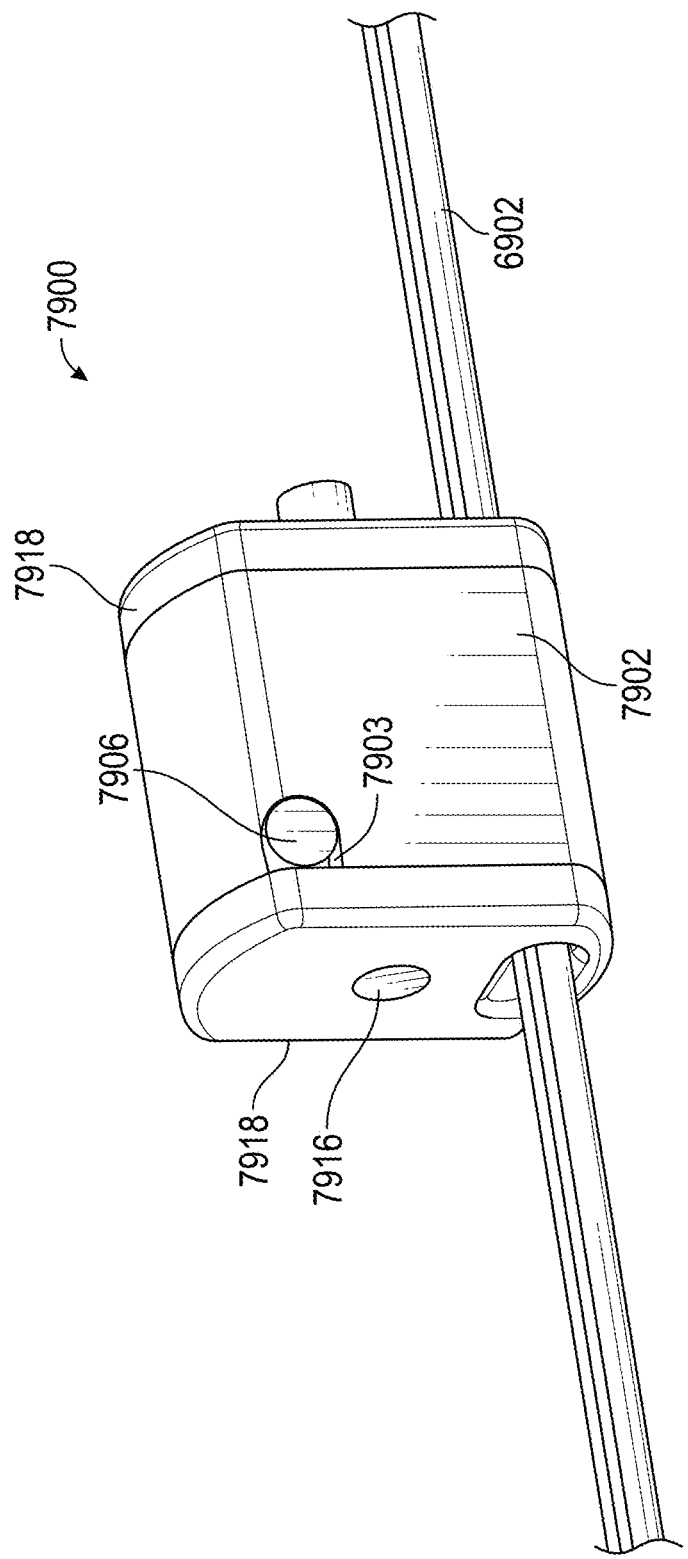
FIG. 79A illustrates a perspective view of an alternative embodiment of a tether lock to be used within a tricuspid valve repair system.
Figure 79B:
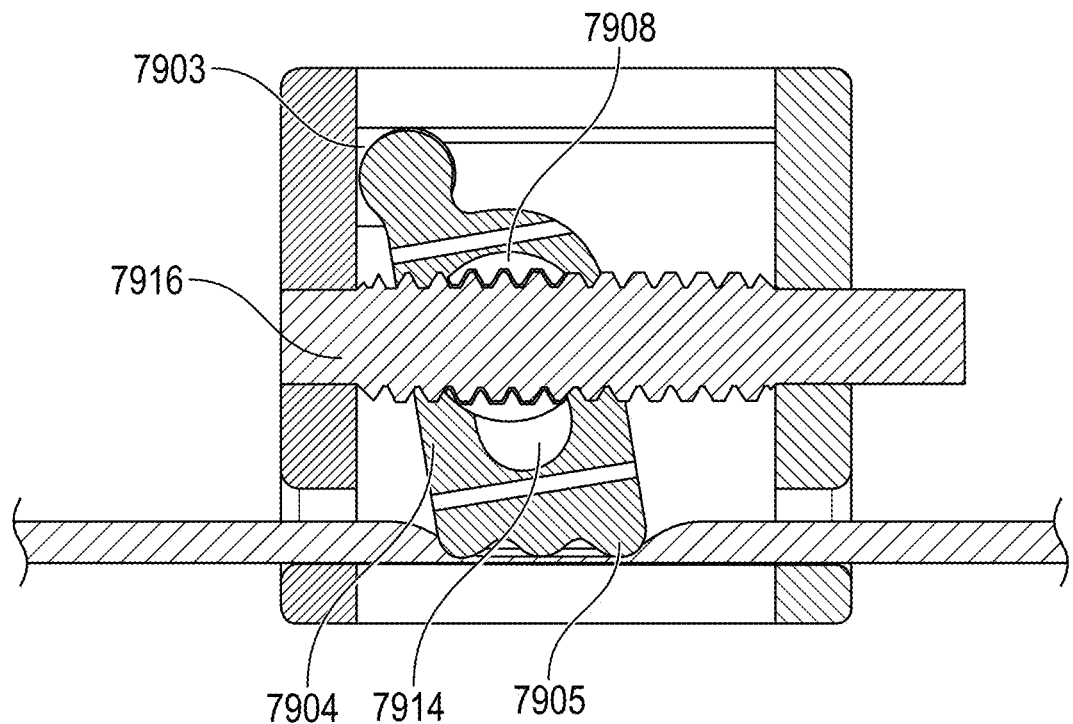
FIG. 79B illustrates a cross-sectional view of the tether lock of FIG. 79A in its locking configuration.
Figure 79C:
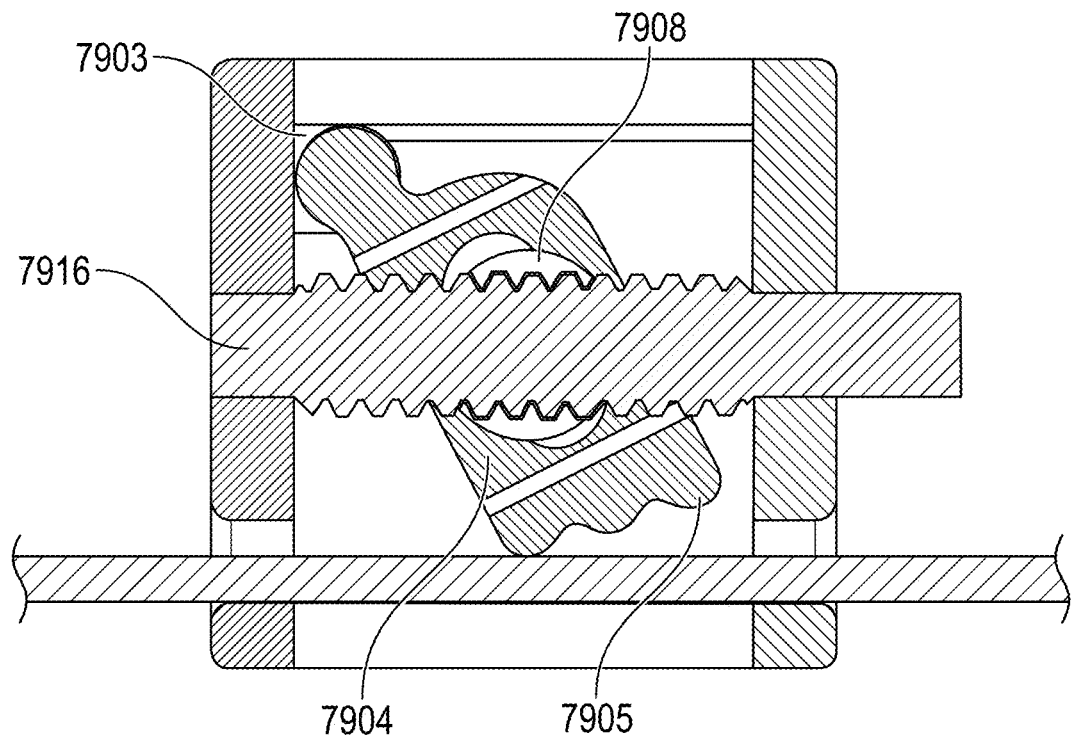
FIG. 79C illustrates a cross-sectional view of the tether lock of FIG. 79A in its non-locking configuration.
Figure 79D:
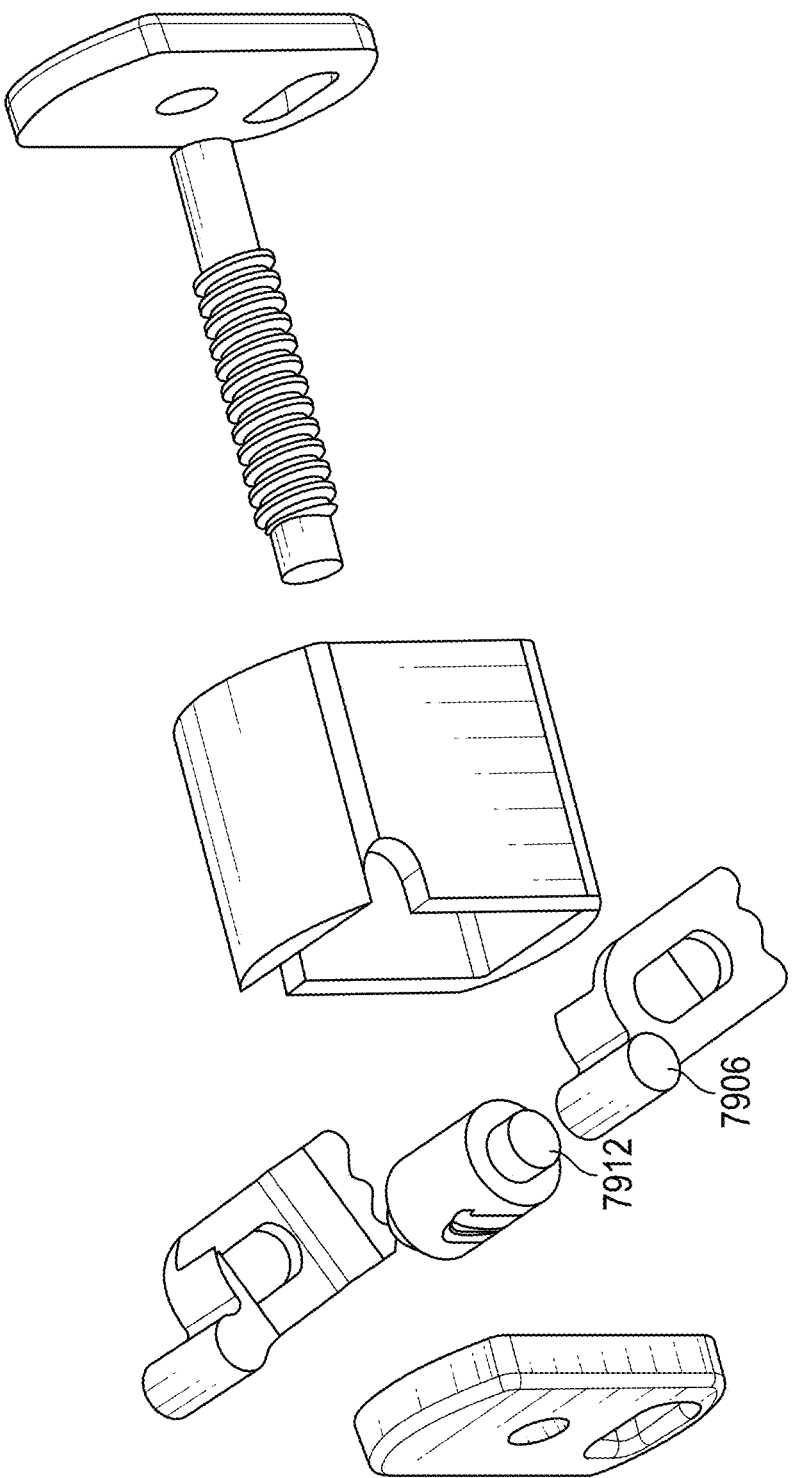
FIG. 79D illustrates an exploded view of the tether lock of FIG. 79A.

FIGS. 79A through 79D illustrate an embodiment of a tether lock 7900 with a threaded rotatable pawl 7904 that engages and clamps one or more tethers, similar to the rotatable pawl tether lock 7700 disclosed herein. The threaded rotatable pawl 7904 features a pawl pin 7906 that rests in a tether lock housing opening 7903, wherein the threaded rotatable pawl 7904 is rotatable about the pawl pin 7906. A cylindrical nut 7908 resides in a pawl groove 7910 within the pawl 7904 that allows the nut to translate up and down within the pawl. The cylindrical nut 7908 features nut pin 7912 at each end that engage a pawl slot 7914 in the threaded rotatable pawl 7904 such that the nut is captive in the pawl and translation of the nut along the axis of the housing will exert a moment on the pawl causing it to rotate. A pawl screw 7916 can be held captive between a cylindrical nut 7908 and a tether lock housing proximal cover 7918 which are attached to the housing, for example, via welding. The pawl screw 7916 is threaded through the cylindrical nut 7908 and rotation of the screw causes translation of the nut which causes the pawl to rotate. The pawl can be constructed from two pieces as shown in FIG. 79D to allow assembly of the nut and once inserted into the housing the nut is held captive in the pawl. The two halves of the pawl could also be joined via welding or other mechanical means.

Figure 80A:
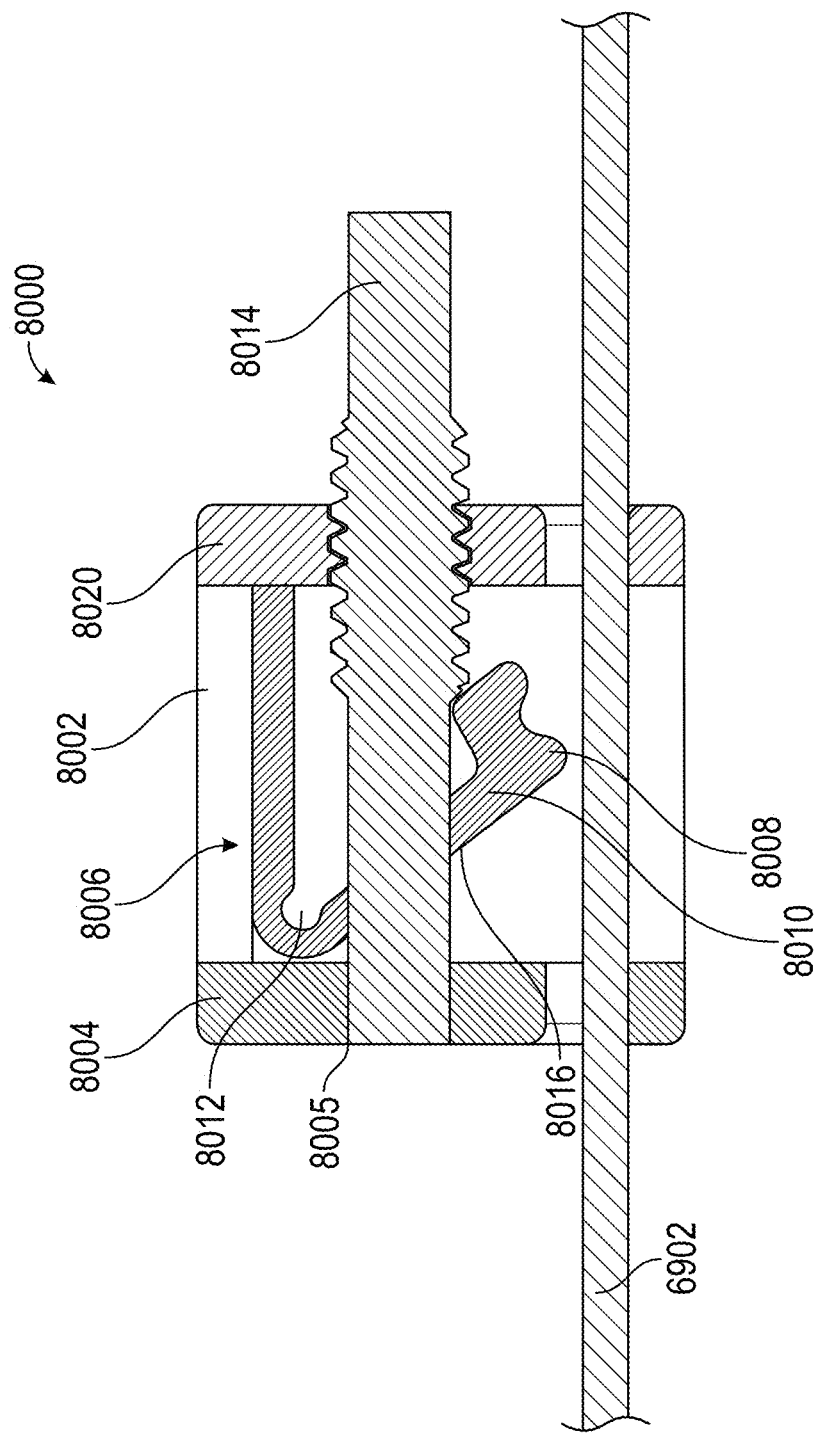
FIG. 80A illustrates a cross-sectional view of an alternative embodiment of a tether lock to be used in a tricuspid valve repair system in its non-locking configuration.
Figure 80B:
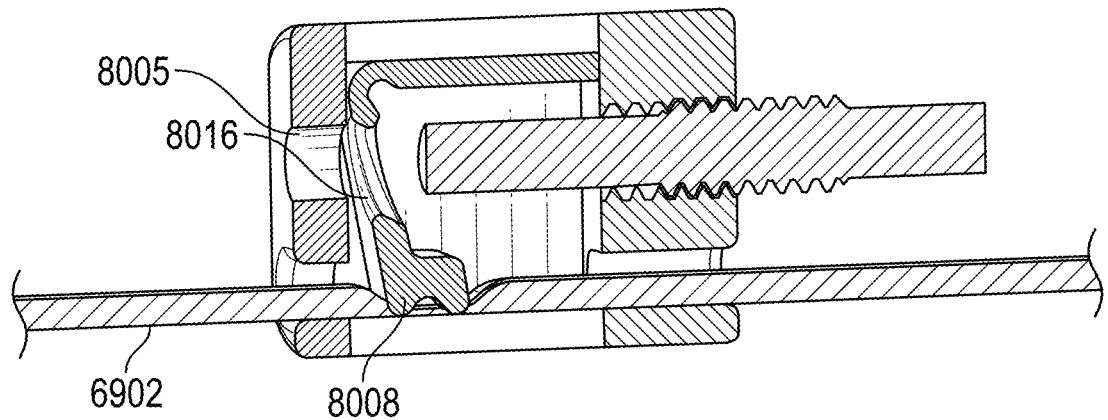
FIG. 80B illustrates a perspective cross-sectional view of the tether lock of FIG. 80A in its locking configuration.
Figure 80C:
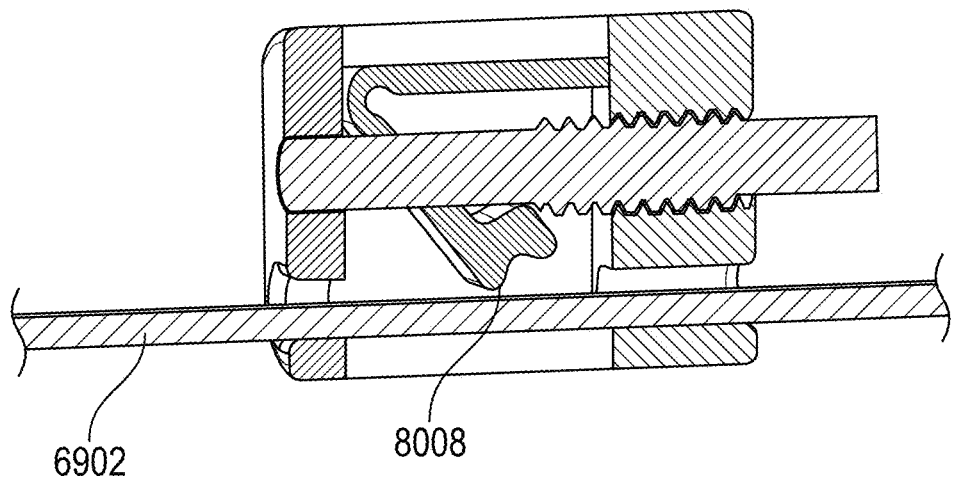
Figure 80D:
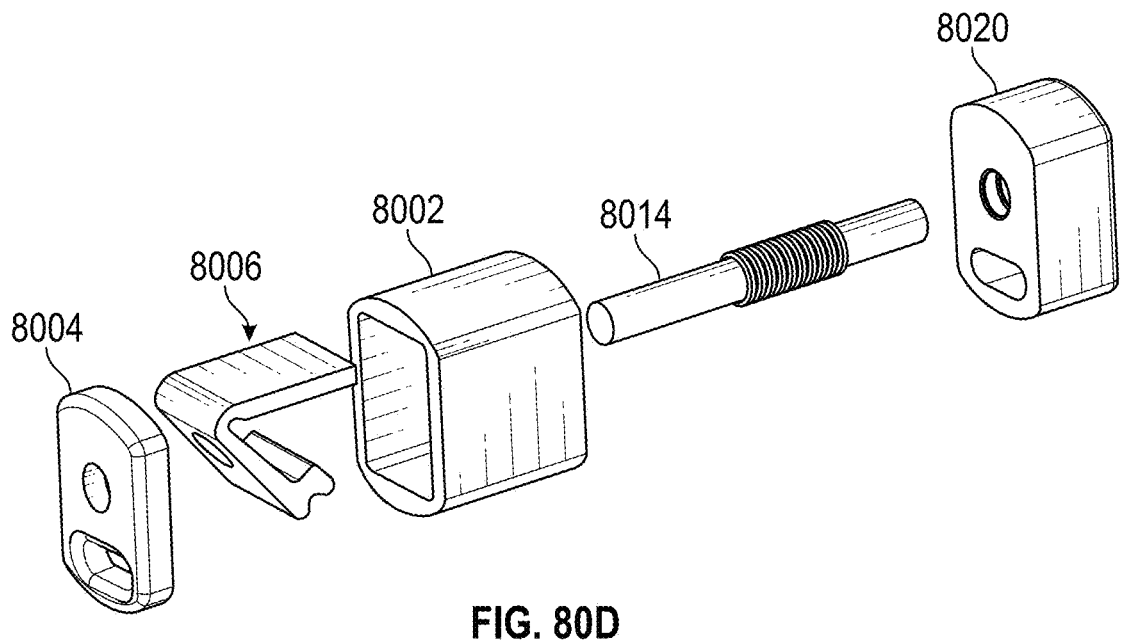

FIG. 80A through 80D illustrate an embodiment of a tether lock with a spring clip 8006 that directly engages and clamps onto a one or more tethers 6902. The spring clip tether lock 8000 is shown in open or unlocked configuration in FIGS. 80A and 80C and a closed or locked configuration in FIG. 80B. The spring clip 8006 is held captive in a tether lock housing 8002 under a preload where the spring clip is deflected from its natural state, thus, the spring clip clamping surface 8008 of the spring clip is naturally in contact with the bottom surface of the housing, thus naturally in the closed position and exerting a clamping force on the tethers. The spring clip 8006 is constrained from translating in the tether lock housing 8002 by the proximal surface of the housing tip 8004 and the housing back surface 8020 which are attached to the housing after insertion of the spring clip, for example, via welding. The spring clip arm 8010 is deflectable about a spring clip deflection node 8012 in the geometry of the spring clip such that when the arm of the spring clip is deflected the spring clip clamping surface 8008 rotates within the housing either into the unlocked configuration or into a locked configuration depending on the direction of the force application. When the tether 6902 is pulled distally the friction force between the tether and the spring clip clamping surface 8008 of the spring clip creates a moment about the spring clip deflection node 8012 that causes the spring clip spring clip arm 8010 to rotate in a direction that drives the spring clip clamping surface 8008 into the tethers 6902 thus clamping the tethers between the spring arm and the housing. The more tension applied to the tethers, the harder the spring arm will clamp down on the tethers. A spring clip pin 8014 can be inserted through a spring clip hole 8016 in the spring clip 8006 and supported in a housing tip hole 8005 in the housing tip 8004 of the lock. The pin can hold the spring clip in an open configuration as illustrated in FIGS. 80A and 80C, which is desirable to smoothly advance the lock over the tethers through a patients anatomy to its intended location and to fine tune tension on the tethers when reducing a heart valve annulus without obstruction. Removal of the spring clip pin 8014 allows the spring clip 8006 to spring into the closed configuration. The spring clip pin 8014 can be threaded and rotatably actuated via a catheter or can be a component of the catheter itself. The threads can serve as the attachment mechanism between the lock and a catheter where unthreading the pin both deploys the spring clip into the locked configuration and releases the lock from the catheter.

While certain embodiments of the inventions have been described, these embodiments have been presented by way of example only, and are not intended to limit the scope of the disclosure. Indeed, the novel methods and systems described herein may be embodied in a variety of other forms. Furthermore, various omissions, substitutions and changes in the systems and methods described herein may be made without departing from the spirit of the disclosure.

Features, materials, characteristics, or groups described in conjunction with a particular aspect, embodiment, or example are to be understood to be applicable to any other aspect, embodiment or example described in this section or elsewhere in this specification unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination, of the steps of any method or process so disclosed.

Furthermore, certain features that are described in this disclosure in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations, one or more features from a claimed combination can, in some cases, be excised from the combination, and the combination may be claimed as a subcombination or variation of a subcombination.

Moreover, while operations may be depicted in the drawings or described in the specification in a particular order, such operations need not be performed in the particular order shown or in sequential order, or that all operations be performed, to achieve desirable results. Other operations that are not depicted or described can be incorporated in the example methods and processes. For example, one or more additional operations can be performed before, after, simultaneously, or between any of the described operations. Further, the operations may be rearranged or reordered in other implementations. Those skilled in the art will appreciate that in some embodiments, the actual steps taken in the processes illustrated and/or disclosed may differ from those shown in the figures. Depending on the embodiment, certain of the steps described above may be removed, others may be added. Furthermore, the features and attributes of the specific embodiments disclosed above may be combined in different ways to form additional embodiments, all of which fall within the scope of the present disclosure. Also, the separation of various system components in the implementations described above should not be understood as requiring such separation in all implementations, and it should be understood that the described components and systems can generally be integrated together in a single product or packaged into multiple products.

For purposes of this disclosure, certain aspects, advantages, and novel features are described herein. Not necessarily all such advantages may be achieved in accordance with any particular embodiment. Thus, for example, those skilled in the art will recognize that the disclosure may be embodied or carried out in a manner that achieves one advantage or a group of advantages as taught herein without necessarily achieving other advantages as may be taught or suggested herein.

Conditional language, such as "can," "could," "might," or "may," unless specifically stated otherwise, or otherwise understood within the context as used, is generally intended to convey that certain embodiments include, while other embodiments do not include, certain features, elements, and/or steps. Thus, such conditional language is not generally intended to imply that features, elements, and/or steps are in any way required for one or more embodiments or that one or more embodiments necessarily include logic for deciding, with or without user input or prompting, whether these features, elements, and/or steps are included or are to be performed in any particular embodiment.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount. As another example, in certain embodiments, the terms "generally parallel" and "substantially parallel"

refer to a value, amount, or characteristic that departs from exactly parallel by less than or equal to 15 degrees, 10 degrees, 5 degrees, 3 degrees, 1 degree, or 0.1 degree. Numbers and values used herein preceded by a term such as "about" or "approximately" include the recited numbers. For example, "approximately 7 mm" includes "7 mm" and numbers and ranges preceded by a term such as "about" or "approximately" should be interpreted as disclosing numbers and ranges with or without such a term in front of the number or value such that this application supports claiming the numbers, values and ranges disclosed in the specification and/or claims with or without the term such as "about" or "approximately" before such numbers, values or ranges such, for example, that "approximately two times to approximately five times" also includes the disclosure of the range of "two times to five times."

The scope of the present disclosure is not intended to be limited by the specific disclosures of preferred embodiments in this section or elsewhere in this specification, and may be defined by claims as presented in this section or elsewhere in this specification or as presented in the future. The language of the claims is to be interpreted broadly based on the language employed in the claims and not limited to the examples described in the present specification or during the prosecution of the application, which examples are to be construed as non-exclusive.

What is claimed is:

1. A method of tricuspid valve repair comprising:
anchoring a first ventricular surface anchor against a first right ventricular surface, wherein the first ventricular surface anchor is connected to a first tension member;
anchoring a first tension anchor against a first tension anchor surface of a heart, wherein the first tension anchor is connected to a second tension member;
anchoring a second tension anchor to a second tension anchor surface of the heart, wherein the second tension anchor is connected to a third tension member;
extending the first tension member connected to the first ventricular surface anchor towards the second tension member connected to the first tension anchor;
extending the third tension member connected to the second tension anchor towards the first tension member connected to the first ventricular surface anchor; and
with the first tension member, the second tension member, and the third tension member, drawing the first right ventricular surface toward the first tension anchor;
wherein the third tension member is connected to the first tension member and the second tension member via a tension member lock.

2. The method of claim 1, wherein the first tension anchor surface is against a left atrial surface of an interatrial septum inferior to a Fossa Ovalis.

3. The method of claim 1, wherein the first tension anchor surface is at a right ventricular surface of an interventricular septum.

4. The method of claim 1, wherein the first tension anchor surface is at a left ventricular surface of an interventricular septum.

5. The method of claim 1, wherein the first tension anchor surface is at a coronary sinus close to a right atrium.

6. The method of claim 1, further comprising anchoring a second ventricular surface anchor against a right ventricular surface near an anterior portion of a tricuspid annulus;
wherein the second ventricular surface anchor is connected to a third tension member;
wherein a center of the first ventricular surface anchor is spaced between 0.5 and 4 centimeters from a center of the second ventricular surface anchor; and
extending the first tension member connected to the first ventricular surface anchor and the second tension member connected to the second ventricular surface anchor towards the first tension anchor; and
with the first tension member, the second tension member, and the third tension member, drawing the first right ventricular surface and the right ventricular surface near the anterior portion of the tricuspid annulus toward the first tension anchor.

7. The method of claim 1, wherein the first right ventricular surface is near an anterior portion of a tricuspid annulus.

8. The method of claim 1, wherein the first right ventricular surface is within a right ventricular outflow tract.

9. The method of claim 1, wherein the first right ventricular surface is within a pulmonary artery proximal to a pulmonary valve.

10. The method of claim 1, wherein drawing the first right ventricular surface toward the first tension anchor further comprises:
advancing a tensioning lock over the first tension member and the second tension member to a location proximal the first tension anchor to draw the first right ventricular surface toward the first tension anchor;
locking the tensioning lock to maintain tension on the first tension member and the second tension member; and
trimming excess material of the first tension member and the second tension member.

11. The method of claim 10, wherein locking the tensioning lock comprises:
adjusting the tensioning lock from a first configuration which can allow tension members to move freely relative to the tensioning lock to a second configuration which prevents the tension members from moving freely relative to the tensioning lock.

12. The method of claim 1, further comprising advancing a grommet over the first tension member connected to the first ventricular surface anchor;
wherein the grommet is positioned against an atrial surface of the heart opposite a ventricular surface anchor attached to the first tension member.

13. The method of claim 1, wherein the first tension member and the second tension member are portions of a single tension element.

14. A method of tricuspid valve repair comprising:
anchoring a first ventricular surface anchor near an anterior portion of a tricuspid annulus, wherein the first ventricular surface anchor is connected to a first tension member;
anchoring a second ventricular surface anchor near a right ventricular surface of a posterior portion of the tricuspid annulus, wherein the second ventricular surface anchor is connected to a second tension member;
anchoring a first tension anchor against a left atrial surface of an interatrial septum, wherein the first tension anchor is connected to a third tension member;
extending the first tension member connected to the first ventricular surface anchor and the second tension member connected to the second ventricular surface anchor towards the third tension member connected to the first tension anchor; and
with the first tension member, the second tension member, and the third tension member, drawing the anterior portion of the tricuspid annulus and the posterior portion of the tricuspid annulus toward the first tension anchor.

15. A tricuspid valve repair system comprising:
two or more surface anchor systems, each surface anchor system comprising:
  a surface anchor comprising a nitinol wire frame defined at its perimeter by a nitinol wire, and comprising an internal nitinol wire feature within an area defined by a perimeter formed by the nitinol wire frame;
    wherein the nitinol wire frame comprises an austenite state in a deployed configuration when a temperature of the nitinol wire frame is body temperature;
  a tether assembly comprising a plurality of tethers, wherein a tether extends from each of the two or more surface anchor systems and connects at a tether connection point; and
  a tether lock advanced over the tether connection point, the tether lock configured to limit relative movement between the two or more surface anchor systems.

16. The tricuspid valve repair system of claim 15, further comprising a grommet and a grommet lock.

17. The tricuspid valve repair system of claim 16, wherein the grommet is a flat grommet comprising an expandable nitinol frame;
  wherein the flat grommet is disposed upon the tether assembly through a hole in the flat grommet; and
  wherein the expandable nitinol frame of the grommet comprises an austenite state in a deployed configuration when a temperature of the expandable nitinol frame is a human body temperature.

18. The tricuspid valve repair system of claim 16, wherein the grommet is a T-bar grommet comprising a singular rigid member with a length along a long axis which is longer than a width along a short axis,
  wherein the width of the T-bar grommet is configured to accommodate the T-bar grommet within an inner diameter of a delivery catheter;
  wherein the T-bar grommet is disposed upon the tether assembly through a hole at or near a center of the T-bar grommet; and
  wherein the T-bar grommet can be pivoted about the tether assembly such that the long axis of the T-bar grommet is approximately parallel to an axis of the tether assembly for insertion into the delivery catheter for deployment; and
  wherein subsequent to deploying from the delivery catheter, the T-bar grommet can be pivoted about the tether assembly such that a longer axis of the T-bar grommet is at an angle relative to the axis of the tether assembly.

19. The tricuspid valve repair system of claim 15, wherein the nitinol wire frame of the surface anchor is formed by laser cutting a nitinol sheet or strip.

* * * * *